United States Patent
Jayasinghe et al.

(10) Patent No.: US 11,685,949 B2
(45) Date of Patent: *Jun. 27, 2023

(54) MUTANT PORE

(71) Applicant: Oxford Nanopore Technologies PLC, Oxford (GB)

(72) Inventors: Lakmal Nishantha Jayasinghe, Oxford (GB); Elizabeth Jayne Wallace, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 52 days.

This patent is subject to a terminal disclaimer.

(21) Appl. No.: 17/194,472

(22) Filed: Mar. 8, 2021

(65) Prior Publication Data

US 2021/0269872 A1    Sep. 2, 2021
US 2022/0154269 A9    May 19, 2022

Related U.S. Application Data

(62) Division of application No. 16/081,894, filed as application No. PCT/GB2017/050569 on Mar. 2, 2017, now Pat. No. 10,975,428.

(30) Foreign Application Priority Data

Mar. 2, 2016   (GB) ..................... 1603656
Mar. 2, 2016   (GB) ..................... 1603657
Mar. 2, 2016   (GB) ..................... 1603658

(51) Int. Cl.
    *C07K 14/245*    (2006.01)
    *C12Q 1/6869*    (2018.01)
    *G01N 33/487*    (2006.01)

(52) U.S. Cl.
    CPC .......... *C12Q 1/6869* (2013.01); *C07K 14/245* (2013.01); *G01N 33/48721* (2013.01); *C12Q 2565/631* (2013.01)

(58) Field of Classification Search
None
See application file for complete search history.

(56) References Cited

U.S. PATENT DOCUMENTS

| | | |
|---|---|---|
| 5,795,782 A | 8/1998 | Church et al. |
| 6,015,714 A | 1/2000 | Baldarelli et al. |
| 6,114,121 A | 9/2000 | Fujiwara et al. |
| 6,150,112 A | 11/2000 | Weissman et al. |
| 6,362,002 B1 | 3/2002 | Denison et al. |
| 6,426,231 B1 | 7/2002 | Bayley et al. |
| 6,627,067 B1 | 9/2003 | Branton et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,189,503 B2 | 3/2007 | Akeson et al. |
| 8,105,846 B2 | 1/2012 | Bayley et al. |
| 8,785,211 B2 | 7/2014 | Bayley et al. |
| 8,822,160 B2 | 9/2014 | Bayley et al. |
| 8,828,208 B2 | 9/2014 | Canas et al. |
| 9,073,990 B2 | 7/2015 | Paas et al. |
| 9,127,313 B2 | 9/2015 | Brown et al. |
| 9,222,082 B2 | 12/2015 | Jayasinghe et al. |
| 9,447,152 B2 | 9/2016 | Clarke et al. |
| 9,562,887 B2 | 2/2017 | Maglia et al. |
| 9,580,480 B2 | 2/2017 | Lu et al. |
| 9,588,079 B2 | 3/2017 | Gundlach et al. |
| 9,732,381 B2 | 8/2017 | Stoddart et al. |
| 9,751,915 B2 | 9/2017 | Clarke et al. |
| 9,777,049 B2 | 10/2017 | Bruce et al. |
| 10,006,905 B2 | 6/2018 | Maglia et al. |
| 10,167,503 B2 | 1/2019 | Clarke et al. |
| 10,266,885 B2 | 4/2019 | Jayasinghe et al. |
| 10,385,389 B2 | 8/2019 | Heron et al. |
| 10,400,014 B2 | 9/2019 | Howorka et al. |
| 10,443,097 B2 | 10/2019 | Jayasinghe et al. |
| 10,472,673 B2 | 11/2019 | Maglia et al. |
| 10,514,378 B2 | 12/2019 | Maglia et al. |
| 10,669,581 B2 | 6/2020 | Stoddart et al. |
| 10,802,015 B2 | 10/2020 | Maglia et al. |
| 10,844,432 B2 | 11/2020 | Jayasinghe et al. |
| 10,882,889 B2 | 1/2021 | Bruce et al. |
| 10,975,428 B2 | 4/2021 | Jayasinghe et al. |
| 10,976,300 B2 | 4/2021 | Maglia et al. |
| 10,976,311 B2 | 4/2021 | Maglia et al. |
| 10,995,372 B2 | 5/2021 | Jayasinghe et al. |
| 11,034,734 B2 | 6/2021 | Howorka et al. |
| 11,104,709 B2 | 8/2021 | Maglia et al. |
| 11,169,138 B2 | 11/2021 | Maglia et al. |
| 11,186,868 B2 | 11/2021 | Jayasinghe et al. |
| 11,307,192 B2 | 4/2022 | Jayasinghe et al. |

(Continued)

FOREIGN PATENT DOCUMENTS

| | | |
|---|---|---|
| CA | 2381139 A1 | 3/2001 |
| CN | 102116783 A | 7/2011 |

(Continued)

OTHER PUBLICATIONS

International Search Report and Written Opinion for Application No. PCT/GB2017/050569, dated Mar. 17, 2017.
International Preliminary Report on Patentability for Application No. PCT/GB2017/050569, dated Sep. 13, 2018.
[No Author Listed] EBI Accession No. GSP:AXX09397. May 13, 2010.
[No Author Listed] EBI Accession No. A0A085GH19. Oct. 29, 2014.
[No Author Listed] EBI Accession No. A0A0D1LDB9. Apr. 29, 2015.
[No Author Listed] EBI Accession No. EMBLCDS:ABV05494. Sep. 11, 2007.
[No Author Listed] Enterobacteria phage vB_EcoM-ACG-C40, complete genome. Genbank Acc. No. NC 019399.1. 2 pages.

(Continued)

*Primary Examiner* — Jennifer E Graser
(74) *Attorney, Agent, or Firm* — Wolf, Greenfield & Sacks, P.C.

(57) ABSTRACT

The invention relates to mutant forms of CsgG. The invention also relates to analyte detection and characterization using CsgG.

16 Claims, 46 Drawing Sheets

Specification includes a Sequence Listing.

(56) References Cited

U.S. PATENT DOCUMENTS

| | | |
|---|---|---|
| 2001/0044137 A1 | 11/2001 | Heyman et al. |
| 2002/0028458 A1 | 3/2002 | Lexow |
| 2002/0094526 A1 | 7/2002 | Bayley et al. |
| 2002/0197614 A1 | 12/2002 | Mosaic |
| 2003/0044816 A1 | 3/2003 | Denison et al. |
| 2003/0099951 A1 | 5/2003 | Akeson et al. |
| 2003/0165936 A1 | 9/2003 | Rabbani et al. |
| 2003/0211502 A1 | 11/2003 | Sauer et al. |
| 2003/0215881 A1 | 11/2003 | Bayley et al. |
| 2004/0209299 A1 | 10/2004 | Pinter et al. |
| 2004/0214177 A1 | 10/2004 | Bension |
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2007/0218471 A1 | 9/2007 | Kim et al. |
| 2008/0121534 A1 | 5/2008 | White et al. |
| 2008/0311582 A1 | 12/2008 | Bayley et al. |
| 2009/0111115 A1 | 4/2009 | Drmanac et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2009/0298188 A1 | 12/2009 | Peti-Peterdi |
| 2010/0120098 A1 | 5/2010 | Grunenwald et al. |
| 2010/0196203 A1 | 8/2010 | Sanghera et al. |
| 2010/0297638 A1 | 11/2010 | Bayley et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0194324 A1 | 7/2014 | Gormley et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0152495 A1 | 6/2015 | Stava et al. |
| 2015/0175663 A1 | 6/2015 | Yokoi et al. |
| 2015/0177237 A1 | 6/2015 | Turner et al. |
| 2015/0191709 A1 | 7/2015 | Heron et al. |
| 2015/0218629 A1 | 8/2015 | Heron et al. |
| 2015/0346149 A1 | 12/2015 | Brown et al. |
| 2016/0005330 A1 | 1/2016 | Maglia et al. |
| 2016/0010147 A1 | 1/2016 | Heron et al. |
| 2016/0053300 A1 | 2/2016 | Maglia et al. |
| 2016/0370358 A1 | 12/2016 | Maglia et al. |
| 2017/0058337 A1 | 3/2017 | Clarke et al. |
| 2017/0058338 A1 | 3/2017 | Jayasinghe et al. |
| 2017/0107569 A1 | 4/2017 | Heron et al. |
| 2017/0233803 A1 | 8/2017 | Stoddart et al. |
| 2017/0306398 A1 | 10/2017 | Jayasinghe et al. |
| 2018/0030526 A1 | 2/2018 | Brown et al. |
| 2018/0095066 A1 | 4/2018 | Jayasinghe et al. |
| 2018/0148481 A2 | 5/2018 | Howorka et al. |
| 2018/0208632 A1 | 7/2018 | Bruce et al. |
| 2018/0209952 A1 | 7/2018 | Maglia et al. |
| 2018/0334707 A1 | 11/2018 | Stoddart et al. |
| 2018/0335425 A1 | 11/2018 | Maglia et al. |
| 2018/0364214 A1 | 12/2018 | Maglia et al. |
| 2019/0071721 A1 | 3/2019 | Jayasinghe et al. |
| 2019/0202876 A1 | 7/2019 | Jayasinghe et al. |
| 2019/0300582 A1 | 10/2019 | Jayasinghe et al. |
| 2019/0330282 A1 | 10/2019 | Jayasinghe et al. |
| 2019/0346431 A1 | 11/2019 | Maglia et al. |
| 2020/0017556 A1 | 1/2020 | Howorka et al. |
| 2020/0072824 A1 | 3/2020 | Maglia et al. |
| 2020/0087724 A1 | 3/2020 | Heron et al. |
| 2020/0224262 A1 | 7/2020 | Jayasinghe et al. |
| 2020/0299336 A9 | 9/2020 | Jayasinghe et al. |
| 2020/0299337 A9 | 9/2020 | Jayasinghe et al. |
| 2020/0407785 A1 | 12/2020 | Stoddart et al. |
| 2021/0139972 A1 | 5/2021 | Jayasinghe et al. |
| 2021/0147486 A1 | 5/2021 | Remaut et al. |
| 2021/0284696 A1 | 9/2021 | Remaut et al. |
| 2021/0292376 A1 | 9/2021 | Howorka et al. |
| 2021/0317520 A1 | 10/2021 | Jayasinghe et al. |
| 2021/0324020 A1 | 10/2021 | Bruce et al. |
| 2021/0405039 A1 | 12/2021 | Maglia et al. |
| 2022/0024985 A9 | 1/2022 | Remaut et al. |
| 2022/0064230 A1 | 3/2022 | Jayasinghe et al. |
| 2022/0091096 A1 | 3/2022 | Maglia et al. |
| 2022/0119879 A1 | 4/2022 | Jayasinghe et al. |
| 2022/0162264 A9 | 5/2022 | Remaut et al. |
| 2022/0283141 A1 | 9/2022 | Jayasinghe et al. |

FOREIGN PATENT DOCUMENTS

| | | |
|---|---|---|
| CN | 102174554 A | 9/2011 |
| CN | 102317310 A | 1/2012 |
| CN | 103460040 A | 12/2013 |
| EP | 2194123 B1 | 8/2012 |
| EP | 2682460 A1 | 1/2014 |
| GB | 2453377 A | 4/2009 |
| GB | 1314695.6 | 8/2013 |
| JP | H10-146190 A | 6/1998 |
| JP | 2005-253427 A | 9/2005 |
| JP | 2015-514128 A | 5/2015 |
| WO | WO 1999/005167 A1 | 2/1999 |
| WO | WO 2000/028312 A1 | 5/2000 |
| WO | WO 2001/042782 A1 | 6/2001 |
| WO | WO 2001/059453 A2 | 8/2001 |
| WO | WO 2002/042496 A2 | 5/2002 |
| WO | WO 2003/095669 A1 | 11/2003 |
| WO | WO 2005/013666 A2 | 2/2005 |
| WO | WO 2005/076010 A2 | 8/2005 |
| WO | WO 2006/028508 A2 | 3/2006 |
| WO | WO 2006/100484 A2 | 9/2006 |
| WO | WO 2007/057668 A1 | 5/2007 |
| WO | WO 2007/075987 A2 | 7/2007 |
| WO | WO 2007/084103 A2 | 7/2007 |
| WO | WO 2008/102120 A1 | 8/2008 |
| WO | WO 2008/102121 A1 | 8/2008 |
| WO | WO 2008/124107 A1 | 10/2008 |
| WO | WO 2009/024775 A1 | 2/2009 |
| WO | WO 2009/035647 A1 | 3/2009 |
| WO | WO 2009/044170 A1 | 4/2009 |
| WO | WO 2009/077734 A2 | 6/2009 |
| WO | WO 2009/143425 A1 | 11/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/055307 A1 | 5/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/122293 A1 | 10/2010 |
| WO | WO 2011/067559 A1 | 6/2011 |
| WO | WO 2012/042226 A1 | 4/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A1 | 4/2013 |
| WO | WO 2013/098561 A1 | 7/2013 |
| WO | WO 2013/098562 A1 | 7/2013 |
| WO | WO 2013/109970 A1 | 7/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A1 | 5/2014 |
| WO | WO 2014/064444 A1 | 5/2014 |
| WO | WO 2014/122654 A2 | 8/2014 |
| WO | WO 2014/135838 A1 | 9/2014 |
| WO | WO 2014/142850 A1 | 9/2014 |
| WO | WO 2014/153047 A1 | 9/2014 |
| WO | WO 2014/153625 A1 | 10/2014 |

(56) References Cited

FOREIGN PATENT DOCUMENTS

| WO | WO 2014/187924 A1 | 11/2014 |
|---|---|---|
| WO | WO 2015/022544 A1 | 2/2015 |
| WO | WO 2015/051378 A1 | 4/2015 |
| WO | WO 2015/055981 A1 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |
| WO | WO 2015/166275 A1 | 11/2015 |
| WO | WO 2015/166276 A1 | 11/2015 |
| WO | WO 2016/034591 A2 | 3/2016 |
| WO | WO 2016/055778 A1 | 4/2016 |
| WO | WO 2016/166232 A1 | 10/2016 |
| WO | WO 2017/149316 A1 | 9/2017 |
| WO | WO 2017/149317 A1 | 9/2017 |
| WO | WO 2017/149318 A1 | 9/2017 |
| WO | WO 2018/211241 A1 | 11/2018 |

OTHER PUBLICATIONS

[No Author Listed] Helicos BioSciences Corporation, "Helicos Genetic Analysis System," Specification Sheet retrieved online at: www.helicosbio.com/Portals/0/Documents/Helicos_SalesSpec. pdf, 4 pages (2008).

[No Author Listed] Uniprot Accession No. A0A081NL13. Oct. 29, 2014. 4 pages.

[No Author Listed] Uniprot Accession No. A0A0P7DN88. Jan. 20, 2016. 4 pages.

[No Author Listed] Uniprot Accession No. Q8Z727. Oct. 24, 2003. 6 pages.

[No Author Listed], *Escherichia coli* HS curli production assembly/ transport subunit. Accession No. ABV05494. Sep. 11, 2007. 2 pages.

Ahern, Biochemical, reagents kits offer scientists good return on investment. The Scientist. Jul. 24, 1995;9(15):20.

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Aoki et al., Single channel properties of lysenin measured in artificial lipid bilayers and their applications to biomolecule detection. Proc Jpn Acad Ser B Phys Biol Sci. 2010;86(9):920-5.

Aravind et al., The DNA-Repair Protein AlkB, EGL-9, and Leprecan Define New Families of 2-oxoglutarate-andIron-Dependent Dioxygenases. Genome Biology. 2001;2:1-8.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Ashton et al., MinION Nanopore Sequencing Identifies the Position and Structure of a Bacterial antibiotic Resistance Island. Nat Biotechnol. Mar. 2015;33(3):296-302.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Atkins et al., Structure-function relationships of a novel bacterial toxin, hemolysin E. The role of alpha G. J Biol Chem. Dec. 29, 2000;275(52):41150-5.

Avrameas, Coupling of enzymes to proteins with glutaraldehyde. Use of the conjugates for the detection of antigens and antibodies. Immunochemistry. Jan. 1969;6(1):43-52.

Bayley et al., Stochastic sensors inspired by biology. Nature. Sep. 13, 2001;413(6852):226-30.

Bayley et al., Wrestling with native chemical ligation. ACS Chem Biol. Dec. 18, 2009;4(12):983-5. doi: 10.1021/cb900304p.

Bayley, Membrane-protein structure: Piercing insights. Nature. Jun. 4, 2009;459(7247):651-2. doi: 10.1038/459651a.

Bayley, Nanopore Sequencing: From Imagination to Reality. Clin Chem. 2015;61(1):25-31.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Bezrukov et al., Counting Polymers Moving Through a Single Ion Channel. Nature. Jul. 28, 1994;370:279-81.

Bianco et al., Helicase unwinding: active or merely perfect? J Mol Biol. Jul. 13, 2012;420(3):139-40. doi: 10.1016/j.jmb.2012.04.030. Epub May 2, 2012.

Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.

Bleijlevens et al., Dynamic States of the DNA Repair Enzyme AlkB regulate Product Release. Eur Mol Biol Org. Jul. 11, 2008;9(9):872-77.

Boersma et al., Continuous stochastic detection of amino acid enantiomers with a protein nanopore. Angew Chem Int Ed Engl. Sep. 17, 2012;51(38):9606-9. doi: 10.1002/anie.201205687. Epub Aug. 29, 2012.

Bourdon et al., Molecular cloning and sequence analysis of a chondroitin sulfate proteoglycan cDNA. Proc Natl Acad Sci USA. Mar. 1985;82(5):1321-5.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi: 10.1038/nbt. 1495.

Braslavsky et al., Sequence information can be obtained from single DNA molecules. Proc Natl Acad Sci USA. Apr. 1, 2003;100(7):3960-4. Epub Mar. 21, 2003.

Butler et al., Determination of RNA orientation during translocation through a biological nanopore. Biophys J. Jan. 1, 2006;90(1):190-9. Epub Oct. 7, 2005.

Butler et al., Single-molecule DNA detection with an engineered MspA protein nanopore. Proc Natl Acad Sci USA. Dec. 30, 2008;105(52):20647-52. doi: 10.1073/pnas.0807514106. Epub Dec. 19, 2008.

Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.

Cao et al., Structure of the nonameric bacterial amyloid secretion channel. Proc Natl Acad Sci USA. Dec. 16, 2014;111(50):E5439-44. doi: 10.1073/pnas.1411942111. Epub Dec. 1, 2014.

Chan, Advances in sequencing technology. Mutat Res. Jun. 3, 2005;573(1-2):13-40.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

Cheley et al., Spontaneous oligomerization of a staphylococcal alpha-hemolysin conformationally constrained by removal of residues that form the transmembrane beta-barrel. Protein Eng. Dec. 1997;10(12):1433-43.

Chen et al., Atomic Layer Deposition to Fine-Tune the Surface Properties and Diameters of Fabricated Nanopores. Nano Lett. Jun. 25, 2004;4(7):1333-1337.

Chen et al., Outer membrane protein G: Engineering a quiet pore for biosensing. Proc Natl Acad Sci USA. Apr. 29, 2008;105(17):6272-7. doi: 10.1073/pnas.0711561105. Epub Apr. 28, 2008.

(56) References Cited

OTHER PUBLICATIONS

Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.

Chin et al., The Metabolite alpha-Ketoglutarate Extends Lifespan by Inhibiting ATP Synthase and TOR. Nature. Jul. 19, 2014;510:397-401.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Comai et al., Protein engineering modulates the transport properties and ion selectivity of the pores formed by staphylococcal gamma-haemolysins in lipid membranes. Mol Microbiol. Jun. 2002;44(5):1251-67.

Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.

Deamer et al., Characterization of nucleic acids by nanopore analysis. Acc Chem Res. Oct. 2002;35(10):817-25.

Deamer et al., Nanopores and nucleic acids: prospects for ultrarapid sequencing. Trends Biotechnol. Apr. 2000;18(4):147-51.

Derrington et al., A Novel DNA Sensing Technique Using Nanopore MSPA. 54th Annual Meeting of the Biophysical Society, Poster 2182-Plat, 2 pages (2010).

Derrington et al., Nanopore DNA sequencing with MspA. Proc Natl Acad Sci USA. Sep. 14, 2010;107(37):16060-5. doi: 10.1073/pnas.1001831107. Epub Aug. 26, 2010.

Dorre et al., Techniques for single molecule sequencing. Bioimaging, vol. 5:139-152 (1997).

Eid et al., Real-time DNA sequencing from single polymerase molecules. Science. Jan. 2, 2009;323(5910):133-8. doi: 10.1126/science.1162986. Epub Nov. 20, 2008.

Eifier et al., Cytotoxin ClyA from *Escherichia coli* assembles to a 13-meric pore independent of its redox-state. EMBO J. Jun. 7, 2006;25(11):2652-61. doi: 10.1038/sj.emboj.7601130. Epub May 11, 2006.

Eliseev et al., Aminocyclodextrins as Selective Hosts with Several Binding Sites for Nucleotides. Angew. Chem. Int. Ed. Engl., vol. 32(9):1331-1333 (1993).

Eliseev et al., Molecular Recognition of Nucleotides, Nucleosides, and Sugars by Aminocyclodextrins. J. Am. Chem. Soc., vol. 116:6081-6088 (1994).

Engelhardt et al., A tetrameric porin limits the cell wall permeability of *Mycobacterium smegmatis*. J Biol Chem. Oct. 4, 2002;277(40):37567-72. Epub Jul. 18, 2002.

Ergel et al., Protein Dynamics Control the Progression and Efficiency of the Catalytic Reaction Cycle of the *Escherichia coli* DNA-Repair Enzyme AlkB. J Biol Chem. Oct. 24, 2014;289(43):29584-601.

Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.

Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

Flusberg et al., Direct detection of DNA methylation during single-molecule, real-time sequencing. Nat Methods. Jun. 2010;7(6):461-5. doi: 10.1038/nmeth.1459. Epub May 9, 2010.

Fologea et al., Potential analytical applications of lysenin channels for detection of multivalent ions. Anal Bioanal Chem. Oct. 2011;401(6):1871-9. doi: 10.1007/s00216-011-5277-8. Epub Aug. 5, 2011.

Franceschini et al., A nanopore machine promotes the vectorial transport of DNA across membranes. Sep. 2013; Nat Commun. 2013;4:2415. doi: 10.1038/ncomms3415.

Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.

Freedman et al., Single Molecule Unfolding and Stretching of Protein Domains Inside a Solid-State Nanopore by Electric Field. Scientific Reports. Apr. 10, 2013;3(1638):1-8.

Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.

Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

Gilbert et al., Two Structural Transitions in Membrane Pore Formation by Pneumolysin, the Pore-Forming Toxin of *Streptococcus Pneumoniae*. Cell. May 28, 1999;97:647-655.

Goedhart et al., Quantitative co-expression of proteins at the single cell level—application to a multimeric FRET sensor. PLoS One. 2011;6(11):e27321. doi: 10.1371/journal.pone.0027321. Epub Nov. 17, 2011.

Gouridis et al., Conformational Dynamics in Substrate-Binding Domains Influences Transport in the ABC Importer GinPQ. Nat Stuct Mol Biol. Dec. 8, 2014;22(1):57-66.

Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.

Goyal et al., Structural and mechanistic insights into the bacterial amyloid secretion channel CsgG. Nature. Dec. 11, 2014;516(7530):250-3. doi: 10.1038/nature13768. Epub Sep. 14, 2014.

Gu et al., Capture of a single molecule in a nanocavity. Science. Jan. 26, 2001;291(5504):636-40.

Gu et al., Electroosmotic enhancement of the binding of a neutral molecule to a transmembrane pore. Proc Natl Acad Sci USA. Dec. 23, 2003;100(26):15498-503. Epub Dec. 15, 2003.

Gu et al., Interaction of the noncovalent molecular adapter, beta-cyclodextrin, with the staphylococcal alpha-hemolysin pore. Biophys J. Oct. 2000;79(4):1967-75.

Gu et al., Prolonged residence time of a noncovalent molecular adapter, beta-cyclodextrin, within the lumen of mutant alpha-hemolysin pores. J Gen Physiol. Nov. 2001;118(5):481-94.

Gu et al., Reversal of charge selectivity in transmembrane protein pores by using noncovalent molecular adapters. Proc Natl Acad Sci USA. Apr. 11, 2000;97(8):3959-64.

Gu et al., Stochastic sensing of organic analytes by a pore-forming protein containing a molecular adapter. Nature. Apr. 22, 1999;398(6729):686-90.

Guan et al., Stochastic sensing of TNT with a genetically engineered pore. Chembiochem. Oct. 2005;6(10):1875-81.

Guasch et al., Detailed architecture of a DNA translocating machine: the high-resolution structure of the bacteriophage phi29 connector particle. J Mol Biol. Jan. 25, 2002;315(4):663-76.

Guo et al., Nanopore sensor for copper ion detection using a polyamine decorated ?-cyclodextrin as the recognition element. RSC Adv. 2017;7:15315. doi: 10.1039/c7ra00454k. 6 pages.

Hall et al., Hybrid pore formation by directed insertion of ?-haemolysin into solid-state nanopores. Nat Nanotechnol. Dec. 2010;5(12):874-7. doi: 10.1038/nnano.2010.237. Epub Nov. 28, 2010.

Han et al., Characterization and optimization of an entropic trap for DNA separation. Anal Chem. Jan. 15, 2002;74(2):394-401.

(56) References Cited

OTHER PUBLICATIONS

Han et al., RecJ exonuclease: substrates, products and interaction with SSB. Nucleic Acids Res. Feb. 18, 2006;34(4):1084-91. Print 2006.

Haque et al., Solid-State and Biological Nanopore for Real-Time Sensing of Single Chemical and Sequencing of DNA. Nano Today. Feb. 2013;8(1):56-74.

He et al. 2012; The T4 phage SF1 B helicase dda is structurally optimized to perform DNA strand separation. Structure. 20:1189-1200.

Henrickson et al., Driven DNA transport into an asymmetric nanometer-scale pore. Phys Rev Lett. Oct. 2, 2000;85(14):3057-60.

Heron et al., Direct detection of membrane channels from gels using water-in-oil droplet bilayers. J Am Chem Soc. Dec. 26, 2007;129(51):16042-7. Epub Dec. 1, 2007.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Hornblower et al., Single-molecule analysis of DNA-protein complexes using nanopores. Nat Methods. Apr. 2007;4(4):315-7. Epub Mar. 4, 2007.

Howorka et al., DNA Duplex Formation of Individual DNA Strands within a Single Protein Pore. Biophysical Journal, vol. 82{ 1, pt. 2):508a, No. 2482-Plat (2002).

Howorka et al., Kinetics of duplex formation for individual DNA strands within a single protein nanopore. Proc Natl Acad Sci USA. Nov. 6, 2001;98(23):12996-3001. Epub Oct. 23, 2001.

Howorka et al., Nanopore Analytics: Sensing of Single Molecules. The Royal Society of Chemistry. Jun. 15, 2009;38:2360-84.

Howorka et al., Nanopores as protein sensors. Nat Biotechnol. Jun. 7, 2012;30(6):506-7. doi: 10.1038/nbt.2264.

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001;19(7):636-9.

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.

Hwang et al., Electrical behavior of droplet interface bilayer networks: experimental analysis and modeling. J Am Chem Soc. Sep. 26, 2007;129(38):11854-64. Epub Sep. 1, 2007.

Iacovache et al., Structure and assembly of pore-forming proteins. Curr Opin Struct Biol. Apr. 2010;20(2):241-6. doi:10.1016/j.sbi.2010.01.013. Epub Feb. 19, 2010.

Ide et al., Lysenin forms a voltage-dependent channel in artificial lipid bilayer membranes. Biochem Biophys Res Commun. Jul. 21, 2006;346(1):288-92. Epub May 26, 2006.

Ivanov et al., DNA tunneling detector embedded in a nanopore. Nano Lett. Jan. 12, 2011;11(1):279-85. doi: 10.1021/nl103873a. Epub Dec. 6, 2010.

Jayasinghe et al., The leukocidin pore: evidence for an octamer with four LukF subunits and four LukS subunits alternating around a central axis. Protein Sci. Oct. 2005;14(10):2550-61.

Johnston et al., Coexpression of proteins in bacteria using T7-based expression plasmids: expression of heteromeric cell-cycle and transcriptional regulatory complexes. Protein Expr Purif. Dec. 2000;20(3):435-43.

Jung et al., The internal cavity of the staphylococcal alpha-hemolysin pore accommodates approximately 175 exogenous amino acid residues. Biochemistry. Jun. 28, 2005;44(25):8919-29.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci USA. Nov. 26, 1996;93(24):13770-3.

Khulbe et al., DNA translocation through a-hemolysin nanopores with potential application to macromolecular data storage. Journal Applied Physics, vol. 97(104317):1-7 (2005).

Kobayashi et al., Comparative Physiology and Biochemistry, 2005, vol. 22, No. 3-4, pp. 139-148.

Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.

Krylova et al., DNA aptamers for as analytical tools for the quantitative analysis of DNA-dealkylating enzymes. Anal Biochem. 2011;414(2):261-265. doi:10.1016/j.ab.2011.03.010.

Kumar et al., PEG-labeled nucleotides and nanopore detection for single molecule DNA sequencing by synthesis. Sci Rep. 2012;2:684. Epub Sep. 21, 2012.

Langecker et al., Synthetic lipid membrane channels formed by designed DNA nanostructures. Science. Nov. 16, 2012;338(6109):932-6. doi: 10.1126/science.1225624.

Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.

Li et al., DNA molecules and configurations in a solid-state nanopore microscope. Nat Mater. Sep. 2003;2(9):611-5. Epub Aug. 24, 2003.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.

Lu et al., Protein Motion and Configurations in a Form-Fitting Nanopore: Avidin in ClyA. Biophys J. Sep. 4, 2018; 115(5): 801-808. Epub Aug. 4, 2018. doi: 10.1016/j.bpj.2018.07.024.

Luchian et al., Single-Molecule Covalent Chemistry with Spatially Separated Reactants. Angew. Chem. Int. Ed. 2003;42:3766-771.

Ludwig et al., Analysis of the SlyA-Controlled Expression, Subcellular Localization and Pore-Forming Activity of a 34 kDa Haemolysin (ClyA) from *Escherichia coli* K-12. Mol Microbiol. 1999;31(2):557-67.

Luo et al., Influence of polymer-pore interactions on translocation. Phys Rev Lett. Oct. 5, 2007;99(14):148102. Epub Oct. 1, 2007.

Maglia et al., DNA strands from denatured duplexes are translocated through engineered protein nanopores at alkaline pH. Nano Lett. Nov. 2009;9(11):3831-6. doi: 10.1021/nl9020232.

Maglia et al., Engineering a Biomimetic Biological Nanopore to Selectively Capture Folded Target Proteins. Biophysical J. Feb. 5, 2013;104(2):518a.

Maglia et al., Enhanced translocation of single DNA molecules through alpha-hemolysin nanopores by manipulation of internal charge. Proc Natl Acad Sci USA. Dec. 16, 2008;105(50):19720-5. doi:10.1073/pnas.0808296105. Epub Dec. 5, 2008.

Makaram et al., Trends in Nanomaterial-Based Non-Invasive Diabetes Sensing Technologies. Diagnostics. Apr. 21, 2014;4:27-46.

Manrao et al., Nucleotide Discrimination with DNA Immobilized in the MspA Nanopore. PLoS One, vol. 6(10):e25723, 7 pages (2011).

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Manrao et al., Single Nucleotide Discrimination in Single Stranded DNA Immobilized within Biological Nanopore MSPA. 54th Annual Meeting of the Biophysical Society, 3 pages (2010).

Martin et al., Nanoscale protein pores modified with PAMAM dendrimers. J Am Chem Soc. Aug. 8, 2007;129(31):9640-9. Epub Jul. 18, 2007.

(56) References Cited

OTHER PUBLICATIONS

Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci USA. Aug. 30, 2005;102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci USA. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Mikheyev et al., A First Look at the Oxford Nanopore MinION Sequencer. Mol Ecol Res. 2014;14:1097-1102.
Miles et al., The Staphylococcal Leukocidin Bicomponent Toxin Forms Large Ionic Channels. Biochemistry. Jun. 28, 2001;40:8514-522.
Mitchell et al., Chemical tags facilitate the sensing of individual DNA strands with nanopores. Angew Chem Int Ed Engl. 2008;47(30):5565-8. doi:10.1002/anie.200800183.
Miyazaki et al., MEGAWHOP Cloning: A Method of Creating Random Mutagenesis Libraries via Megaprimer PCR of Whole Plasmids. Methods in Enzymology. 2011;498:399-406.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Moreau et al., Coupling ion channels to receptors for biomolecule sensing. Nat Nanotechnol. Oct. 2008;3(10):620-5. doi: 10.1038/nnano.2008.242. Epub Sep. 7, 2008.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Moyer et al., Correlation Between Sweat Glucose and Blood Glucose in Subjects with Diabetes. Diabetes Technol Ther. 2012:14(5):398-402.
Mueller et al., RCSB Protein Data Bank No. 2WCD. Mar. 11, 2009. doi: 10.2210/pdb2WCD/pdb. 5 pages.
Mueller et al., The Structure of Cytolytic alpha-Helical Toxin Pore Reveals its Assembly Mechanism. Nature. Jun. 4, 2009;459:726-731.
Mueller et al., The Structure of Cytolytic alpha-Helical Toxin Pore Reveals its Assembly Mechanism. Nature. Jun. 4, 2009;459:Supplemental Information.
Muller et al., DNA-directed assembly of artificial multienzyme complexes. Biochem Biophys Res Commun. Dec. 5, 2008;377(1):62-7. doi: 10.1016/j.bbrc.2008.09.078. Epub Sep. 25, 2008.
Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niedzwiecki et al., Inspection of the Engineered FhuA deltaC/delta4L Protein Nanopore by Polymer Exclusion. Biophys J. Nov. 2012;103:2115-124.

Nikolaidou et al., alpha-Ketoglutarate: Biological Effects of a Novel Biomarker of Heart Failure. Heart. Sep. 2010;96(17). 2 pages.
Nivala et al., Unfoldase-mediated protein translocation through an ?-hemolysin nanopore. Nat Biotechnol. Mar. 2013;31(3):247-50. doi: 10.1038/nbt.2503. Epub Feb. 3, 2013.
Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. Nov. 2009;32(11):1819-18223.
Oukhaled et al., Dynamics of Completely Unfolded and Native Proteins through Solid-State Nanopores as a Function of Electric Driving Force. Am Chem Soc. Apr. 8, 2011;5(5):3628-38.
Pavlenok et al., Hetero-oligomeric MspA pores in *Mycobacterium smegmatis*. FEMS Microbiol Lett. Apr. 2016;363(7). pii: fnw046. doi:10.1093/femsle/fnw046. Epub Feb. 23, 2016.
Pavlenok et al., MspA nanopores from subunit dimers. PLoS One. 2012;7(6):e38726. doi: 10.1371/journal.pone.0038726. Epub Jun. 18, 2012.
Pfeiffer et al., Bivalent cholesterol-based coupling of oligonucleotides to lipid membrane assemblies. J Am Chem Soc. Aug. 25, 2004;126(33):10224-5.
Plesa et al., Fast Translocation of Proteins through Solid State Nanopores. Nano Lett. Jan. 23, 2013;13:658-663.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Quick et al., A reference Bacterial Genome Dataset Generated on the MinION Portable Single-Molecule Nanopore Sequencer. GigaScience. 2014;3(22):1-6.
Rajagopalan et al., Interaction of Dihydrofolate Reductase with Methotrexate: Ensemble and Single-Molecule Kinetics. PNAS. Oct. 15, 2002;99(21):13481-6.
Rasko et al., The pangenome structure of *Escherichia coli*: comparative genomic analysis of *E. coli* commensal and pathogenic isolates. J Bacteriol. Oct. 2008;190(20):6881-93. doi: 10.1128/JB.00619-08. Epub Aug. 1, 2008.
Rhee et al., Nanopore sequencing technology: research trends and applications. Trends Biotechnol. Dec. 2006;24(12):580-6. Epub Oct. 19, 2006.
Robinson et al., Secretion of curli fibre subunits is mediated by the outer membrane-localized CsgG protein. Mol Microbiol. Feb. 2006;59(3):870-81.
Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.
Rotem et al., Protein detection by nanopores equipped with aptamers. J Am Chem Soc. Feb. 8, 2012;134(5):2781-7. doi:10.1021/ja2105653. Epub Jan. 26, 2012.
Rucker et al., Recombinant ferritin: modulation of subunit stoichiometry in bacterial expression systems. Protein Eng. 1997;10(8):967-973. doi:10.1093/protein/10.8.967.
Russo et al., Reversible permeabilization of plasma membranes with an engineered switchable pore. Nat Biotechnol. Mar. 1997;15(3):278-82.
Saariaho et al., Characteristics of MuA transposase-catalyzed processing of model transposon end DNA hairpin substrates. Nucleic Acids Res. Jun. 6, 2006;34(10):3139-49.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Skocaj et al., The sensing of membrane microdomains based on pore-forming toxins. Curr Med Chem. 2013;20(4):491-501.

(56) References Cited

OTHER PUBLICATIONS

Smeets et al., Salt dependence of ion transport and DNA translocation through solid-state nanopores. Nano Lett. Jan. 2006;6(1):89-95.
Soni et al., Synchronous optical and electrical detection of biomolecules traversing through solid-state nanopores. Rev Sci Instrum. Jan. 2010;81(1):014301. doi: 10.1063/1.3277116.
Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012.
Soskine et al., Single-Molecule Analyte Recognition with ClyA Nanopores Equipped with Internal Protein Adaptors. J Am Chem Soc. 2015;137:5793-97.
Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci USA. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Taylor et al., Atomic resolution insights into curli fiber biogenesis. Structure. Sep. 7, 2011;19(9):1307-16. doi: 10.1016/j.str.2011.05.015.
Trewick et al., Oxidative Demethylation by *Escherichia coli* AlkB Directly Reverts DNA Base Damage. Nature. Sep. 12, 2002:419:174-78.
Van De Goor, Nanopore Detection: Threading DNA Through a Tiny Hole. PharmaGenomics, vol. 4 (3):28-30 (2004).
Van Gerven et al., Secretion and functional display of fusion proteins through the curli biogenesis pathway. Mol Microbiol. Mar. 2014;91(5):1022-35. doi:10.1111/mmi.12515. Epub Feb. 12, 2014.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Van Meervelt et al., Detection of Two Isomeric Binding Configurations in a Protein-Aptamer Complex with a Biological Nanopore. Am Chem Soc. Dec. 10, 2014;8(12):12826-35.
Van Meervelt et al., Real-Time Conformational Changes and Controlled Orientation of Native Proteins Inside a Protein Nanoreactor. J Am Chem Soc. Dec. 27, 2017; 139(51): 18640-18646. EPub Dec. 5, 2017. doi: 10.1021/jacs.7b10106.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wallace et al., *E. coli* hemolysin E (HlyE, ClyA, SheA): X-ray crystal structure of the toxin and observation of membrane pores by electron microscopy. Cell. Jan. 21, 2000;100(2):265-76.
Wang et al., Nanopores with a spark for single-molecule detection. Nat Biotechnol. Jul. 2001;19(7):622-3.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wanunu, Nanopores: A journey towards DNA sequencing. Phys Life Rev. Jun. 2012;9(2):125-58. doi:10.1016/j.phev.2012.05.010. Epub May 18, 2012.
Welford et al., The Selectivity and Inhibition of AlkB. J. Biol. Chem. Mar. 21, 2003;278(12):10157-161.
Wendell et al., Translocation of double-stranded DNA through membrane-adapted phi29 motor protein nanopores. Nat Nanotechnol. 2009;4(11):765-772. doi:10.1038/nnano.2009.259.

White et al., Single Ion-Channel Recordings Using Glass Nanopore Membranes. J Am Chem Soc. 2007;129:11766-775.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
Wu et al., Single-molecule detection of nitrogen mustards by covalent reaction within a protein nanopore. J Am Chem Soc. May 28, 2008;130(21):6813-9. doi: 10.1021/ja8004607. Epub Apr. 30, 2008.
Yoo et al., Glucose Biosensors: An Overview of Use in Clinical Practice. Sensores. May 4, 2010;10:4558-4576.
Zernia et al., Current Blockades of Proteins inside Nanopores for Real-Time Metabolome Analysis. ACS Nano. Feb. 25, 2020; 14(2): 2296-2307. EPub Jan. 31, 2020. doi: 10.1021/acsnano.9b09434.
Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano.9b09434. 19 pages.
Zhou et al., Ion Channel Probes for Scanning Ion Conductance Microscopy. Langmuir. Nov. 25, 2014;30:15351-355.
U.S. Appl. No. 17/108,536, filed Dec. 1, 2020, Bruce et al.
U.S. Appl. No. 17/196,810, filed Mar. 9, 2021, Maglia et al.
U.S. Appl. No. 17/179,641, filed Feb. 19, 2021, Maglia et al.
U.S. Appl. No. 17/194,821, filed Mar. 8, 2021, Howorka et al.
U.S. Appl. No. 17/215,506, filed Mar. 29, 2021, Jayasinghe et al.
[No Author Listed] Nextera™ DNA Sample Preparation Kits (Illumina) Oct. 2011. (2 pages).
[No Author Listed] Oxford Nanopore "Product" brochure (2020) https://nanoporetech.com/sites/default/files/s3/literature/product-brochure.Pdf (36 pages).
[No Author Listed] Protein Databank entries of AlphaFold structure prediction for POAE98 and POA202, 2 pages.
[No Author Listed] Uniprot Accession No. POAE98 and POA202 search results, last accessed Mar. 29, 2022. 4 pages.
[No Author Listed] UniProt, "SubName: Full=Curli production assembly/transport component {ECO:0000313:EMBL:CTR43957.1};", XP002783536, retrieved from EBI accession No. UNIPROT:A0A0K3UZP3, Nov. 11, 2015.
Afonine et al., Real-space refinement in PHENIX for cryo-EM and crystallography. Acta Crystallogr D Struct Biol. 2018;74(Pt 6):531-544. doi:10.1107/S2059798318006551.
Altschul et al. Basic local alignment search tool. J Mol Biol. Oct. 5, 1990;215(3):403-10. doi: 10.1016/S0022-2836(05)80360-2.
Altschul, A protein alignment scoring system sensitive at all evolutionary distances. J Mol Evol. Mar. 1993;36(3):290-300. doi: 10.1007/BF00160485.
Ayub et al., Engineered transmembrane pores. Curr Opin Chem Biol. 2016;34:117-126. doi:10.1016/j.cbpa.2016.08.005. Author Manuscript, 16 pages.
Brown et al., Tools for macromolecular model building and refinement into electron cryo-microscopy reconstructions. Acta Crystallogr D Biol Crystallogr. 2015;71(Pt 1):136-153. doi:10.1107/S1399004714021683.
Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.
Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.
Chapman et al., Role of *Escherichia coli* curli operons in directing amyloid fiber formation. Science. 2002;295(5556):851-855. doi:10.1126/science.1067484. Author Manuscript, 9 pages.
Chin et al., Addition of a photocrosslinking amino acid to the genetic code of *Escherichia coli*. Proc Natl Acad Sci USA. Aug. 20, 2002;99(17):11020-4. doi: 10.1073/pnas. 172226299. Epub Aug. 1, 2002.

(56) References Cited

OTHER PUBLICATIONS

De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.
Devereux et al., A comprehensive set of sequence analysis programs for the VAX. Nucleic Acids Res. Jan. 11, 1984;12(1 Pt 1):387-95. doi: 10.1093/nar/12.1part1.387.
Epstein, Assembly, Spatial Distribution, and Secretion Activity of the Curlin Secretion Lipoprotein, CsgG. Dissertation. The University of Michigan. 2008. 167 pages.
Fiume et al., Savant: genome browser for high-throughput sequencing data. Bioinformatics. Aug. 15, 2010;26(16):1938-44. doi: 10.1093/bioinformatics/btq332. Epub Jun. 20, 2010.
Gibson et al., AgfC and AgfE facilitate extracellular thin aggregative fimbriae synthesis in *Salmonella enteritidis*. Microbiology. Apr. 2007;153(Pt 4):1131-1140. doi: 10.1099/mic.0.2006/000935-0.
Goryshin et al., Tn5 in vitro transposition. J Biol Chem. Mar. 27, 1998;273(13):7367-74. doi: 10.1074/jbc.273.13.7367.
Goyal et al., Crystallization and preliminary X-ray crystallographic analysis of the curli transporter CsgG. Acta Crystallographica Section F: Structural Biology and Crystallization Communications. Dec. 1, 2013;69(12):1349-53.
Hammar et al., Expression of two csg operons is required for production of fibronectin- and congo red-binding curli polymers in *Escherichia coli* K-12. Mol Microbiol. Nov. 1995;18(4):661-70. doi: 10.1111/j.1365-2958.1995.mmi_18040661.x.
Haque et al., DNA-associated click chemistry. Science China Chemistry. Feb. 2014;57(2):215-231. doi:10.1007/s11426-013-5035-1.
Heng et al., Sizing DNA using a nanometer-diameter pore. Biophys J. Oct. 2004;87(4):2905-11. doi: 10.1529/biophysj.104.041814. Epub Aug. 23, 2004.
Higgins et al., DNA-joining enzymes: a review. Methods Enzymol. 1979;68:50-71. doi: 10.1016/0076-6879(79)68006-0.
Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016;17 (1):256.
Juncker et al., Prediction of lipoprotein signal peptides in Gram-negative bacteria. Protein Sci. 2003;12(8):1652-1662. doi:10.1110/ps.0303703.
Kanaan et al., UPF1-like helicase grip on nucleic acids dictates processivity. Nat Commun. Sep. 14, 2018;9(1):3752. doi: 10.1038/s41467-018-06313-y.
Kimanius et al., Accelerated cryo-EM structure determination with parallelisation using GPUs in RELION-2. Elife. 2016;5:e18722. Published Nov. 15, 2016. doi:10.7554/eLife.18722. 21 pages.
Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.
Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.
Li et al., ChIA-PET tool for comprehensive chromatin interaction analysis with paired-end tag sequencing. Genome Biol. 2010;11(2):R22. doi: 10.1186/gb-2010-11-2-r22. Epub Feb. 25, 2010.
Li, Minimap2: pairwise alignment for nucleotide sequences. Bioinformatics. 2018;34(18):3094-3100. doi:10.1093/bioinformatics/bty191.
Loferer et al., Availability of the fibre subunit CsgA and the nucleator protein CsgB during assembly of fibronectin-binding curli is limited by the intracellular concentration of the novel lipoprotein CsgG. Mol Microbiol. 1997;26(1):11-23. doi: 10.1046/j.1365-2958.1997.5231883.x.
Lovett, The DNA Exonucleases of *Escherichia coli*. EcoSal Plus. Dec. 2011;4(2):10.1128/ecosalplus.4.4.7. doi: 10.1128/ecosalplus.4.4.7. Author Manuscript, 45 pages.

Lu et al., Expression, purification and structural analysis of csgF gene of curli systems from *Escherichia coli* CFT073. Microbiol China. 2016, 43(9):2063-2071. doi:10.13344/j.microbiol.china.150752.
Ludtke, Single-Particle Refinement and Variability Analysis in EMAN2.1. Methods Enzymol. 2016;579:159-89. doi: 10.1016/bs.mie.2016.05.001. Epub Jul. 1, 2016.
Nivala et al., Unfoldase-mediated protein translocation through an α-hemolysin nanopore. Nat Biotechnol. Mar. 2013;31(3):247-50. doi: 10.1038/nbt.2503. Epub Feb. 3, 2013. Author Manuscript, 10 pages.
Notice of Opposition for European Patent No. EP3097210 dated Aug. 12, 2019.
Peabody et al., Type II protein secretion and its relationship to bacterial type IV pili and archaeal flagella. Microbiology. Nov. 2003;149(Pt 11):3051-3072. doi: 10.1099/mic.0.26364-0.
Pud et al., Mechanical Trapping of DNA in a Double-Nanopore System. Nano Lett. 2016;16(12):8021-8028. doi:10.1021/acs.nanolett.6b04642. Author Manuscript, 17 pages.
Reznikoff, Tn5 as a model for understanding DNA transposition. Mol Microbiol. Mar. 2003;47(5):1199-206. doi: 10.1046/j.1365-2958.2003.03382.x.
Rhee et al., Comprehensive genome-wide protein-DNA interactions detected at single-nucleotide resolution. Cell. Dec. 9, 2011;147(6):1408-19. doi: 10.1016/j.cell.2011.11.013.
Rohou et al., CTFFIND4: Fast and accurate defocus estimation from electron micrographs. J Struct Biol. Nov. 2015;192(2):216-21. doi: 10.1016/j.jsb.2015.08.008. Epub Aug. 13, 2015.
Scheres, Relion: implementation of a Bayesian approach to cryo-EM structure determination. J Struct Biol. Dec. 2012;180(3):519-30. doi: 10.1016/j.jsb.2012.09.006. Epub Sep. 19, 2012.
Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.
Sivanathan et al., Generating extracellular amyloid aggregates using *E. coli* cells. Genes Dev. Dec. 1, 2012;26(23):2659-67. doi: 10.1101/gad.205310.112. Epub Nov. 19, 2012.
Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.
Taylor et al., New insight into the molecular control of bacterial functional amyloids. Front Cell Infect Microbiol. Apr. 8, 2015;5:33. doi: 10.3389/fcimb.2015.00033.
Third Party Observation for Application No. EP 15759438.3, dated Sep. 17, 2021. 21 pages.
Third Party Observation for Application No. EP 18734933.7, dated Apr. 11, 2022. 14 pages.
Third Party Observation for European Application No. EP18734933.7, dated Sep. 27, 2021.
Tuteja et al., Helicases as molecular motors: An insight. Physica A. Dec. 1, 2006;372(1):70-83. doi: 10.1016/j.physa.2006.05.014. Epub Jun. 5, 2006.
Van Der Verren et al., A dual-constriction biological nanopore resolves homonucleotide sequences with high fidelity. Nat Biotechnol. Dec. 2020;38(12):1415-1420. doi: 10.1038/s41587-020-0570-8. Epub Jul. 6, 2020. Author Manuscript, 25 pages.
Van Gerven et al., Bacterial amyloid formation: structural insights into curli biogenesis. Trends Microbiol. Nov. 2015; 23(11): 693-706. EPub Oct. 1, 2015. doi: 10.1016/j.tim.2015.07.010. Author Manuscript, 24 pages.
Wang et al., Engineering of protein nanopores for sequencing, chemical or protein sensing and disease diagnosis. Curr Opin Biotechnol. Jun. 2018;51:80-89. doi: 10.1016/j.copbio.2017.11.006. Epub Dec. 10, 2017.
Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.
Wang et al., Protein engineering with non-natural amino acids. InTechOpen; Feb. 24, 2012. DOI: 10.5772/28719.

(56) References Cited

OTHER PUBLICATIONS

Wiedmann et al., Ligase chain reaction (LCR)—overview and applications. PCR Methods Appl. Feb. 1994;3(4):S51-64. doi: 10.1101/gr.3.4.s51.

Wilkinson et al., Bacterial DNA ligases. Mol Microbiol. Jun. 2001;40(6):1241-8. doi: 10.1046/j.1365-2958.2001.02479.x.

Wu et al., Sequence-specific capture of protein-DNA complexes for mass spectrometric protein identification. PLoS One. 2011;6(10):e26217. doi: 10.1371/journal.pone.0026217. Epub Oct. 20, 2011.

Yen et al., SWR-C and INO80 chromatin remodelers recognize nucleosome-free regions near +1 nucleosomes. Cell. Sep. 12, 2013;154(6):1246-56. doi: 10.1016/j.cell.2013.08.043.

Zheng et al., MotionCor2: anisotropic correction of beam-induced motion for improved cryo-electron microscopy. Nat Methods. Apr. 2017;14(4):331-332. doi: 10.1038/nmeth.4193. Epub Feb. 27, 2017.

U.S. Appl. No. 17/933,061, filed Sep. 16, 2022, Remaut et al.

Fig. 34
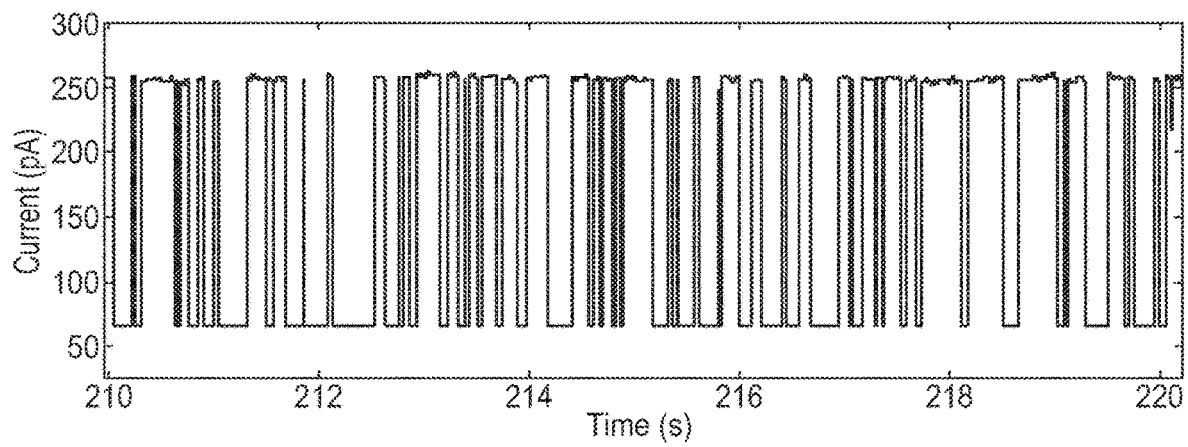
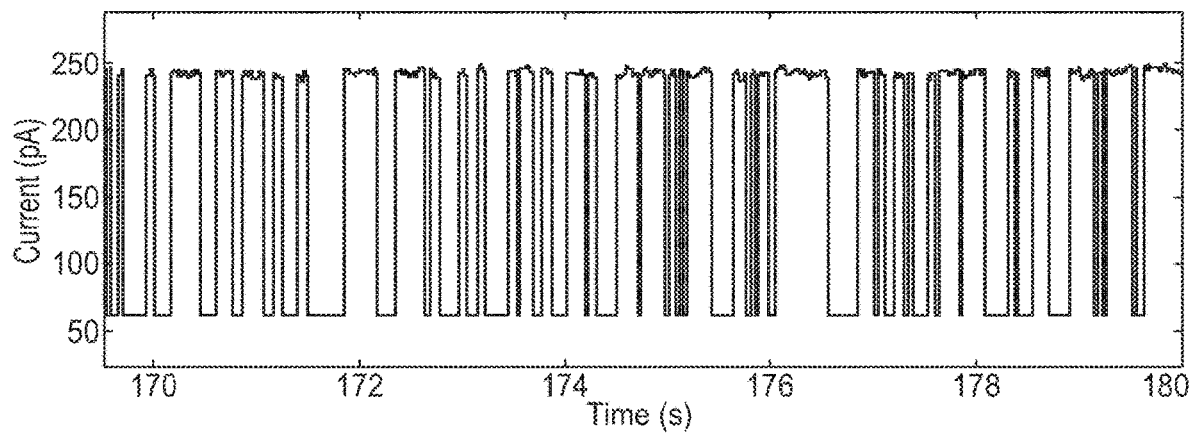

Fig. 35
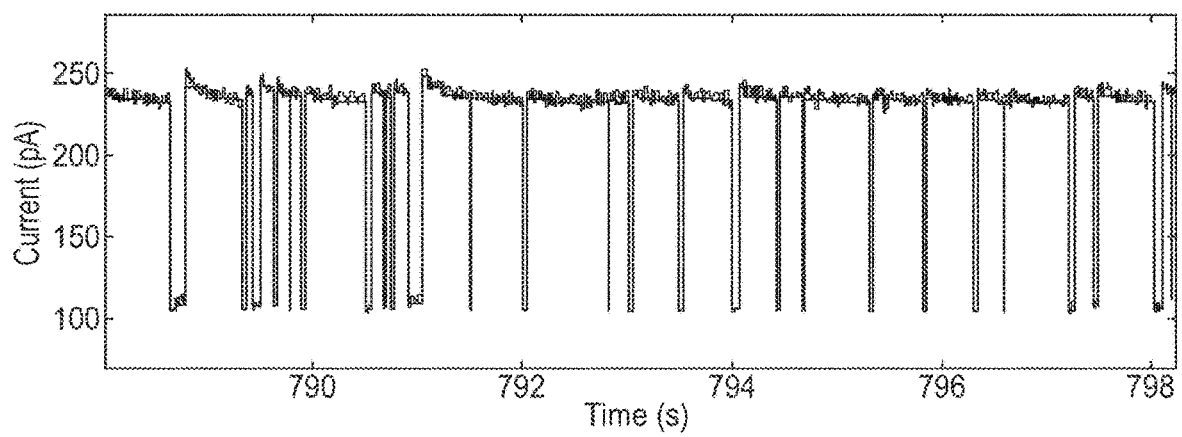
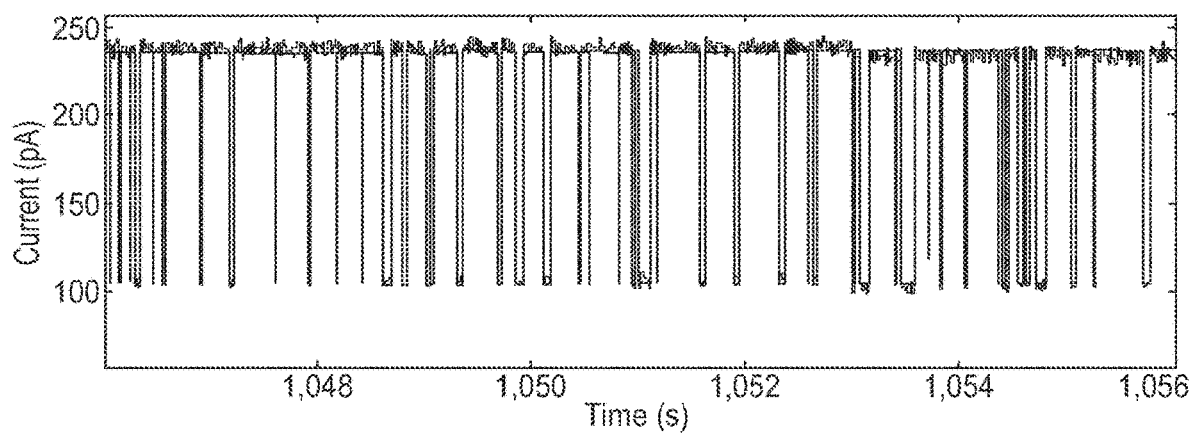

Fig. 36
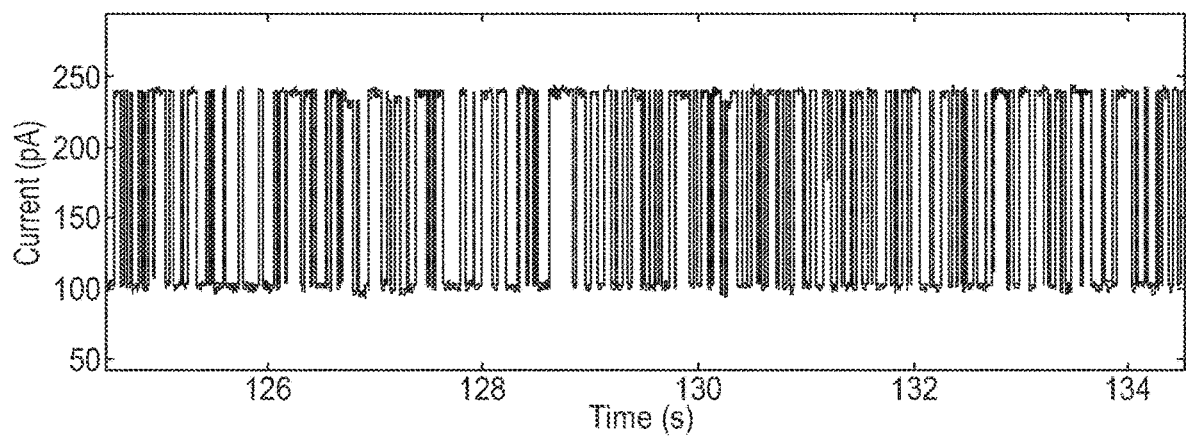
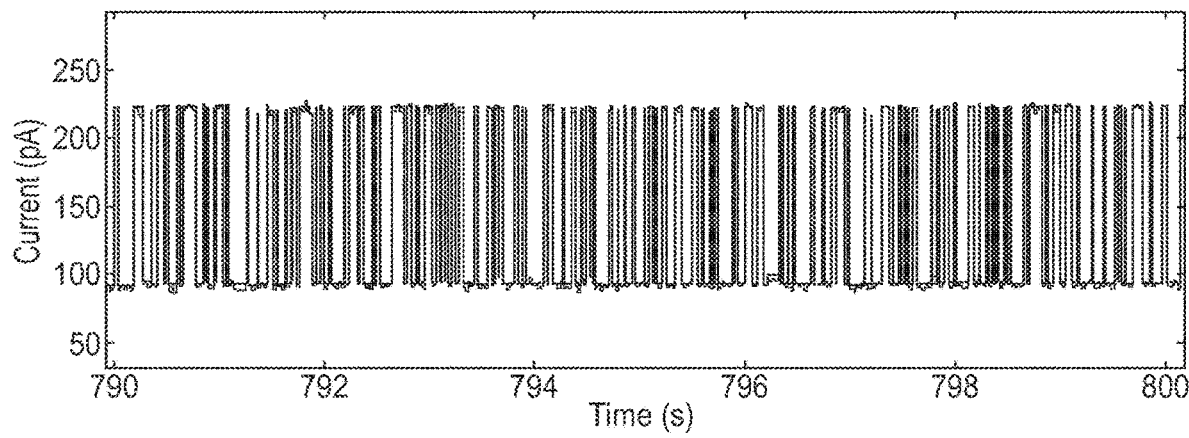

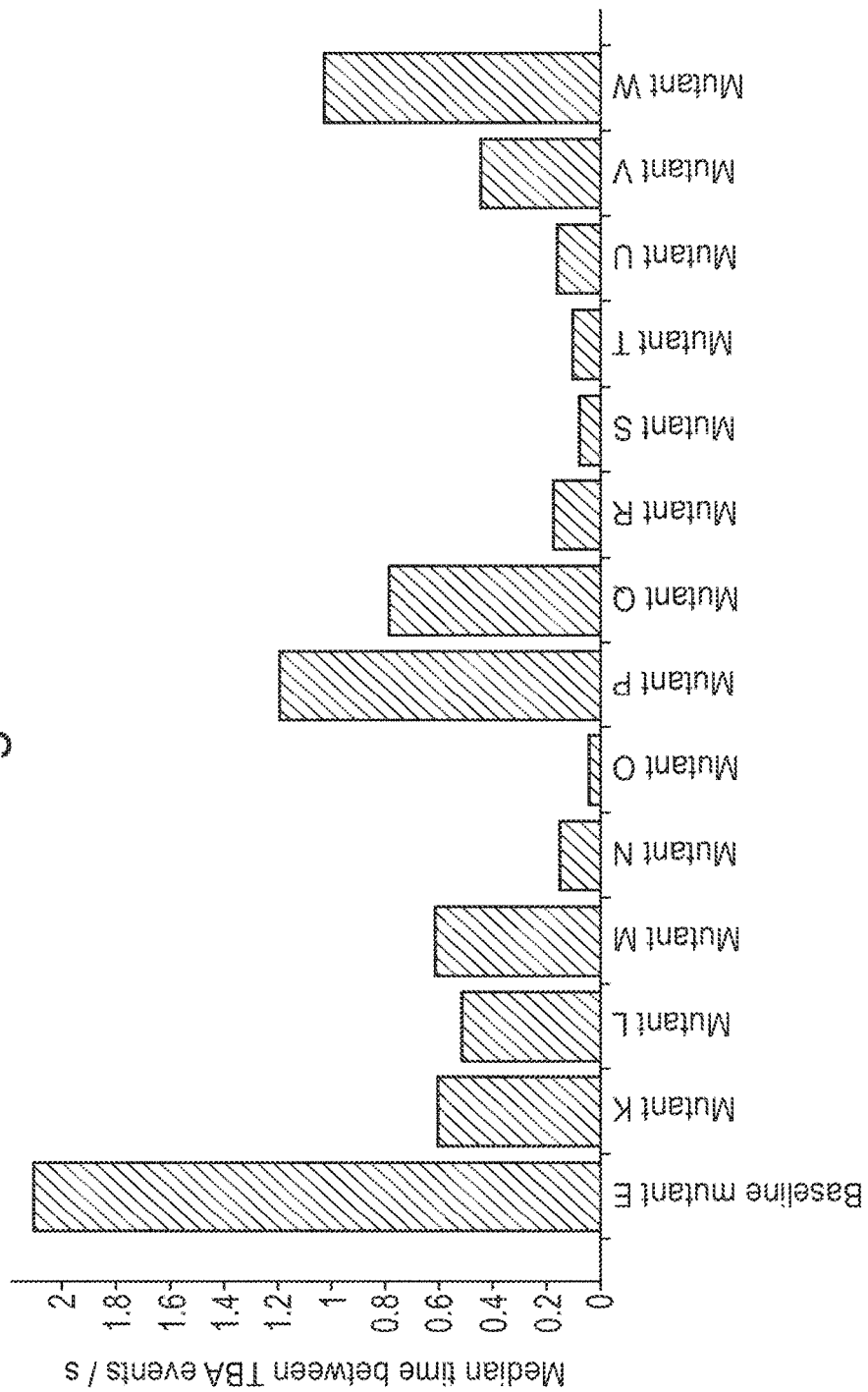

Fig. 45A

```
SEQ_ID_NO_2    1 CLT--APPKEAARPTLMPRAQSYKDLTHLPAPTGKIFVS
SEQ_ID_NO_5    1 CLT--APPKEAAKPTLMPRAQSYKDLTHLPIPTGKIFVS
SEQ_ID_NO_6    1 CLT--TPPKEAAKPTLMPRAQSYKDLTHLPVPTGKIFVS
SEQ_ID_NO_7    1 CLT--APPKEAAKPTLMPRAQSYRDLTHLPAPTGKIFVS
SEQ_ID_NO_27   1 CLT--APPKEAAKPTLMPRAQSYRDLTNLPDPKGKLFVS
SEQ_ID_NO_28   1 CLT--AAPKEAARPTLLPRAPSYTDLTHLPSPQGRIFVS
SEQ_ID_NO_29   1 CIT--SPPKQAAKPTLLPRSQSYQDLTHLPEPQGRLFVS
SEQ_ID_NO_30   1 CLT--APPKQAAKPTLMPRAQSYQDLTHLPEPAGKLFVS
SEQ_ID_NO_32   1-IT--EVPKEAAKPTLMPRASTYKDLVALPKPNGKIIVS
SEQ_ID_NO_36   1 CATHIGSPVADEKATLMPRSVSYKELISLPKPKGKIVAA
SEQ_ID_NO_3    1---------------MPRAQSYKDLTHLPMPTGKIFVS
SEQ_ID_NO_35   1--------PETSKEPTLMARGTAYQDLVSLPLPKGKVYVS
SEQ_ID_NO_31   1 CIT--TPPQEAAKPTLLPRDATYKDLVSLPQPRGKIYVA
SEQ_ID_NO_40   1--------------LTRRMSTYQDLIDMPAPRGKIVTA
SEQ_ID_NO_33   1--------PETSESPTLMQRGANYIDLISLPKPQGKIFVS
SEQ_ID_NO_34   1--------PDASESPTLMQRGATYLDLISLPKPQGKIYVS
SEQ_ID_NO_37   1-------------ASSSLMPKGESYYDLINLPAPQGVMLAA
SEQ_ID_NO_39   1--------------MPKSDTYYDLIGLPHPQGSMLAA
SEQ_ID_NO_38   1--------QDSETPTLTPRASTYYDLINMPRPKGRLMAV
SEQ_ID_NO_41   1--------PSDPERSTMGELTPSTAELRNLPLPNEKIVIG
SEQ_ID_NO_4    1 CLT--APPKQAAKPTLMPRAQSYKDLTHLPAPTGKIFVS
```

Conservation

```
---------20010112152542772 9 * 429 * 1 * 4438656 *
```

```
SEQ_ID_NO_2   120 YESNVKSGGVGARYFGIGADTQYQLDQIAVNLRVVNVST
SEQ_ID_NO_5   130 YESNVKSGGVGARYFGIGADTQYQLDQIAVNLRVVNVST
SEQ_ID_NO_6   130 YESNVKSGGAGARYFGIGADTQYQLDQIAVNLRVVNVST
SEQ_ID_NO_7   130 YESNVKSGGVGARYFGIGADTQYQLDQIAVNLRVVNVST
SEQ_ID_NO_27  130 YESNVKSGGVGARYFGIGGDTQYQLDQIAVNLRVVNVST
SEQ_ID_NO_28  130 YESNVKSGGVGARYFGIGASTQYQLDQIAVNLRAVDVNT
SEQ_ID_NO_29  120 YESNVKSGGAGARYFGIGASTQYQLDQIAVNLRVVNVST
SEQ_ID_NO_30  130 YESNVKSGGAGARFFGIGASTQYQLDQIAVNLRVVDVNT
SEQ_ID_NO_32  129 YDSDIKTGGAGARYFGIGADGKYRVDQVAVNLRAVDVRT
SEQ_ID_NO_36  132 YDSNVRTGGAGAKYFGIGASGEYRVDQVTVNLRAVDIRS
SEQ_ID_NO_3   116 YESNVKSGGVGARYFGIGADTQYQLDQIAVNLRVVNVST
SEQ_ID_NO_35  125 YDTNIQTGGAGARYLGVGASGQYRTDQVTVNIRAVDVRT
SEQ_ID_NO_31  130 YASNVKTGGFGARYFGIGGSTQYQLDQVAVNLRIVNVHT
SEQ_ID_NO_40  117 YDSNIHTGGAGARYFGIGASEKYRVDEVTVNLRAIDIRT
SEQ_ID_NO_33  125 YDSNIKTGGAGARYLGIGGSGQYRADQVTVNIRAVDVRS
SEQ_ID_NO_34  125 YDSNIKTGGAGARYLGIGGSGQYRADQVTVNIRAVDVRS
SEQ_ID_NO_37  115 YDTNVRTGGAGARYLGIGAATQFRVDTVTVNLRAVDIRT
SEQ_ID_NO_39  110 YDTNIKTGGAGARYLGIGVNSKFRVDTVTVNLRAVDIRT
SEQ_ID_NO_38  124 YDTNVRSGGEGARYLGIDISREYRVDQVTVNLRAVDVRT
SEQ_ID_NO_41  127 YDSNTMTGGFGARYFGIGASTQYRQDRITIYLRAVSTLN
SEQ_ID_NO_4   130 YESNVKSGGVGARYFGIGADTQYQLDQIAVNLRVVNVST
```

Conservation

```
VYNIQDETGQFKPYPA-SNFSTAVPQSATAMLVTALKDSRWFIPLEROGLQNL
VYNIQDETGQFKPYPA-SNFSTAVPQSATAMLVTALKDSRWFVPLEROGLQNL
VYNIQDETGQFKPYPA-SNFSTAVPQSATAMLVTALKDSRWFIPLEROGLQNL
VYNIQDETGQFKPYPA-SNFSTAVPQSATAMLVTALKDSHWFIPLEROGLQNL
VYNIQDETGQFKPYPA-SNFSTAVPQSATSMLVTALKDSRWFIPLEROGLQNL
VYNIQDETGQFKPYPA-CNFSTAVPQSATAMLVSALKDSKWFIPLEROGLQNL
VYNISDETGQFKPYPA-SNFSTSVPQSATAMLVSALKDSNWFIPLEROGLQNL
VYNIQDETGQFKPYPA-SNFSTAVPQSATAMLVSALKDSGWFIPLEROGLQNL
VYSVQDETGQFKPLPA-SNFSTAVPQSGNAMLTSALKDSGWFVPLEREGLQNL
VYDFRDQTGQYLPAPA-SNFSTAVTQGGVAMLSTALWDSQWFVPLEREGLQNL
VYNIQDETGQFKPYPA-SNFSTAVPQSATAMLVTALKDSRWFIPLEROGLQNL
VYDFRDQTGQYKPQN-SNFSTAVPQGGAALLTTALLDSRWFMPLEREGLQNL
VYNIQDETGQFQPYPA-SNFSTSVPQSATAMLVSSLKDSRWFVPLEROGLNNL
VYSFRDQSGQYKPAPS-SSFSTAVTQGAAAMLVNVLNDSGWFIPLEREGLQNI
VYDFRDQTGQYKPQN-SNFSTAVPQGGTALLTMALLDSEWFYPLEROGLQNL
VYDFRDQTGQYKPQN-SNFSTAVPQGGTALLTMALLDSEWFYPLEROGLQNL
VYDFRDQTGQYKPIPS-SNFSTAVPQSGTAFLAQALNDSSWFIPVEREGLQNL
VYDFRDQTGQYKAIPS-SNFSTAVPQSGTAFLAQALNDSSWFVPVEREGLQNL
VYGFRDQTGQYKPTPA-SSFSTSVTQGAASMLMDALSASGWFVVLEREGLQNL
VYKFRDQTGQYKPSENGNNWSTAVPQGTTTILIKALEDSRWFIPIERENIANL
VYNIQDETGQFKPYPA-SNFSTAVPQSATAMLVTALKDSRWFIPLEROGLQNL
```

`*376*89957457-7998*8*87678*536*15*267987+6**`

R192
`                              *`

```
GEILSSVNTSKTILSYEVQAGVFRFIDYQRLLEGEVGYTSNEPVMLCLMSAIE
GEILSSVNTSKTILSYEVQAGVFRFIDYQRLLEGEIGYTSNEPVMLCLMSAIE
GEILSSVNTSKTILSYEVQAGVFRFIDYQRLLEGEIGYTSNEPVMLCLMSAIE
GEVLSSVNTSKTILSYEVQAGVFRFIDYQRLLEGEIGYTSNEPVMMCLMSAIE
GEVLSSVNTSKTILSYEVQAGVFRFIDYQRLLEGEIGYTANEPVMLCLMSAIE
GEVLSSVNTSKTILSYEVQAGVFRFIDYQRLLEGELGYTTNEPVMLCLMSAIE
GEVLSSVNTSKTILSYEFQAGVFRYIDYQRLLEGEVGYTVNEPVMLCLMSAIE
GQVLSSVNTSKTILSYEVQAGVFRYIDYQRLLEGEIGYTTNEPVMLCVMSAIE
GEVLLSVNTSKTILSSELSAGVFRFIEYQRLLELAGYTTNEPVMMCMMSALE
GRILNSVTTSKTVMSQQVQAGVFRFVEYKRLLEAEADFSTNEPVQMCVMSAIE
GEILSSVNTSKTILSYEVQAGVFRFIDYQRLLEGEIGYTSNEPVMLCLMSAIE
GRILLSVTTSKTILSKELQTGVFKFVDYKDLLEAELGYTTNEPVNLAVMSAID
GEVLSSVNTSKTILSYEIQAGVFRFIDYQRLLEGEADFTTNEPVMTCLMSAIE
GRILHSVLTSKKILSREIRSDVYRFIEFKHLLEMEAGITTNDPAQLCVLSAIE
GKILTSVTTSKTILSYEVSAGAFRFVDYKELLEVELGYTNNEPVNIALMSAID
GKILTSVTTSKTILSYELSAGAFRFVDYKELLEVELGYTNNEPVNIALMSAID
GRLLSSVTTTKSILSKEITAGVFKFIDAQELLESELGYTSNEPVSLCVASAIE
GRLLSSVTTTKSILSKEVSAGVFKFIDAQDLLESELGYTSNEPVSLCVADAIE
GQVLANVMTSKTIYSVGRSAGVFKFIEFKKLLEAEVGYTTNEPAQLCVLSAIE
GEILKTVYTSKTILSTSVNGSFFRYIDTERLLEAEVGLTQNEPVQLAVTEAIE
GEILSSVNTSKTILSYEVQAGVFRFIDYQRLLEGEIGYTSNEPVMLCLMSAIE
```

```
LNERKIIRAAQENGTVAINNRI-PLQSLTAANIMVEGSIIG 129
LNERKIIRAAQENGTVAINNRI-PLQSLTAANIMVEGSIIG 129
LNERKIIRAAQENGTVAINNRI-PLPSLTAANIMVEGSIIG 129
LNERKIIRAAQENGTVANNNRM-PLQSLAAANVMIEGSIIG 129
LNERKIIRAAQENGTVAENNRM-PLQSLVAANVMIEGSIIG 129
LNERKIIRAAQENGSVAINNQR-PLSSLVAANILIEGSIIG 129
LNERKIIRAAQENGTVAVNNRT-QLPSLVAANILIEGSIIG 129
LNERKIIRAAQENGTAAVNNQH-QLSSLVAANVLVEGSIIG 129
LNERKIIRAAQENGTVAANNQQ-PLPSLLSANVVIEGAIIG 129
LTERKIVRAAQNKPNVPGNNAN-QLPSLVAANILIEGGIVA 131
LNERKIIRAAQENGTVAINNRI-PLQSLTAANIMVEGSIIG 115
LTERKIIRAAQKKDEIPTNHGV-HLPSLASANIMVEGGIVA 124
LNERKIIRAAQQNGTVGDNNAS-PLPSLYSANVIVEGSIIG 129
LTERKIIRAALKKDNVPVNNSA-GLPSLLAANIMLEGGIVG 116
LTERKIIRAAQKKQESISNHGS-TLPSLLSANVMIEGGIVA 124
LTERKIIRAAQKKQESISNHGS-TLPSLLSANVMIEGGIVA 124
LTERKIVRAGLK------GDAN-KLPQLNSAQILMEGGIVA 114
LTERKIVRAGLK------GEAN-QLPQLSSAQILMEGGIVA 109
LTERKIIRASQKKPDVAENIMG-ELPPLQAANLMLEGGIIA 123
LNERQIIRSTRQEYMKDADKNSQSLPPLLYAGILLEGGVIS 126
LNERKIIRAAQENGTVAMNNRI-PLQSLTAANIMVEGSIIG 129
```

```
++**7*9*8755100005242-1*66*45*6988**8998
```

```
TGVIFLINDGIDRGLWDLQNKAE-RQNDILVKYRHMSVPPE 261
TGVIFLINDGIDRGLWDLQNKAD-RQNDILVKYRHMSVPPE 261
TGVIFLINDGIDRGLWDLQNKAD-RQNDILVKYRDMSVPPE 261
TGVIFLINDGIDRGLWDLQNKAD-AQNPVLVKYRDMSVPPE 261
TGVIHLINDGINRGLWELKNKGD-AKNTILAKYRSMAVPPE 261
SGVIYLVNDGIERNLWQLQNPSE-INSPILQRYKNNIVPAE 261
TGVIYLVNDGISRNLWQLKNASD-INSFVLEKYKSIIVP-- 259
TGVIYLVNDGINRNLWTLKNPQD-AKSSVLERYKSTIVP-- 259
AGVAHLIVEGIRQNLWSLQNPSD-INNPIIQRYMKEDVP-- 258
SGVIRLIANGVRDNLWQLADQRD-IDNPILQEYLQDNAP-- 261
TGVIFLINDGIDRGLWDLQNKAE-RQNDILVKYRHMSVPPE 247
AAVVHVIVDGIKTGLWEPLRGED-LQHPIIQEYMNRSKP-- 254
EGVIHLINDGINKKLWALSNAAD-INSEVLTRYRK------ 255
SAVAHLIVDGVIKKSWSLADPNE-LNSPVIQAYQQRI---- 245
SAVIHLIVKGVQQGLWRPANLDT-RNNPIFKKY-------- 248
SAVIHLIVKGIEEGLWRPENQNG-KENPIFRKY-------- 248
SAVVHMIADGIWKGAWNLADQASGLRSPVLQKY-------- 239
SAVVHMIADGIWKRAWNLADTASGLNNPVLQKY-------- 234
SAVGHLLAQGIEQRLWQV---------------------- 233
KAVRSLIIEGTRDKIW------------------------ 234
TG---------------------------------- 223
```

```
SEQ_ID_NO_2    1 CLT--APPKEAARPTLMPR        LPAPTGKIFVS
SEQ_ID_NO_5    1 CLT--APPKEAAKPTLMPR        LPIPTGKIFVS
SEQ_ID_NO_6    1 CLT--TPPKEAAKPTLMPR        LPVPTGKIFVS
SEQ_ID_NO_7    1 CLT--APPKEAAKPTLMPRA       LPAPTGKIFVS
SEQ_ID_NO_27   1 CLT--APPKEAAKPTLMPRA       LPDPKGKLFVS
SEQ_ID_NO_28   1 CLT--AAPKEAARPTLLPRA       LPSPQGRIFVS
SEQ_ID_NO_29   1 CIT--SPPKQAAKPTLLPRS       LPEPQGRLFVS
SEQ_ID_NO_30   1 CLT--APPKQAAKPTLMPR        HLPEPAGKLFVS
SEQ_ID_NO_32   1-IT--EVPKEAAKPTLMPRA       ALPKPNGKIIVS
SEQ_ID_NO_36   1 CATHIGSPVADEKATLMPRS       LPKPKGKIVAA
SEQ_ID_NO_3    1 ---------------MPRA        LPMTGKIFVS
SEQ_ID_NO_35   1 --------PETSKEPTLMAR       LPLPKGKVYVS
SEQ_ID_NO_31   1 CIT--TPPQEAAKPTLLPRD       SLPQPRGKIYVA
SEQ_ID_NO_40   1 --------------LTRRM        DMPAPRGKIVTA
SEQ_ID_NO_33   1 --------PETSESPTLMQRGAN    SLPKPQGKIFVS
SEQ_ID_NO_34   1 --------PDASESPTLMQRG      SLPKPQGKIYVS
SEQ_ID_NO_37   1 -------------ASSSLMPK      NLPAPQGVMLAA
SEQ_ID_NO_39   1 ----------------MPKS       GLPHPQGSMLAA
SEQ_ID_NO_38   1 --------QDSETPTLTPR        NMPRPKGRLMAV
SEQ_ID_NO_41   1 --------PSDPERSTMGELT      LPLPNEKIVIG
SEQ_ID_NO_4    1 CLT--APPKQAAKPTLMPR        LPAPTGKIFVS
```

Conservation

```
--------2001011215254 27729*429*1*4438656*
```

```
SEQ_ID_NO_2   130 YESNVKSGGVGARYFGIGADTQYQLDQIAVNLRVVNVST
SEQ_ID_NO_5   130 YESNVKSGGVGARYFGIGADTQYQLDQIAVNLRVVNVST
SEQ_ID_NO_6   130 YESNVKSGGAGARYFGIGADTQYQLDQIAVNLRVVNVST
SEQ_ID_NO_7   130 YESNVKSGGVGARYFGIGADTQYQLDQIAVNLRVVNVST
SEQ_ID_NO_27  130 YESNVKSGGVGARYFGIGGDTQYQLDQIAVNLRVVNVST
SEQ_ID_NO_28  130 YESNVKSGGVGARYFGIGASTQYQLDQIAVNLRAVDVNT
SEQ_ID_NO_29  130 YESNVKSGGAGARYFGIGASTQYQLDQIAVNLRVVNVST
SEQ_ID_NO_30  130 YESNVKSGGAGARFFGIGASTQYQLDQIAVNLRVVDVNT
SEQ_ID_NO_32  129 YDSDIKTGGAGARYFGIGADGKYRVDQVAVNLRAVDVRT
SEQ_ID_NO_36  132 YDSNVRTGGAGAKYFGIGASGEYRVDQVTVNLRAVDIRS
SEQ_ID_NO_3   115 YESNVKSGGVGARYFGIGADTQYQLDQIAVNLRVVNVST
SEQ_ID_NO_35  125 YDTNIQTGGAGARYLGVGASGQYRTDQVTVNIRAVDVRT
SEQ_ID_NO_31  130 YASNVKTGGFGARYFGIGGSTQYQLDQVAVNLRIVNHT
SEQ_ID_NO_40  117 YDSNIHTGGAGARYFGIGASEKYRVDEVTVNLRAIDIRT
SEQ_ID_NO_33  125 YDSNIKTGGAGARYLGIGGSGQYRADQVTVNIRAVDVRS
SEQ_ID_NO_34  125 YDSNIKTGGAGARYLGIGGSGQYRADQVTVNIRAVDVRS
SEQ_ID_NO_37  115 YDTNVRTGGAGARYLGIGAATQFRVDTVTVNLRAVDIRT
SEQ_ID_NO_39  110 YDTNIKTGGAGARYLGIGVNSKFRVDTVTVNLRAVDIRT
SEQ_ID_NO_38  124 YDTNVRSGGEGARYLGIDISREYRVDQVTVNLRAVDVRT
SEQ_ID_NO_41  127 YDSNTMTGGFGARYFGIGASTQYRQDRITIYLRAVSTLN
SEQ_ID_NO_4   130 YESNVKSGGVGARYFGIGADTQYQLDQIAVNLRVVNVST
```

Conservation

```
VYNIQDETGQFKPYPA-SNFSTA...           ...SRWFIPLE...
VYNIQDETGQFKPYPA-SNFSTA...           ...SRWFVPLE...
VYNIQDETGQFKPYPA-SNFSTA...           ...SRWFIPLE...
VYNIQDETGQFKPYPA-SNFSTA...           ...SHWFIPLE...
VYNIQDETGQFKPYPA-SNFSTA...           ...SRWFIPLE...
VYNIQDETGQFKPYPA-CNFSTAVP...          ...SKWFIPLE...
VYNIGDETGQFKPYPA-SNFSTSVP...          ...SNWFIPLE...
VYNIQDETGQFKPYPA-SNFSTA...           ...SGWFIPLE...
VYSVQDETGQFKPLPA-SNFS...             ...SGWFVPLE...
VYDFRDQTGQYLPAPA-SNFST...            ...SQWFVPLE...
VYNIQDETGQFKPYPA-SNFSTAV...          ...SRWFIPLE...
VYDFRDQTGQYKPQPN-SNFST...            ...SRWFMPLE...
VYNIQDETGQFQPYPA-SNFSTSVP...         ...SRWFVPLE...
VYSFRDQSGQYKPAPS-SSFSTAVT...         ...SGWFIPLE...
VYDFRDQTGQYKPQPN-SNFSTAVPG...        ...SEWFYPLE...
VYDFRDQTGQYKPQPN-SNFSTA...           ...SEWFYPLE...
VYDFRDQTGQYEPIPS-SNFSTA...           ...SWFIPVE...
VYDFRDQTGQYKAIPS-SNFSTA...           ...SSWFVPVE...
VYGFRDQTGQYKPTPA-SSFST...            ...SGWFVVLE...
VYKFRDQTGQYEPSENGNNWSTAVPC...        ...SRWFIPIEREN...
VYNIQDETGQFKPYPA-SNFSTA...           ...SRWFIPLE...
```

`*376*89957457-7998*8*87678*536*15*267987+6*+`

R192
*

```
GEILSSVNTSKTILSYEVQAGVFRFIDYQRLLEGEVGYTSN...
GEILSSVNTSKTILSYEVQAGVFRFIDYQRLLEGEIGYTSN...
GEILSSVNTSKTILSYEVQAGVFRFIDYQRLLEGEIGYTSN...
GEVLSSVNTSKTILSYEVQAGVFRFIDYQRLLEGEIGYTSN...
GEVLSSVNTSKTILSYEVQAGVFRFIDYQRLLEGEIGYTAN...
GEVLSSVNTSKTILSYEVQAGVFRFIDYQRLLEGELGYTTN...
GEVLSSVNTSKTILSYEFQAGVFRYIDYQRLLEGEVGYTVN...
GQVLSSVNTSKTILSYEVQAGVFRYIDYQRLLEGEIGYTTN...
GEVLLSVNTSKTILSSELSAGVFRFIEYQRLLELEAGYTTN...
GRILNSVTTSKTVMSQQVQAGVFRFVEYKRLLEAEAGFSTN...
GEILSSVNTSKTILSYEVQAGVFRFIDYQRLLEGEIGYTSN...
GRILLSVTTSKTILSKELQTGVFKFVDYKDLLEAELGYTTN...
GEVLSSVNTSKTILSYEIQAGVFRFIDYQRLLEGEAGFTTN...
GRILHSVLTSKKILSREIRSQVYRFIEFKHLLEMEAGITTND...
GKILTSVTTSKTILSYEVSAGAFRFVDYKELLEVELGYTNN...
GKILTSVTTSKTILSYELSAGAFRFVDYKELLEVELGYTNN...
GRLLSSVTTTKSILSKEITAGVFKFIDAQELLESELGYTSN...
GRLLSSVTTTKSILSKEVSAGVFKFIDAQDLLESELGYTSN...
GQVLANVNTSKTIYSVGRSAGVFEFIEFKKLLEAEVGYTTN...
GEILKTVYTSKTILSTSVNGSFFRYIQTERLLEAEVGLTQN...
GEILSSVNTSKTILSYEVQAGVFRFIDYQRLLEGEIGYTSN...
```

```
              R97
               *
              ENGTVAINN    LQSLTAANIMVEGSIIG 129
              ENGTVAINN    LQSLTAANIMVEGSIIG 129
              NGTVAINN     LPSLTAANIMVEGSIIG 129
              NGTVANNN     LQSLAAANVMIEGSIIG 129
           AQENGTVAENN     LQSLVAANVMIEGSIIG 129
              ENGSV   NQR-PLSSLVAANILIEGSIIG 129
              ENGTVAVNN    LPSLVAANILIEGSIIG 129
              NGTAAVNN     LSSLVAANVLVEGSIIG 129
              NGTVAANNQQ-PLPSLLSANVVIEGAIIG 128
           AAQNKPNVPGNNAN-QLPSLVAANILIEGGIVA 131
              NGTVAINN     LQSLTAANIMVEGSIIG 115
              KKDEIPTNH    LPSLASANIMVEGGIVA 124
              NGTVGDNNAS-PLPSLYSANVIVEGSIIG 129
             LKKDNVPVNN    LPSLLAANIMLEGGIVG 116
              KQESISNHGS-TLPSLLSANVMIEGGIVA 124
              KQESISNHGS-TLPSLLSANVMIEGGIVA 124
              GLK------GDAN-KLPQLNSAQILMEGGIVA 114
              GLK------GEAN-QLPQLSSAQILMEGGIVA 108
              SQKKPQ      IMG-ELPPLQAANLMLEGGIIA 123
              RQEYMKDAQKNSQSLPPLLYAGILLEGGVIS 126
              NGTVAMNN     LQSLTAANIMVEGSIIG 129

+**7*9*8755100005242-1*66*45*6988**8998

RGLWDLQN                  SVPPE 261
              RGLWDLQN                  SVPPE 261
              RGLWDLQN                  MSVPPE 261
              RGLWDLQN                  SVPPE 261
              GLWELKN KGD               AVPPE 261
              NLWDLQNPSE-INS            NIVPAE 261
              RLWQLK                    IIVP-- 259
              LWTLKN                    TIVP-- 259
              LWSLQN PSD                DVP-- 258
              LWDLAD QRD-IDN            DNAP-- 261
              RLWDLQN                   MSVPPE 247
              GLWEPLR                   RSKP-- 254
              KLWALSNAAD                K----- 255
              SWSLADPNE-LN              QRI--- 245
              GLWRPANLDT-RN       KY........ 249
              GLWRPENQNG          KY........ 248
              AWNLADQASGLR        KY-------- 239
              RAWNLADTASGLN       KY-------- 234
              RLWQV--------------------- 233
              KIW----------------------- 234
TG--------------------------------------- 229

```
SEQ_ID_NO_2    1 CLT--APPKEAARPTLMPRAQSYKDLTHLPAPTGK
SEQ_ID_NO_5    1 CLT--APPKEAAKPTLMPRAQSYKDLTHLPIPTGK
SEQ_ID_NO_6    1 CLT--TPPKEAAKPTLMPRAQSYKDLTHLPVFTGK
SEQ_ID_NO_7    1 CLT--APPKEAAKPTLMPRAQSYRDLTHLPAPTGK
SEQ_ID_NO_27   1 CLT--APPKEAAKPTLMPRAQSYRDLTNLPDPKGKL
SEQ_ID_NO_28   1 CLT--AAPKEAARPTLLPRAPSYTDLTHLPSPQGRL
SEQ_ID_NO_29   1 CIT--SPPKQAAKPTLLPRSQSYQDLTHLPEPQGRL
SEQ_ID_NO_30   1 CLT--APPKQAAKPTLMPRAQSYQDLTHLPEPAGKL
SEQ_ID_NO_32   1 -IT--EVPKEAAKPTLMPRASTYKDLVALPKPNGK
SEQ_ID_NO_36   1 CATHIGSPVADEKATLMPRSVGYKELISLPKPKGK
SEQ_ID_NO_3    1 ----------------MPRAQSYKDLTHLPMPTGK
SEQ_ID_NO_35   1 --------PETSKEPTLMARGTAYQDLVSLPLPKGKV
SEQ_ID_NO_31   1 CIT--TPPQEAAKPTLLPRDATYKDLVSLPQPRGK
SEQ_ID_NO_40   1 --------------LTRRMSTYQDLIDMPAPRGK
SEQ_ID_NO_33   1 --------PETSESPTLMQRGANYIDLISLPKQGK
SEQ_ID_NO_34   1 --------PDASESP  MQRGATYLDLISLPKQGK
SEQ_ID_NO_37   1 -----------ASSSLMPKGESYYDLINLPAPQGVM
SEQ_ID_NO_39   1 -------------MPKSDTYYDLIGLPHPQGSM
SEQ_ID_NO_38   1 -------QDSETPTLTPRASTYYDLINMPRPKGRLM
SEQ_ID_NO_41   1 --------PSDPERSTMGELTPSTAELRNLPLPNEK
SEQ_ID_NO_4    1 CLT--APPKQAAKPTLMPRAQSYKDLTHLPAPTGK
```

Conservation

`--------20010112152542772 9*429*1*4438656*`

```
SEQ_ID_NO_2   130 ESNVKSGGVGA     ADTQ          VST
SEQ_ID_NO_5   130 ESNVKSGGVGA     ADT           VST
SEQ_ID_NO_6   130 ESNVKSGGAGA     ADT           VST
SEQ_ID_NO_7   130 ESNVKSGGVGA     ADT           VST
SEQ_ID_NO_27  130 ESNVKSGGVGA     GGDT          VST
SEQ_ID_NO_28  130 ESNVKSGGVGA     ASTQ          VNT
SEQ_ID_NO_29  130 ESNVKSGGAGA     AST           VST
SEQ_ID_NO_30  130 ESNVKSGGAGA     AST           VNT
SEQ_ID_NO_32  129 DSDIKTGGAGA     ADGK          VRT
SEQ_ID_NO_36  132 DSNVRTGGAGA     GASGE         IRS
SEQ_ID_NO_3   116 ESNVKSGGVGA     GADT          VST
SEQ_ID_NO_35  125 DTN  GGAGA      VGASGQ        VRT
SEQ_ID_NO_31  130 ASNVKTGGFGA     GGST          VHT
SEQ_ID_NO_40  117 DSNIHTGGAGA     ASE           IRT
SEQ_ID_NO_33  125 DSN  GGAG       GGSG          VRS
SEQ_ID_NO_34  125 YDSNIKTGGAG     GGSG          VRS
SEQ_ID_NO_37  115 YDTN  GGAGA     AAT           IRT
SEQ_ID_NO_39  110 DTN  GGAGA      VNS           IRT
SEQ_ID_NO_38  124 DTNVRSGGEGA     DISR          VRT
SEQ_ID_NO_41  127  SN  GGFGA      GAST          TLN
SEQ_ID_NO_4   130 ESNVKSGGVGA     ADT           VST
```

Conservation

```
 NIQDETGQFKPYPA-SNFSTAVPQSATAMLVTALKDSRWF   EROGLQNL
 NIQDETGQFKP   -SNFSTAVPQSATAMLVTALKDSRWF   EROGLQNL
 NIQDETGQFKP   -SNFSTAVPQSATAMLVTALKDSRWF   EROGLQNL
  QDETGQFKP   -SNFSTAVPQSATAMLVTALKDSHWF   EROGLQNL
 NIQDETGQFKP   -SNFSTAVPQSATSMLVTALKDSRWF   EROGLQNL
 NIQDETGQFKPYPA-CNFSTAVPQSATAMLVSALKDSRWF   EROGLQNL
 NISDETGQFKPYPA-SNFSTSVPQSATAMLVSALKDSNWF   EROGLQNL
 NIQDETGQFKPYPA-SNFSTAVPQSATAMLVSALKDSGWF   EROGLQNL
 S DETGQFKPLPA-SNFSTAVPQSNAMLTSALKDSGWF   EREGLQNL
 DFRQTGQYLPAPA-SNFSTAVTQGGVAMLSTALWDSQWF   EREGLQNL
 NIQDETGQFKP   -SNFSTAVPQSATAMLVTALKDSRWF   EREGLQNL
 DFRQTGQYKPQN-SNFSTAVPQGGAALLTTALLDSRWF    REGLQNL
 NIQDETGQFQP  A-SNFSTSVPQSATAMLVSSLKDSRWF   ROGLNNL
  RQSGQYKPAPS-SSFSTAVTQGAAAMLVNVLNDSGWF   EREGLQNI
 DFRQTGQYKPQN-SNFSTAVPQGGTALLTMALLDSEWFY   EROGLQNL
 DFRQTGQYKPQN-SNFSTAVPQGGTALLTMALLDSEWFY   ROGLQNL
 DFRQTGQYKPIPS-SNFSTAVPQSGTAFLAQALNDSSWF    EREGLQNL
 DFRQTGQYKA   S-SNFSTAVPQSGTAFLAQALNDSSWF   EREGLQNL
  RQTGQYKPTPA-SSFSTSVTQGAASMLMDALSASGWF   EREGLQNL
 YKFRQTGQYKPSENGN STAVPQGTTTILIKALEDSRWF   RENIANL
  IQDETGQFKP   -SNFSTAVPQSATAMLVTALKDSRWF   EROGLQNL
```

*376*89957457-7998*8*87678*536*15*267987+6*+

R192
*

```
G            VQ       IDYQ         SNEPVMLCLMSAIE
G            VT       FIDYQ    EIQ  SNEPVMLCLMSAIE
G            VT       FIDYQ         TSNEPVMLCLMSAIE
G            V        FIDYQ         SNEPVMMCLMSAIE
G            V        IDYQ         ANEPVMLCLMSAIE
G            VKT         DYQ LLE  GYTTNEPVMLCLMSAIE
G            V          IDYQ         NEPVMLCLMSAIE
G            V          DYQ         TNEPVMLCVMSAIE
G            VN        EYQ         TNEPVMMCMMSALE
G                       EYK         GFSTNEPVQMCVMSAIE
G            V        FIDYQ         SNEPVMLCLMSAIE
G            VKT    SK KF DYK LE   LGYTTNEPVNLAVMSAID
G            V          DYQ         GFTTNEPVMTCLMSAIE
G            VT        FK         TNDPAQLCVLSAIE
G            L          DYK         NNEPVNIALMSAID
G            L          VDYK    ELG  NNEPVNIALMSAID
G                       AQ         SNEPVSLCVASAIE
G                       DAQ         SNEPVSLCVAQAIE
G                       EFK   VGYTTNEPAQLCVLSAIE
G                       DTE   VGLTQNEPVQLAVTEAIE
G            V         FIDYQ         SNEPVMLCLMSAIE
```

```
        R97
         *
LNERKIIRAAQENGTVAINNRI-PLQSLTAAN▒▒▒▒    129
LNERKIIRAAQENGTVAINNRI-PLQSLTAAN▒▒▒▒    129
LNERKIIRAAQENGTVAINNRI-PLPSLTAAN▒▒▒▒    129
LNERKIIRAAQENGTVANNNRM-PLQSLAAAN▒▒▒▒    129
LNERKIIRAAQENGTVAENNRM-PLQSLVAAN▒▒▒▒    129
LNERKIIRAAQENGSVAINNQR-PLSSLVAAN▒▒▒▒    129
LNERKIIRAAQENGTVAVNNRT-QLPSLVAAN▒▒▒▒    129
LNERKIIRAAQENGTAAVNNQH-QLSSLVAAN▒▒▒▒    129
LNERKIIRAAQENGTVAANNQQ-PLPSLLSAN▒▒▒▒    128
LTERKIVRAAQNKPNVPGNNAN-QLPSLVAAN▒▒▒▒    131
LNERKIIRAAQENGTVAINNRI-PLQSLTAAN▒▒▒▒    115
LTERKIIRAAQKKDEIPTNHGV-HLPSLASAN▒▒▒▒    124
LNERKIIRAAQQNGTVGDNNAS-PLPSLYSAN▒▒▒▒    129
LTERKIIRAALKKDNVPVNNSA-GLPSLLAAN▒▒▒▒    116
LTERKIIRAAQKKQESISNHGS-TLPSLLSAN▒▒▒▒    124
LTERKIIRAAQKKQESISNHGS-TLPSLLSAN▒▒▒▒    124
LTERKIVRAGLK-----GDAN-KLPQLNSAQ▒▒▒▒     114
LTERKIVRAGLK-----GEAN-QLPQLSSAQ▒▒▒▒     109
LTERKIIRASQKKPDVAENIMG-ELPPLQAAN▒▒▒▒    123
LNERQIIRSTRQEYMKDADKNSQLPPLLYAG▒▒▒▒     126
LNERKIIRAAQENGTVAMNNRI-PLQSLTAAN▒▒▒▒    129

*+**7*9*87551000005242-1*66*45*6988**8998

TGVIFLINDGIDRGLWDLQNKAE-RQNDILVKYRHMSVPPE    261
TGVIFLINDGIDRGLWDLQNKAD-RQNDILVKYRHMSVPPE    261
TGVIFLINDGIDRGLWDLQNKAD-RQNDILVKYRQMSVPPE    261
TGVIFLINDGIDRGLWDLQNKAD-AQNPVLVKYRDMSVPPE    261
TGVIHLINDGINRGLWELKNKGD-AKNTILAKYRSMAVPPE    261
SGVIYLVNDGIERNLWQLQNPSE-INSPILQRYKNNIVPAE    261
TGVIYLVNDGISRNLWQLKNASD-INSPVLEKYKSIIVP--   259
TGVIYLVNDGINRNLWTLKNPQD-AKSSVLERYKSTIVP--   259
AGVAHLIVEGIRQNLWSLQNPSD-INNPIIQRYMKEDVP--   258
SGVIRLIANGVRDNLW▒▒ADQRD-IDNPILQEYLQDNAP--   261
TGVIFLINDGIDRGLWDLQNKAE-RQNDILVKYRHMSVPPE    247
AAVHVIVDGIKTGLWEPLRGED-LQHPIIQEYMNRSKP--    254
EGVIHLINDGINKKLWALSNAAD-INSEVLTRYRK-----    255
SAVAHLIVDGVIKKSWSLADPNE-LNSPVIQAYQQQRI---   245
SAVIHLIVKGVQQGLWRPANLDT-RNNPIFKKY--------  248
SAVIHLIVKGIEEGLWRPENQNG-KENPIFRKY--------  248
SAVVHMIADGIWKGAWNLADQASGLRSPVLQKY--------  239
SAVVHMIADGIWKRAWNLADTASGLNNPVLQKY--------  234
SAVGHLLAQGIEQRLWQV----------------------   233
KAVRSLIIEGTRDKIW-----------------------   294
TG------------------------------------   229

3+300120130010030001000-011021003--------
```

MUTANT PORE

RELATED APPLICATIONS

This Application is a division of U.S. application Ser. No. 16/081,894, filed Aug. 31, 2018, entitled "MUTANT PORE", now granted as U.S. Pat. No. 10,975,428, which is a national stage filing under 35 U.S.C. 371 of International Patent Application Serial No. PCT/GB2017/050569, filed Mar. 2, 2017, entitled "MUTANT PORE", claims the benefit of United Kingdom application number 1603656.8, filed Mar. 2, 2016, United Kingdom application number 1603657.6, filed Mar. 2, 2016, and United Kingdom application number 1603658.4, filed Mar. 2, 2016. The contents of these applications are incorporated herein by reference in their entireties.

FIELD OF THE INVENTION

The invention relates to mutant forms of CsgG. The invention also relates to analyte detection and characterisation using CsgG.

BACKGROUND OF THE INVENTION

Nanopore sensing is an approach to sensing that relies on the observation of individual binding or interaction events between analyte molecules and a receptor. Nanopore sensors can be created by placing a single pore of nanometer dimensions in an insulating membrane and measuring voltage-driven ionic transport through the pore in the presence of analyte molecules. The identity of an analyte is revealed through its distinctive current signature, notably the duration and extent of current block and the variance of current levels. Such nanopore sensors are commercially available, such as the MinION™ device sold by Oxford Nanopore Technologies Ltd, comprising an array of nanopores integrated with an electronic chip.

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection. Nanopore sensing has the potential to provide rapid and cheap nucleic acid sequencing by reducing the quantity of nucleotide and reagents required.

Two of the essential components of sequencing nucleic acids using nanopore sensing are (1) the control of nucleic acid movement through the pore and (2) the discrimination of nucleotides as the nucleic acid polymer is moved through the pore. In the past, to achieve nucleotide discrimination the nucleic acid has been passed through a mutant of hemolysin. This has provided current signatures that have been shown to be sequence dependent. It has also been shown that a large number of nucleotides contribute to the observed current when a hemolysin pore is used, making a direct relationship between observed current and polynucleotide challenging.

While the current range for nucleotide discrimination has been improved through mutation of the hemolysin pore, a sequencing system would have higher performance if the current differences between nucleotides could be improved further. In addition, it has been observed that when the nucleic acids are moved through a pore, some current states show high variance. It has also been shown that some mutant hemolysin pores exhibit higher variance than others. While the variance of these states may contain sequence specific information, it is desirable to produce pores that have low variance to simplify the system. It is also desirable to reduce the number of nucleotides that contribute to the observed current.

SUMMARY OF THE INVENTION

The inventors have surprisingly demonstrated that CsgG and novel mutants thereof may be used to characterise analytes, such as polynucleotides. The invention concerns mutant CsgG monomers. The inventors have surprisingly demonstrated that pores comprising the novel mutant monomers have an enhanced ability to estimate the characteristics of analytes, such as the sequence of polynucleotides. The inventors have made mutant pores that surprisingly provide more consistent movement of a target polynucleotide with respect to, such as through, the pores. The inventors have made mutant pores that surprisingly display improved characterisation accuracy. In particular, the inventors have made mutant pores that surprisingly display an increased current range, which makes it easier to discriminate between different nucleotides, and a reduced variance of states, which increases the signal-to-noise ratio. In addition, the inventors have made mutant pores that surprisingly capture nucleotides and polynucleotides more easily. In the mutant CsgG monomers the arginine (R) at position 192 may be substituted with aspartic acid (D), glutamine (Q), phenylalanine (F), serine (S) or threonine (T). The inventors have surprisingly demonstrated that such monomers, and in particular a monomer comprising a R192D substitution, are much easier to express than monomers without a substitution at position 192.

All amino-acid substitutions, deletions and/or additions disclosed herein are with reference to a mutant CsgG monomer comprising a variant of the sequence shown in SEQ ID NO: 2, unless stated to the contrary.

Reference to a mutant CsgG monomer comprising a variant of the sequence shown in SEQ ID NO: 2 encompasses mutant CsgG monomers comprising variants of sequences as set out in the further SEQ ID NOS as disclosed below. Amino-acid substitutions, deletions and/or additions may be made to CsgG monomers comprising a variant of the sequence other than shown in SEQ ID NO:2 that are equivalent to those substitutions, deletions and/or additions disclosed herein with reference to a mutant CsgG monomer comprising a variant of the sequence shown in SEQ ID NO:2.

A mutant monomer may be considered as an isolated monomer.

The invention concerns in particular mutant CsgG monomers in which the arginine (R) at position 97 has been substituted with tryptophan (W), in which the arginine (R) at position 93 has been substituted with tryptophan (W), in which the arginines (R) at position 93 and 97 have been substituted with tryptophan (W).

The invention also provides a mutant CsgG monomer comprising a variant of the sequence shown in SEQ ID NO: 2, wherein the variant comprises (a) F191T (b) deletion of V105, A106 and I107 and/or deletion of one or more of positions R192, F193, I194, D195, Y196, Q197, R198, L199, L200 and E201, such as deletion of F193, I194, D195, Y196, Q197, R198 and L199 or deletion of D195, Y196, Q197, R198 and L199.

The invention also provides:

a mutant CsgG monomer comprising a variant of the sequence shown in SEQ ID NO: 2 which comprises R192D/Q/F/S/T;

a mutant CsgG monomer which comprises (a) R192D; (b) R97W/Y and/or R93W/Y, preferably R97W, R93W or R93Y and R97Y; (c) K94Q/N; (d) G103K/R and/or T104K/R; and/or (e) F191T, deletion of V105, A106 and I107 and/or deletion of F193, I194, D195, Y196, Q197, R198 and L199.

The mutant CsgG monomer preferably further comprises Y51A and F56Q.

Particular mutant CsgG monomers provided by the invention comprise variants of the sequence shown in SEQ ID NO: 2 that comprise the following mutations:
(1) Y51A, F56Q and R192D;
(2) Y51A, F56Q and R97W.
(3) Y51A, F56Q, R192D and R97W;
(4) Y51A, F56Q, R192D and R93W;
(5) Y51A, F56Q, R192D, R93Y and R97Y; or
(6) Y51A, F56Q, R192D and R93W.
(7) the mutations of any one of (1)-(6) and:
(a) deletion of V105, A106 and I107.
(b) K94Q or K94N;
(c) deletion of D195, Y196, Q197, R198 and L199 or deletion of F193, I194, D195, Y196, Q197, R198 and L199; and/or
(d) F191T.
(8) the mutations of any one of (1)-(6) and:
(i) K94Q and deletion of V105, A106 and I107;
(ii) K94N and deletion of V105, A106 and I107;
(iii) F191T and deletion of V105, A106 and I107;
(iv) K94Q and F191T;
(v) K94N and F191T;
(vi) K94Q, F191T and deletion of V105, A106 and I107; or
(vii) K94N, F191T and deletion of V105, A106 and I107.
(9) the mutations of any one of (1)-(8) and:
T104K or T104R;
L90R;
N91R;
I95R;
A99R;
E101K, E101N, E101Q, E101T or E101H;
E44N or E44Q; and/or
Q42K.

The invention also provides:
a construct comprising two or more covalently attached CsgG monomers, wherein at least one of the monomers is a mutant monomer of the invention;
a polynucleotide which encodes a mutant monomer of the invention or a construct of the invention;
a homo-oligomeric pore derived from CsgG comprising identical mutant monomers of the invention or identical constructs of the invention;
a hetero-oligomeric pore derived from CsgG comprising at least one mutant monomer of the invention or at least one construct of the invention;
a method for determining the presence, absence or one or more characteristics of a target analyte, comprising:
(a) contacting the target analyte with a pore of the invention such that the target analyte moves with respect to the pore; and
(b) taking one or more measurements as the analyte moves with respect to the pore and thereby determining the presence, absence or one or more characteristics of the analyte;
a method of forming a sensor for characterising a target polynucleotide, comprising forming a complex between a pore of the invention and a polynucleotide binding protein and thereby forming a sensor for characterising the target polynucleotide;

a sensor for characterising a target polynucleotide, comprising a complex between a pore of the invention and a polynucleotide binding protein;
use of a pore of the invention to determine the presence, absence or one or more characteristics of a target analyte;
a kit for characterising a target analyte comprising (a) a pore of the invention and (b) the components of a membrane;
an apparatus for characterising target analytes in a sample, comprising (a) a plurality of a pores of the invention and (b) a plurality of membranes;
a method of characterising a target polynucleotide, comprising:
a) contacting the polynucleotide with a pore of the invention, a polymerase and labelled nucleotides such that phosphate labelled species are sequentially added to the target polynucleotide by the polymerase, wherein the phosphate species contain a label specific for each nucleotide; and
b) detecting the phosphate labelled species using the pore and thereby characterising the polynucleotide; and
a method of producing a mutant monomer of the invention or a construct of the invention, comprising expressing a polynucleotide of the invention in a suitable host cell and thereby producing a mutant monomer of the invention or a construct.

DESCRIPTION OF THE FIGURES

FIG. 34 shows two ten second screen shots of current traces showing translocation of DNA (SEQ ID NO: 51) through MspA mutant x=MspA-((Del-L74/G75/D118/L119)D56F/E59R/L88N/D90N/D91N/Q126R/D134R/E139K)8 (SEQ ID NO: 50 with mutations D56F/E59R/L88N/D90N/D91N/Q126R/D134R/E139K and deletion of the amino acids L74/G75/D118/L119) without the control of an enzyme.

FIG. 35 shows two ten second screen shots of current traces showing translocation of DNA (SEQ ID NO: 51) through CsgG-Eco-(Y51A/F56Q/R97W/R192D-StrepII(C))9 (SEQ ID NO: 2 with mutations Y51A/F56Q/R97W/R192D where StrepII(C) is SEQ ID NO: 47 and is attached at the C-terminus) without the control of an enzyme.

FIG. 36 shows two ten second screen shots of current traces showing translocation of DNA (SEQ ID NO: 51) through CsgG-Eco-(Y51A/F56Q/R97W/E101S/R192D-StrepII(C))9 (SEQ ID NO: 2 with mutations Y51A/F56Q/R97W/E101S/R192D where StrepII(C) is SEQ ID NO: 47 and is attached at the C-terminus) without the control of an enzyme.

FIG. 40A shows that the speed distribution was tighter when Mutant D was used compared to the baseline mutant. FIG. 40B shows that mutant D has a tighter distribution of template accuracy compared to the baseline mutant.

FIG. 44 shows the median time between Thrombin Binding Aptamer (TBA) events for mutant CsgG nanopores comprising one of the following substitutions: Q42K (Mutant K), E44N (Mutant L), E44Q (Mutant M), L90R (Mutant N), N91R (Mutant O), I95R (Mutant P), A99R (Mutant Q), E101H (Mutant R), E101K (Mutant S), E101N (Mutant T), E101Q (Mutant U), E101T (Mutant V) and Q114K (Mutant W). The median time was significantly reduced compared to the baseline pore comprising the mutations Y51A/F56Q/K94Q/R97W/R192D-del(V105-I107) (Baseline mutant E), all of which are also included in each of the 13 mutants tested. FIG. 44 shows that each of the Q42K, E44N, E44Q, L90R, N91R, I95R, A99R, E101H, E101K, E101N, E101Q, E101T and Q114K substitutions increase template DNA capture rates.

FIGS. 45A-45C show sequence alignments of the 21 CsgG homologues corresponding to SEQ ID Nos 2, 5, 6, 7, 27, 28, 29, 30, 32, 36, 3, 35, 31, 40, 33, 34, 37, 39, 38, 41 and 4 FIGS. 46A-46C show the same relative sequence alignments as FIGS. 45A-45C with predicted alpha helical secondary structure regions additionally shaded.

FIGS. 47A-47C show the same relative sequence alignments as FIGS. 45A-45C with predicted beta sheet secondary structure regions additionally shaded.

DESCRIPTION OF THE SEQUENCE LISTING

Figure 1:
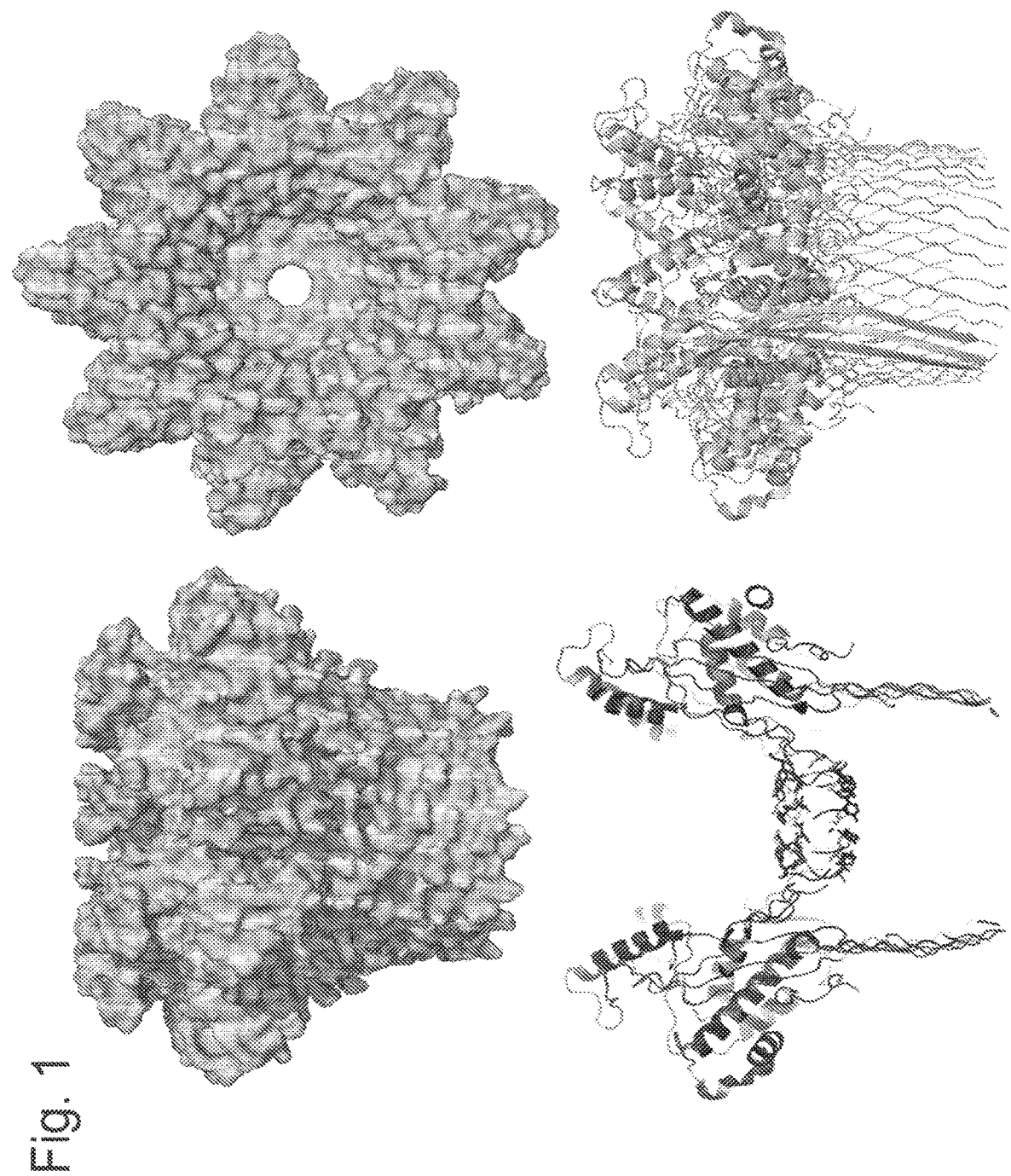
FIG. 1: Illustrates CsgG from *E. coli*.
Figure 2:
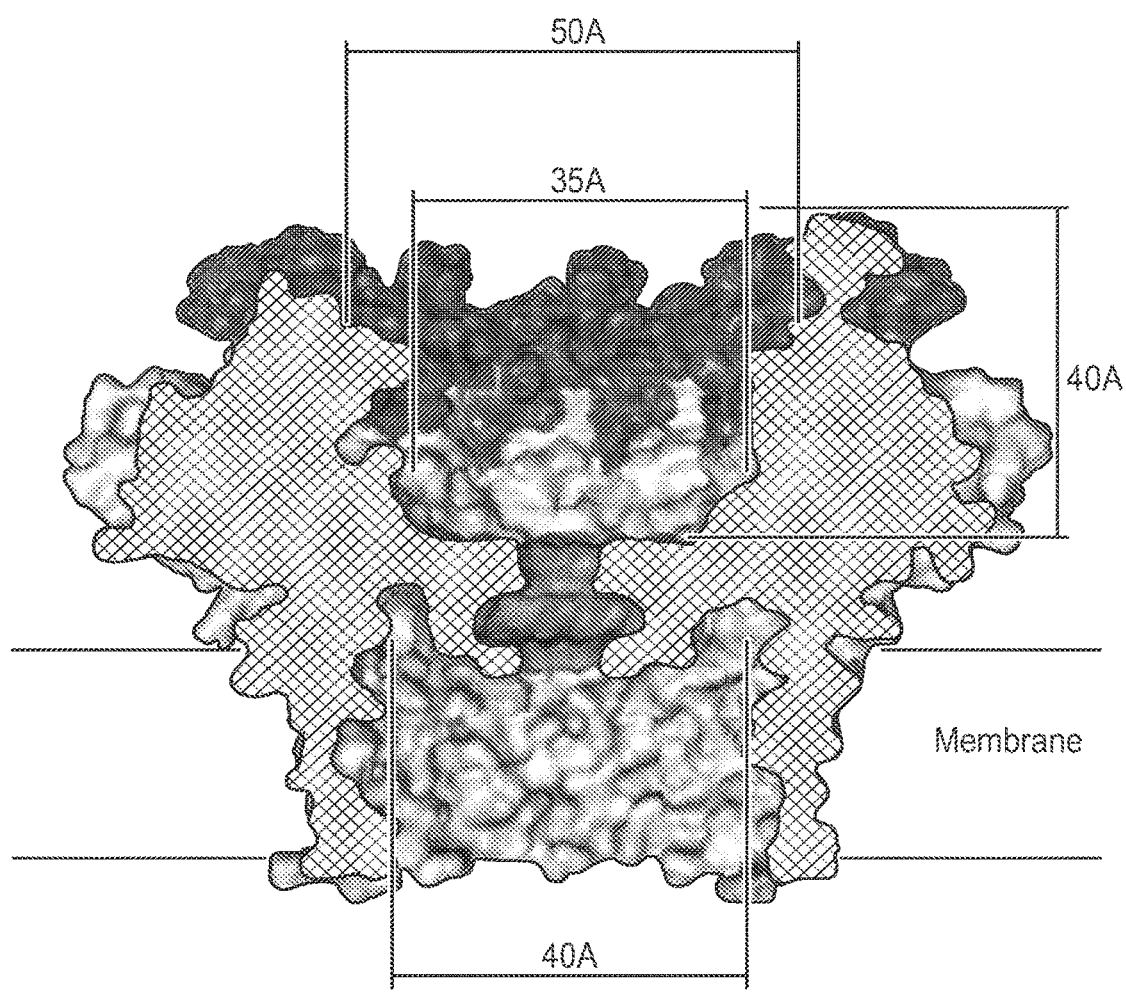
FIG. 2: Illustrates the dimensions of CsgG.

SEQ ID NO: 1 shows the codon optimised polynucleotide sequence encoding the wild-type CsgG monomer from *Escherichia coli* Str. K-12 substr. MC4100. This monomer lacks the signal sequence.

SEQ ID NO: 2 shows the amino acid sequence of the mature form of the wild-type CsgG monomer from *Escherichia coli* Str. K-12 substr. MC4100. This monomer lacks the signal sequence. The abbreviation used for this CsgG=CsgG-Eco.

SEQ ID NO: 3 shows the amino acid sequence of YP_001453594.1: 1-248 of hypothetical protein CKO_02032 [*Citrobacter koseri* ATCC BAA-895], which is 99% identical to SEQ ID NO: 2.

SEQ ID NO: 4 shows the amino acid sequence of WP_001787128.1: 16-238 of curli production assembly/transport component CsgG, partial [*Salmonella enterica*], which is 98% to SEQ ID NO: 2.

SEQ ID NO: 5 shows the amino acid sequence of KEY44978.1|: 16-277 of curli production assembly/transport protein CsgG [*Citrobacter amalonaticus*], which is 98% identical to SEQ ID NO: 2.

SEQ ID NO: 6 shows the amino acid sequence of YP_003364699.1: 16-277 of curli production assembly/transport component [*Citrobacter rodentium* ICC168], which is 97% identical to SEQ ID NO: 2.

SEQ ID NO: 7 shows the amino acid sequence of YP_004828099.1: 16-277 of curli production assembly/transport component CsgG [*Enterobacter asburiae* LF7a], which is 94% identical to SEQ ID NO: 2.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3'direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows the amino acid sequence of WP_006819418.1: 19-280 of transporter [*Yokenella regensburgei*], which is 91% identical to SEQ ID NO: 2.

SEQ ID NO: 27 shows the amino acid sequence of WP_024556654.1: 16-277 of curli production assembly/transport protein CsgG [*Cronobacter pulveris*], which is 89% identical to SEQ ID NO: 2.

SEQ ID NO: 28 shows the amino acid sequence of YP_005400916.1:16-277 of curli production assembly/transport protein CsgG [*Rahnella aquatilis* HX2], which is 84% identical to SEQ ID NO: 2.

SEQ ID NO: 29 shows the amino acid sequence of KFC99297.1: 20-278 of CsgG family curli production assembly/transport component [*Kluyvera ascorbata* ATCC 33433], which is 82% identical to SEQ ID NO: 2.

SEQ ID NO: 30 shows the amino acid sequence of KFC86716.1|:16-274 of CsgG family curli production assembly/transport component [*Hafnia alvei* ATCC 13337], which is 81% identical to SEQ ID NO: 2.

SEQ ID NO: 31 shows the amino acid sequence of YP_007340845.11:16-270 of uncharacterised protein involved in formation of curli polymers [Enterobacteriaceae bacterium strain FGI 57], which is 76% identical to SEQ ID NO: 2.

SEQ ID NO: 32 shows the amino acid sequence of WP_010861740.1: 17-274 of curli production assembly/transport protein CsgG [*Plesiomonas shigelloides*], which is 70% identical to SEQ ID NO: 2.

SEQ ID NO: 33 shows the amino acid sequence of YP_205788.1: 23-270 of curli production assembly/transport outer membrane lipoprotein component CsgG [*Vibrio fischeri* ES114], which is 60% identical to SEQ ID NO: 2.

SEQ ID NO: 34 shows the amino acid sequence of WP_017023479.1: 23-270 of curli production assembly protein CsgG [*Aliivibrio logei*], which is 59% identical to SEQ ID NO: 2.

SEQ ID NO: 35 shows the amino acid sequence of WP_007470398.1: 22-275 of Curli production assembly/transport component CsgG [*Photobacterium* sp. AK15], which is 57% identical to SEQ ID NO: 2.

SEQ ID NO: 36 shows the amino acid sequence of WP_021231638.1: 17-277 of curli production assembly protein CsgG [*Aeromonas veronii*], which is 56% identical to SEQ ID NO: 2.

SEQ ID NO: 37 shows the amino acid sequence of WP_033538267.1: 27-265 of curli production assembly/transport protein CsgG [*Shewanella* sp. ECSMB14101], which is 56% identical to SEQ ID NO: 2.

SEQ ID NO: 38 shows the amino acid sequence of WP_003247972.1: 30-262 of curli production assembly protein CsgG [*Pseudomonas putida*], which is 54% identical to SEQ ID NO: 2.

SEQ ID NO: 39 shows the amino acid sequence of YP_003557438.1: 1-234 of curli production assembly/transport component CsgG [*Shewanella violacea* DSS12], which is 53% identical to SEQ ID NO: 2.

SEQ ID NO: 40 shows the amino acid sequence of WP_027859066.1: 36-280 of curli production assembly/transport protein CsgG [*Marinobacterium jannaschii*], which is 53% identical to SEQ ID NO: 2.

SEQ ID NO: 41 shows the amino acid sequence of CEJ70222.1: 29-262 of Curli production assembly/transport component CsgG [*Chryseobacterium oranimense* G311], which is 50% identical to SEQ ID NO: 2.

SEQ ID NO: 42 shows a polynucleotide sequence used in Example 2.

SEQ ID NO: 43 shows a polynucleotide sequence used in Example 2.

SEQ ID NO: 44 shows a polynucleotide sequence used in Example 2.

SEQ ID NO: 45 shows a polynucleotide sequence used in Example 2.

SEQ ID NO: 46 shows a polynucleotide sequence used in Example 2. Attached to the 3' end of SEQ ID NO: 46 is six iSp18 spacers which are attached at the opposite end to two thymines and a 3' cholesterol TEG.

SEQ ID NO: 47 shows the polynucleotide sequence of StrepII(C).

SEQ ID NO: 48 shows the polynucleotide sequence of Pro.

SEQ ID NO: 49 shows the codon optimised polynucleotide sequence encoding the wild-type MspA monomer. This mutant lacks the signal sequence.

SEQ ID NO: 50 shows the amino acid sequence of the mature form of the wild-type MspA monomer. This mutant lacks the signal sequence.

SEQ ID NO: 51 shows the polynucleotide sequence of Thrombin Binding Aptamer used in Examples 7 and 11.

SEQ ID NO: 52 shows the polynucleotide sequence of a Y-adaptor top strand.

SEQ ID NO: 53 shows the polynucleotide sequence of a Y-adaptor blocker strand.

SEQ ID NO: 54 shows the polynucleotide sequence of a Y-adaptor cholesterol tether strand.

SEQ ID NO: 55 shows the polynucleotide sequence of a Y-adaptor bottom strand.

SEQ ID NO: 56 shows the polynucleotide sequence of a 3.6 kb double stranded DNA target sequence used in the Examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "a polynucleotide binding protein" includes two or more such proteins, reference to "a helicase" includes two or more helicases, reference to "a monomer" refers to two or more monomers, reference to "a pore" includes two or more pores and the like.

All publications, patents and patent applications cited herein, whether supra or infra, are hereby incorporated by reference in their entirety.

Mutant CsgG Monomers

An aspect of the present invention provides mutant CsgG monomers. The mutant CsgG monomers may be used to form the pores of the invention. A mutant CsgG monomer is a monomer whose sequence varies from that of a wild-type CsgG monomer and which retains the ability to form a pore. Methods for confirming the ability of mutant monomers to form pores are well-known in the art and are discussed in more detail below.

Pores constructed from the CsgG monomers of some embodiments of the invention comprising the modification R97W display an increased accuracy as compared to otherwise identical pores without the modification at 97 when characterizing (or sequencing) target polynucleotides. An increased accuracy is also seen when instead of R97W the CsgG monomers of the invention comprise the modification R93W or the modifications R93Y and R97Y. Accordingly, pores may be constructed from one or more mutant CsgG monomers that comprise a modification at R97 or R93 of SEQ ID NO: 2 such that the modification increases the hydrophobicity of the amino acid. For example, such modification may include an amino acid substitution with any amino acid containing a hydrophobic side chain, including, e.g., but not limited to W and Y.

The CsgG monomers of some embodiments of the invention that comprise R192D/Q/F/S/T are easier to express than monomers which do not have a substitution at position 192 which may be due to the reduction of positive charge. Accordingly position 192 may be substituted with an amino-acid which reduces the positive charge. The monomers of the invention that comprise R192D/Q/F/S/T may also comprise additional modifications which improve the ability of mutant pores formed from the monomers to interact with and characterise analytes, such as polynucleotides.

Pores comprising the CsgG monomers of some embodiments of the invention that comprise a deletion of V105, A106 and I107, a deletion of F193, I194, D195, Y196, Q197, R198 and L199 or a deletion of D195, Y196, Q197, R198 and L199, and/or F191T display an increased accuracy when characterizing (or sequencing) target polynucleotides. The amino-acids at positions 105 to 107 correspond to the cis-loops in the cap of the nanopore and the amino-acids at positions 193 to 199 correspond to the trans-loops at the other end of the pore. Without wishing to be bound by theory it is thought that deletion of the cis-loops improves the interaction of the enzyme with the pore and removal of the trans-loops decreases any unwanted interaction between DNA on the trans side of the pore.

Pores comprising the CsgG monomers of some embodiments of the invention that comprise K94Q or K94N show a reduction in the number of noisy pores (namely those pores that give rise to an increased signal:noise ratio) as compared to identical pores without the mutation at 94 when characterizing (or sequencing) target polynucleotides. Position 94 is found within the vestibule of the pore and was found to be a particularly sensitive position in relation to the noise of the current signal.

Pores comprising the CsgG monomers of some embodiments of the invention that comprise T104K or T104R, N91R, E101K/N/Q/T/H, E44N/Q, Q114K, A99R, I95R, N91R, L90R, E44Q/N and/or Q42K all demonstrate an improved ability to capture target polynucleotides when used to characterize (or sequence) target polynucleotides as compounds to identical pores without substitutions at these positions.

Characterisation, such as sequencing, of a polynucleotide using a transmembrane pore may be carried out such as disclosed in International Application No. PCT/GB2012/052343 (published as WO 2013/041878). As the target polynucleotide moves with respect to, or through the pore, the analyte may be characterised from the distinctive ion current signature produced, typically by measuring the ion current flow through the pore. The level of current measured at any particular time is typically dependent on a group of k polymer (for example nucleotide) units where k is a positive integer and the typical current signature may be represented as a series of current levels indicative of a particular k-mer. The movement of the polynucleotide with respect to, such as through, the pore can be viewed as movement from one k-mer to another or from k-mer to k-mer. Analytical techniques to characterise the polynucleotide may for example involve the use of an HMM, a neural network and for example a Forwards Backwards algorithm or Viterbi algorithm to determine the likelihood of the series of measurements corresponding to a particular sequence. Alternatively the polynucleotide may be characterised by determining a feature vector and comparing the feature vector to another feature vector, which may be known, such as disclosed in International Application No. PCT/GB2013/050381 (published as WO 2013/121224). However, the analytical techniques used to characterise the polynucleotide are not necessarily restricted to the above examples.

When a monomer of the invention forms a transmembrane pore and is used with a polynucleotide binding protein to characterise a target polynucleotide, some of the modified positions interact with the polynucleotide binding protein. For example, when the monomer forms a transmembrane pore and is used with a polynucleotide binding protein to characterise a target polynucleotide, R97W interacts with the polynucleotide binding protein. Modifying the CsgG monomer in accordance with the invention typically provides more consistent movement of the target polynucleotide with respect to, such as through, a transmembrane pore comprising the monomer. The modification(s) typically provide more consistent movement from one k-mer to another or from k-mer to k-mer as the target polynucleotide moves with respect to, such as through, the pore. The modification(s) typically allow the target polynucleotide to move with respect to, such as through, the transmembrane pore more smoothly. The modification(s) typically provide more regular or less irregular movement of the target polynucleotide with respect to, such as through, the transmembrane pore.

Modifying the CsgG monomer in accordance with the invention (e.g. R97W) typically reduces the amount of slipping forward associated with the movement of the target polynucleotide with respect to, such as through, a pore comprising the monomer. Some helicases including the Dda helicase used in the Example move along the polynucleotide in a 5' to 3' direction. When the 5' end of the polynucleotide (the end away from which the helicase moves) is captured by the pore, the helicase works with the direction of the field resulting from the applied potential and moves the threaded polynucleotide into the pore and into the trans chamber. Slipping forward involves the DNA moving forwards relative to the pore (i.e. towards its 3' and away from its 5' end) at least 4 consecutive nucleotides and typically more than 10 consecutive nucleotides. Slipping forward may involve movement forward of 100 consecutive nucleotides or more and this may happen more than once in each strand.

Modifying the CsgG monomer may reduce the noise associated with the movement of the target polynucleotide with respect to, such as through, a transmembrane pore comprising the monomer. Unwanted movement of the target polynucleotide in any dimension as the signal is being analysed typically results in noise in the current signature or level for the k-mer. The modification may reduce this noise by reducing unwanted movement associated with one or more k-mers, such as each k-mer, in the target polynucleotide. The modification may reduce the noise associated with the current level or signature for one or more k-mers, such as each k-mer, in the target polynucleotide.

The enzyme motors employed for moving the polynucleotide have multiple sub-steps in the full catalytic cycle where ATP is hydrolysed to move the polynucleotide forward one base (eg. binding ATP.Mg, hydrolysing to produce ADP.P.Mg, moving the polynucleotide one base forward, and releasing the ADP/P/Mg by-products). Each sub-step process has a characteristic dwell time distribution determined by the kinetics of the process. If any of these sub-steps of the catalytic cycle move the position of the polynucleotide in the reader (e.g. by moving the polynucleotide relative to the enzyme, or by changing the position of the enzyme on the top of the pore) then this may be observed as a change in current through the pore, as long the change lasts sufficiently long to be detected by the acquisition electronics. If the sub-step processes result in no change of conformation or shift in polynucleotide, or occur too quickly to observe, then in an ideal system the full catalytic cycle will result in only one step change in current for the polynucleotide moving one integer base forward.

Figure 48:
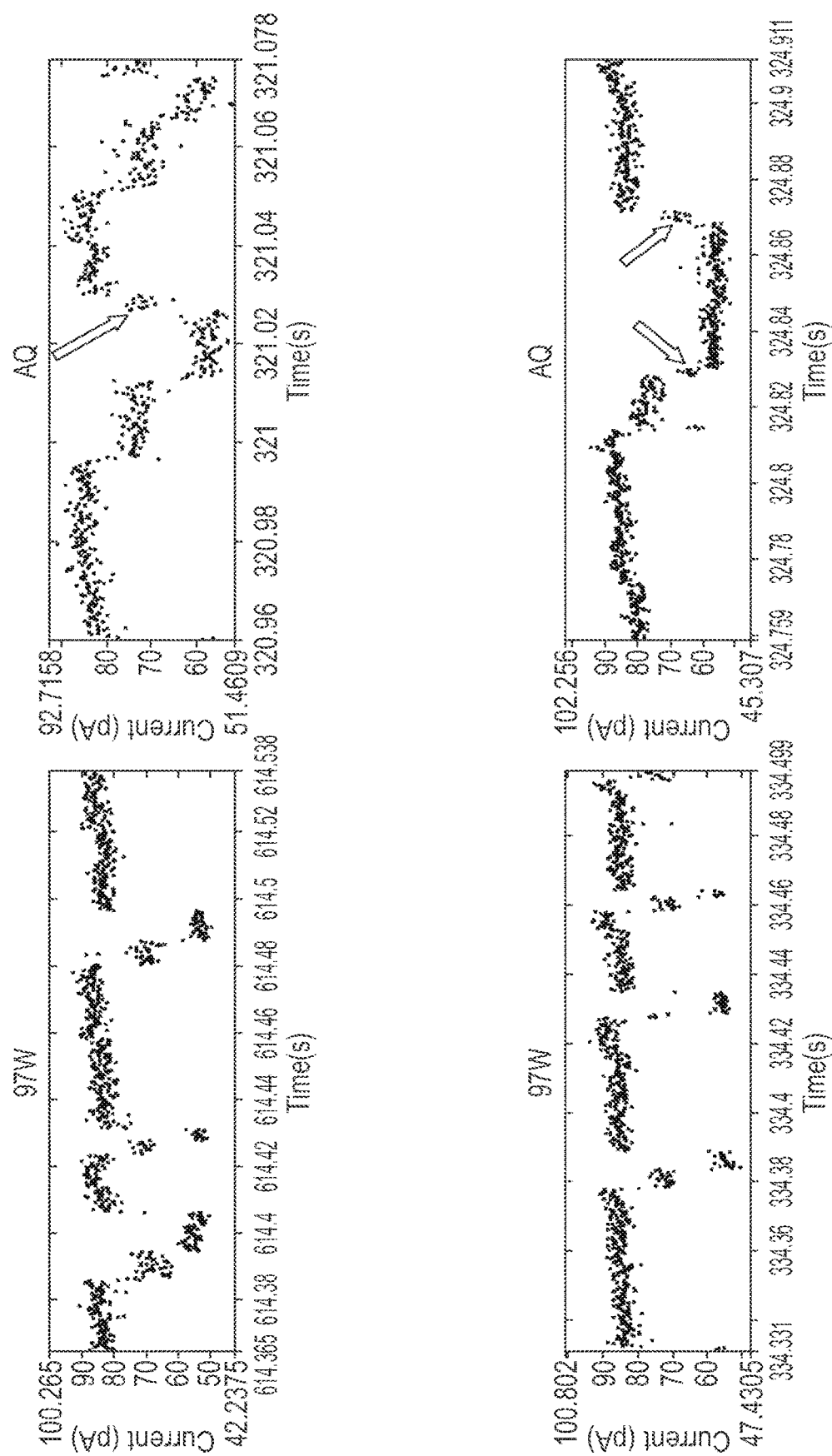
FIG. 48 shows two examples of raw electrical data for poreAQ and pore97W.

For pores that do not contain R97W (eg Pro-CP1-Eco-(WT-Y51A/F56Q-StrepII(C))9), we observe long dwell time levels where predicted by the model, with an approximately exponential dwell distribution that is dependent on ATP.Mg concentration. For poreAQ we also short-lived substeps current levels in between the major levels, as marked in FIG. 48. Because the sub-step current levels are short-lived, they are most easily observed in the gap between two widely separated current levels. The sub-steps levels correspond to an intermediate approximately 0.5 base movement of the polynucleotide, and under these conditions have an ATP.Mg independent dwell time of approximately 3 milliseconds.

Pores containing R97W (e.g. Pro-CP1-Eco-(WT-Y51A/F56Q/R97W-StrepII(C))9) shows similar longer lived main levels with ATP.Mg dependent dwell times, but shows no signs of distinct intermediate sub-step current levels under these conditions or at this acquisition frequency (possible explanations being that they do not occur, occur too quickly to be observed, or that the substeps do occur and are slow enough in principle to be observed but that in practice they are not observed due to for example the way in which the enzyme interacts with the pore).

The raw data traces (FIG. 48) show the ionic current (y-axis, pA) vs. time (x-axis, seconds) trace of an enzyme controlled DNA strand translocation through a nanopore for the pores Pro-CP1-Eco-(WT-Y51A/F56Q/R97W-StrepII(C))9 (Pore 97W) and Pro-CP1-Eco-(WT-Y51A/F56Q-StrepII(C))9 (Pore AQ). Each current level is the result of the sequence held in the nanopore reader altering the flow of ions, and step-wise changes in current are observed when the polynucleotide changes position in the nanopore, for example when the enzyme moves the entire strand forward one base. In this case the DNA strand contains in part a repeating sequence (GGTT)n. The data was acquired by loading a Dda enzyme onto synthetic DNA polynucleotides and running on a MinION recording raw data output (Cis buffer: 500 mM KCl, 25 mM HEPES, pH8, 0.6 mM MgCl2, 0.6 mM ATP, 140 mV, 37 deg C., 5 kHz acquisition frequency). Pore97W only shows the main current levels from integer step-wise movements of the polynucleotide, with no significant data density between the levels. In comparison, PoreAQ has significant intermediate sub-step levels, as marked by the arrows in FIG. 48.

The mutant monomers preferably have improved polynucleotide reading properties i.e. display improved polynucleotide capture and nucleotide discrimination. In particular, pores constructed from the mutant monomers preferably capture nucleotides and polynucleotides more easily than the wild type. In addition, pores constructed from the mutant monomers preferably display an increased current range, which makes it easier to discriminate between different nucleotides, and a reduced variance of states, which increases the signal-to-noise ratio.

In addition, the number of nucleotides contributing to the current as the polynucleotide moves through pores constructed from the mutants is preferably decreased. This makes it easier to identify a direct relationship between the observed current as the polynucleotide moves through the pore and the polynucleotide sequence. In addition, pores constructed from the mutant monomers may display an increased throughput, i.e. are more likely to interact with an analyte, such as a polynucleotide. This makes it easier to characterise analytes using the pores. Pores constructed from the mutant monomers may insert into a membrane more easily. A mutant monomer of the invention comprises a variant of the sequence shown in SEQ ID NO: 2. SEQ ID NO: 2 is the wild-type CsgG monomer from *Escherichia coli* Str. K-12 substr. MC4100. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state.

In all of the discussion herein, the standard one letter codes for amino acids are used. These are as follows: alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y) and valine (V). Standard substitution notation is also used, i.e. Q42R means that Q at position 42 is replaced with R.

In one embodiment of the mutant monomers of the invention, the variant of SEQ ID NO: 2 comprises (a) one or more mutations at the following positions (i.e. mutations at one or more of the following positions) I41, R93, A98, Q100, G103, T104, A106, I107, N108, L113, S115, T117, Y130, K135, E170, S208, D233, D238 and E244 and/or (b) one or more of D43S, E44S, F48S/N/Q/Y/W/I/V/H/R/K, Q87N/R/K, N91K/R, K94R/F/Y/W/L/S/N, R97F/Y/W/V/I/K/S/Q/H, E101I/L/A/H, N102K/Q/L/I/V/S/H, R110F/G/N, Q114R/K, R142Q/S, T150Y/A/V/L/S/Q/N, R192D/Q/F/S/T and D248S/N/Q/K/R. The variant may comprise (a); (b); or (a) and (b).

In some embodiments of the invention, the variant of SEQ ID NO: 2 comprises R97W.

In some embodiments of the invention, the variant of SEQ ID NO: 2 comprises R192D/Q/F/S/T, preferably R192D/Q, more preferably R192D. In (a), the variant may comprise modifications at any number and combination of the positions, such as 1, 2, 3, 4, 5, 6, 7, 8, 9, 10, 11, 12, 13, 14, 15, 16, 17, 18 or 19 of the positions. In (a), the variant preferably comprises one or more of I41N, R93F/Y/W/L/I/V/N/Q/S, A98K/R, Q100K/R, G103F/W/S/N/K/R, T104R/K, A106R/K, I107R/K/W/F/Y/L/V, N108R/K, L113K/R, S115R/K, T117R/K, Y130W/F/H/Q/N, K135L/V/N/Q/S, E170S/N/Q/K/R, S208V/I/F/W/Y/L/T, D233S/N/Q/K/R, D238S/N/Q/K/R and E244S/N/Q/K/R.

In (a), the variant preferably comprises one or more modifications which provide more consistent movement of a target polynucleotide with respect to, such as through, a transmembrane pore comprising the monomer. In particular, in (a), the variant preferably comprises one or more mutations at the following positions (i.e. mutations at one or more of the following positions) R93, G103 and I107. The variant may comprise R93; G103; I107; R93 and G103; R93 and I107; G103 and I107; or R93, G103 and I107. The variant preferably comprises one or more of R93F/Y/W/L/I/V/N/Q/S, G103F/W/S/N/K/R and I107R/K/W/F/Y/L/V. These may be present in any combination shown for the positions R93, G103 and I107.

In (a), the variant preferably comprises one or modifications which allow pores constructed from the mutant monomers preferably capture nucleotides and polynucleotides more easily. In particular, in (a), the variant preferably comprises one or more mutations at the following positions (i.e. mutations at one or more of the following positions) I41, T104, A106, N108, L113, S115, T117, E170, D233, D238 and E244. The variant may comprise modifications at any number and combination of the positions, such as 1, 2, 3, 4, 5, 6, 7, 8, 9, 10 or 11 of the positions. The variant preferably comprises one or more of I41N, T104R/K, A106R/K, N108R/K, L113K/R, S115R/K, T117R/K, E170S/N/Q/K/R, D233S/N/Q/K/R, D238S/N/Q/K/R and E244S/N/Q/K/R. Additionally or alternatively the variant may comprise (c) Q42K/R, E44N/Q, L90R/K, N91R/K, I95R/K, A99R/K, E101H/K/N/Q/T and/or Q114K/R.

In (a), the variant preferably comprises one or more modifications which provide more consistent movement and increase capture. In particular, in (a), the variant preferably comprises one or more mutations at the following positions (i.e. mutations at one or more of the following positions) (i) A98, (ii) Q100, (iii) G103 and (iv) I107. The variant preferably comprises one or more of (i) A98R/K, (ii) Q100K/R, (iii) G103K/R and (iv) I107R/K. The variant may comprise {i}; {ii}; {iii}; {iv}; {i,ii}; {i,iii}; {i,iv}; {ii,iii}; {ii,iv}; {iii,iv}; {i,ii,iii}; {i,ii,iv}; {i,iii,iv}; {ii,iii,iv}; or {i,ii,iii,iv}.

Particularly preferred mutant monomers which provide for increased capture of analytes, such as a polynucleotides include a mutation at one or more of positions Q42, E44, E44, L90, N91, I95, A99, E101 and Q114, which mutation removes the negative charge and/or increases the positive charge at the mutated positions. In particular, the following mutations may be included in a mutant monomer of the invention to produce a CsgG pore that has an improved ability to capture an analyte, preferably a polynucleotide: Q42K, E44N, E44Q, L90R, N91R, I95R, A99R, E101H, E101K, E101N, E101Q, E101T and Q114K. Examples of particular mutant monomers which comprise one of these mutations in combination with other beneficial mutations are described in Example 11.

In (a), the variant preferably comprises one or more modifications which provide increased characterisation accuracy. In particular, in (a), the variant preferably comprises one or more mutations at the following positions (i.e. mutations at one or more of the following positions) Y130, K135 and S208, such as Y130; K135; S208; Y130 and K135; Y130 and S208; K135 and S208; or Y130, K135 and S208. The variant preferably comprises one or more of Y130W/F/H/Q/N, K135L/V/N/Q/S and R142Q/S. These substitutions may be present in any number and combination as set out for Y130, K135 and S208.

In (b), the variant may comprise any number and combination of the substitutions, such as 1, 2, 3, 4, 5, 6, 7, 8, 9, 10, 11 or 12 of the substitutions. In (b), the variant preferably comprises one or more modifications which provide more consistent movement of a target polynucleotide with respect to, such as through, a transmembrane pore comprising the monomer. In particular, in (b), the variant preferably comprises one or more one or more of (i) Q87N/R/K, (ii) K94R/F/Y/W/L/S/N, (iii) R97F/Y/W/V/I/K/S/Q/H, (iv) N102K/Q/L/I/V/S/H and (v) R110F/G/N. More preferably, the variant comprises K94D or K94Q and/or R97W or R97Y. The variant may comprise {i}; {ii}; {iii}; {iv}; {v}; {i,ii}; {i,iii}; {i,iv}; {i,v}; {ii,iii}; {ii,iv}; {ii,v}; {iii,iv}; {iii,v}; {iv,v}; {i,ii,iii}; {i,ii,iv}; {i,ii,v}; {i,iii,iv}; {i,iii,v}; {i,iv,v}; {ii,iii,iv}; {ii,iii,v}; {ii,iv,v}; {iii,iv,v}; {i,ii,iii,iv}; {i,i,iii,v}; {i,ii,iv,v}; {i,iii,iv,v}; {ii,iii,iv,v}; or {i,ii,iii,iv,v}. Other preferred variants that are modified to provide more consistent movement of a target polynucleotide with respect to, such as through, a transmembrane pore comprising the monomer include (vi) R93W and R93Y. A preferred variant may comprise R93W and R97W, R93Y and R97W, R93W and R97W, or more preferably R93Y and R97Y. The variant may comprise {vi}; {i,vi}; {ii,vi}; {iii,vi}; {iv,vi}; {v,vi}; {i,ii,vi}; {i,iii,vi}; {i,iv,vi}; {i,v,vi}; {ii,iii,vi}; {ii,iv,vi}; {ii,v,vi}; {iii,iv,vi}; {iii,v,vi}; {iv,v,vi}, {i,ii,iii,vi}; {i,ii,iv,vi}, {i,ii,v,vi}, {i,iii,iv,vi}; {i,iii,v,vi}; {i,iv,v,vi}; {ii,iii,iv,vi}; {ii,iii,v,vi}; {ii,iv,v,vi}; {iii,iv,v,vi}, {i,ii,iii,iv,vi}, {i,ii,iii,v,vi}; {i,ii,iv,v,vi}; {i,iii,iv,v,vi}; {ii,iii,iv,v,vi}; or {i,ii,iii,iv,v,vi}.

In (b), the variant preferably comprises one or modifications which allow pores constructed from the mutant monomers preferably capture nucleotides and polynucleotides more easily. In particular, in (b), the variant preferably comprises one or more of (i) D43S, (ii) E44S, (iii) N91K/R, (iv) Q114R/K and (v) D248S/N/Q/K/R. The variant may comprise {i}; {ii}; {iii}; {iv}; {v}; {i,ii}; {i,iii}; {i,iv}; {i,v}; {ii,iii}; {ii,iv}; {ii,v}; {iii,iv}; {iii,v}; {iv,v}; {i,ii,iii}; {i,ii,iv}; {i,ii,v}; {i,iii,iv}; {i,iii,v}; {i,iv,v}; {ii,iii,iv}; {ii,iii,v}; {ii,iv,v}; {iii,iv,v}; {i,ii,iii,iv}; {i,ii,iii,v}; {i,ii,iv,v}; {i,iii,iv,v}; {ii,iii,iv,v}; or {i,ii,iii,iv,v}.

In (b), the variant preferably comprises one or more modifications which provide more consistent movement and increase capture. In particular, in (b), the variant preferably comprises one or more of Q87R/K, E101I/L/A/H and N102K, such as Q87R/K; E101I/L/A/H; N102K; Q87R/K and E101I/L/A/H; Q87R/K and N102K; E101I/L/A/H and N102K; or Q87R/K, E101I/L/A/H and N102K.

In (b), the variant preferably comprises one or more modifications which provide increased characterisation accuracy. In particular, in (a), the variant preferably comprises F48S/N/Q/Y/W/I/V.

In (b), the variant preferably comprises one or more modifications which provide increased characterisation accuracy and increased capture. In particular, in (a), the variant preferably comprises F48H/R/K.

The variant may comprise modifications in both (a) and (b) which provide more consistent movement. The variant may comprise modifications in both (a) and (b) which provide increased capture.

The invention provides variants of SEQ ID NO: 2 which provide an increased throughput of an assay for characterising an analyte, such as a polynucleotide, using a pore comprising the variant. Such variants may comprise a mutation at K94, preferably K94Q or K94N, more preferably K94Q. Examples of particular mutant monomers which comprise a K94Q or K94N mutation in combination with other beneficial mutations are described in Examples 10 and 11.

The invention provides variants of SEQ ID NO: 2 which provide increased characterisation accuracy in an assay for characterising an analyte, such as a polynucleotide, using a pore comprising the variant. Such variants include variants that comprise: a mutation at F191, preferably F191T; deletion of V105-I107; deletion of F193-L199 or of D195-L199; and/or a mutation at R93 and/or R97, preferably R93Y, R97Y, or more preferably, R97W, R93W or both R97Y and R97Y. Examples of particular mutant monomers which comprise one or more of these mutations in combination with other beneficial mutations are described in Example 9.

In another embodiment of the mutant monomers of the invention, the variant of SEQ ID NO: 2 comprises (A) deletion of one or more positions R192, F193, I194, D195, Y196, Q197, R198, L199, L200 and E201 and/or (B) deletion of one or more of V139/G140/D149/T150/V186/Q187/V204/G205 (called band 1 herein), G137/G138/Q151/Y152/Y184/E185/Y206/T207 (called band 2 herein) and A141/R142/G147/A148/A188/G189/G202/E203 (called band 3 herein).

In (A), the variant may comprise deletion of any number and combination of the positions, such as 1, 2, 3, 4, 5, 6, 7, 8, 9 or 10 of the positions. In (A), the variant preferably comprises deletion of D195, Y196, Q197, R198 and L199;
R192, F193, I194, D195, Y196, Q197, R198, L199 and L200;
Q197, R198, L199 and L200;
I194, D195, Y196, Q197, R198 and L199;
D195, Y196, Q197, R198, L199 and L200;
Y196, Q197, R198, L199, L200 and E201;
Q197, R198, L199, L200 and E201;
Q197, R198, L199; or
F193, I194, D195, Y196, Q197, R198 and L199.

More preferably, the variant comprises deletion of D195, Y196, Q197, R198 and L199 or F193, I194, D195, Y196, Q197, R198 and L199. In (B), any number and combination of bands 1 to 3 may be deleted, such as band 1; band 2; band 3; bands 1 and 2; bands 1 and 3; bands 2 and 3; or bands 1, 2 and 3.

The variant may comprise deletions according to (A); (B); or (A) and (B).

The variants comprising deletion of one or more positions according to (A) and/or (B) above may further comprise any of the modifications or substitutions discussed above and below. If the modifications or substitutions are made at one or more positions which appear after the deletion positions in SEQ ID NO: 2, the numbering of the one or more positions of the modifications or substitutions must be adjusted accordingly. For instance, if L199 is deleted, E244 becomes E243. Similarly, if band 1 is deleted, R192 becomes R186.

In another embodiment of the mutant monomers of the invention, the variant of SEQ ID NO: 2 comprises (C) deletion of one or more positions V105, A106 and I107. The deletions in accordance with (C) may be made in addition to deletions according to (A) and/or (B).

The above-described deletions typically reduce the noise associated with the movement of the target polynucleotide with respect to, such as through, a transmembrane pore comprising the monomer. As a result the target polynucleotide can be characterised more accurately.

In the paragraphs above where different amino acids at a specific positon are separated by the / symbol, the / symbol means "or". For instance, Q87R/K means Q87R or Q87K.

The invention provides variants of SEQ ID NO: 2 which provide increased capture of an an analyte, such as a polynucleotide. Such variants may comprise a mutation at T104, preferably T104R or T104K, a mutation at N91, preferably N91R, a mutation at E101, preferably E101K/N/Q/T/H, a mutation at position E44, preferably E44N or E44Q and/or a mutation at position Q42, preferably Q42K.

The mutations at different positions in SEQ ID NO: 2 may be combined in any possible way. In particular, a monomer of the invention may comprise one or more mutation that improves accuracy, one ore more mutation that reduces noise and/ore one or more mutation that enhances capture of an analyte.

In the mutant monomers of the invention, the variant of SEQ ID NO: 2 preferably comprises one or more of the following (i) one or more mutations at the following positions (i.e. mutations at one or more of the following positions) N40, D43, E44, S54, S57, Q62, R97, E101, E124, E131, R142, T150 and R192, such as one or more mutations at the following positions (i.e. mutations at one or more of the following positions) N40, D43, E44, S54, S57, Q62, E101, E131 and T150 or N40, D43, E44, E101 and E131; (ii) mutations at Y51/N55, Y51/F56, N55/F56 or Y51/N55/F56; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57. The variant may comprise any combination of (i) to (xi). In particular, the variant may comprise: (where each variant in parentheses { } separated by a space represents an optional variant from the list of variants, namely {i} or {ii} or {iii} or {iv} or {v} and so on) {i} {ii} {iii} {iv} {v} {vi} {vii} {viii} {ix} {x} {xi} {i,ii} {i,iii} {i,iv} {i,v} {i,vi} {i,vii} {i,viii} {i,ix} {i,x} {i,xi} {ii,iii} {ii,iv} {ii,v} {ii,vi} {ii,vii} {ii,viii} {ii,ix} {ii,x} {ii,xi} {iii,iv} {iii,v} {iii,vi} {iii,vii} {iii,viii} {iii,ix} {iii,x} {iii,xi} {iv,v} {iv,vi} {iv,vii} {iv,viii} {iv,ix} {iv,x} {iv,xi} {v,vi} {v,vii} {v,viii} {v,ix} {v,x} {v,xi} {vi,vii} {vi,viii} {vi,ix} {vi,x} {vi,xi} {vii,viii} {vii,ix} {vii,x} {vii,xi} {viii,ix} {viii,x} {viii,xi} {ix,x} {ix,xi} {x,xi} {i,ii,iii} {i,ii,iv} {i,ii,v} {i,ii,vi} {i,ii,vii} {i,ii,viii} {i,ii,ix} {i,ii,x} {i,ii,xi} {i,iii,iv} {i,iii,v} {i,iii,vi} {i,iii,vii} {i,iii,viii} {i,iii,ix} {i,iii,x} {i,iii,xi} {i,iv,v} {i,iv,vi} {i,iv,vii} {i,iv,viii} {i,iv,ix} {i,iv,x} {i,iv,xi} {i,v,vi} {i,v,vii} {i,v,viii} {i,v,ix} {i,v,x} {i,v,xi} {i,vi,vii} {i,vi,viii} {i,vi,ix} {i,vi,x} {i,vi,xi} {i,vii,viii} {i,vii,ix} {i,vii,x} {i,vii,xi} {i,viii,ix} {i,viii,x} {i,viii,xi} {i,ix,x} {i,ix,xi} {i,x,xi} {ii,iii,iv} {ii,iii,v} {ii,iii,vi} {ii,iii,vii} {ii,iii,viii} {ii,iii,ix} {ii,iii,x} {ii,iii,xi} {ii,iv,v} {ii,iv,vi} {ii,iv,vii} {i,ii,iv,viii} {i,ii,iv,ix} {ii,iv,x} {ii,iv,xi} {ii,v,vi} {ii,v,vii} {ii,v,viii} {ii,v,ix} {ii,v,x} {ii,v,xi} {ii,vi,vii} {ii,vi,viii} {ii,vi,ix} {ii,vi,x} {ii,vi,xi} {ii,vii,viii} {ii,vii,ix} {ii,vii,x} {ii,vii,xi} {ii,viii,ix} {ii,viii,x} {ii,viii,xi} {ii,ix,x} {ii,ix,xi} {ii,x,xi} {iii,iv,v} {iii,iv,vi} {iii,iv,vii} {iii,iv,viii} {iii,iv,ix} {iii,iv,x} {iii,iv,xi} {iii,v,vi} {iii,v,vii} {iii,v,viii} {iii,v,ix} {iii,v,x} {iii,v,xi} {iii,vi,vii} {iii,vi,viii} {iii,vi,ix} {iii,vi,x} {iii,vi,xi} {iii,vii,viii} {iii,vii,ix} {iii,vii,x} {iii,vii,xi} {iii,viii,ix} {iii,viii,x} {i,ii,iii,iv} {i,ii,iii,v} {i,ii,iii,vi} {i,ii,iii, vii} {i,ii,iii,viii} {i,ii,iii,ix} {i,ii,iii,x} {i,ii,iii,xi} {i,ii,iv,v} {i,ii,iv,vi} {i,ii,iv,vii} {i,ii,iv,viii} {i,ii,iv,ix} {i,ii,iv,x} {i,ii,iv,xi} {i,ii,v,vi} {i,ii,v,vii} {i,ii,v,viii} {i,ii,v,ix} {i,ii,v,x} {i,ii,v,xi} {i,ii,vi,vii} {i,ii,vi,viii} {i,ii,vi,ix} {i,ii,vi,x} {i,ii,vi,xi} {i,ii,vii,viii} {i,ii,vii,ix} {i,ii,vii,x} {i,ii,vii,xi} {i,ii,viii,ix} {i,ii,viii,x} {i,ii,viii,xi} {i,ii,ix,x} {i,ii,ix,xi} {i,ii,x,xi} {i,iii,iv,v} {i,iii,iv,vi} {i,iii,iv,vii} {i,iii,iv,viii} {i,iii,iv,ix} {i,iii,iv,x} {i,iii,iv,xi} {i,iii,v,vi} {i,iii,v,vii} {i,iii,v,viii} {i,iii,v,ix} {i,iii,v,x} {i,iii,v,xi} {i,iii,vi,vii} {i,iii,vi,viii} {i,iii,vi,ix} {i,iii,vi,x} {i,iii,vi,xi} {i,iii,vii,viii} {i,iii,vii,ix} {i,iii,vii,x} {i,iii,vii,xi} {i,iii,viii,ix} {i,iii,viii,x} {i,iii,viii,xi} {i,iii,ix,x} {i,iii,ix,xi} {i,iii,x,xi} {i,iv,v,vi} {i,iv,v,vii} {i,iv,v,viii} {i,iv,v,ix} {i,iv,v,x} {i,iv,v,xi} {i,iv,vi,vii} {i,iv,vi,viii} {i,iv,vi,ix} {i,iv,vi,x} {i,iv,vi,xi} {i,iv,vii,viii} {i,iv,vii,ix} {i,iv,vii,x} {i,iv,vii,xi} {i,iv,viii,ix} {i,iv,viii,x} {i,iv,viii,xi} {i,iv,ix,x} {i,iv,ix,xi} {i,iv,x,xi} {i,v,vi,vii} {i,v,vi,viii} {i,v,vi,ix} {i,v,vi,x} {i,v,vi,xi} {i,v,vii,viii} {i,v,vii,ix} {i,v,vii,x} {i,v,vii,xi} {i,v,viii,ix} {i,v,viii,x} {i,v,viii,xi} {i,v,ix,x} {i,v,ix,xi} {i,v,x,xi} {i,vi,vii,viii} {i,vi,vii,ix} {i,vi,vii,x} {i,vi,vii,xi} {i,vi,viii,ix} {i,vi,viii,x} {i,vi,viii,xi} {i,vi,ix,x} {i,vi,ix,xi} {i,vi,x,xi} {i,vii,viii,ix} {i,vii,viii,x} {i,vii,viii,xi} {i,vii,ix,x} {i,vii,ix,xi} {i,vii,x,xi} {i,viii,ix,x} {i,viii,ix,xi} {i,viii,x,xi} {i,ix,x,xi} {ii,iii,iv,v} {ii,iii,iv,vi} {ii,iii,iv,vii} {ii,iii,iv,viii} {ii,iii,iv,ix} {ii,iii,iv,x} {ii,iii,iv,xi} {ii,iii,v,vi} {ii,iii,v,vii} {ii,iii,v,viii} {ii,iii,v,ix} {ii,iii,v,x} {ii,iii,v,xi} {ii,iii,vi,vii} {ii,iii,vi,viii} {ii,iii,vi,ix} {ii,iii,vi,x} {ii,iii,vi,xi} {ii,iii,vii,viii} {ii,iii,vii,ix} {ii,iii,vii,x} {ii,iii,vii,xi} {ii,iii,viii,ix} {ii,iii,viii,x} {ii,iii,viii,xi} {ii,iii,ix,x} {ii,iii,ix,xi} {ii,iii,x,xi} {ii,iv,v,vi} {ii,iv,v,vii} {ii,iv,v,viii} {ii,iv,v,ix} {ii,iv,v,x} {ii,iv,v,xi} {ii,iv,vi,vii} {ii,iv,vi,viii} {ii,iv,vi,ix} {ii,iv,vi,x} {ii,iv,vi,xi} {ii,iv,vii,viii} {ii,iv,vii,ix} {ii,iv,vii,x} {ii,iv,vii,xi} {ii,iv,viii,ix} {ii,iv,viii,x} {ii,iv,viii,xi} {ii,iv,ix,x} {ii,iv,ix,xi} {ii,iv,x,xi} {ii,v,vi,vii} {ii,v,vi,viii} {ii,v,vi,ix} {ii,v,vi,x} {ii,v,vi,xi} {ii,v,vii,viii} {ii,v,vii,ix} {ii,v,vii,x} {ii,v,vii,xi} {ii,v,viii,ix} {ii,v,viii,x} {ii,v,viii,xi} {ii,v,ix,x} {ii,v,ix,xi} {ii,v,x,xi} {ii,vi,vii,viii} {ii,vi,vii,ix} {ii,vi,vii,x} {ii,vi,vii,xi} {ii,vi,viii,ix} {ii,vi,viii,x} {ii,vi,viii,xi} {ii,vi,ix,x} {ii,vi,ix,xi} {ii,vi,x,xi} {ii,vii,viii,ix} {ii,vii,viii,x} {ii,vii,viii,xi} {ii,vii,ix,x} {ii,vii,ix,xi} {ii,vii,x,xi} {ii,viii,ix,x} {ii,viii,ix,xi} {ii,viii,x,xi} {ii,ix,x,xi} {iii,iv,v,vi} {iii,iv,v,vii} {iii,iv,v,viii} {iii,iv,v,ix} {iii,iv,v,x} {iii,iv,v,xi} {iii,iv,vi,vii} {iii,iv,vi,viii} {iii,iv,vi,ix} {iii,iv,vi,x} {iii,iv,vi,xi} {iii,iv,vii,viii} {iii,iv,vii,ix} {iii,iv,vii,x} {iii,iv,vii,xi} {iii,iv,viii,ix} {iii,iv,viii,x} {iii,iv,viii,xi} {iii,iv,ix,x} {iii,iv,ix,xi} {iii,iv,x,xi} {iii,v,vi,vii} {iii,v,vi,viii} {iii,v,vi,ix} {iii,v,vi,x} {iii,v,vi,xi} {iii,v,vii,viii} {iii,v,vii,ix} {iii,v,vii,x} {iii,v,vii,xi} {iii,v,viii,ix} {iii,v,viii,x} {iii,v,viii,xi} {iii,v,ix,x} {iii,v,ix,xi} {iii,v,x,xi} {iii,vi,vii,viii} {iii,vi,vii,ix} {iii,vi,vii,x} {iii,vi,vii,xi} {iii,vi,viii,ix} {iii,vi,viii,x} {iii,vi,viii,xi} {iii,vi,ix,x} {iii,vi,ix,xi} {iii,vi,x,xi} {iii,vii,viii,ix} {iii,vii,viii,x} {iii,vii,viii,xi} {iii,vii,ix,x} {iii,vii,ix,xi} {iii,vii,x,xi} {iii,viii,ix,x} {iii,viii,ix,xi} {iii,viii,x,xi} {iii,ix,x,xi} {iv,v,vi,vii} {iv,v,vi,viii} {iv,v,vi,ix} {iv,v,vi,x} {iv,v,vi,xi} {iv,v,vii,viii} {iv,v,vii,ix} {iv,v,vii,x} {iv,v,vii,xi} {iv,v,viii,ix} {iv,v,viii,x} {iv,v,viii,xi} {iv,v,ix,x} {iv,v,ix,xi} {iv,v,x,xi} {iv,vi,vii,viii} {iv,vi,vii,ix} {iv,vi,vii,x} {iv,vi,vii,xi} {iv,vi,viii,ix} {iv,vi,viii,x} {iv,vi,viii,xi} {iv,vi,ix,x} {iv,vi,ix,xi} {iv,vi,x,xi} {iv,vii,viii,ix} {iv,vii,viii,x} {iv,vii,viii,xi} {iv,vii,ix,x} {iv,vii,ix,xi} {iv,vii,x,xi} {iv,viii,ix,x} {iv,viii,ix,xi} {iv,viii,x,xi} {iv,ix,x,xi} {v,vi,vii,viii} {v,vi,vii,ix} {v,vi,vii,x} {v,vi,vii,xi} {v,vi,viii,ix} {v,vi,viii,x} {v,vi,viii,xi} {v,vi,ix,x} {v,vi,ix,xi} {v,vi,x,xi} {v,vii,viii,ix} {v,vii,viii,x} {v,vii,viii,xi} {v,vii,ix,x} {v,vii,ix,xi} {v,vii,x,xi} {v,viii,ix,x} {v,viii,ix,xi} {v,viii,x,xi} {v,ix,x,xi} {vi,vii,viii,ix} {vi,vii,viii,x} {vi,vii,viii,xi} {vi,vii,ix,x} {vi,vii,ix,xi} {vi,vii,x,xi} {vi,viii,ix,x} {vi,viii,ix,xi} {vi,viii,x,xi} {vi,ix,x,xi} {vii,viii,ix,x} {vii,viii,ix,xi} {vii,viii,x,xi} {vii,ix,x,xi} {viii,ix,x,xi} {i,ii,iii,iv,v} {i,ii,iii,iv,vi} {i,ii,iii,iv,vii} {i,ii,iii,iv,viii} {i,ii,iii,iv,ix} {i,ii,iii,iv,x} {i,ii,iii,iv,xi} {i,ii,iii,v,vi} {i,ii,iii,v,vii} {i,ii,iii,v,viii} {i,ii,iii,v,ix} {i,ii,iii,v,x} {i,ii,iii,v,xi} {i,ii,iii,vi,vii} {i,ii,iii,vi,viii} {i,ii,iii,vi,ix} {i,ii,iii,vi,x} {i,ii,iii,vi,xi} {i,ii,iii,vii,viii} {i,ii,iii,vii,ix} {i,ii,iii,vii,x} {i,ii,iii,vii,xi} {i,ii,iii,viii,ix} {i,ii,iii,viii,x} {i,ii,ui,viii,xi} {i,ii,iii,ix,x} {i,ii,iii,ix,xi} {i,ii,iii,x,xi} {i,ii,iv,v,vi} {i,ii,iv,v,vii} {i,ii,iv,v,viii} {i,ii,iv,v,ix} {i,ii,iv,v,x} {i,ii,iv,v,xi} {i,ii,iv,vi,vii} {i,ii,iv,vi,viii} {i,ii,iv,vi,ix} {i,ii,iv,vi,x} {i,ii,iv,vi,xi} {i,ii,iv,vii,viii} {i,ii,iv,vii,ix} {i,ii,iv,vii,x} {i,ii,iv,vii,xi} {i,ii,iv,viii,ix} {i,ii,iv,viii,x} {i,ii,iv,viii,xi} {i,ii,iv,ix,x} {i,ii,iv,ix,xi} {i,ii,iv,x,xi} {i,ii,v,vi,vii} {i,ii,v,vi,viii} {i,ii,v,vi,ix} {i,ii,v,vi,x} {i,ii,v,vi,xi} {i,ii,v,vii,viii} {i,ii,v,vii,ix} {i,ii,v,vii,x} {i,ii,v,vii,xi} {i,ii,v,viii,ix} {i,ii,v,viii,x} {i,ii,v,viii,xi} {i,ii,v,ix,x} {i,ii,v,ix,xi} {i,ii,v,x,xi} {i,ii,vi,vii,viii} {i,ii,vi,vii,ix} {i,ii,vi,vii,x} {i,ii,vi,vii,xi} {i,ii,vi,viii,ix} {i,ii,vi,viii,x} {i,ii,vi,viii,xi} {i,ii,vi,ix,x} {i,ii,vi,ix,xi} {i,ii,vi,x,xi} {i,ii,vii,viii,ix} {i,ii,vii,viii,x} {i,ii,vii,viii,xi} {i,ii,vii,ix,x} {i,ii,vii,ix,xi} {i,ii,vii,x,xi} {i,ii,viii,ix,x} {i,ii,viii,ix,xi} {i,ii,viii,x,xi} {i,ii,ix,x,xi} {i,iii,iv,v,vi} {i,iii,iv,v,vii} {i,iii,iv,v,viii} {i,iii,iv,v,ix} {i,iii,iv,v,x} {i,iii,iv,v,xi} {i,iii,iv,vi,vii} {i,iii,iv,vi,viii} {i,iii,iv,vi,ix} {i,iii,iv,vi,x} {i,iii,iv,vi,xi} {i,iii,iv,vii,viii} {i,iii,iv,vii,ix} {i,iii,iv,vii,x} {i,iii,iv,vii,xi} {i,iii,iv,viii,ix} {i,iii,iv,viii,x} {i,iii,iv,viii,xi} {i,iii,iv,ix,x} {i,iii,iv,ix,xi} {i,iii,iv,x,xi} {i,iii,v,vi,vii} {i,iii,v,vi,viii} {i,iii,v,vi,ix} {i,iii,v,vi,x} {i,iii,v,vi,xi} {i,iii,v,vii,viii} {i,iii,v,vii,ix} {i,iii,v,vii,x} {i,iii,v,vii,xi} {i,iii,v,viii,ix} {i,iii,v,viii,x} {i,iii,v,viii,xi} {i,iii,v,ix,x} {i,iii,v,ix,xi} {i,iii,v,x,xi} {i,iii,vi,vii,viii} {i,iii,vi,vii,ix} {i,iii,vi,vii,x} {i,iii,vi,vii,xi} {i,iii,vi,viii,ix} {i,iii,vi,viii,x} {i,iii,vi,viii,xi} {i,iii,vi,ix,x} {i,iii,vi,ix,xi} {i,iii,vi,x,xi} {i,iii,vii,viii,ix} {i,iii,vii,viii,x} {i,iii,vii,viii,xi} {i,iii,vii,ix,x} {i,iii,vii,ix,xi} {i,iii,vii,x,xi} {i,iii,viii,ix,x} {i,iii,viii,ix,xi} {i,iii,viii,x,xi} {i,iii,ix,x,xi} {i,iv,v,vi,vii} {i,iv,v,vi,viii} {i,iv,v,vi,ix} {i,iv,v,vi,x} {i,iv,v,vi,xi} {i,iv,v,vii,viii} {i,iv,v,vii,ix} {i,iv,v,vii,x} {i,iv,v,vii,xi} {i,iv,v,viii,ix} {i,iv,v,viii,x} {i,iv,v,viii,xi} {i,iv,v,ix,x} {i,iv,v,ix,xi} {i,iv,v,x,xi} {i,iv,vi,vii,viii} {i,iv,vi,vii,ix} {i,iv,vi,vii,x} {i,iv,vi,vii,xi} {i,iv,vi,viii,ix} {i,iv,vi,viii,x} {i,iv,vi,viii,xi} {i,iv,vi,ix,x} {i,iv,vi,ix,xi} {i,iv,vi,x,xi} {i,iv,vii,viii,ix} {i,iv,vii,viii,x} {i,iv,vii,viii,xi} {i,iv,vii,ix,x} {i,iv,vii,ix,xi} {i,iv,vii,x,xi} {i,iv,viii,ix,x} {i,iv,viii,ix,xi} {i,iv,viii,x,xi} {i,iv,ix,x,xi} {i,v,vi,vii,viii} {i,v,vi,vii,ix} {i,v,vi,vii,x} {i,v,vi,vii,xi} {i,v,vi,viii,ix} {i,v,vi,viii,x} {i,v,vi,viii,xi} {i,v,vi,ix,x} {i,v,vi,ix,xi} {i,v,vi,x,xi} {i,v,vii,viii,ix} {i,v,vii,viii,x} {i,v,vii,viii,xi} {i,v,vii,ix,x} {i,v,vii,ix,xi} {i,v,vii,x,xi} {i,v,viii,ix,x} {i,v,viii,ix,xi} {i,v,viii,x,xi} {i,v,ix,x,xi} {i,vi,vii,viii,ix} {i,vi,vii,viii,x} {i,vi,vii,viii,xi} {i,vi,vii,ix,x} {i,vi,vii,ix,xi} {i,vi,vii,x,xi} {i,vi,viii,ix,x} {i,vi,viii,ix,xi} {i,vi,viii,x,xi} {i,vi,ix,x,xi} {i,vii,viii,ix,x} {i,vii,viii,ix,xi} {i,vii,viii,x,xi} {i,vii,ix,x,xi} {i,viii,ix,x,xi} {ii,iii,iv,v,vi} {ii,iii,iv,v,vii} {ii,iii,iv,v,viii} {ii,iii,iv,v,ix} {ii,iii,iv,v,x} {ii,iii,iv,v,xi} {ii,iii,iv,vi,vii} {ii,iii,iv,vi,viii} {ii,iii,iv,vi,ix} {ii,iii,iv,vi,x} {ii,iii,iv,vi,xi} {ii,iii,iv,vii,viii} {ii,iii,iv,vii,ix} {ii,iii,iv,vii,x} {ii,iii,iv,vii,xi} {ii,iii,iv,viii,ix} {ii,iii,iv,viii,x} {ii,iii,iv,viii,xi} {ii,iii,iv,ix,x} {ii,iii,iv,ix,xi} {ii,iii,iv,x,xi} {ii,iii,v,vi,vii} {ii,iii,v,vi,viii} {ii,iii,v,vi,ix} {ii,iii,v,vi,x} {ii,iii,v,vi,xi} {ii,iii,v,vii,viii} {ii,iii,v,vii,ix} {ii,iii,v,vii,x} {ii,iii,v,vii,xi} {ii,iii,v,viii,ix} {ii,iii,v,viii,x} {ii,iii,v,viii,xi} {ii,iii,v,ix,x} {ii,iii,v,ix,xi} {ii,iii,v,x,xi} {ii,iii,vi,vii,viii} {ii,iii,vi,vii,ix} {ii,iii,vi,vii,x} {ii,iii,vi,vii,xi} {ii,iii,vi,viii,ix} {ii,iii,vi,viii,x} {ii,iii,vi,viii,xi} {ii,iii,vi,ix,x} {ii,iii,vi,ix,xi} {ii,iii,vi,x,xi} {ii,iii,vii,viii,ix} {ii,iii,vii,viii,x} {ii,iii,vii,viii,xi} {ii,iii,vii,ix,x} {ii,iii,vii,ix,xi} {ii,iii,vii,x,xi} {ii,iii,viii,ix,x} {ii,iii,viii,ix,xi} {ii,iii,viii,x,xi} {ii,iii,ix,x,xi} {ii,iv,v,vi,vii} {ii,iv,v,vi,viii} {ii,iv,v,vi,ix} {ii,iv,v,vi,x} {ii,iv,v,vi,xi} {ii,iv,v,vii,viii} {ii,iv,v,vii,ix} {ii, iv,v,vii,x} {ii,iv,v,vii,xi} {ii,iv,v,viii,ix} {ii,iv,v,viii,x} {ii,iv,v,viii,xi} {ii,iv,v,ix,x} {ii,iv,v,ix,xi} {ii,iv,v,x,xi} {ii,iv,vi,vii,viii} {ii,iv,vi,vii,ix} {ii,iv,vi,vii,x} {ii,iv,vi,vii,xi} {ii,iv,vi,viii,ix} {ii,iv,vi,viii,x} {ii,iv,vi,viii,xi} {ii,iv,vi,ix,x} {ii,iv,vi,ix,xi} {ii,iv,vi,x,xi} {ii,iv,vii,viii,ix} {ii,iv,vii,viii,x} {ii,iv,vii,viii,xi} {ii,iv,vii,ix,x} {ii,iv,vii,ix,xi} {ii,iv,vii,x,xi} {ii,iv,viii,ix,x} {ii,iv,viii,ix,xi} {ii,iv,viii,x,xi} {ii,iv,ix,x,xi} {ii,v,vi,vii,viii} {ii,v,vi,vii,ix} {ii,v,vi,vii,x} {ii,v,vi,vii,xi} {ii,v,vi,viii,ix} {ii,v,vi,viii,x} {ii,v,vi,viii,xi} {ii,v,vi,ix,x} {ii,v,vi,ix,xi} {ii,v,vi,x,xi} {ii,v,vii,viii,ix} {ii,v,vii,viii,x} {ii,v,vii,viii,xi} {ii,v,vii,ix,x} {ii,v,vii,ix,xi} {ii,v,vii,x,xi} {ii,v,viii,ix,x} {ii,v,viii,ix,xi} {ii,v,viii,x,xi} {ii,v,ix,x,xi} {ii,vi,vii,viii,ix} {ii,vi,vii,viii,x} {ii,vi,vii,viii,xi} {ii,vi,vii,ix,x} {ii,vi,vii,ix,xi} {ii,vi,vii,x,xi} {ii,vi,viii,ix,x} {ii,vi,viii,ix,xi} {ii,vi,viii,x,xi} {ii,vi,ix,x,xi} {ii,vii,viii,ix,x} {ii,vii,viii,ix,xi} {ii,vii,viii,x,xi} {ii,vii,ix,x,xi} {ii,viii,ix,x,xi} {iii,iv,v,vi,vii} {iii,iv,v,vi,viii} {iii,iv,v,vi,ix} {iii,iv,v,vi,x} {iii,iv,v,vi,xi} {iii,iv,v,vii,viii} {iii,iv,v,vii,ix} {iii,iv,v,vii,x} {iii,iv,v,vii,xi} {iii,iv,v,viii,ix} {iii,iv,v,viii,x} {iii,iv,v,viii,xi} {iii,iv,v,ix,x} {iii,iv,v,ix,xi} {iii,iv,v,x,xi} {iii,iv,vi,vii,viii} {iii,iv,vi,vii,ix} {iii,iv,vi,vii,x} {iii,iv,vi,vii,xi} {iii,iv,vi,viii,ix} {iii,iv,vi,viii,x} {iii,iv,vi,viii,xi} {iii,iv,vi,ix,x} {iii,iv,vi,ix,xi} {iii,iv,vi,x,xi} {iii,iv,vii,viii,ix} {iii,iv,vii,viii,x} {iii,iv,vii,viii,xi} {iii,iv,vii,ix,x} {iii,iv,vii,ix,xi} {iii,iv,vii,x,xi} {iii,iv,viii,ix,x} {iii,iv,viii,ix,xi} {iii,iv,viii,x,xi} {iii,iv,ix,x,xi} {iii,v,vi,vii,viii} {iii,v,vi,vii,ix} {iii,v,vi,vii,x} {iii,v,vi,vii,xi} {iii,v,vi,viii,ix} {iii,v,vi,viii,x} {iii,v,vi,viii,xi} {iii,v,vi,ix,x} {iii,v,vi,ix,xi} {iii,v,vi,x,xi} {iii,v,vii,viii,ix} {iii,v,vii,viii,x} {iii,v,vii,viii,xi} {iii,v,vii,ix,x} {iii,v,vii,ix,xi} {iii,v,vii,x,xi} {iii,v,viii,ix,x} {iii,v,viii,ix,xi} {iii,v,viii,x,xi} {iii,v,ix,x,xi} {iii,vi,vii,viii,ix} {iii,vi,vii,viii,x} {iii,vi,vii,viii,xi} {iii,vi,vii,ix,x} {iii,vi,vii,ix,xi} {iii,vi,vii,x,xi} {iii,vi,viii,ix,x} {iii,vi,viii,ix,xi} {iii,vi,viii,x,xi} {iii,vi,ix,x,xi} {iii,vii,viii,ix,x} {iii,vii,viii,ix,xi} {iii,vii,viii,x,xi} {iii,vii,ix,x,xi} {iii,viii,ix,x,xi} {iv,v,vi,vii,viii} {iv,v,vi,vii,ix} {iv,v,vi,vii,x} {iv,v,vi,vii,xi} {iv,v,vi,viii,ix} {iv,v,vi,viii,x} {iv,v,vi,viii,xi} {iv,v,vi,ix,x} {iv,v,vi,ix,xi} {iv,v,vi,x,xi} {iv,v,vii,viii,ix} {iv,v,vii,viii,x} {iv,v,vii,viii,xi} {iv,v,vii,ix,x} {iv,v,vii,ix,xi} {iv,v,vii,x,xi} {iv,v,viii,ix,x} {iv,v,viii,ix,xi} {iv,v,viii,x,xi} {iv,v,ix,x,xi} {iv,vi,vii,viii,ix} {iv,vi,vii,viii,x} {iv,vi,vii,viii,xi} {iv,vi,vii,ix,x} {iv,vi,vii,ix,xi} {iv,vi,vii,x,xi} {iv,vi,viii,ix,x} {iv,vi,viii,ix,xi} {iv,vi,viii,x,xi} {iv,vi,ix,x,xi} {iv,vii,viii,ix,x} {iv,vii,viii,ix,xi} {iv,vii,viii,x,xi} {iv,vii,ix,x,xi} {iv,viii,ix,x,xi} {v,vi,vii,viii,ix} {v,vi,vii,viii,x} {v,vi,vii,viii,xi} {v,vi,vii,ix,x} {v,vi,vii,ix,xi} {v,vi,vii,x,xi} {v,vi,viii,ix,x} {v,vi,viii,ix,xi} {v,vi,viii,x,xi} {v,vi,ix,x,xi} {v,vii,viii,ix,x} {v,vii,viii,ix,xi} {v,vii,viii,x,xi} {v,vii,ix,x,xi} {v,viii,ix,x,xi} {vi,vii,viii,ix,x} {vi,vii,viii,ix,xi} {vi,vii,viii,x,xi} {vi,vii,ix,x,xi} {vi,viii,ix,x,xi} {vii,viii,ix,x,xi} {i,ii,iii,iv,v,vi} {i,ii,iii,iv,v,vii} {i,ii,iii,iv,v,viii} {i,ii,iii,iv,v,ix} {i,ii,iii,iv,v,x} {i,ii,iii,iv,v,xi} {i,ii,iii,iv,vi,vii} {i,ii,iii,iv,vi,viii} {i,ii,iii,iv,vi,ix} {i,ii,iii,iv,vi,x} {i,ii,iii,iv,vi,xi} {i,ii,iii,iv,vii,viii} {i,ii,iii,iv,vii,ix} {i,ii,iii,iv,vii,x} {i,ii,iii,iv,vii,xi} {i,ii,iii,iv,viii,ix} {i,ii,iii,iv,viii,x} {i,ii,iii,iv,viii,xi} {i,ii,iii,iv,ix,x} {i,ii,iii,iv,ix,xi} {i,ii,iii,iv,x,xi} {i,ii,iii,v,vi,vii} {i,ii,iii,v,vi,viii} {i,ii,iii,v,vi,ix} {i,ii,iii,v,vi,x} {i,ii,iii,v,vi,xi} {i,ii,iii,v,vii,viii} {i,ii,iii,v,vii,ix} {i,ii,iii,v,vii,x} {i,ii,iii,v,vii,xi} {i,ii,iii,v,viii,ix} {i,ii,iii,v,viii,x} {i,ii,iii,v,viii,xi} {i,ii,iii,v,ix,x} {i,ii,iii,v,ix,xi} {i,ii,iii,v,x,xi} {i,ii,iii,vi,vii,viii} {i,ii,iii,vi,vii,ix} {i,ii,iii,vi,vii,x} {i,ii,iii,vi,vii,xi} {i,ii,iii,vi,viii,ix} {i,ii,iii,vi,viii,x} {i,ii,iii,vi,viii,xi} {i,ii,iii,vi,ix,x} {i,ii,iii,vi,ix,xi} {i,ii,iii,vi,x,xi} {i,ii,iii,vii,viii,ix} {i,ii,iii,vii,viii,x} {i,ii,iii,vii,viii,xi} {i,ii,iii,vii,ix,x} {i,ii,iii,vii,ix,xi} {i,ii,iii,vii,x,xi} {i,ii,iii,viii,ix,x} {i,ii,iii,viii,ix,xi} {i,ii,iii,viii,x,xi} {i,ii,iii,ix,x,xi} {i,ii,iv,v,vi,vii} {i,ii,iv,v,vi,viii} {i,ii,iv,v,vi,ix} {i,ii,iv,v,vi,x} {i,ii,iv,v,vi,xi} {i,ii,iv,v,vii,viii} {i,ii,iv,v,vii,ix} {i,ii,iv,v,vii,x} {i,ii,iv,v,vii,xi} {i,ii,iv,v,viii,ix} {i,ii,iv,v,viii,x} {i,ii,iv,v,viii,xi} {i,ii,iv,v,ix,x} {i,ii,iv,v,ix,xi} {i,ii,iv,v,x,xi} {i,ii,iv,vi,vii,viii} {i,ii,iv,vi,vii,ix} {i,ii,iv,vi,vii,x} {i,ii,iv,vi,vii,xi} {i,ii,iv,vi,viii,ix} {i,ii,iv,vi,viii,x} {i,ii,iv,vi,viii,xi} {i,ii,iv,vi,ix,x} {i,ii,iv,vi,ix,xi} {i,ii,iv,vi,x,xi} {i,ii,iv,vii,viii,ix} {i,ii,iv,vii,viii,x} {i,ii,iv,vii,viii,xi} {i,ii,iv,vii,ix,x} {i,ii,iv,vii,ix,xi} {i,ii,iv,vii,x,xi} {i,ii,iv,viii,ix,x} {i,ii,iv,viii,ix,xi} {i,ii,iv,viii,x,xi} {i,ii,iv,ix,x,xi} {i,ii,v,vi,vii,viii} {i,ii,v,vi,vii,ix} {i,ii,v,vi,vii,x} {i,ii,v,vi,vii,xi} {i,ii,v,vi,viii,ix} {i,ii,v,vi,viii,x} {i,ii,v,vi,viii,xi} {i,ii,v,vi,ix,x} {i,ii,v,vi,ix,xi} {i,ii,v,vi,x,xi} {i,ii,v,vii,viii,ix} {i,ii,v,vii,viii,x} {i,ii,v,vii,viii,xi} {i,ii,v,vii,ix,x} {i,ii,v,vii,ix,xi} {i,ii,v,vii,x,xi} {i,ii,v,viii,ix,x} {i,ii,v,viii,ix,xi} {i,ii,v,viii,x,xi} {i,ii,v,ix,x,xi} {i,ii,vi,vii,viii,ix} {i,ii,vi,vii,viii,x} {i,ii,vi,vii,viii,xi} {i,ii,vi,vii,ix,x} {i,ii,vi,vii,ix,xi} {i,ii,vi,vii,x,xi} {i,ii,vi,viii,ix,x} {i,ii,vi,viii,ix,xi} {i,ii,vi,viii,x,xi} {i,ii,vi,ix,x,xi} {i,ii,vii,viii,ix,x} {i,ii,vii,viii,ix,xi} {i,ii,vii,viii,x,xi} {i,ii,vii,ix,x,xi} {i,ii,viii,ix,x,xi} {i,iii,iv,v,vi,vii} {i,iii,iv,v,vi,viii} {i,iii,iv,v,vi,ix} {i,iii,iv,v,vi,x} {i,iii,iv,v,vi,xi} {i,iii,iv,v,vii,viii} {i,iii,iv,v,vii,ix} {i,iii,iv,v,vii,x} {i,iii,iv,v,vii,xi} {i,iii,iv,v,viii,ix} {i,iii,iv,v,viii,x} {i,iii,iv,v,viii,xi} {i,iii,iv,v,ix,x} {i,iii,iv,v,ix,xi} {i,iii,iv,v,x,xi} {i,iii,iv,vi,vii,viii} {i,iii,iv,vi,vii,ix} {i,iii,iv,vi,vii,x} {i,iii,iv,vi,vii,xi} {i,iii,iv,vi,viii,ix} {i,iii,iv,vi,viii,x} {i,iii,iv,vi,viii,xi} {i,iii,iv,vi,ix,x} {i,iii,iv,vi,ix,xi} {i,iii,iv,vi,x,xi} {i,iii,iv,vii,viii,ix} {i,iii,iv,vii,viii,x} {i,iii,iv,vii,viii,xi} {i,iii,iv,vii,ix,x} {i,iii,iv,vii,ix,xi} {i,iii,iv,vii,x,xi} {i,iii,iv,viii,ix,x} {i,iii,iv,viii,ix,xi} {i,iii,iv,viii,x,xi} {i,iii,iv,ix,x,xi} {i,iii,v,vi,vii,viii} {i,iii,v,vi,vii,ix} {i,iii,v,vi,vii,x} {i,iii,v,vi,vii,xi} {i,iii,v,vi,viii,ix} {i,iii,v,vi,viii,x} {i,iii,v,vi,viii,xi} {i,iii,v,vi,ix,x} {i,iii,v,vi,ix,xi} {i,iii,v,vi,x,xi} {i,iii,v,vii,viii,ix} {i,iii,v,vii,viii,x} {i,iii,v,vii,viii,xi} {i,iii,v,vii,ix,x} {i,iii,v,vii,ix,xi} {i,iii,v,vii,x,xi} {i,iii,v,viii,ix,x} {i,iii,v,viii,ix,xi} {i,iii,v,viii,x,xi} {i,iii,v,ix,x,xi} {i,iii,vi,vii,viii,ix} {i,iii,vi,vii,viii,x} {i,iii,vi,vii,viii,xi} {i,iii,vi,vii,ix,x} {i,iii,vi,vii,ix,xi} {i,iii,vi,vii,x,xi} {i,iii,vi,viii,ix,x} {i,iii,vi,viii,ix,xi} {i,iii,vi,viii,x,xi} {i,iii,vi,ix,x,xi} {i,iii,vii,viii,ix,x} {i,iii,vii,viii,ix,xi} {i,iii,vii,viii,x,xi} {i,iii,vii,ix,x,xi} {i,iii,viii,ix,x,xi} {i,iv,v,vi,vii,viii} {i,iv,v,vi,vii,ix} {i,iv,v,vi,vii,x} {i,iv,v,vi,vii,xi} {i,iv,v,vi,viii,ix} {i,iv,v,vi,viii,x} {i,iv,v,vi,viii,xi} {i,iv,v,vi,ix,x} {i,iv,v,vi,ix,xi} {i,iv,v,vi,x,xi} {i,iv,v,vii,viii,ix} {i,iv,v,vii,viii,x} {i,iv,v,vii,viii,xi} {i,iv,v,vii,ix,x} {i,iv,v,vii,ix,xi} {i,iv,v,vii,x,xi} {i,iv,v,viii,ix,x} {i,iv,v,viii,ix,xi} {i,iv,v,viii,x,xi} {i,iv,v,ix,x,xi} {i,iv,vi,vii,viii,ix} {i,iv,vi,vii,viii,x} {i,iv,vi,vii,viii,xi} {i,iv,vi,vii,ix,x} {i,iv,vi,vii,ix,xi} {i,iv,vi,vii,x,xi} {i,iv,vi,viii,ix,x} {i,iv,vi,viii,ix,xi} {i,iv,vi,viii,x,xi} {i,iv,vi,ix,x,xi} {i,iv,vii,viii,ix,x} {i,iv,vii,viii,ix,xi} {i,iv,vii,viii,x,xi} {i,iv,vii,ix,x,xi} {i,iv,viii,ix,x,xi} {i,v,vi,vii,viii,ix} {i,v,vi,vii,viii,x} {i,v,vi,vii,viii,xi} {i,v,vi,vii,ix,x} {i,v,vi,vii,ix,xi} {i,v,vi,vii,x,xi} {i,v,vi,viii,ix,x} {i,v,vi,viii,ix,xi} {i,v,vi,viii,x,xi} {i,v,vi,ix,x,xi} {i,v,vii,viii,ix,x} {i,v,vii,viii,ix,xi} {i,v,vii,viii,x,xi} {i,v,vii,ix,x,xi} {i,v,viii,ix,x,xi} {i,vi,vii,viii,ix,x} {i,vi,vii,viii,ix,xi} {i,vi,vii,viii,x,xi} {i,vi,vii,ix,x,xi} {i,vi,viii,ix,x,xi} {i,vii,viii,ix,x,xi} {ii,iii,iv,v,vi,vii} {ii,iii,iv,v,vi,viii} {ii,iii,iv,v,vi,ix} {ii,iii,iv,v,vi,x} {ii,iii,iv,v,vi,xi} {ii,iii,iv,v,vii,viii} {ii,iii,iv,v,vii,ix} {ii,iii,iv,v,vii,x} {ii,iii,iv,v,vii,xi} {ii,iii,iv,v,viii,ix} {ii,iii,iv,v,viii,x} {ii,iii,iv,v,viii,xi} {ii,iii,iv,v,ix,x} {ii,iii,iv,v,ix,xi} {ii,iii,iv,v,x,xi} {ii,iii,iv,vi,vii,viii} {ii,iii,iv,vi,vii,ix} {ii,iii,iv,vi,vii,x} {ii,iii,iv,vi,vii,xi} {ii,iii,iv,vi,viii,ix} {ii,iii,iv,vi,viii,x} {ii,iii,iv,vi,viii,xi} {ii,iii,iv,vi,ix,x} {ii,iii,iv,vi,ix,xi} {ii,iii,iv,vi,x,xi} {ii,iii,iv,vii,viii,ix} {ii,iii,iv,vii,viii,x} {ii,iii,iv,vii,viii,xi} {ii,iii,iv,vii,ix,x} {ii,iii,iv,vii,ix,xi} {ii,iii,iv,vii,x,xi} {ii,iii,iv,viii,ix,x} {ii,iii,iv,viii,ix,xi} {ii,iii,iv,viii,x,xi} {ii,iii,iv,ix,x,xi} {ii,iii,v,vi,vii,viii} {ii,iii,v,vi,vii,ix} {ii,iii,v,vi,vii,x} {ii,iii,v,vi,vii,xi} {ii,iii,v,vi,viii,ix} {ii,iii,v,vi,viii,x} {ii,iii,v,vi,viii,xi} {ii,iii,v,vi,ix,x} {ii,iii,v,vi,ix,xi} {ii,iii,v,vi,x,xi} {ii,iii,v,vii,viii,ix}

{ii,iii,v,vii,viii,x} {ii,iii,v,vii,viii,xi} {ii,iii,v,vii,ix,x} {ii,iii,v,vii,ix,xi} {ii,iii,v,vii,x,xi} {ii,iii,v,viii,ix,x} {ii,iii,v,viii,ix,xi} {ii,iii,v,viii,x,xi} {ii,iii,v,ix,x,xi} {ii,iii,vi,vii,ix,x} {ii,iii,vi,vii,ix,xi} {ii,iii,vi,vii,viii,ix} {ii,iii,vi,vii,viii,x} {ii,iii,vi,vii,viii,xi} {ii,iii,vi,vii,x,xi} {ii,iii,vi,viii,ix,x} {ii,iii,vi,viii,ix,xi} {ii,iii,vi,viii,x,xi} {ii,iii,vi,ix,x,xi} {ii,iii,vii,viii,ix,x} {ii,iii,vii,viii,ix,xi} {ii,iii,vii,viii,x,xi} {ii,iii,vii,ix,x,xi} {ii,iii,viii,ix,x,xi} {ii,iv,v,vi,vii,viii} {ii,iv,v,vi,vii,ix} {ii,iv,v,vi,vii,x} {ii,iv,v,vi,vii,xi} {ii,iv,v,vi,viii,ix} {ii,iv,v,vi,viii,x} {ii,iv,v,vi,viii,xi} {ii,iv,v,vi,ix,x} {ii,iv,v,vi,ix,xi} {ii,iv,v,vi,x,xi} {ii,iv,v,vii,viii,ix} {ii,iv,v,vii,viii,x} {ii,iv,v,vii,viii,xi} {ii,iv,v,vii,ix,x} {ii,iv,v,vii,ix,xi} {ii,iv,v,vii,x,xi} {ii,iv,v,viii,ix,x} {ii,iv,v,viii,ix,xi} {ii,iv,v,viii,x,xi} {ii,iv,v,ix,x,xi} {ii,iv,vi,vii,viii,ix} {ii,iv,vi,vii,viii,x} {ii,iv,vi,vii,viii,xi} {ii,iv,vi,vii,ix,x} {ii,iv,vi,vii,ix,xi} {ii,iv,vi,vii,x,xi} {ii,iv,vi,viii,ix,x} {ii,iv,vi,viii,ix,xi} {ii,iv,vi,viii,x,xi} {ii,iv,vi,ix,x,xi} {ii,iv,vii,viii,ix,x} {ii,iv,vii,viii,ix,xi} {ii,iv,vii,viii,x,xi} {ii,iv,vii,ix,x,xi} {ii,iv,viii,ix,x,xi} {ii,vi,vii,viii,ix} {ii,v,vi,vii,viii,x} {ii,v,vi,vii,viii,xi} {ii,v,vi,vii,ix,x} {ii,v,vi,vii,ix,xi} {ii,v,vi,vii,x,xi} {ii,v,vi,viii,ix,x} {ii,v,vi,viii,ix,xi} {ii,v,vi,viii,x,xi} {ii,v,vi,ix,x,xi} {ii,v,vii,viii,ix,x} {ii,v,vii,viii,ix,xi} {ii,v,vii,viii,x,xi} {ii,v,vii,ix,x,xi} {ii,v,viii,ix,x,xi} {ii,vi,vii,viii,ix,x} {ii,vi,vii,viii,ix,xi} {ii,vi,vii,viii,x,xi} {ii,vi,vii,ix,x,xi} {ii,vi,viii,ix,x,xi} {ii,vii,viii,ix,x,xi} {iii,iv,v,vi,vii,viii} {iii,iv,v,vi,vii,ix} {iii,iv,v,vi,vii,x} {iii,iv,v,vi,vii,xi} {iii,iv,v,vi,viii,ix} {iii,iv,v,vi,viii,x} {iii,iv,v,vi,viii,xi} {iii,iv,v,vi,ix,x} {iii,iv,v,vi,ix,xi} {iii,iv,v,vi,x,xi} {iii,iv,v,vii,viii,ix} {iii,iv,v,vii,viii,x} {iii,iv,v,vii,viii,xi} {iii,iv,v,vii,ix,x} {iii,iv,v,vii,ix,xi} {iii,iv,v,vii,x,xi} {iii,iv,v,viii,ix,x} {iii,iv,v,viii,ix,xi} {iii,iv,v,viii,x,xi} {iii,iv,v,ix,x,xi} {iii,iv,vi,vii,viii,ix} {iii,iv,vi,vii,viii,x} {iii,iv,vi,vii,viii,xi} {iii,iv,vi,vii,ix,x} {iii,iv,vi,vii,ix,xi} {iii,iv,vi,vii,x,xi} {iii,iv,vi,viii,ix,x} {iii,iv,vi,viii,ix,xi} {iii,iv,vi,viii,x,xi} {iii,iv,vi,ix,x,xi} {iii,iv,vii,viii,ix,x} {iii,iv,vii,viii,ix,xi} {iii,iv,vii,viii,x,xi} {iii,iv,vii,ix,x,xi} {iii,iv,viii,ix,x,xi} {iii,v,vi,vii,viii,ix} {iii,v,vi,vii,viii,x} {iii,v,vi,vii,viii,xi} {iii,v,vi,vii,ix,x} {iii,v,vi,vii,ix,xi} {iii,v,vi,vii,x,xi} {iii,v,vi,viii,ix,x} {iii,v,vi,viii,ix,xi} {iii,v,vi,viii,x,xi} {iii,v,vi,ix,x,xi} {iii,v,vii,viii,ix,x} {iii,v,vii,viii,ix,xi} {iii,v,vii,viii,x,xi} {iii,v,vii,ix,x,xi} {iii,v,viii,ix,x,xi} {iii,vi,vii,viii,ix,x} {iii,vi,vii,viii,ix,xi} {iii,vi,vii,viii,x,xi} {iii,vi,vii,ix,x,xi} {iii,vi,viii,ix,x,xi} {iii,vii,viii,ix,x,xi} {iv,v,vi,vii,viii,ix} {iv,v,vi,vii,viii,x} {iv,v,vi,vii,viii,xi} {iv,v,vi,vii,ix,x} {iv,v,vi,vii,ix,xi} {iv,v,vi,vii,x,xi} {iv,v,vi,viii,ix,x} {iv,v,vi,viii,ix,xi} {iv,v,vi,viii,x,xi} {iv,v,vi,ix,x,xi} {iv,v,vii,viii,ix,x} {iv,v,vii,viii,ix,xi} {iv,v,vii,viii,x,xi} {iv,v,vii,ix,x,xi} {iv,v,viii,ix,x,xi} {iv,vi,vii,viii,ix,x} {iv,vi,vii,viii,ix,xi} {iv,vi,vii,viii,x,xi} {iv,vi,vii,ix,x,xi} {iv,vi,viii,ix,x,xi} {iv,vii,viii,ix,x,xi} {v,vi,vii,viii,ix,x} {v,vi,vii,viii,ix,xi} {v,vi,vii,viii,x,xi} {v,vi,vii,ix,x,xi} {v,vi,viii,ix,x,xi} {v,vii,viii,ix,x,xi} {vi,vii,viii,ix,x,xi} {i,ii,iii,iv,v,vi,vii} {i,ii,iii,iv,v,vi,viii} {i,ii,iii,iv,v,vi,ix} {i,ii,iii,iv,v,vi,x} {i,ii,iii,iv,v,vi,xi} {i,ii,iii,iv,v,vii,viii} {i,ii,iii,iv,v,vii,ix} {i,ii,iii,iv,v,vii,x} {i,ii,iii,iv,v,vii,xi} {i,ii,iii,iv,v,viii,ix} {i,ii,iii,iv,v,viii,x} {i,ii,iii,iv,v,viii,xi} {i,ii,iii,iv,v,ix,x} {i,ii,iii,iv,v,ix,xi} {i,ii,iii,iv,v,x,xi} {i,ii,iii,iv,vi,vii,viii} {i,ii,iii,iv,vi,vii,ix} {i,ii,iii,iv,vi,vii,x} {i,ii,iii,iv,vi,vii,xi} {i,ii,iii,iv,vi,viii,ix} {i,ii,iii,iv,vi,viii,x} {i,ii,iii,iv,vi,viii,xi} {i,ii,iii,iv,vi,ix,x} {i,ii,iii,iv,vi,ix,xi} {i,ii,iii,iv,vi,x,xi} {i,ii,iii,iv,vii,viii,ix} {i,ii,iii,iv,vii,viii,x} {i,ii,iii,iv,vii,viii,xi} {i,ii,iii,iv,vii,ix,x} {i,ii,iii,iv,vii,ix,xi} {i,ii,iii,iv,vii,x,xi} {i,ii,iii,iv,viii,ix,x} {i,ii,iii,iv,viii,ix,xi} {i,ii,iii,iv,viii,x,xi} {i,ii,iii,iv,ix,x,xi} {i,ii,iv,v,vi,vii,viii} {i,ii,iv,v,vi,vii,ix} {i,ii,iv,v,vi,vii,x} {i,ii,iv,v,vi,vii,xi} {i,ii,iv,v,vi,viii,ix} {i,ii,iv,v,vi,viii,x} {i,ii,iv,v,vi,viii,xi} {i,ii,iv,v,vi,ix,x} {i,ii,iv,v,vi,ix,xi} {i,ii,iv,v,vi,x,xi} {i,ii,iv,v,vii,viii,ix} {i,ii,iv,v,vii,viii,x} {i,ii,iv,v,vii,viii,xi} {i,ii,iv,v,vii,ix,x} {i,ii,iv,v,vii,ix,xi} {i,ii,iv,v,vii,x,xi} {i,ii,iv,v,viii,ix,x} {i,ii,iv,v,viii,ix,xi} {i,ii,iv,v,viii,x,xi} {i,ii,iv,v,ix,x,xi} {i,ii,iv,vi,vii,viii,ix} {i,ii,iv,vi,vii,viii,x} {i,ii,iv,vi,vii,viii,xi} {i,ii,iv,vi,vii,ix,x} {i,ii,iv,vi,vii,ix,xi} {i,ii,iv,vi,vii,x,xi} {i,ii,iv,vi,viii,ix,x} {i,ii,iv,vi,viii,ix,xi} {i,ii,iv,vi,viii,x,xi} {i,ii,iv,vi,ix,x,xi} {i,ii,iv,vii,viii,ix,x} {i,ii,iv,vii,viii,ix,xi} {i,ii,iv,vii,viii,x,xi} {i,ii,iv,vii,ix,x,xi} {i,ii,iv,viii,ix,x,xi} {i,ii,v,vi,vii,viii,ix} {i,ii,v,vi,vii,viii,x} {i,ii,v,vi,vii,viii,xi} {i,ii,v,vi,vii,ix,x} {i,ii,v,vi,vii,ix,xi} {i,ii,v,vi,vii,x,xi} {i,ii,v,vi,viii,ix,x} {i,ii,v,vi,viii,ix,xi} {i,ii,v,vi,viii,x,xi} {i,ii,v,vi,ix,x,xi} {i,ii,v,vii,viii,ix,x} {i,ii,v,vii,viii,ix,xi} {i,ii,v,vii,viii,x,xi} {i,ii,v,vii,ix,x,xi} {i,ii,v,viii,ix,x,xi} {i,ii,vi,vii,viii,ix,x} {i,ii,vi,vii,viii,ix,xi} {i,ii,vi,vii,viii,x,xi} {i,ii,vi,vii,ix,x,xi} {i,ii,vi,viii,ix,x,xi} {i,ii,vii,viii,ix,x,xi} {i,iii,iv,v,vi,vii,viii} {i,iii,iv,v,vi,vii,ix} {i,iii,iv,v,vi,vii,x} {i,iii,iv,v,vi,vii,xi} {i,iii,iv,v,vi,viii,ix} {i,iii,iv,v,vi,viii,x} {i,iii,iv,v,vi,viii,xi} {i,iii,iv,v,vi,ix,x} {i,iii,iv,v,vi,ix,xi} {i,iii,iv,v,vi,x,xi} {i,iii,iv,v,vii,viii,ix} {i,iii,iv,v,vii,viii,x} {i,iii,iv,v,vii,viii,xi} {i,iii,iv,v,vii,ix,x} {i,iii,iv,v,vii,ix,xi} {i,iii,iv,v,vii,x,xi} {i,iii,iv,v,viii,ix,x} {i,iii,iv,v,viii,ix,xi} {i,iii,iv,v,viii,x,xi} {i,iii,iv,v,ix,x,xi} {i,iii,iv,vi,vii,viii,ix} {i,iii,iv,vi,vii,viii,x} {i,iii,iv,vi,vii,viii,xi} {i,iii,iv,vi,vii,ix,x} {i,iii,iv,vi,vii,ix,xi} {i,iii,iv,vi,vii,x,xi} {i,iii,iv,vi,viii,ix,x} {i,iii,iv,vi,viii,ix,xi} {i,iii,iv,vi,viii,x,xi} {i,iii,iv,vi,ix,x,xi} {i,iii,iv,vii,viii,ix,x} {i,iii,iv,vii,viii,ix,xi} {i,iii,iv,vii,viii,x,xi} {i,iii,iv,vii,ix,x,xi} {i,iii,iv,viii,ix,x,xi} {i,iii,v,vi,vii,viii,ix} {i,iii,v,vi,vii,viii,x} {i,iii,v,vi,vii,viii,xi} {i,iii,v,vi,vii,ix,x} {i,iii,v,vi,vii,ix,xi} {i,iii,v,vi,vii,x,xi} {i,iii,v,vi,viii,ix,x} {i,iii,v,vi,viii,ix,xi} {i,iii,v,vi,viii,x,xi} {i,iii,v,vi,ix,x,xi} {i,iii,v,vii,viii,ix,x} {i,iii,v,vii,viii,ix,xi} {i,iii,v,vii,viii,x,xi} {i,iii,v,vii,ix,x,xi} {i,iii,v,viii,ix,x,xi} {i,iii,vi,vii,viii,ix,x} {i,iii,vi,vii,viii,ix,xi} {i,iii,vi,vii,viii,x,xi} {i,iii,vi,vii,ix,x,xi} {i,iii,vi,viii,ix,x,xi} {i,iii,vii,viii,ix,x,xi} {i,iv,v,vi,vii,viii,ix} {i,iv,v,vi,vii,viii,x} {i,iv,v,vi,vii,viii,xi} {i,iv,v,vi,vii,ix,x} {i,iv,v,vi,vii,ix,xi} {i,iv,v,vi,vii,x,xi} {i,iv,v,vi,viii,ix,x} {i,iv,v,vi,viii,ix,xi} {i,iv,v,vi,viii,x,xi} {i,iv,v,vi,ix,x,xi} {i,iv,v,vii,viii,ix,x} {i,iv,v,vii,viii,ix,xi} {i,iv,v,vii,viii,x,xi} {i,iv,v,vii,ix,x,xi} {i,iv,v,viii,ix,x,xi} {i,iv,vi,vii,viii,ix,x} {i,iv,vi,vii,viii,ix,xi} {i,iv,vi,vii,viii,x,xi} {i,iv,vi,vii,ix,x,xi} {i,iv,vi,viii,ix,x,xi} {i,iv,vii,viii,ix,x,xi} {i,v,vi,vii,viii,ix,x} {i,v,vi,vii,viii,ix,xi} {i,v,vi,vii,viii,x,xi} {i,v,vi,vii,ix,x,xi} {i,v,vi,viii,ix,x,xi} {i,v,vii,viii,ix,x,xi} {i,vi,vii,viii,ix,x,xi} {ii,iii,iv,v,vi,vii,viii} {ii,iii,iv,v,vi,vii,ix} {ii,iii,iv,v,vi,vii,x} {ii,iii,iv,v,vi,vii,xi} {ii,iii,iv,v,vi,viii,ix} {ii,iii,iv,v,vi,viii,x} {ii,iii,iv,v,vi,viii,xi} {ii,iii,iv,v,vi,ix,x} {ii,iii,iv,v,vi,ix,xi} {ii,iii,iv,v,vi,x,xi} {ii,iii,iv,v,vii,viii,ix} {ii,iii,iv,v,vii,viii,x} {ii,iii,iv,v,vii,viii,xi} {ii,iii,iv,v,vii,ix,x} {ii,iii,iv,v,vii,ix,xi} {ii,iii,iv,v,vii,x,xi} {ii,iii,iv,v,viii,ix,x} {ii,iii,iv,v,viii,ix,xi} {ii,iii,iv,v,viii,x,xi} {ii,iii,iv,v,ix,x,xi} {ii,iii,iv,vi,vii,viii,ix} {ii,iii,iv,vi,vii,viii,x} {ii,iii,iv,vi,vii,viii,xi} {ii,iii,iv,vi,vii,ix,x} {ii,iii,iv,vi,vii,ix,xi} {ii,iii,iv,vi,vii,x,xi} {ii,iii,iv,vi,viii,ix,x} {ii,iii,iv,vi,viii,ix,xi} {ii,iii,iv,vi,viii,x,xi} {ii,iii,iv,vi,ix,x,xi} {ii,iii,iv,vii,viii,ix,x} {ii,iii,iv,vii,viii,ix,xi} {ii,iii,iv,vii,viii,x,xi} {ii,iii,iv,vii,ix,x,xi} {ii,iii,iv,viii,ix,x,xi} {ii,iii,v,vi,vii,viii,ix} {ii,iii,v,vi,vii,viii,x} {ii,iii,v,vi,vii, viii,ix,x} {ii,iii,v,vii,viii,ix,xi} {ii,iii,v,vii,viii,x,xi} {ii,iii,v,vii,ix,x,xi} {ii,iii,v,viii,ix,x,xi} {ii,iii,vi,vii,viii,ix,x} {ii,iii,vi,vii,viii,ix,xi} {ii,iii,vi,vii,viii,x,xi} {ii,iii,vi,vii,ix,x,xi} {ii,iii,vi,viii,ix,x,xi} {ii,iii,vii,viii,ix,x,xi} {ii,iv,v,vi,vii,viii,ix} {ii,iv,v,vi,vii,viii,x} {ii,iv,v,vi,vii,viii,xi} {ii,iv,v,vi,vii,ix,x} {ii,iv,v,vi,vii,ix,xi} {ii,iv,v,vi,vii,x,xi} {ii,iv,v,vi,viii,ix,x} {ii,iv,v,vi,viii,ix,xi} {ii,iv,v,vi,viii,x,xi} {ii,iv,v,vi,ix,x,xi} {ii,iv,v,vii,viii,ix,x} {ii,iv,v,vii,viii,ix,xi} {ii,iv,v,vii,viii,x,xi} {ii,iv,v,vii,ix,x,xi} {ii,iv,v,viii,ix,x,xi} {ii,iv,vi,vii,viii,ix,x} {ii,iv,vi,vii,viii,ix,xi} {ii,iv,vi,vii,viii,x,xi} {ii,iv,vi,vii,ix,x,xi} {ii,iv,vi,viii,ix,x,xi} {ii,iv,vii,viii,ix,x,xi} {ii,v,vi,vii,viii,ix,x} {ii,v,vi,vii,viii,ix,xi} {ii,v,vi,vii,viii,x,xi} {ii,v,vi,vii,ix,x,xi} {ii,v,vi,viii,ix,x,xi} {ii,v,vii,viii,ix,x,xi} {ii,vi,vii,viii,ix,x,xi} {iii,iv,v,vi,vii,viii,ix} {iii,iv,v,vi,vii,viii,x} {iii,iv,v,vi,vii,viii,xi} {iii,iv,v,vi,vii,ix,x} {iii,iv,v,vi,vii,ix,xi} {iii,iv,v,vi,vii,x,xi} {iii,iv,v,vi,viii,ix,x} {iii,iv,v,vi,viii,ix,xi} {iii,iv,v,vi,viii,x,xi} {iii,iv,v,vi,ix,x,xi} {iii,iv,v,vii,viii,ix,x} {iii,iv,v,vii,viii,ix,xi} {iii,iv,v,vii,viii,x,xi} {iii,iv,v,vii,ix,x,xi} {iii,iv,v,viii,ix,x,xi} {iii,iv,vi,vii,viii,ix,x} {iii,iv,vi,vii,viii,ix,xi} {iii,iv,vi,vii,viii,x,xi} {iii,iv,vi,vii,ix,x,xi} {iii,iv,vi,viii,ix,x,xi} {iii,iv,vii,viii,ix,x,xi} {iii,v,vi,vii,viii,ix,x} {iii,v,vi,vii,viii,ix,xi} {iii,v,vi,vii,viii,x,xi} {iii,v,vi,vii,ix,x,xi} {iii,v,vi,viii,ix,x,xi} {iii,v,vii,viii,ix,x,xi} {iii,vi,vii,viii,ix,x,xi} {iv,v,vi,vii,viii,ix,x} {iv,v,vi,vii,viii,ix,xi} {iv,v,vi,vii,viii,x,xi} {iv,v,vi,vii,ix,x,xi} {iv,v,vi,viii,ix,x,xi} {iv,v,vii,viii,ix,x,xi} {iv,vi,vii,viii,ix,x,xi} {v,vi,vii,viii,ix,x,xi} {i,ii,iii,iv,v,vi,vii,viii} {i,ii,iii,iv,v,vi,vii,ix} {i,ii,iii,iv,v,vi,vii,x} {i,ii,iii,iv,v,vi,vii,xi} {i,ii,iii,iv,v,vi,viii,ix} {i,ii,iii,iv,v,vi,viii,x} {i,ii,iii,iv,v,vi,viii,xi} {i,ii,iii,iv,v,vi,ix,x} {i,ii,iii,iv,v,vi,ix,xi} {i,ii,ii,iv,v,vi,x,xi} {i,ii,ii,iv,v,vii,viii,ix} {i,ii,iii,iv,v,vii,viii,x} {i,ii,iii,iv,v,vii,viii,xi} {i,ii,ii,iv,v,vii,ix,x} {i,ii,iii,iv,v,vii,ix,xi} {i,ii,iii,iv,v,vii,x,xi} {i,ii,ii,iv,v,viii,ix,x} {i,ii,ii,iv,v,viii,ix,xi} {i,ii,iii,iv,v,viii,x,xi} {i,ii,iii,iv,v,ix,x,xi} {i,ii,iii,iv,vi,vii,viii,ix} {i,ii,iii,iv,vi,vii,viii,x} {i,ii,iii,iv,vi,vii,viii,xi} {i,ii,ii,iv,vi,vii,ix,x} {i,ii,ii,iv,vi,vii,ix,xi} {i,ii,iii,iv,vi,vii,x,xi} {i,ii,iii,iv,vi,viii,ix,x} {i,ii,ii,iv,vi,viii,ix,xi} {i,ii,ii,iv,vi,viii,x,xi} {i,ii,iii,iv,vi,ix,x,xi} {i,ii,ii,iv,vii,viii,ix,x} {i,ii,ii,iv,vii,viii,ix,xi} {i,ii,iii,iv,vii,viii,x,xi} {i,ii,ii,iv,vii,ix,x,xi} {i,ii,iii,iv,viii,ix,x,xi} {i,ii,iii,v,vi,vii,viii,ix} {i,ii,iii,v,vi,vii,viii,x} {i,ii,iii,v,vi,vii,viii,xi} {i,ii,iii,v,vi,vii,ix,x} {i,ii,iii,v,vi,vii,ix,xi} {i,ii,iii,v,vi,vii,x,xi} {i,ii,iii,v,vi,viii,ix,x} {i,ii,iii,v,vi,viii,ix,xi} {i,ii,iii,v,vi,viii,x,xi} {i,ii,iii,v,vi,ix,x,xi} {i,ii,iii,v,vii,viii,ix,x} {i,ii,iii,v,vii,viii,ix,xi} {i,ii,iii,v,vii,viii,x,xi} {i,ii,iii,v,vii,ix,x,xi} {i,ii,iii,v,viii,ix,x,xi} {i,ii,iii,vi,vii,viii,ix,x} {i,ii,iii,vi,vii,viii,ix,xi} {i,ii,iii,vi,vii,viii,x,xi} {i,ii,iii,vi,vii,ix,x,xi} {i,ii,iii,vi,viii,ix,x,xi} {i,ii,iii,vii,viii,ix,x,xi} {i,ii,iv,v,vi,vii,viii,ix} {i,ii,iv,v,vi,vii,viii,x} {i,ii,iv,v,vi,vii,viii,xi} {i,ii,iv,v,vi,vii,ix,x} {i,ii,iv,v,vi,vii,ix,xi} {i,ii,iv,v,vi,vii,x,xi} {i,ii,iv,v,vi,viii,ix,x} {i,ii,iv,v,vi,viii,ix,xi} {i,ii,iv,v,vi,viii,x,xi} {i,ii,iv,v,vi,ix,x,xi} {i,ii,iv,v,vii,viii,ix,x} {i,ii,iv,v,vii,viii,ix,xi} {i,ii,iv,v,vii,viii,x,xi} {i,ii,iv,v,vii,ix,x,xi} {i,ii,iv,v,viii,ix,x,xi} {i,ii,iv,vi,vii,viii,ix,x} {i,ii,iv,vi,vii,viii,ix,xi} {i,ii,iv,vi,vii,viii,x,xi} {i,ii,iv,vi,vii,ix,x,xi} {i,ii,iv,vi,viii,ix,x,xi} {i,ii,iv,vii,viii,ix,x,xi} {i,ii,v,vi,vii,viii,ix,x} {i,ii,v,vi,vii,viii,ix,xi} {i,ii,v,vi,vii,viii,x,xi} {i,ii,v,vi,vii,ix,x,xi} {i,ii,v,vi,viii,ix,x,xi} {i,ii,v,vii,viii,ix,x,xi} {i,ii,vi,vii,viii,ix,x,xi} {i,iii,iv,v,vi,vii,viii,ix} {i,iii,iv,v,vi,vii,viii,x} {i,iii,iv,v,vi,vii,viii,xi} {i,iii,iv,v,vi,vii,ix,x} {i,iii,iv,v,vi,vii,ix,xi} {i,iii,iv,v,vi,vii,x,xi} {i,iii,iv,v,vi,viii,ix,x} {i,iii,iv,v,vi,viii,ix,xi} {i,iii,iv,v,vi,viii,x,xi} {i,iii,iv,v,vi,ix,x,xi} {i,iii,iv,v,vii,viii,ix,x} {i,iii,iv,v,vii,viii,ix,xi} {i,iii,iv,v,vii,viii,x,xi} {i,iii,iv,v,vii,ix,x,xi} {i,iii,iv,v,viii,ix,x,xi} {i,iii,iv,vi,vii,viii,ix,x} {i,iii,iv,vi,vii,viii,ix,xi} {i,iii,iv,vi,vii,viii,x,xi} {i,iii,iv,vi,vii,ix,x,xi} {i,iii,iv,vi,viii,ix,x,xi} {i,iii,iv,vii,viii,ix,x,xi} {i,iii,v,vi,vii,viii,ix,x} {i,iii,v,vi,vii,viii,ix,xi} {i,iii,v,vi,vii,viii,x,xi} {i,iii,v,vi,vii,ix,x,xi} {i,iii,v,vi,viii,ix,x,xi} {i,iii,v,vii,viii,ix,x,xi} {i,iii,vi,vii,viii,ix,x,xi} {i,iv,v,vi,vii,viii,ix,x} {i,iv,v,vi,vii,viii,ix,xi} {i,iv,v,vi,vii,viii,x,xi} {i,iv,v,vi,vii,ix,x,xi} {i,iv,v,vi,viii,ix,x,xi} {i,iv,v,vii,viii,ix,x,xi} {i,iv,vi,vii,viii,ix,x,xi} {i,v,vi,vii,viii,ix,x,xi} {ii,iii,iv,v,vi,vii,viii,ix} {ii,iii,iv,v,vi,vii,viii,x} {ii,iii,iv,v,vi,vii,viii,xi} {ii,iii,iv,v,vi,vii,ix,x} {ii,iii,iv,v,vi,vii,ix,xi} {ii,iii,iv,v,vi,vii,x,xi} {ii,iii,iv,v,vi,viii,ix,x} {ii,iii,iv,v,vi,viii,ix,xi} {ii,iii,iv,v,vi,viii,x,xi} {ii,iii,iv,v,vi,ix,x,xi} {ii,iii,iv,v,vii,viii,ix,x} {ii,iii,iv,v,vii,viii,ix,xi} {ii,iii,iv,v,vii,viii,x,xi} {ii,iii,iv,v,vii,ix,x,xi} {ii,iii,iv,v,viii,ix,x,xi} {ii,iii,iv,vi,vii,viii,ix,x} {ii,iii,iv,vi,vii,viii,ix,xi} {ii,iii,iv,vi,vii,viii,x,xi} {ii,iii,iv,vi,vii,ix,x,xi} {ii,iii,iv,vi,viii,ix,x,xi} {ii,iii,iv,vii,viii,ix,x,xi} {ii,iii,v,vi,vii,viii,ix,x} {ii,iii,v,vi,vii,viii,ix,xi} {ii,iii,v,vi,vii,viii,x,xi} {ii,iii,v,vi,vii,ix,x,xi} {ii,iii,v,vi,viii,ix,x,xi} {ii,iii,v,vii,viii,ix,x,xi} {ii,iii,vi,vii,viii,ix,x,xi} {ii,iv,v,vi,vii,viii,ix,x} {ii,iv,v,vi,vii,viii,ix,xi} {ii,iv,v,vi,vii,viii,x,xi} {ii,iv,v,vi,vii,ix,x,xi} {ii,iv,v,vi,viii,ix,x,xi} {ii,iv,v,vii,viii,ix,x,xi} {ii,iv,vi,vii,viii,ix,x,xi} {ii,v,vi,vii,viii,ix,x,xi} {iii,iv,v,vi,vii,viii,ix,x} {iii,iv,v,vi,vii,viii,ix,xi} {iii,iv,v,vi,vii,viii,x,xi} {iii,iv,v,vi,vii,ix,x,xi} {iii,iv,v,vi,viii,ix,x,xi} {iii,iv,v,vii,viii,ix,x,xi} {iii,iv,vi,vii,viii,ix,x,xi} {iii,v,vi,vii,viii,ix,x,xi} {iv,v,vi,vii,viii,ix,x,xi} {i,ii,iii,iv,v,vi,vii,viii,ix} {i,ii,iii,iv,v,vi,vii,viii,x} {i,ii,iii,iv,v,vi,vii,viii,xi} {i,ii,iii,iv,v,vi,vii,ix,x} {i,ii,iii,iv,v,vi,vii,ix,xi} {i,ii,iii,iv,v,vi,vii,x,xi} {i,ii,iii,iv,v,vi,viii,ix,x} {i,ii,iii,iv,v,vi,viii,ix,xi} {i,ii,iii,iv,v,vi,viii,x,xi} {i,ii,iii,iv,v,vi,ix,x,xi} {i,ii,iii,iv,v,vii,viii,ix,x} {i,ii,iii,iv,v,vii,viii,ix,xi} {i,ii,iii,iv,v,vii,viii,x,xi} {i,ii,iii,iv,v,vii,ix,x,xi} {i,ii,iii,iv,v,viii,ix,x,xi} {i,ii,iii,iv,vi,vii,viii,ix,x} {i,ii,iii,iv,vi,vii,viii,ix,xi} {i,ii,iii,iv,vi,vii,viii,x,xi} {i,ii,iii,iv,vi,vii,ix,x,xi} {i,ii,iii,iv,vi,viii,ix,x,xi} {i,ii,iii,iv,vii,viii,ix,x,xi} {i,ii,iii,v,vi,vii,viii,ix,x} {i,ii,iii,v,vi,vii,viii,ix,xi} {i,ii,iii,v,vi,vii,viii,x,xi} {i,ii,iii,v,vi,vii,ix,x,xi} {i,ii,iii,v,vi,viii,ix,x,xi} {i,ii,iii,v,vii,viii,ix,x,xi} {i,ii,iii,vi,vii,viii,ix,x,xi} {i,ii,iv,v,vi,vii,viii,ix,x} {i,ii,iv,v,vi,vii,viii,ix,xi} {i,ii,iv,v,vi,vii,viii,x,xi} {i,ii,iv,v,vi,vii,ix,x,xi} {i,ii,iv,v,vi,viii,ix,x,xi} {i,ii,iv,v,vii,viii,ix,x,xi} {i,ii,iv,vi,vii,viii,ix,x,xi} {i,ii,v,vi,vii,viii,ix,x,xi} {i,iii,iv,v,vi,vii,viii,ix,x} {i,iii,iv,v,vi,vii,viii,ix,xi} {i,iii,iv,v,vi,vii,viii,x,xi} {i,iii,iv,v,vi,vii,ix,x,xi} {i,iii,iv,v,vi,viii,ix,x,xi} {i,iii,iv,v,vii,viii,ix,x,xi} {i,iii,iv,vi,vii,viii,ix,x,xi} {i,iii,v,vi,vii,viii,ix,x,xi} {i,iv,v,vi,vii,viii,ix,x,xi} {ii,iii,iv,v,vi,vii,viii,ix,x} {ii,iii,iv,v,vi,vii,viii,ix,xi} {ii,iii,iv,v,vi,vii,viii,x,xi} {ii,iii,iv,v,vi,vii,ix,x,xi} {ii,iii,iv,v,vi,viii,ix,x,xi} {ii,iii,iv,v,vii,viii,ix,x,xi} {ii,iii,iv,vi,vii,viii,ix,x,xi} {ii,iii,v,vi,vii,viii,ix,x,xi} {ii,iv,v,vi,vii,viii,ix,x,xi} {iii,iv,v,vi,vii,viii,ix,x,xi} {i,ii,iii,iv,v,vi,vii,viii,ix,x} {i,ii,iii,iv,v,vi,vii,viii,ix,xi} {i,ii,iii,iv,v,vi,vii,viii,x,xi} {i,ii,iii,iv,v,vi,vii,ix,x,xi} {i,ii,iii,iv,v,vi,viii,ix,x,xi} {i,ii,iii,iv,v,vii,viii,ix,x,xi} {i,ii,iii,iv,vi,vii,viii,ix,x,xi} {i,ii,iii,v,vi,vii,viii,ix,x,xi} {i,ii,iv,v,vi,vii,viii,ix,x,xi} {i,iii,iv,v,vi,vii,viii,ix,x,xi} {ii,iii,iv,v,vi,vii,viii,ix,x,xi} or {i,ii,iii,iv,v,vi,vii,viii,ix,x,xi}.

If the variant comprises any one of (i) and (iii) to (xi), it may further comprise a mutation at one or more of Y51, N55 and F56, such as at Y51, N55, F56, Y51/N55, Y51/F56, N55/F56 or Y51/N55/F56.

In (i), the variant may comprises mutations at any number and combination of N40, D43, E44, S54, S57, Q62, R97, E101, E124, E131, R142, T150 and R192. In (i), the variant preferably comprises one or more mutations at at the following positions (i.e. mutations at one or more of the following positions) N40, D43, E44, S54, S57, Q62, E101, E131 and T150. In (i), the variant preferably comprises one or more mutations at the following positions (i.e. mutations at one or more of the following positions) N40, D43, E44, E101 and E131. In (i), the variant preferably comprises a mutation at S54 and/or S57. In (i), the variant more preferably comprises a mutation at (a) S54 and/or S57 and (b) one or more of Y51, N55 and F56, such as at Y51, N55, F56, Y51/N55, Y51/F56, N55/F56 or Y51/N55/F56. If S54 and/or S57 are deleted in (xi), it/they cannot be mutated in (i) and vice versa. In (i), the variant preferably comprises a mutation at T150, such as T150I. Alternatively the variant preferably comprises a mutation at (a) T150 and (b) one or more of Y51, N55 and F56, such as at Y51, N55, F56, Y51/N55, Y51/F56, N55/F56 or Y51/N55/F56. In (i), the variant preferably comprises a mutation at Q62, such as Q62R or Q62K. Alternatively the variant preferably comprises a mutation at (a) Q62 and (b) one or more of Y51, N55 and F56, such as at Y51, N55, F56, Y51/N55, Y51/F56, N55/F56 or Y51/N55/F56. The variant may comprise a mutation at D43, E44, Q62 or any combination thereof, such as D43, E44, Q62, D43/E44, D43/Q62, E44/Q62 or D43/E44/Q62. Alternatively the variant preferably comprises a mutation at (a) D43, E44, Q62, D43/E44, D43/Q62, E44/Q62 or D43/E44/Q62 and (b) one or more of Y51, N55 and F56, such as at Y51, N55, F56, Y51/N55, Y51/F56, N55/F56 or Y51/N55/F56.

In (ii) and elsewhere in this application where different positions are separated by the / symbol, the/symbol means "and" such that Y51/N55 is Y51 and N55. In (ii), the variant preferably comprises mutations at Y51/N55. It has been proposed that the constriction in CsgG is composed of three stacked concentric rings formed by the side chains of residues Y51, N55 and F56 (Goyal et al, 2014, Nature, 516, 250-253). Mutation of these residues in (ii) may therefore decrease the number of nucleotides contributing to the current as the polynucleotide moves through the pore and thereby make it easier to identify a direct relationship between the observed current (as the polynucleotide moves through the pore) and the polynucleotide. F56 may be mutated in any of the ways discussed below with reference to variants and pores useful in the method of the invention.

In (v), the variant may comprise N102R, N102F, N102Y or N102W. The variant preferably comprises (a) N102R, N102F, N102Y or N102W and (b) a mutation at one or more of Y51, N55 and F56, such as at Y51, N55, F56, Y51/N55, Y51/F56, N55/F56 or Y51/N55/F56.

In (xi), any number and combination of K49, P50, Y51, P52, A53, S54, N55, F56 and S57 may be deleted. Preferably one or more of K49, P50, Y51, P52, A53, S54, N55 and S57 may be deleted. If any of Y51, N55 and F56 are deleted in (xi), it/they cannot be mutated in (ii) and vice versa.

In (i), the variant preferably comprises one of more of the following substitutions N40R, N40K, D43N, D43Q, D43R, D43K, E44N, E44Q, E44R, E44K, S54P, S57P, Q62R, Q62K, R97N, R97G, R97L, E101N, E101Q, E101R, E101K, E101F, E101Y, E101W, E124N, E124Q, E124R, E124K, E124F, E124Y, E124W, E131D, R142E, R142N, T150I, R192E and R192N, such as one or more of N40R, N40K, D43N, D43Q, D43R, D43K, E44N, E44Q, E44R, E44K, S54P, S57P, Q62R, Q62K, E101N, E101Q, E101R, E101K, E101F, E101Y, E101W, E131D and T150I, or one or more of N40R, N40K, D43N, D43Q, D43R, D43K, E44N, E44Q, E44R, E44K, E101N, E101Q, E101R, E101K, E101F, E101Y, E101W and E131D. The variant may comprise any number and combination of these substitutions. In (i), the variant preferably comprises S54P and/or S57P. In (i), the variant preferably comprises (a) S54P and/or S57P and (b) a mutation at one or more of Y51, N55 and F56, such as at Y51, N55, F56, Y51/N55, Y51/F56, N55/F56 or Y51/N55/F56. The mutations at one or more of Y51, N55 and F56 may be any of those discussed below. In (i), the variant preferably comprises F56A/S57P or S54P/F56A. The variant preferably comprises T150I. Alternatively the variant preferably comprises a mutation at (a) T150I and (b) one or more of Y51, N55 and F56, such as at Y51, N55, F56, Y51/N55, Y51/F56, N55/F56 or Y51/N55/F56.

In (i), the variant preferably comprises Q62R or Q62K. Alternatively the variant preferably comprises (a) Q62R or Q62K and (b) a mutation at one or more of Y51, N55 and F56, such as at Y51, N55, F56, Y51/N55, Y51/F56, N55/F56 or Y51/N55/F56. The variant may comprise D43N, E44N, Q62R or Q62K or any combination thereof, such as D43N, E44N, Q62R, Q62K, D43N/E44N, D43N/Q62R, D43N/Q62K, E44N/Q62R, E44N/Q62K, D43N/E44N/Q62R or D43N/E44N/Q62K. Alternatively the variant preferably comprises (a) D43N, E44N, Q62R, Q62K, D43N/E44N, D43N/Q62R, D43N/Q62K, E44N/Q62R, E44N/Q62K, D43N/E44N/Q62R or D43N/E44N/Q62K and (b) a mutation at one or more of Y51, N55 and F56, such as at Y51, N55, F56, Y51/N55, Y51/F56, N55/F56 or Y51/N55/F56.

In (i), the variant preferably comprises D43N.

In (i), the variant preferably comprises E101R, E101S, E101F or E101N.

In (i), the variant preferably comprises E124N, E124Q, E124R, E124K, E124F, E124Y, E124W or E124D, such as E124N.

In (i), the variant preferably comprises R142E and R142N.

In (i), the variant preferably comprises R97N, R97G or R97L.

In (i), the variant preferably comprises R192E and R192N.

In (ii), the variant preferably comprises F56N/N55Q, F56N/N55R, F56N/N55K, F56N/N55S, F56N/N55G, F56N/N55A, F56N/N55T, F56Q/N55Q, F56Q/N55R, F56Q/N55K, F56Q/N55S, F56Q/N55G, F56Q/N55A, F56Q/N55T, F56R/N55Q, F56R/N55R, F56R/N55K, F56R/N55S, F56R/N55G, F56R/N55A, F56R/N55T, F56S/N55Q, F56S/N55R, F56S/N55K, F56S/N55S, F56S/N55G, F56S/N55A, F56S/N55T, F56G/N55Q, F56G/N55R, F56G/N55K, F56G/N55S, F56G/N55G, F56G/N55A, F56G/N55T, F56A/N55Q, F56A/N55R, F56A/N55K, F56A/N55S, F56A/N55G, F56A/N55A, F56A/N55T, F56K/N55Q, F56K/N55R, F56K/N55K, F56K/N55S, F56K/N55G, F56K/N55A, F56K/N55T, F56N/Y51L, F56N/Y51V, F56N/Y51A, F56N/Y51N, F56N/Y51Q, F56N/Y51S, F56N/Y51G, F56Q/Y51L, F56Q/Y51V, F56Q/Y51A, F56Q/Y51N, F56Q/Y51Q, F56Q/Y51S, F56Q/Y51G, F56R/Y51L, F56R/Y51V, F56R/Y51A, F56R/Y51N, F56R/Y51Q, F56R/Y51S, F56R/Y51G, F56S/Y51L, F56S/Y51V, F56S/Y51A, F56S/Y51N, F56S/Y51Q, F56S/Y51S, F56S/Y51G, F56G/Y51L, F56G/Y51V, F56G/Y51A, F56G/Y51N, F56G/Y51Q, F56G/Y51S, F56G/Y51G, F56A/Y51L, F56A/Y51V, F56A/Y51A, F56A/Y51N, F56A/Y51Q, F56A/Y51S, F56A/Y51G, F56K/Y51L, F56K/Y51V, F56K/Y51A, F56K/Y51N, F56K/Y51Q, F56K/Y51S, F56K/Y51G, N55Q/Y51L, N55Q/Y51V, N55Q/Y51A, N55Q/Y51N, N55Q/Y51Q, N55Q/Y51S, N55Q/Y51G, N55R/Y51L, N55R/Y51V, N55R/Y51A, N55R/Y51N, N55R/Y51Q, N55R/Y51S, N55R/Y51G, N55K/Y51L, N55K/Y51V, N55K/Y51A, N55K/Y51N, N55K/Y51Q, N55K/Y51S, N55K/Y51G, N55S/Y51L, N55S/Y51V, N55S/Y51A, N55S/Y51N, N55S/Y51Q, N55S/Y51S, N55S/Y51G, N55G/Y51L, N55G/Y51V, N55G/Y51A, N55G/Y51N, N55G/Y51Q, N55G/Y51S, N55G/Y51G, N55A/Y51L, N55A/Y51V, N55A/Y51A, N55A/Y51N, N55A/Y51Q, N55A/Y51S, N55A/Y51G, N55T/Y51L, N55T/Y51V, N55T/Y51A, N55T/Y51N, N55T/Y51Q, N55T/Y51S, N55T/Y51G, F56N/N55Q/Y51L, F56N/N55Q/Y51V, F56N/N55Q/Y51A, F56N/N55Q/Y51N, F56N/N55Q/Y51Q, F56N/N55Q/Y51S, F56N/N55Q/Y51G, F56N/N55R/Y51L, F56N/N55R/Y51V, F56N/N55R/Y51A, F56N/N55R/Y51N, F56N/N55R/Y51Q, F56N/N55R/Y51S, F56N/N55R/Y51G, F56N/N55K/Y51L, F56N/N55K/Y51V, F56N/N55K/Y51A, F56N/N55K/Y51N, F56N/N55K/Y51Q, F56N/N55K/Y51S, F56N/N55K/Y51G, F56N/N55S/Y51L, F56N/N55S/Y51V, F56N/N55S/Y51A, F56N/N55S/Y51N, F56N/N55S/Y51Q, F56N/N55S/Y51S, F56N/N55S/Y51G, F56N/N55G/Y51L, F56N/N55G/Y51V, F56N/N55G/Y51A, F56N/N55G/Y51N, F56N/N55G/Y51Q, F56N/N55G/Y51S, F56N/N55G/Y51G, F56N/N55A/Y51L, F56N/N55A/Y51V, F56N/N55A/Y51A, F56N/N55A/Y51N, F56N/N55A/Y51Q, F56N/N55A/Y51S, F56N/N55A/Y51G, F56N/N55T/Y51L, F56N/N55T/Y51V, F56N/N55T/Y51A, F56N/N55T/Y51N, F56N/N55T/Y51Q, F56N/N55T/Y51S, F56N/N55T/Y51G, F56Q/N55Q/Y51L, F56Q/N55Q/Y51V, F56Q/N55Q/Y51A, F56Q/N55Q/Y51N, F56Q/N55Q/Y51Q, F56Q/N55Q/Y51S, F56Q/N55Q/Y51G, F56Q/N55R/Y51L, F56Q/N55R/Y51V, F56Q/N55R/Y51A, F56Q/N55R/Y51N, F56Q/N55R/Y51Q, F56Q/N55R/Y51S, F56Q/N55R/Y51G, F56Q/N55K/Y51L, F56Q/N55K/Y51V, F56Q/N55K/Y51A, F56Q/N55K/Y51N, F56Q/N55K/Y51Q, F56Q/N55K/Y51S, F56Q/N55K/Y51G, F56Q/N55S/Y51L, F56Q/N55S/Y51V, F56Q/N55S/Y51A, F56Q/N55S/Y51N, F56Q/N55S/Y51Q, F56Q/N55S/Y51S, F56Q/N55S/Y51G, F56Q/N55G/Y51L, F56Q/N55G/Y51V, F56Q/N55G/Y51A, F56Q/N55G/Y51N, F56Q/N55G/Y51Q, F56Q/N55G/Y51S, F56Q/N55G/Y51G, F56Q/N55A/Y51L, F56Q/N55A/Y51V, F56Q/N55A/Y51A, F56Q/N55A/Y51N, F56Q/N55A/Y51Q, F56Q/N55A/Y51S, F56Q/N55A/Y51G, F56Q/N55T/Y51L, F56Q/N55T/Y51V, F56Q/N55T/Y51A, F56Q/N55T/Y51N, F56Q/N55T/Y51Q, F56Q/N55T/Y51S, F56Q/N55T/Y51G, F56R/N55Q/Y51L, F56R/N55Q/Y51V, F56R/N55Q/Y51A, F56R/N55Q/Y51N, F56R/N55Q/Y51Q, F56R/N55Q/Y51S, F56R/N55Q/Y51G, F56R/N55R/Y51L, F56R/N55R/Y51V, F56R/N55R/Y51A, F56R/N55R/Y51N, F56R/N55R/Y51Q, F56R/N55R/Y51S, F56R/N55R/Y51G, F56R/N55K/Y51L, F56R/N55K/Y51V, F56R/N55K/Y51A, F56R/N55K/Y51N, F56R/N55K/Y51Q, F56R/N55K/Y51S, F56R/N55K/Y51G, F56R/N55S/Y51L, F56R/N55S/Y51V, F56R/N55S/Y51A, F56R/N55S/Y51N, F56R/N55S/Y51Q, F56R/N55S/Y51S, F56R/N55S/Y51G, F56R/N55G/Y51L, F56R/N55G/Y51V, F56R/N55G/Y51A, F56R/N55G/Y51N, F56R/N55G/Y51Q, F56R/N55G/Y51S, F56R/N55G/Y51G, F56R/N55A/Y51L, F56R/N55A/Y51V, F56R/N55A/Y51A, F56R/N55A/Y51N, F56R/N55A/Y51Q, F56R/N55A/Y51S, F56R/N55A/Y51G, F56R/N55T/Y51L, F56R/N55T/Y51V, F56R/N55T/Y51A, F56R/N55T/Y51N, F56R/N55T/Y51Q, F56R/N55T/Y51S, F56R/N55T/Y51G, F56S/N55Q/Y51L, F56S/N55Q/Y51V, F56S/N55Q/Y51A, F56S/N55Q/Y51N, F56S/N55Q/Y51Q, F56S/N55Q/Y51S, F56S/N55Q/Y51G, F56S/N55R/Y51L, F56S/N55R/Y51V, F56S/N55R/Y51A, F56S/N55R/Y51N, F56S/N55R/Y51Q, F56S/N55R/Y51S, F56S/N55R/Y51G, F56S/N55K/Y51L, F56S/N55K/Y51V, F56S/N55K/Y51A, F56S/N55K/Y51N, F56S/N55K/Y51Q, F56S/N55K/Y51S, F56S/N55K/Y51G, F56S/N55S/Y51L, F56S/N55S/Y51V, F56S/N55S/Y51A, F56S/N55S/Y51N, F56S/N55S/Y51Q, F56S/N55S/Y51S, F56S/N55S/Y51G, F56S/N55G/Y51L, F56S/N55G/Y51V, F56S/N55G/Y51A, F56S/N55G/Y51N, F56S/N55G/Y51Q, F56S/N55G/Y51S, F56S/N55G/Y51G, F56S/N55A/Y51L, F56S/N55A/Y51V, F56S/N55A/Y51A, F56S/N55A/Y51N, F56S/N55A/Y51Q, F56S/N55A/Y51S, F56S/N55A/Y51G, F56S/N55T/Y51L, F56S/N55T/Y51V, F56S/N55T/Y51A, F56S/N55T/Y51N, F56S/N55T/Y51Q, F56S/N55T/Y51S, F56S/N55T/Y51G, F56G/N55Q/Y51L, F56G/N55Q/Y51V, F56G/N55Q/Y51A, F56G/N55Q/Y51N, F56G/N55Q/Y51Q, F56G/N55Q/Y51S, F56G/N55Q/Y51G, F56G/N55R/Y51L, F56G/N55R/Y51V, F56G/N55R/Y51A, F56G/N55R/Y51N, F56G/N55R/Y51Q, F56G/N55R/Y51S, F56G/N55R/Y51G, F56G/N55K/Y51L, F56G/N55K/Y51V, F56G/N55K/Y51A, F56G/N55K/Y51N, F56G/N55K/Y51Q, F56G/N55K/Y51S, F56G/N55K/Y51G, F56G/N55S/Y51L, F56G/N55S/Y51V, F56G/N55S/Y51A, F56G/N55S/Y51N, F56G/N55S/Y51Q, F56G/N55S/Y51S, F56G/N55S/Y51G, F56G/N55G/Y51L, F56G/N55G/Y51V, F56G/N55G/Y51A, F56G/N55G/Y51N, F56G/N55G/Y51Q, F56G/N55G/Y51S, F56G/N55G/Y51G, F56G/N55A/Y51L, F56G/N55A/Y51V, F56G/N55A/Y51A, F56G/N55A/Y51N, F56G/N55A/Y51Q, F56G/N55A/Y51S, F56G/N55A/Y51G, F56G/N55T/Y51L, F56G/N55T/Y51V, F56G/N55T/Y51A, F56G/N55T/Y51N, F56G/N55T/Y51Q, F56G/N55T/Y51S, F56G/N55T/Y51G, F56A/N55Q/Y51L, F56A/N55Q/Y51V, F56A/N55Q/Y51A, F56A/N55Q/Y51N, F56A/N55Q/Y51Q, F56A/N55Q/Y51S, F56A/N55Q/Y51G, F56A/N55R/Y51L, F56A/N55R/Y51V, F56A/N55R/Y51A, F56A/N55R/Y51N, F56A/N55R/Y51Q, F56A/N55R/Y51S, F56A/N55R/Y51G, F56A/N55K/Y51L, F56A/N55K/Y51V, F56A/N55K/Y51A, F56A/N55K/Y51N, F56A/N55K/Y51Q, F56A/N55K/Y51S, F56A/N55K/Y51G, F56A/N55S/Y51L, F56A/N55S/Y51V, F56A/N55S/Y51A, F56A/N55S/Y51N, F56A/N55S/Y51Q, F56A/N55S/Y51S, F56A/N55S/Y51G, F56A/N55G/Y51L, F56A/N55G/Y51V, F56A/N55G/Y51A, F56A/N55G/Y51N, F56A/N55G/Y51Q, F56A/N55G/Y51S, F56A/N55G/Y51G, F56A/N55A/Y51L, F56A/N55A/Y51V, F56A/N55A/Y51A, F56A/N55A/Y51N, F56A/N55A/Y51Q, F56A/N55A/Y51S, F56A/N55A/Y51G, F56A/N55T/Y51L, F56A/N55T/Y51V, F56A/N55T/Y51A, F56A/N55T/Y51N, F56A/N55T/Y51Q, F56A/N55T/Y51S, F56A/N55T/Y51G, F56K/N55Q/Y51L, F56K/N55Q/Y51V, F56K/N55Q/Y51A, F56K/N55Q/Y51N, F56K/N55Q/Y51Q, F56K/N55Q/Y51S, F56K/N55Q/Y51G, F56K/N55R/Y51L, F56K/N55R/Y51V, F56K/N55R/Y51A, F56K/N55R/Y51N, F56K/N55R/Y51Q, F56K/N55R/Y51S, F56K/N55R/Y51G, F56K/N55K/Y51L, F56K/N55K/Y51V, F56K/N55K/Y51A, F56K/N55K/Y51N, F56K/N55K/Y51Q, F56K/N55K/Y51S, F56K/N55K/Y51G, F56K/N55S/Y51L, F56K/N55S/Y51V, F56K/N55S/Y51A, F56K/N55S/Y51N, F56K/N55S/Y51Q, F56K/N55S/Y51S, F56K/N55S/Y51G, F56K/N55G/Y51L, F56K/N55G/Y51V, F56K/N55G/Y51A, F56K/N55G/Y51N, F56K/N55G/Y51Q, F56K/N55G/Y51S, F56K/N55G/Y51G, F56K/N55A/Y51L, F56K/N55A/Y51V, F56K/N55A/Y51A, F56K/N55A/Y51N, F56K/N55A/Y51Q, F56K/N55A/Y51S, F56K/N55A/Y51G, F56K/N55T/Y51L, F56K/N55T/Y51V, F56K/N55T/Y51A, F56K/N55T/Y51N, F56K/N55T/Y51Q, F56K/N55T/Y51S, F56K/N55T/Y51G, F56E/N55R, F56E/N55K, F56D/N55R, F56D/N55K, F56R/N55E, F56R/N55D, F56K/N55E or F56K/N55D.

In (ii), the variant preferably comprises Y51R/F56Q, Y51N/F56N, Y51M/F56Q, Y51L/F56Q, Y51/1F56Q, Y51V/F56Q, Y51A/F56Q, Y51P/F56Q, Y51G/F56Q, Y51C/F56Q, Y51Q/F56Q, Y51N/F56Q, Y51S/F56Q, Y51E/F56Q, Y51D/F56Q, Y51K/F56Q or Y51H/F56Q.

In (ii), the variant preferably comprises Y51T/F56Q, Y51Q/F56Q or Y51A/F56Q.

In (ii), the variant preferably comprises Y51T/F56F, Y51T/F56M, Y51T/F56L, Y51T/F56I, Y51T/F56V, Y51T/F56A, Y51T/F56P, Y51T/F56G, Y51T/F56C, Y51T/F56Q, Y51T/F56N, Y51T/F56T, Y51T/F56S, Y51T/F56E, Y51T/ F56D, Y51T/F56K, Y51T/F56H or Y51T/F56R.

In (ii), the variant preferably comprises Y51T/N55Q, Y51T/N55S or Y51T/N55A.

In (ii), the variant preferably comprises Y51A/F56F, Y51A/F56L, Y51A/F56I, Y51A/F56V, Y51A/F56A, Y51A/ F56P, Y51A/F56G, Y51A/F56C, Y51A/F56Q, Y51A/F56N, Y51A/F56T, Y51A/F56S, Y51A/F56E, Y51A/F56D, Y51A/ F56K, Y51A/F56H or Y51A/F56R.

In (ii), the variant preferably comprises Y51C/F56A, Y51E/F56A, Y51D/F56A, Y51K/F56A, Y51H/F56A, Y51Q/F56A, Y51N/F56A, Y51S/F56A, Y51P/F56A or Y51V/F56A.

In (xi), the variant preferably comprises deletion of Y51/ P52, Y51/P52/A53, P50 to P52, P50 to A53, K49 to Y51, K49 to A53 and replacement with a single proline (P), K49 to S54 and replacement with a single P, Y51 to A53, Y51 to S54, N55/F56, N55 to S57, N55/F56 and replacement with a single P, N55/F56 and replacement with a single glycine (G), N55/F56 and replacement with a single alanine (A), N55/F56 and replacement with a single P and Y51N, N55/ F56 and replacement with a single P and Y51Q, N55/F56 and replacement with a single P and Y51S, N55/F56 and replacement with a single G and Y51N, N55/F56 and replacement with a single G and Y51Q, N55/F56 and replacement with a single G and Y51S, N55/F56 and replacement with a single A and Y51N, N55/F56 and replacement with a single A/Y51Q or N55/F56 and replacement with a single A and Y51S.

The variant more preferably comprises D195N/E203N, D195Q/E203N, D195N/E203Q, D195Q/E203Q, E201N/ E203N, E201Q/E203N, E201N/E203Q, E201Q/E203Q, E185N/E203Q, E185Q/E203Q, E185N/E203N, E185Q/ E203N, D195N/E201N/E203N, D195Q/E201N/E203N, D195N/E201Q/E203N, D195N/E201N/E203Q, D195Q/ E201Q/E203N, D195Q/E201N/E203Q, D195N/E201Q/ E203Q, D195Q/E201Q/E203Q, D149N/E201N, D149Q/ E201N, D149N/E201Q, D149Q/E201Q, D149N/E201N/ D195N, D149Q/E201N/D195N, D149N/E201Q/D195N, D149N/E201N/D195Q, D149Q/E201Q/D195N, D149Q/ E201N/D195Q, D149N/E201Q/D195Q, D149Q/E201Q/ D195Q, D149N/E203N, D149Q/E203N, D149N/E203Q, D149Q/E203Q, D149N/E185Q/E201N, D149Q/E185N/ E201N, D149N/E185Q/E201N, D149N/E185N/E201Q, D149Q/E185Q/E201N, D149Q/E185N/E201Q, D149N/ E185Q/E201Q, D149Q/E185Q/E201Q, D149N/E185N/ E203N, D149Q/E185N/E203N, D149N/E185Q/E203N, D149N/E185N/E203Q, D149Q/E185Q/E203N, D149Q/ E185N/E203Q, D149N/E185Q/E203Q, D149Q/E185Q/ E203Q, D149N/E185N/E201N/E203N, D149Q/E185N/ E201N/E203N, D149N/E185Q/E201N/E203N, D149N/ E185N/E201Q/E203N, D149N/E185N/E201N/E203Q, D149Q/E185Q/E201N/E203N, D149Q/E185N/E201Q/ E203N, D149Q/E185N/E201N/E203Q, D149N/E185Q/ E201Q/E203N, D149N/E185Q/E201N/E203Q, D149N/ E185N/E201Q/E203Q, D149Q/E185Q/E201Q/E203Q, D149Q/E185Q/E201N/E203Q, D149Q/E185N/E201Q/ E203Q, D149N/E185Q/E201Q/E203Q, D149Q/E185Q/ E201Q/E203N, D149N/E185N/D195N/E201N/E203N, D149Q/E185N/D195N/E201N/E203N, D149N/E185Q/ D195N/E201N/E203N, D149N/E185N/D195Q/E201N/ E203N, D149N/E185N/D195N/E201Q/E203N, D149N/ E185N/D195N/E201N/E203Q, D149Q/E185Q/D195N/ E201N/E203N, D149Q/E185N/D195Q/E201N/E203N, D149Q/E185N/D195N/E201Q/E203N, D149N/E185N/ D195N/E201N/E203Q, D149N/E185Q/D195N/E201Q/E203N, D149N/ E185Q/D195N/E201N/E203Q, D149N/E185N/D195Q/ E201Q/E203N, D149N/E185N/D195Q/E201N/E203Q, D149N/E185N/D195N/E201Q/E203Q, D149Q/E185Q/ D195Q/E201N/E203N, D149Q/E185Q/D195N/E201Q/ E203N, D149Q/E185Q/D195N/E201N/E203Q, D149Q/ E185N/D195Q/E201Q/E203N, D149Q/E185N/D195Q/ E201N/E203Q, D149Q/E185N/D195N/E201Q/E203Q, D149N/E185Q/D195Q/E201Q/E203N, D149N/E185Q/ D195Q/E201N/E203N, D149Q/E185Q/D195N/E201Q/ E203N, D149Q/E185Q/D195N/E201N/E203Q, D149Q/ E185N/D195Q/E201Q/E203N, D149Q/E185N/D195Q/ E201N/E203Q, D149Q/E185N/D195N/E201Q/E203Q, D149N/E185Q/D195Q/E201Q/E203N, D149N/E185Q/ D195Q/E201N/E203Q, D149N/E185Q/D195N/E201Q/ E203Q, D149N/E185N/D195Q/E201Q/E203Q, D149Q/ E185Q/D195Q/E201Q/E203N, D149Q/E185Q/D195Q/E201N/E203Q, D149Q/E185Q/D195N/E201Q/E203Q, D149Q/E185N/D195Q/E201Q/E203Q, D149N/E185Q/ D195Q/E201Q/E203Q, D149Q/E185Q/D195Q/E201Q/ E203Q, D149N/E185R/E201N/E203N, D149Q/E185R/ E201N/E203N, D149N/E185R/E201Q/E203N, D149N/ E185R/E201N/E203Q, D149Q/E185R/E201Q/E203N, D149Q/E185R/E201N/E203Q, D149N/E185R/E201Q/ E203Q, D149Q/E185R/E201Q/E203Q, D149R/E185N/ E201N/E203N, D149R/E185Q/E201N/E203N, D149R/ E185N/E201Q/E203N, D149R/E185N/E201N/E203Q, D149R/E185Q/E201Q/E203N, D149R/E185Q/E201N/ E203Q, D149R/E185N/E201Q/E203Q, D149R/E185Q/ E201Q/E203Q, D149R/E185N/D195N/E201N/E203N, D149R/E185Q/D195N/E201N/E203N, D149R/E185N/ D195Q/E201N/E203N, D149R/E185N/D195N/E201Q/ E203N, D149R/E185Q/D195N/E201N/E203Q, D149R/ E185Q/D195Q/E201N/E203N, D149R/E185Q/D195N/ E201Q/E203N, D149R/E185Q/D195N/E201N/E203Q, D149R/E185N/D195Q/E201Q/E203N, D149R/E185N/ D195Q/E201N/E203Q, D149R/E185N/D195N/E201Q/ E203Q, D149R/E185Q/D195Q/E201Q/E203N, D149R/ E185Q/D195Q/E201N/E203Q, D149R/E185Q/D195N/ E201Q/E203Q, D149R/E185N/D195Q/E201Q/E203Q, D149R/E185Q/D195Q/E201Q/E203Q, D149N/E185R/ D195N/E201N/E203N, D149Q/E185R/D195N/E201N/ E203N, D149N/E185R/D195Q/E201N/E203N, D149N/ E185R/D195N/E201Q/E203N, D149N/E185R/D195N/ E201N/E203Q, D149Q/E185R/D195Q/E201N/E203N, D149Q/E185R/D195N/E201Q/E203N, D149Q/E185R/ D195N/E201N/E203Q, D149N/E185R/D195Q/E201Q/ E203N, D149N/E185R/D195Q/E201N/E203Q, D149N/ E185R/D195N/E201Q/E203Q, D149Q/E185R/D195Q/ E201Q/E203N, D149Q/E185R/D195N/E201Q/E203Q, D149Q/E185R/D195Q/E201N/E203Q, D149N/E185R/ D195Q/E201Q/E203Q, D149Q/E185R/D195Q/E201Q/ E203Q, D149N/E185R/D195N/E201R/E203N, D149Q/ E185R/D195N/E201R/E203N, D149N/E185R/D195Q/ E201R/E203N, D149N/E185R/D195N/E201R/E203Q, D149Q/E185R/D195Q/E201R/E203N, D149Q/E185R/ D195N/E201R/E203Q, D149N/E185R/D195Q/E201R/ E203Q, D149Q/E185R/D195Q/E201R/E203Q, E131D/ K49R, E101N/N102F, E101N/N102Y, E101N/N102W, E101F/N102F, E101F/N102Y, E101F/N102W, E101Y/ N102F, E101Y/N102Y, E101Y/N102W, E101W/N102F, E101W/N102Y, E101W/N102W, E101N/N102R, E101F/ N102R, E101Y/N102R or E101W/N102F.

Preferred variants of the invention which form pores in which fewer nucleotides contribute to the current as the polynucleotide moves through the pore comprise Y51A/ F56A, Y51I/F56N, Y51I/F56A, Y51L/F56A, Y51T/F56A, Y51I/F56N, Y51L/F56N or Y51T/F56N or more preferably Y51I/F56A, Y51L/F56A or Y51T/F56A. As discussed above, this makes it easier to identify a direct relationship between the observed current (as the polynucleotide moves through the pore) and the polynucleotide.

Preferred variants which form pores displaying an increased range comprise mutations at the following positions:
Y51, F56, D149, E185, E201 and E203;
N55 and F56;
Y51 and F56;
Y51, N55 and F56; or
F56 and N102.

Preferred variants which form pores displaying an increased range comprise:
Y51N, F56A, D149N, E185R, E201N and E203N;
N55S and F56Q;
Y51A and F56A;
Y51A and F56N;
Y51I and F56A;
Y51L and F56A;
Y51T and F56A;
Y51I and F56N;
Y51L and F56N;
Y51T and F56N;
Y51T and F56Q;
Y51A, N55S and F56A;
Y51A, N55S and F56N;
Y51T, N55S and F56Q; or
F56Q and N102R.

Preferred variants which form pores in which fewer nucleotides contribute to the current as the polynucleotide moves through the pore comprise mutations at the following positions:
N55 and F56, such as N55X and F56Q, wherein X is any amino acid; or
Y51 and F56, such as Y51X and F56Q, wherein X is any amino acid.

Particularly preferred variants comprise Y51A and F56Q.

Preferred variants which form pores displaying an increased throughput comprise mutations at the following positions:
D149, E185 and E203;
D149, E185, E201 and E203; or
D149, E185, D195, E201 and E203.

Preferred variants which form pores displaying an increased throughput comprise:
D149N, E185N and E203N;
D149N, E185N, E201N and E203N;
D149N, E185R, D195N, E201N and E203N; or
D149N, E185R, D195N, E201R and E203N.

Preferred variants which form pores in which capture of the polynucleotide is increased comprise the following mutations:
D43N/Y51T/F56Q;
E44N/Y51T/F56Q;
D43N/E44N/Y51T/F56Q;
Y51T/F56Q/Q62R;
D43N/Y51T/F56Q/Q62R;
E44N/Y51T/F56Q/Q62R; or
D43N/E44N/Y51T/F56Q/Q62R.

Preferred variants comprise the following mutations:
D149R/E185R/E201R/E203R or Y51T/F56Q/D149R/E185R/E201R/E203R;
D149N/E185N/E201N/E203N or Y51T/F56Q/D149N/E185N/E201N/E203N;
E201R/E203R or Y51T/F56Q/E201R/E203R
E201N/E203N or Y51T/F56Q/E201N/E203N;
E203R or Y51T/F56Q/E203R;
E203N or Y51T/F56Q/E203N;
E201R or Y51T/F56Q/E201R;
E201N or Y51T/F56Q/E201N;
E185R or Y51T/F56Q/E185R;
E185N or Y51T/F56Q/E185N;
D149R or Y51T/F56Q/D149R;
D149N or Y51T/F56Q/D149N;
R142E or Y51T/F56Q/R142E;
R142N or Y51T/F56Q/R142N;
R192E or Y51T/F56Q/R192E; or
R192N or Y51T/F56Q/R192N.

Preferred variants comprise the following mutations:
Y51A/F56Q/E101N/N102R;
Y51A/F56Q/R97N/N102G;
Y51A/F56Q/R97N/N102R;
Y51A/F56Q/R97N;
Y51A/F56Q/R97G;
Y51A/F56Q/R97L;
Y51A/F56Q/N102R;
Y51A/F56Q/N102F;
Y51A/F56Q/N102G;
Y51A/F56Q/E101R;
Y51A/F56Q/E101F;
Y51A/F56Q/E101N; or
Y51A/F56Q/E101G The variant preferably further comprises a mutation at T150. A preferred variant which forms a pore displaying an increased insertion comprises T150I. A mutation at T150, such as T150I, may be combined with any of the mutations or combinations of mutations discussed above.

A preferred variant of SEQ ID NO: 2 comprises (a) R97W and (b) a mutation at Y51 and/or F56. A preferred variant of SEQ ID NO: 2 comprises (a) R97W and (b) Y51R/H/K/D/E/S/T/N/Q/C/G/P/A/V/I/L/M and/or F56 R/H/K/D/E/S/T/N/Q/C/G/P/A/V/I/L/M. A preferred variant of SEQ ID NO: 2 comprises (a) R97W and (b) Y51L/V/A/N/Q/S/G and/or F56A/Q/N. A preferred variant of SEQ ID NO: 2 comprises (a) R97W and (b) Y51A and/or F56Q. A preferred variant of SEQ ID NO: 2 comprises R97W, Y51A and F56Q.

In the mutant monomers of the invention, the variant of SEQ ID NO: 2 preferably comprises a mutation at R192. The variant preferably comprises R192D/Q/F/S/T/N/E, R192D/Q/F/S/T or R192D/Q. A preferred variant of SEQ ID NO: 2 comprises (a) R97W, (b) a mutation at Y51 and/or F56 and (c) a mutation at R192, such as R192D/Q/F/S/T/N/E, R192D/Q/F/S/T or R192D/Q. A preferred variant of SEQ ID NO: 2 comprises (a) R97W, (b) Y51R/H/K/D/E/S/T/N/Q/C/G/P/A/V/I/L/M and/or F56 R/H/K/D/E/S/T/N/Q/C/G/P/A/V/I/L/M and (c) a mutation at R192, such as R192D/Q/F/S/T/N/E, R192D/Q/F/S/T or R192D/Q. A preferred variant of SEQ ID NO: 2 comprises (a) R97W, (b) Y51L/V/A/N/Q/S/G and/or F56A/Q/N and (c) a mutation at R192, such as R192D/Q/F/S/T/N/E, R192D/Q/F/S/T or R192D/Q. A preferred variant of SEQ ID NO: 2 comprises (a) R97W, (b) Y51A and/or F56Q and (c) a mutation at R192, such as R192 D/Q/F/S/T/N/E, R192D/Q/F/S/T or R192D/Q. A preferred variant of SEQ ID NO: 2 comprises R97W, Y51A, F56Q and R192D/Q/F/S/T or R192D/Q. A preferred variant of SEQ ID NO: 2 comprises R97W, Y51A, F56Q and R192D. A preferred variant of SEQ ID NO: 2 comprises R97W, Y51A, F56Q and R192Q. In the paragraphs above where different amino acids at a specific positon are separated by the/symbol, the/symbol means "or". For instance, R192D/Q means R192D or R192Q.

In the mutant monomers of the invention, the variant of SEQ ID NO: 2 preferably comprises a mutation at R93. A preferred variant of SEQ ID NO: 2 comprises (a) R93W and (b) a mutation at Y51 and/or F56, preferably Y51A and F56Q. D or R192N.deletion of V105, A106 and I107.

Any of the above preferred variants of SEQ ID NO: 2 may comprise a K94N/Q mutation. Any of the above preferred variants of SEQ ID NO: 2 may comprise a F191T mutation. The invention also provides a mutant CsgG monomer comprising a variant of the sequence shown in SEQ ID NO: 2 comprising the combination of mutations present in a variant disclosed in the Examples.

Methods for introducing or substituting naturally-occurring amino acids are well known in the art. For instance, methionine (M) may be substituted with arginine (R) by replacing the codon for methionine (ATG) with a codon for arginine (CGT) at the relevant position in a polynucleotide encoding the mutant monomer. The polynucleotide can then be expressed as discussed below.

Methods for introducing or substituting non-naturally-occurring amino acids are also well known in the art. For instance, non-naturally-occurring amino acids may be introduced by including synthetic aminoacyl-tRNAs in the IVTT system used to express the mutant monomer. Alternatively, they may be introduced by expressing the mutant monomer in *E. coli* that are auxotrophic for specific amino acids in the presence of synthetic (i.e. non-naturally-occurring) analogues of those specific amino acids. They may also be produced by naked ligation if the mutant monomer is produced using partial peptide synthesis.

Variants

In addition to the specific mutations discussed above, the variant may include other mutations. Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the wild-type CsgG monomer from *Escherichia coli* Str. K-12 substr. MC4100. The variant of SEQ ID NO: 2 may comprise any of the substitutions present in another CsgG homologue. Preferred CsgG homologues are shown in SEQ ID NOs: 3 to 7 and 26 to 41. The variant may comprise combinations of one or more of the substitutions present in SEQ ID NOs: 3 to 7 and 26 to 41 compared with SEQ ID NO: 2. For example, mutations may be made at any one or more of the positions in SEQ ID NO: 2 that differ between SEQ ID NO: 2 and any one of SEQ ID NOs: 3 to 7 and SEQ ID NOs: 26 to 41. Such a mutation may be a substitution of an amino acid in SEQ ID NO: 2 with an amino acid from the corresponding position in any one of SEQ ID NOs: 3 to 7 and SEQ ID NOs: 26 to 41. Alternatively, the mutation at any one of these positions may be a substitution with any amino acid, or may be a deletion or insertion mutation, such as deletion or insertion of 1 to 10 amino acids, such as of 2 to 8 or 3 to 6 amino acids. Other than the mutations disclosed herein, the amino acids that are conserved between SEQ ID NO: 2 and all of SEQ ID NOs: 3 to 7 and SEQ ID NOs: 26 to 41 are preferably present in a variant of the invention. However, conservative mutations may be made at any one or more of these positions that are conserved between SEQ ID NO: 2 and all of SEQ ID NOs: 3 to 7 and SEQ ID NOs: 26 to 41.

The invention provides a pore-forming CsgG mutant monomer that comprises any one or more of the amino acids described herein as being substituted into a specific position of SEQ ID NO: 2 at a position in the structure of the CsgG monomer that corresponds to the specific position in SEQ ID NO: 2. Corresponding positions may be determined by standard techniques in the art. For example, the PILEUP and BLAST algorithms mentioned above can be used to align the sequence of a CsgG monomer with SEQ ID NO: 2 and hence to identify corresponding residues.

In particular, the invention provides a pore-forming CsgG mutant monomer that comprises any one or more of the following:

a W at a position corresponding to R97 in SEQ ID NO:2;
a W at a position corresponding to R93 in SEQ ID NO:2;
a Y at a position corresponding to R97 in SEQ ID NO: 2;
a Y at a position corresponding to R93 in SEQ ID NO: 2;
a Y at each of the positions corresponding to R93 and R97 in SEQ ID NO: 2;
a D at the position corresponding to R192 in SEQ ID NO:2;
deletion of the residues at the positions corresponding to V105-I107 in SEQ ID NO:2;
deletion of the residues at one or more of the positions corresponding to F193 to L199 in SEQ ID NO: 2;
deletion of the residues the positions corresponding to F195 to L199 in SEQ ID NO: 2;
deletion of the residues the positions corresponding to F193 to L199 in SEQ ID NO: 2;
a T at the position corresponding to F191 in SEQ ID NO: 2;
a Q at the position corresponding to K49 in SEQ ID NO: 2;
a N at the position corresponding to K49 in SEQ ID NO: 2;
a Q at the position corresponding to K42 in SEQ ID NO: 2;
a Q at the position corresponding to E44 in SEQ ID NO: 2;
a N at the position corresponding to E44 in SEQ ID NO: 2;
a R at the position corresponding to L90 in SEQ ID NO: 2;
a R at the position corresponding to L91 in SEQ ID NO: 2;
a R at the position corresponding to I95 in SEQ ID NO: 2;
a R at the position corresponding to A99 in SEQ ID NO: 2;
a H at the position corresponding to E101 in SEQ ID NO: 2;
a K at the position corresponding to E101 in SEQ ID NO: 2;
a N at the position corresponding to E101 in SEQ ID NO: 2;

a Q at the position corresponding to E101 in SEQ ID NO: 2;
a T at the position corresponding to E101 in SEQ ID NO: 2;
a K at the position corresponding to Q114 in SEQ ID NO: 2.

The CsgG pore-forming monomer of the invention preferably further comprises an A at the position corresponding to Y51 in SEQ ID NO: 2 and/or a Q at the position corresponding to F56 in SEQ ID NO: 2.

The pore-forming mutant monomer typically retains the ability to form the same 3D structure as the wild-type CsgG monomer, such as the same 3D structure as a CsgG monomer having the sequence of SEQ ID NO: 2. The 3D structure of CsgG is known in the art and is disclosed, for example, in Cao et al (2014) PNAS E5439-E5444. Any number of mutations may be made in the wild-type CsgG sequence in addition to the mutations described herein provided that the CsgG mutant monomer retains the improved properties imparted on it by the mutations of the present invention.

Typically the CsgG monomer will retain the ability to form a structure comprising three alpha-helicies and five beta-sheets. The present inventors have shown in particular that mutations may be made at least in the region of CsgG which is N-terminal to the first alpha helix (which starts at S63 in SEQ ID NO:2), in the second alpha helix (from G85 to A99 of SEQ ID NO: 2), in the loop between the second alpha helix and the first beta sheet (from Q100 to N120 of SEQ ID NO: 2), in the fourth and fifth beta sheets (S173 to R192 and R198 to T107 of SEQ ID NO: 2, respectively) and in the loop between the fourth and fifth beta sheets (F193 to Q197 of SEQ ID NO: 2) without affecting the ability of the CsgG monomer to form a transmembrane pore, which transmembrane pore is capable of translocating polypeptides. Therefore, it is envisaged that further mutations may be made in any of these regions in any CsgG monomer without affecting the ability of the monomer to form a pore that can translocate polynucleotides. It is also expected that mutations may be made in other regions, such as in any of the alpha helicies (S63 to R76, G85 to A99 or V211 to L236 of SEQ ID NO: 2) or in any of the beta sheets (I121 to N133, K135 to R142, I146 to R162, S173 to R192 or R198 to T107 of SEQ ID NO: 2) without affecting the ability of the monomer to form a pore that can translocate polynucleotides. It is also expected that deletions of one or more amino acids can be made in any of the loop regions linking the alpha helicies and beta sheets and/or in the N-terminal and/or C-terminal regions of the CsgG monomer without affecting the ability of the monomer to form a pore that can translocate polynucleotides.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

| Chemical properties of amino acids | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged (+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

TABLE 3

| Hydropathy scale | |
|---|---|
| Side Chain | Hydropathy |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 or more residues may be deleted.

Variants may include fragments of SEQ ID NO: 2. Such fragments retain pore forming activity. Fragments may be at least 50, at least 100, at least 150, at least 200 or at least 250 amino acids in length. Such fragments may be used to produce the pores. A fragment preferably comprises the membrane spanning domain of SEQ ID NO: 2, namely K135-Q153 and S183-S208.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of CsgG, which contains a β-barrel, is provided by β-sheets in each subunit. A variant of SEQ ID NO: 2 typically comprises the regions in SEQ ID NO: 2 that form β-sheets, namely K135-Q153 and S183-S208. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from CsgG may be modified to assist their identification or purification, for example by the addition of a streptavidin tag or by the addition of a signal sequence to promote their secretion from a cell where the monomer does not naturally contain such a sequence. Other suitable tags are discussed in more detail below. The monomer may be labelled with a revealing label. The revealing label may be any suitable label which allows the monomer to be detected. Suitable labels are described below.

The monomer derived from CsgG may also be produced using D-amino acids. For instance, the monomer derived from CsgG may comprise a mixture of L-amino acids and D-amino acids. This is conventional in the art for producing such proteins or peptides.

The monomer derived from CsgG contains one or more specific modifications to facilitate nucleotide discrimination. The monomer derived from CsgG may also contain other non-specific modifications as long as they do not interfere with pore formation. A number of non-specific side chain modifications are known in the art and may be made to the side chains of the monomer derived from CsgG. Such modifications include, for example, reductive alkylation of amino acids by reaction with an aldehyde followed by reduction with $NaBH_4$, amidination with methylacetimidate or acylation with acetic anhydride.

The monomer derived from CsgG can be produced using standard methods known in the art. The monomer derived from CsgG may be made synthetically or by recombinant means. For example, the monomer may be synthesised by in vitro translation and transcription (IVTT). Suitable methods for producing pores and monomers are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

In some embodiments, the mutant monomer is chemically modified. The mutant monomer can be chemically modified in any way and at any site. The mutant monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The mutant monomer may be chemically modified by the attachment of any molecule. For instance, the mutant monomer may be chemically modified by attachment of a dye or a fluorophore.

In some embodiments, the mutant monomer is chemically modified with a molecular adaptor that facilitates the interaction between a pore comprising the monomer and a target nucleotide or target polynucleotide sequence. The presence of the adaptor improves the host-guest chemistry of the pore and the nucleotide or polynucleotide sequence and thereby improves the sequencing ability of pores formed from the mutant monomer. The principles of host-guest chemistry are well-known in the art. The adaptor has an effect on the physical or chemical properties of the pore that improves its interaction with the nucleotide or polynucleotide sequence. The adaptor may alter the charge of the barrel or channel of the pore or specifically interact with or bind to the nucleotide or polynucleotide sequence thereby facilitating its interaction with the pore.

The molecular adaptor is preferably a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore. The adaptor preferably has eight-fold or nine-fold symmetry since CsgG typically has eight or nine subunits around a central axis. This is discussed in more detail below.

The adaptor typically interacts with the nucleotide or polynucleotide sequence via host-guest chemistry. The adaptor is typically capable of interacting with the nucleotide or polynucleotide sequence. The adaptor comprises one or more chemical groups that are capable of interacting with the nucleotide or polynucleotide sequence. The one or more chemical groups preferably interact with the nucleotide or polynucleotide sequence by non-covalent interactions, such as hydrophobic interactions, hydrogen bonding, Van der Waal's forces, π-cation interactions and/or electrostatic forces. The one or more chemical groups that are capable of interacting with the nucleotide or polynucleotide sequence are preferably positively charged. The one or more chemical groups that are capable of interacting with the nucleotide or polynucleotide sequence more preferably comprise amino groups. The amino groups can be attached to primary, secondary or tertiary carbon atoms. The adaptor even more preferably comprises a ring of amino groups, such as a ring of 6, 7 or 8 amino groups. The adaptor most preferably comprises a ring of eight amino groups. A ring of protonated amino groups may interact with negatively charged phosphate groups in the nucleotide or polynucleotide sequence.

The correct positioning of the adaptor within the pore can be facilitated by host-guest chemistry between the adaptor and the pore comprising the mutant monomer. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, π-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that facilitates the interaction between the pore and the nucleotide or polynucleotide sequence can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H-J. (1994) *J. Am. Chem.*

Soc. 116, 6081-6088. The adaptor is more preferably heptakis-6-amino-β-cyclodextrin (am$_7$-βCD), 6-monodeoxy-6-monoamino-β-cyclodextrin (am$_1$-βCD) or heptakis-(6-deoxy-6-guanidino)-cyclodextrin (gu$_7$-βCD). The guanidino group in gu$_7$-βCD has a much higher pKa than the primary amines in am$_7$-βCD and so it is more positively charged. This gu$_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono (2-pyridyl)dithiopropanoyl-β-cyclodextrin (am$_6$amPDP$_1$-βCD).

More suitable adaptors include γ-cyclodextrins, which comprise 9 sugar units (and therefore have nine-fold symmetry). The γ-cyclodextrin may contain a linker molecule or may be modified to comprise all or more of the modified sugar units used in the β-cyclodextrin examples discussed above.

The molecular adaptor is preferably covalently attached to the mutant monomer. The adaptor can be covalently attached to the pore using any method known in the art. The adaptor is typically attached via chemical linkage. If the molecular adaptor is attached via cysteine linkage, the one or more cysteines have preferably been introduced to the mutant, for instance in the barrel, by substitution. The mutant monomer may be chemically modified by attachment of a molecular adaptor to one or more cysteines in the mutant monomer. The one or more cysteines may be naturally-occurring, i.e. at positions 1 and/or 215 in SEQ ID NO: 2. Alternatively, the mutant monomer may be chemically modified by attachment of a molecule to one or more cysteines introduced at other positions. The cysteine at position 215 may be removed, for instance by substitution, to ensure that the molecular adaptor does not attach to that position rather than the cysteine at position 1 or a cysteine introduced at another position.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the mutant monomer before a linker is attached. The molecule may be attached directly to the mutant monomer. The molecule is preferably attached to the mutant monomer using a linker, such as a chemical crosslinker or a peptide linker.

Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and Maleimide-based linkers.

In other embodiment, the monomer may be attached to a polynucleotide binding protein. This forms a modular sequencing system that may be used in the methods of sequencing of the invention. Polynucleotide binding proteins are discussed below.

The polynucleotide binding protein is preferably covalently attached to the mutant monomer. The protein can be covalently attached to the monomer using any method known in the art. The monomer and protein may be chemically fused or genetically fused. The monomer and protein are genetically fused if the whole construct is expressed from a single polynucleotide sequence. Genetic fusion of a monomer to a polynucleotide binding protein is discussed in International Application No. PCT/GB09/001679 (published as WO 2010/004265).

If the polynucleotide binding protein is attached via cysteine linkage, the one or more cysteines have preferably been introduced to the mutant by substitution. The one or more cysteines are preferably introduced into loop regions which have low conservation amongst homologues indicating that mutations or insertions may be tolerated. They are therefore suitable for attaching a polynucleotide binding protein. In such embodiments, the naturally-occurring cysteine at position 251 may be removed. The reactivity of cysteine residues may be enhanced by modification as described above.

The polynucleotide binding protein may be attached directly to the mutant monomer or via one or more linkers. The molecule may be attached to the mutant monomer using the hybridization linkers described in International Application No. PCT/GB10/000132 (published as WO 2010/086602). Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16, serine and/or glycine amino acids. More preferred flexible linkers include (SG)$_1$, (SG)$_2$, (SG)$_3$, (SG)$_4$, (SG)$_5$ and (SG)$_8$ wherein S is serine and G is glycine. Preferred rigid linkers are stretches of 2 to 30, such as 4, 6, 8, 16 or 24, proline amino acids. More preferred rigid linkers include (P)$_{12}$ wherein P is proline.

The mutant monomer may be chemically modified with a molecular adaptor and a polynucleotide binding protein.

The molecule (with which the monomer is chemically modified) may be attached directly to the monomer or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the mutant monomers and pores of the invention, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the protein. An example of this would be to react a gel-shift reagent to a cysteine engineered on the outside of the protein. This has been demonstrated as a method for separating hemolysin hetero-oligomers (Chem Biol. 1997 July; 4(7):497-505).

Any of the proteins described herein, such as the mutant monomers and pores of the invention, may be labelled with a revealing label. The revealing label may be any suitable label which allows the protein to be detected. Suitable labels include, but are not limited to, fluorescent molecules, radio-isotopes, e.g. $^{125}$I, $^{35}$S, enzymes, antibodies, antigens, polynucleotides and ligands such as biotin.

Any of the proteins described herein, such as the monomers or pores of the invention, may be made synthetically or by recombinant means. For example, the protein may be synthesised by in vitro translation and transcription (IVTT). The amino acid sequence of the protein may be modified to include non-naturally occurring amino acids or to increase the stability of the protein. When a protein is produced by synthetic means, such amino acids may be introduced during production. The protein may also be altered following either synthetic or recombinant production.

Proteins may also be produced using D-amino acids. For instance, the protein may comprise a mixture of L-amino acids and D-amino acids. This is conventional in the art for producing such proteins or peptides.

The protein may also contain other non-specific modifications as long as they do not interfere with the function of the protein. A number of non-specific side chain modifications are known in the art and may be made to the side chains of the protein(s). Such modifications include, for example, reductive alkylation of amino acids by reaction with an aldehyde followed by reduction with NaBH$_4$, amidination with methylacetimidate or acylation with acetic anhydride.

Any of the proteins described herein, including the monomers and pores of the invention, can be produced using standard methods known in the art. Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Constructs

The invention also provides a construct comprising two or more covalently attached CsgG monomers, wherein at least one of the monomers is a mutant monomer of the invention. The construct of the invention retains its ability to form a pore. This may be determined as discussed above. One or more constructs of the invention may be used to form pores for characterising, such as sequencing, polynucleotides. The construct may comprise at least 2, at least 3, at least 4, at least 5, at least 6, at least 7, at least 8, at least 9 or at least 10 monomers. The construct preferably comprises two monomers. The two or more monomers may be the same or different.

At least one monomer in the construct is a mutant monomer of the invention. 2 or more, 3 or more, 4 or more, 5 or more, 6 or more, 7 or more, 8 or more, 9 or more or 10 or more monomers in the construct may be mutant monomers of the invention. All of the monomers in the construct are preferably mutant monomers of the invention. The mutant monomers may be the same or different. In a preferred embodiment, the construct comprises two mutant monomers of the invention.

The mutant monomers of the invention in the construct are preferably approximately the same length or are the same length. The barrels of the mutant monomers of the invention in the construct are preferably approximately the same length or are the same length. Length may be measured in number of amino acids and/or units of length.

The construct may comprise one or more monomers which are not mutant monomers of the invention. CsgG mutant monomers which are non mutant monomers of the invention include monomers comprising SEQ ID NO: 2, 3, 4, 5, 6, 7, 26, 27, 28, 29, 30, 31, 32, 33, 34, 35, 36, 37, 38, 39, 40 or 41 or a comparative variant of SEQ ID NO: 2, 3, 4, 5, 6, 7, 26, 27, 28, 29, 30, 31, 32, 33, 34, 35, 36, 37, 38, 39, 40 or 41 in which none of the amino acids/positions discussed above have been mutated. At least one monomer in the construct may comprise SEQ ID NO: 2, 3, 4, 5, 6, 7, 26, 27, 28, 29, 30, 31, 32, 33, 34, 35, 36, 37, 38, 39, 40 or 41 or a comparative variant of the sequence shown in SEQ ID NO: 2, 3, 4, 5, 6, 7, 26, 27, 28, 29, 30, 31, 32, 33, 34, 35, 36, 37, 38, 39, 40 or 41. A comparative variant of SEQ ID NO: 2, 3, 4, 5, 6, 7, 26, 27, 28, 29, 30, 31, 32, 33, 34, 35, 36, 37, 38, 39, 40 or 41 is at least 50% homologous to SEQ ID NO: 2, 3, 4, 5, 6, 7, 26, 27, 28, 29, 30, 31, 32, 33, 34, 35, 36, 37, 38, 39, 40 or 41 over its entire sequence based on amino acid identity. More preferably, the comparative variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2, 3, 4, 5, 6, 7, 26, 27, 28, 29, 30, 31, 32, 33, 34, 35, 36, 37, 38, 39, 40 or 41 over the entire sequence.

The monomers in the construct are preferably genetically fused. Monomers are genetically fused if the whole construct is expressed from a single polynucleotide sequence. The coding sequences of the monomers may be combined in any way to form a single polynucleotide sequence encoding the construct.

The monomers may be genetically fused in any configuration. The monomers may be fused via their terminal amino acids. For instance, the amino terminus of the one monomer may be fused to the carboxy terminus of another monomer. The second and subsequent monomers in the construct (in the amino to carboxy direction) may comprise a methionine at their amino terminal ends (each of which is fused to the carboxy terminus of the previous monomer). For instance, if M is a monomer (without an amino terminal methionine) and mM is a monomer with an amino terminal methionine, the construct may comprise the sequence M-mM, M-mM-mM or M-mM-mM-mM. The presences of these methionines typically results from the expression of the start codons (i.e. ATGs) at the 5' end of the polynucleotides encoding the second or subsequent monomers within the polynucleotide encoding entire construct. The first monomer in the construct (in the amino to carboxy direction) may also comprise a methionine (e.g. mM-mM, mM-mM-mM or mM-mM-mM-mM).

The two or more monomers may be genetically fused directly together. The monomers are preferably genetically fused using a linker. The linker may be designed to constrain the mobility of the monomers. Preferred linkers are amino acid sequences (i.e. peptide linkers). Any of the peptide linkers discussed above may be used.

In another preferred embodiment, the monomers are chemically fused. Two monomers are chemically fused if the two parts are chemically attached, for instance via a chemical crosslinker. Any of the chemical crosslinkers discussed above may be used. The linker may be attached to one or more cysteine residues introduced into a mutant monomer of the invention. Alternatively, the linker may be attached to a terminus of one of the monomers in the construct.

If a construct contains different monomers, crosslinkage of monomers to themselves may be prevented by keeping the concentration of linker in a vast excess of the monomers. Alternatively, a "lock and key" arrangement may be used in which two linkers are used. Only one end of each linker may react together to form a longer linker and the other ends of the linker each react with a different monomers. Such linkers are described in International Application No. PCT/GB10/000132 (published as WO 2010/086602).

Polynucleotides

The present invention also provides polynucleotide sequences which encode a mutant monomer of the invention. The mutant monomer may be any of those discussed above. The polynucleotide sequence preferably comprises a sequence at least 50%, 60%, 70%, 80%, 90% or 95% homologous based on nucleotide identity to the sequence of SEQ ID NO: 1 over the entire sequence. There may be at least 80%, for example at least 85%, 90% or 95% nucleotide identity over a stretch of 300 or more, for example 375, 450, 525 or 600 or more, contiguous nucleotides ("hard homology"). Homology may be calculated as described above. The polynucleotide sequence may comprise a sequence that differs from SEQ ID NO: 1 on the basis of the degeneracy of the genetic code.

The present invention also provides polynucleotide sequences which encode any of the genetically fused constructs of the invention. The polynucleotide preferably comprises two or more variants of the sequence shown in SEQ ID NO: 1. The polynucleotide sequence preferably comprises two or more sequences having at least 50%, 60%, 70%, 80%, 90% or 95% homology to SEQ ID NO: 1 based on nucleotide identity over the entire sequence. There may be at least 80%, for example at least 85%, 90% or 95% nucleotide identity over a stretch of 600 or more, for example 750, 900, 1050 or 1200 or more, contiguous nucleotides ("hard homology"). Homology may be calculated as described above.

Polynucleotide sequences may be derived and replicated using standard methods in the art. Chromosomal DNA encoding wild-type CsgG may be extracted from a pore producing organism, such as *Escherichia coli*. The gene encoding the pore subunit may be amplified using PCR involving specific primers. The amplified sequence may then undergo site-directed mutagenesis. Suitable methods of site-directed mutagenesis are known in the art and include, for example, combine chain reaction. Polynucleotides encoding a construct of the invention can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, N.Y.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The expression vector may then be introduced into a suitable host cell. Thus, a mutant monomer or construct of the invention can be produced by inserting a polynucleotide sequence into an expression vector, introducing the vector into a compatible bacterial host cell, and growing the host cell under conditions which bring about expression of the polynucleotide sequence. The recombinantly-expressed monomer or construct may self-assemble into a pore in the host cell membrane. Alternatively, the recombinant pore produced in this manner may be removed from the host cell and inserted into another membrane. When producing pores comprising at least two different monomers or constructs, the different monomers or constructs may be expressed separately in different host cells as described above, removed from the host cells and assembled into a pore in a separate membrane, such as a rabbit cell membrane or a synthetic membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\lambda_L$ promoter is typically used.

The host cell typically expresses the monomer or construct at a high level. Host cells transformed with a polynucleotide sequence will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter. In addition to the conditions listed above any of the methods cited in Cao et al, 2014, PNAS, Structure of the nonameric bacterial amyloid secretion channel, doi-1411942111 and Goyal et al, 2014, Nature, 516, 250-253 structural and mechanistic insights into the bacterial amyloid secretion channel CsgG may be used to express the CsgG proteins.

The invention also comprises a method of producing a mutant monomer of the invention or a construct of the invention. The method comprises expressing a polynucleotide of the invention in a suitable host cell. The polynucleotide is preferably part of a vector and is preferably operably linked to a promoter.

Pores

The invention also provides various pores. The pores of the invention are ideal for characterising, such as sequencing, polynucleotide sequences because they can discriminate between different nucleotides with a high degree of sensitivity. The pores can surprisingly distinguish between the four nucleotides in DNA and RNA. The pores of the invention can even distinguish between methylated and unmethylated nucleotides. The base resolution of pores of the invention is surprisingly high. The pores show almost complete separation of all four DNA nucleotides. The pores further discriminate between deoxycytidine monophosphate (dCMP) and methyl-dCMP based on the dwell time in the pore and the current flowing through the pore.

The pores of the invention can also discriminate between different nucleotides under a range of conditions. In particular, the pores will discriminate between nucleotides under conditions that are favourable to the characterising, such as sequencing, of nucleic acids. The extent to which the pores of the invention can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The pores of the invention may also be used to identify polynucleotide polymers from the interaction with one or more monomers rather than on a nucleotide by nucleotide basis.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as triblock copolymers, lipids or other pores. Alternatively, a pore of the invention may be present in a membrane. Suitable membranes are discussed below.

A pore of the invention may be present as an individual or single pore. Alternatively, a pore of the invention may be present in a homologous or heterologous population of two or more pores.

Homo-Oligomeric Pores

The invention also provides a homo-oligomeric pore derived from CsgG comprising identical mutant monomers of the invention. The homo-oligomeric pore may comprise any of the mutants of the invention. The homo-oligomeric pore of the invention is ideal for characterising, such as sequencing, polynucleotides. The homo-oligomeric pore of the invention may have any of the advantages discussed above.

The homo-oligomeric pore may contain any number of mutant monomers. The pore typically comprises at least 7, at least 8, at least 9 or at least 10 identical mutant monomers, such as 7, 8, 9 or 10 mutant monomers. The pore preferably comprises eight or nine identical mutant monomers. One or more, such as 2, 3, 4, 5, 6, 7, 8, 9 or 10, of the mutant monomers is preferably chemically modified as discussed above.

Methods for making pores are discussed in more detail below.

Hetero-Oligomeric Pores

The invention also provides a hetero-oligomeric pore derived from CsgG comprising at least one mutant monomer of the invention. The hetero-oligomeric pore of the invention is ideal for characterising, such as sequencing, polynucleotides. Hetero-oligomeric pores can be made using methods known in the art (e.g. Protein Sci. 2002 July; 11(7):1813-24).

The hetero-oligomeric pore contains sufficient monomers to form the pore. The monomers may be of any type. The pore typically comprises at least 7, at least 8, at least 9 or at least 10 monomers, such as 7, 8, 9 or 10 monomers. The pore preferably comprises eight or nine monomers.

In a preferred embodiment, all of the monomers (such as 10, 9, 8 or 7 of the monomers) are mutant monomers of the invention and at least one of them differs from the others. In a more preferred embodiment, the pore comprises eight or nine mutant monomers of the invention and at least one of them differs from the others. They may all differ from one another.

The mutant monomers of the invention in the pore are preferably approximately the same length or are the same length. The barrels of the mutant monomers of the invention in the pore are preferably approximately the same length or are the same length. Length may be measured in number of amino acids and/or units of length.

In another preferred embodiment, at least one of the mutant monomers is not a mutant monomer of the invention. In this embodiment, the remaining monomers are preferably mutant monomers of the invention. Hence, the pore may comprise 9, 8, 7, 6, 5, 4, 3, 2 or 1 mutant monomers of the invention. Any number of the monomers in the pore may not be a mutant monomer of the invention. The pore preferably comprises seven or eight mutant monomers of the invention and a monomer which is not a monomer of the invention. The mutant monomers of the invention may be the same or different.

The mutant monomers of the invention in the construct are preferably approximately the same length or are the same length. The barrels of the mutant monomers of the invention in the construct are preferably approximately the same length or are the same length. Length may be measured in number of amino acids and/or units of length.

The pore may comprise one or more monomers which are not mutant monomers of the invention. CsgG monomers which are not mutant monomers of the invention include monomers comprising SEQ ID NO: 2, 3, 4, 5, 6, 7, 26, 27, 28, 29, 30, 31, 32, 33, 34, 35, 36, 37, 38, 39, 40 or 41 or a comparative variant of SEQ ID NO: 2, 3, 4, 5, 6, 7, 26, 27, 28, 29, 30, 31, 32, 33, 34, 35, 36, 37, 38, 39, 40 or 41 in which none of the amino acids/positions discussed above in relation to the invention have been mutated/substituted. A comparative variant of SEQ ID NO: 2, 3, 4, 5, 6, 7, 26, 27, 28, 29, 30, 31, 32, 33, 34, 35, 36, 37, 38, 39, 40 or 41 is typically at least 50% homologous to SEQ ID NO: 2, 3, 4, 5, 6, 7, 26, 27, 28, 29, 30, 31, 32, 33, 34, 35, 36, 37, 38, 39, 40 or 41 over its entire sequence based on amino acid identity. More preferably, the comparative variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2, 3, 4, 5, 6, 7, 26, 27, 28, 29, 30, 31, 32, 33, 34, 35, 36, 37, 38, 39, 40 or 41 over the entire sequence.

In all the embodiments discussed above, one or more, such as 2, 3, 4, 5, 6, 7, 8, 9 or 10, of the mutant monomers is preferably chemically modified as discussed above.

Methods for making pores are discussed in more detail below.

Construct-Containing Pores

The invention also provides a pore comprising at least one construct of the invention. A construct of the invention comprises two or more covalently attached monomers derived from CsgG wherein at least one of the monomers is a mutant monomer of the invention. In other words, a construct must contain more than one monomer. The pore contains sufficient constructs and, if necessary, monomers to form the pore. For instance, an octameric pore may comprise (a) four constructs each comprising two constructs, (b) two constructs each comprising four monomers or (b) one construct comprising two monomers and six monomers that do not form part of a construct. For instance, an nonameric pore may comprise (a) four constructs each comprising two constructs and one monomer that does not form part of a construct, (b) two constructs each comprising four monomers and a monomer that does not form part of a construct or (b) one construct comprising two monomers and seven monomers that do not form part of a construct. Other combinations of constructs and monomers can be envisaged by the skilled person.

At least two of the monomers in the pore are in the form of a construct of the invention. The construct, and hence the pore, comprises at least one mutant monomer of the invention. The pore typically comprises at least 7, at least 8, at least 9 or at least 10 monomers, such as 7, 8, 9 or 10 monomers, in total (at least two of which must be in a construct). The pore preferably comprises eight or nine monomers (at least two of which must be in a construct).

The construct containing pore may be a homo-oligomer (i.e. include identical constructs) or be a hetero-oligomer (i.e. where at least one construct differs from the others).

A pore typically contains (a) one construct comprising two monomers and (b) 5, 6, 7 or 8 monomers. The construct may be any of those discussed above. The monomers may be any of those discussed above, including mutant monomers of the invention, monomers comprising SEQ ID NO: 2, 3, 4, 5, 6, 7, 26, 27, 28, 29, 30, 31, 32, 33, 34, 35, 36, 37, 38, 39, 40 or 41 and mutant monomers comprising a comparative variant of SEQ ID NO: 2, 3, 4, 5, 6, 7, 26, 27, 28, 29, 30, 31, 32, 33, 34, 35, 36, 37, 38, 39, 40 or 41 as discussed above.

Another typical pore comprises more than one construct of the invention, such as two, three or four constructs of the invention. If necessary, such pores further comprise sufficient additional monomers or constructs to form the pore. The additional monomer(s) may be any of those discussed above, including mutant monomers of the invention, monomers comprising SEQ ID NO: 2, 3, 4, 5, 6, 7, 26, 27, 28, 29, 30, 31, 32, 33, 34, 35, 36, 37, 38, 39, 40 or 41 and mutant monomers comprising a comparative variant of SEQ ID NO: 2, 3, 4, 5, 6, 7, 26, 27, 28, 29, 30, 31, 32, 33, 34, 35, 36, 37, 38, 39, 40 or 41 as discussed above. The additional construct(s) may be any of those discussed above or may be a construct comprising two or more covalently attached CsgG monomers each comprising a monomer comprising SEQ ID NO: 2, 3, 4, 5, 6, 7, 26, 27, 28, 29, 30, 31, 32, 33, 34, 35, 36, 37, 38, 39, 40 or 41 or a comparative variant of SEQ ID NO: 2, 3, 4, 5, 6, 7, 26, 27, 28, 29, 30, 31, 32, 33, 34, 35, 36, 37, 38, 39, 40 or 41 as discussed above.

A further pore of the invention comprises only constructs comprising 2 monomers, for example a pore may comprise 4, 5, 6, 7 or 8 constructs comprising 2 monomers. At least one construct is a construct of the invention, i.e. at least one monomer in the at least one construct, and preferably each monomer in the at least one construct, is a mutant monomer of the invention. All of the constructs comprising 2 monomers may be constructs of the invention.

A specific pore according to the invention comprises four constructs of the invention each comprising two monomers, wherein at least one monomer in each construct, and preferably each monomer in each construct, is a mutant monomer of the invention. The constructs may oligomerise into a pore with a structure such that only one monomer of each construct contributes to the channel of the pore. Typically the other monomers of the construct will be on the outside of the channel of the pore. For example, pores of the invention may comprise 7, 8, 9 or 10 constructs comprising 2 monomers where the channel comprises 7, 8, 9 or 10 monomers.

Mutations can be introduced into the construct as described above. The mutations may be alternating, i.e. the mutations are different for each monomer within a two monomer construct and the constructs are assembled as a homo-oligomer resulting in alternating modifications. In other words, monomers comprising MutA and MutB are fused and assembled to form an A-B:A-B:A-B:A-B pore. Alternatively, the mutations may be neighbouring, i.e. identical mutations are introduced into two monomers in a construct and this is then oligomerised with different mutant monomers or constructs. In other words, monomers comprising MutA are fused follow by oligomerisation with MutB-containing monomers to form A-A:B:B:B:B:B.

One or more of the monomers of the invention in a construct-containing pore may be chemically-modified as discussed above.

Analyte Characterisation

The invention provides a method of determining the presence, absence or one or more characteristics of a target analyte. The method involves contacting the target analyte with a pore of the invention such that the target analyte moves with respect to, such as through, the pore and taking one or more measurements as the analyte moves with respect to the pore and thereby determining the presence, absence or one or more characteristics of the analyte. The target analyte may also be called the template analyte or the analyte of interest.

Steps (a) and (b) are preferably carried out with a potential applied across the pore. As discussed in more detail below, the applied potential typically results in the formation of a complex between the pore and a polynucleotide binding protein. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The method is for determining the presence, absence or one or more characteristics of a target analyte. The method may be for determining the presence, absence or one or more characteristics of at least one analyte. The method may concern determining the presence, absence or one or more characteristics of two or more analytes. The method may comprise determining the presence, absence or one or more characteristics of any number of analytes, such as 2, 5, 10, 15, 20, 30, 40, 50, 100 or more analytes. Any number of characteristics of the one or more analytes may be determined, such as 1, 2, 3, 4, 5, 10 or more characteristics.

The target analyte is preferably a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. The method may concern determining the presence, absence or one or more characteristics of two or more analytes of the same type, such as two or more proteins, two or more nucleotides or two or more pharmaceuticals. Alternatively, the method may concern determining the presence, absence or one or more characteristics of two or more analytes of different types, such as one or more proteins, one or more nucleotides and one or more pharmaceuticals.

The target analyte can be secreted from cells. Alternatively, the target analyte can be an analyte that is present inside cells such that the analyte must be extracted from the cells before the invention can be carried out.

The analyte is preferably an amino acid, a peptide, a polypeptides and/or a protein. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are above. For the purposes of the invention, it is to be understood that the target analyte can be modified by any method available in the art.

The protein can be an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, preferably IL-γ, and other cytokines such as TNF-α. The protein may be a bacterial protein, a fungal protein, a virus protein or a parasite-derived protein.

The target analyte is preferably a nucleotide, an oligonucleotide or a polynucleotide. Nucleotides and polynucleotides are discussed below. Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed below, including the abasic and modified nucleotides.

The target analyte, such as a target polynucleotide, may be present in any of the suitable samples discussed below.

The pore is typically present in a membrane as discussed below. The target analyte may be coupled or delivered to the membrane using of the methods discussed below.

Any of the measurements discussed below can be used to determine the presence, absence or one or more characteristics of the target analyte. The method preferably comprises contacting the target analyte with the pore such that the analyte moves with respect to, such as moves through, the pore and measuring the current passing through the pore as the analyte moves with respect to the pore and thereby determining the presence, absence or one or more characteristics of the analyte.

The target analyte is present if the current flows through the pore in a manner specific for the analyte (i.e. if a distinctive current associated with the analyte is detected flowing through the pore). The analyte is absent if the current does not flow through the pore in a manner specific for the nucleotide. Control experiments can be carried out in the presence of the analyte to determine the way in which if affects the current flowing through the pore.

The invention can be used to differentiate analytes of similar structure on the basis of the different effects they have on the current passing through a pore. Individual analytes can be identified at the single molecule level from their current amplitude when they interact with the pore. The invention can also be used to determine whether or not a particular analyte is present in a sample. The invention can also be used to measure the concentration of a particular analyte in a sample. Analyte characterisation using pores other than CsgG is known in the art.

Polynucleotide Characterisation

The invention provides a method of characterising a target polynucleotide, such as sequencing a polynucleotide. There are two main strategies for characterising or sequencing polynucleotides using nanopores, namely strand characterisation/sequencing and exonuclease characterisation/sequencing. The method of the invention may concern either method.

In strand sequencing, the DNA is translocated through the nanopore either with or against an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

In one embodiment, the method of characterising a target polynucleotide involves contacting the target sequence with a pore of the invention and a helicase enzyme. Any helicase may be used in the method. Suitable helicases are discussed below. Helicases may work in two modes with respect to the pore. First, the method is preferably carried out using a helicase such that it controls movement of the target sequence through the pore with the field resulting from the applied voltage. In this mode the 5' end of the DNA is first captured in the pore, and the enzyme controls movement of the DNA into the pore such that the target sequence is passed through the pore with the field until it finally translocates through to the trans side of the bilayer. Alternatively, the method is preferably carried out such that a helicase enzyme controls movement of the target sequence through the pore against the field resulting from the applied voltage. In this mode the 3' end of the DNA is first captured in the pore, and the enzyme controls movement of the DNA through the pore such that the target sequence is pulled out of the pore against the applied field until finally ejected back to the cis side of the bilayer.

In exonuclease sequencing, an exonuclease releases individual nucleotides from one end of the target polynucleotide and these individual nucleotides are identified as discussed below. In another embodiment, the method of characterising a target polynucleotide involves contacting the target sequence with a pore and an exonuclease enzyme. Any of the exonuclease enzymes discussed below may be used in the method. The enzyme may be covalently attached to the pore as discussed below.

Exonucleases are enzymes that typically latch onto one end of a polynucleotide and digest the sequence one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method involves contacting the polynucleotide with the exonuclease so that the nucleotides are digested from the end of the polynucleotide at a rate that allows characterisation or identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease functions is typically slower than the optimal rate of a wild-type exonuclease. A suitable rate of activity of the exonuclease in the method of the invention involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used in accordance with the invention.

In the strand characterisation embodiment, the method comprises contacting the polynucleotide with a pore of the invention such that the polynucleotide moves with respect to, such as through, the pore and taking one or more measurements as the polynucleotide moves with respect to the pore, wherein the measurements are indicative of one or more characteristics of the polynucleotide, and thereby characterising the target polynucleotide.

In the exonucleotide characterisation embodiment, the method comprises contacting the polynucleotide with a pore of the invention and an exonuclease such that the exonuclease digests individual nucleotides from one end of the target polynucleotide and the individual nucleotides move with respect to, such as through, the pore and taking one or more measurements as the individual nucleotides move with respect to the pore, wherein the measurements are indicative of one or more characteristics of the individual nucleotides, and thereby characterising the target polynucleotide.

An individual nucleotide is a single nucleotide. An individual nucleotide is one which is not bound to another nucleotide or polynucleotide by a nucleotide bond. A nucleotide bond involves one of the phosphate groups of a nucleotide being bound to the sugar group of another nucleotide. An individual nucleotide is typically one which is not bound by a nucleotide bond to another polynucleotide of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand. The nucleotide can be any of those discussed below.

The individual nucleotides may interact with the pore in any manner and at any site. The nucleotides preferably reversibly bind to the pore via or in conjunction with an adaptor as discussed above. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane.

During the interaction between the individual nucleotide and the pore, the nucleotide typically affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide in the sample or determine whether a particular nucleotide is present in the sample. The frequency at which the current flowing through the pore is affected in a manner indicative of a particular nucleotide can be used to determine the concentration of that nucleotide in the sample. The ratio of different nucleotides within a sample can also be calculated. For instance, the ratio of dCMP to methyl-dCMP can be calculated.

The method involves measuring one or more characteristics of the target polynucleotide. The target polynucleotide may also be called the template polynucleotide or the polynucleotide of interest.

This embodiment also uses a pore of the invention. Any of the pores and embodiments discussed above with reference to the target analyte may be used.

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. The polynucleotide is preferably single stranded. Single stranded polynucleotide characterization is referred to as 1D in the Examples. At least a portion of the polynucleotide may be double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety. Bridged nucleic acids (BNAs) are modified RNA nucleotides. They may also be called constrained or inaccessible RNA. BNA monomers can contain a five-membered, six-membered or even a seven-membered bridged structure with a "fixed" C3'-endo sugar puckering. The bridge is synthetically incorporated at the 2', 4'-position of the ribose to produce a 2', 4'-BNA monomer.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Any number of polynucleotides can be investigated. For instance, the method of the invention may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide.

The polynucleotide can be naturally occurring or artificial. For instance, the method may be used to verify the sequence of a manufactured oligonucleotide. The method is typically carried out in vitro.

Sample

The polynucleotide is typically present in any suitable sample. The invention is typically carried out on a sample that is known to contain or suspected to contain the polynucleotide. Alternatively, the invention may be carried out on a sample to confirm the identity of a polynucleotide whose presence in the sample is known or expected.

The sample may be a biological sample. The invention may be carried out in vitro using a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum.

Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The may be measured immediately upon being taken. The sample may also be typically stored prior to assay, preferably below −70° C.

Characterisation

The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iiii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

The target polynucleotide is contacted with a pore of the invention. The pore is typically present in a membrane. Suitable membranes are discussed below. The method may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The method may be carried out using the apparatus described in International Application No. PCT/GB08/000562 (WO 2008/102120).

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The method may involve measuring the current passing through the pore as the polynucleotide moves with respect to the pore. Therefore the apparatus used in the method may also comprise an electrical circuit capable of applying a potential and measuring an electrical signal across the membrane and pore. The methods may be carried out using a patch clamp or a voltage clamp. The methods preferably involve the use of a voltage clamp.

The method of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The method is typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The method is typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The method may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Polynucleotide Binding Protein

The strand characterisation method preferably comprises contacting the polynucleotide with a polynucleotide binding protein such that the protein controls the movement of the polynucleotide with respect to, such as through, the pore.

More preferably, the method comprises (a) contacting the polynucleotide with a pore of the invention and a polynucleotide binding protein such that the protein controls the movement of the polynucleotide with respect to, such as through, the pore and (b) taking one or more measurements as the polynucleotide moves with respect to the pore, wherein the measurements are indicative of one or more characteristics of the polynucleotide, and thereby characterising the polynucleotide.

More preferably, the method comprises (a) contacting the polynucleotide with a pore of the invention and a polynucleotide binding protein such that the protein controls the movement of the polynucleotide with respect to, such as through, the pore and (b) measuring the current through the pore as the polynucleotide moves with respect to the pore, wherein the current is indicative of one or more characteristics of the polynucleotide, and thereby characterising the polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The protein may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17), TatD exonuclease and variants thereof. Three subunits comprising the sequence shown in SEQ ID NO: 15 or a variant thereof interact to form a trimer exonuclease. These exonucleases can also be used in the exonuclease method of the invention. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Tga (SEQ ID NO: 20), Hel308 Mhu (SEQ ID NO: 21), TraI Eco (SEQ ID NO: 22), XPD Mbu (SEQ ID NO: 23) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736.

The helicase preferably comprises the sequence shown in SEQ ID NO: 25 (Trwc Cba) or as variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 24 comprises (a) E94C and A360C or (b) E94C, A360C, C109A and C136A and then optionally (ΔM1)G1G2 (i.e. deletion of M1 and then addition G1 and G2).

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

A variant of SEQ ID NOs: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane.

Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Helicase(s) and Molecular Brake(s)

In a preferred embodiment, the method comprises:
(a) providing the polynucleotide with one or more helicases and one or more molecular brakes attached to the polynucleotide;
(b) contacting the polynucleotide with a pore of the invention and applying a potential across the pore such that the one or more helicases and the one or more molecular brakes are brought together and both control the movement of the polynucleotide with respect to, such as through, the pore;
(c) taking one or more measurements as the polynucleotide moves with respect to the pore wherein the measurements are indicative of one or more characteristics of the polynucleotide and thereby characterising the polynucleotide.

This type of method is discussed in detail in the International Application PCT/GB2014/052737

The one or more helicases may be any of those discussed above. The one or more molecular brakes may be any compound or molecule which binds to the polynucleotide and slows the movement of the polynucleotide through the pore. The one or more molecular brakes preferably comprise one or more compounds which bind to the polynucleotide. The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD).

The one or more molecular brakes are preferably one or more single stranded binding proteins (SSB). The one or more molecular brakes are more preferably a single-stranded binding protein (SSB) comprising a carboxy-terminal (C-terminal) region which does not have a net negative charge or (ii) a modified SSB comprising one or more modifications in its C-terminal region which decreases the net negative charge of the C-terminal region. The one or more molecular brakes are most preferably one of the SSBs disclosed in International Application No. PCT/GB2013/051924 (published as WO 2014/013259).

The one or more molecular brakes are preferably one or more polynucleotide binding proteins. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase (SEQ ID NO: 8) which act as molecular brakes are disclosed in U.S. Pat. No. 5,576,204. The one or more molecular brakes are preferably derived from a helicase.

Any number of molecular brakes derived from a helicase may be used. For instance, 1, 2, 3, 4, 5, 6, 7, 8, 9, 10 or more helicases may be used as molecular brakes. If two or more helicases are used as molecular brakes, the two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. The one or more molecular brakes derived from helicases are preferably modified to reduce the size of an opening in the polynucleotide binding domain through which in at least one conformational state the polynucleotide can unbind from the helicase. This is disclosed in WO 2014/013260.

Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

If the one or more helicases are used in the active mode (i.e. when the one or more helicases are provided with all the necessary components to facilitate movement, e.g. ATP and $Mg^{2+}$), the one or more molecular brakes are preferably (a) used in an inactive mode (i.e. are used in the absence of the necessary components to facilitate movement or are incapable of active movement), (b) used in an active mode where the one or more molecular brakes move in the opposite direction to the one or more helicases or (c) used in an active mode where the one or more molecular brakes move in the same direction as the one or more helicases and more slowly than the one or more helicases.

If the one or more helicases are used in the inactive mode (i.e. when the one or more helicases are not provided with all the necessary components to facilitate movement, e.g. ATP and $Mg^{2+}$ or are incapable of active movement), the one or more molecular brakes are preferably (a) used in an inactive mode (i.e. are used in the absence of the necessary components to facilitate movement or are incapable of active movement) or (b) used in an active mode where the one or more molecular brakes move along the polynucleotide in the same direction as the polynucleotide through the pore.

The one or more helicases and one or more molecular brakes may be attached to the polynucleotide at any positions so that they are brought together and both control the movement of the polynucleotide through the pore. The one or more helicases and one or more molecular brakes are at least one nucleotide apart, such as at least 5, at least 10, at least 50, at least 100, at least 500, at least 1000, at least 5000, at least 10,000, at least 50,000 nucleotides or more apart. If the method concerns characterising a double stranded polynucleotide provided with a Y adaptor at one end and a hairpin loop adaptor at the other end, the one or more helicases are preferably attached to the Y adaptor and the one or more molecular brakes are preferably attached to the hairpin loop adaptor. In this embodiment, the one or more molecular brakes are preferably one or more helicases that are modified such that they bind the polynucleotide but do not function as a helicase. The one or more helicases attached to the Y adaptor are preferably stalled at a spacer as discussed in more detail below. The one or more molecular brakes attach to the hairpin loop adaptor are preferably not stalled at a spacer. The one or more helicases and the one or more molecular brakes are preferably brought together when the one or more helicases reach the hairpin loop. The one or more helicases may be attached to the Y adaptor before the Y adaptor is attached to the polynucleotide or after the Y adaptor is attached to the polynucleotide. The one or more molecular brakes may be attached to the hairpin loop adaptor before the hairpin loop adaptor is attached to the polynucleotide or after the hairpin loop adaptor is attached to the polynucleotide.

The one or more helicases and the one or more molecular brakes are preferably not attached to one another. The one or more helicases and the one or more molecular brakes are more preferably not covalently attached to one another. The one or more helicases and the one or more molecular brakes are preferably not attached as described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

Spacers

The one or more helicases may be stalled at one or more spacers as discussed in International Application No. PCT/GB2014/050175. Any configuration of one or more helicases and one or more spacers disclosed in the International Application may be used in this invention.

When a part of the polynucleotide enters the pore and moves through the pore along the field resulting from the applied potential, the one or more helicases are moved past the spacer by the pore as the polynucleotide moves through the pore. This is because the polynucleotide (including the one or more spacers) moves through the pore and the one or more helicases remain on top of the pore.

The one or more spacers are preferably part of the polynucleotide, for instance they interrupt(s) the polynucleotide sequence. The one or more spacers are preferably not part of one or more blocking molecules, such as speed bumps, hybridised to the polynucleotide.

There may be any number of spacers in the polynucleotide, such as 1, 2, 3, 4, 5, 6, 7, 8, 9, 10 or more spacers. There are preferably two, four or six spacers in the polynucleotide. There may be one or more spacers in different regions of the polynucleotide, such as one or more spacers in the Y adaptor and/or hairpin loop adaptor.

The one or more spacers each provides an energy barrier which the one or more helicases cannot overcome even in the active mode. The one or more spacers may stall the one or more helicases by reducing the traction of the helicase (for instance by removing the bases from the nucleotides in the polynucleotide) or physically blocking movement of the one or more helicases (for instance using a bulky chemical group).

The one or more spacers may comprise any molecule or combination of molecules that stalls the one or more helicases. The one or more spacers may comprise any molecule or combination of molecules that prevents the one or more helicases from moving along the polynucleotide. It is straightforward to determine whether or not the one or more helicases are stalled at one or more spacers in the absence of a transmembrane pore and an applied potential. For instance, the ability of a helicase to move past a spacer and displace a complementary strand of DNA can be measured by PAGE.

The one or more spacers typically comprise a linear molecule, such as a polymer. The one or more spacers typically have a different structure from the polynucleotide. For instance, if the polynucleotide is DNA, the one or more spacers are typically not DNA. In particular, if the polynucleotide is deoxyribonucleic acid (DNA) or ribonucleic acid (RNA), the one or more spacers preferably comprise peptide nucleic acid (PNA), glycerol nucleic acid (GNA), threose nucleic acid (TNA), locked nucleic acid (LNA) or a synthetic polymer with nucleotide side chains. The one or more spacers may comprise one or more nucleotides in the opposite direction from the polynucleotide. For instance, the one or more spacers may comprise one or more nucleotides in the 3' to 5' direction when the polynucleotide is in the 5' to 3' direction. The nucleotides may be any of those discussed above.

The one or more spacers preferably comprises one or more nitroindoles, such as one or more 5-nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT® (Integrated DNA Technologies®).

The one or more spacers may contain any number of these groups. For instance, for 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, the one or more spacers preferably comprise 2, 3, 4, 5, 6, 7, 8, 9, 10, 11, 12 or more. The one or more spacers preferably comprise 2, 3, 4, 5, 6, 7, 8 or more iSp9 groups. The one or more spacers preferably comprise 2, 3, 4, 5 or 6 or more iSp18 groups. The most preferred spacer is four iSp18 groups.

The polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The one or more spacers preferably comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into polynucleotides by removing the nucleobases from one or more adjacent nucleotides. For instance, polynucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polynucleotides may be modified to include uracil and the nucleobases removed with Uracil-DNA Glycosylase (UDG). In one embodiment, the one or more spacers do not comprise any abasic nucleotides.

The one or more helicases may be stalled by (i.e. before) or on each linear molecule spacers. If linear molecule spacers are used, the polynucleotide is preferably provided with a double stranded region of polynucleotide adjacent to the end of each spacer past which the one or more helicases are to be moved. The double stranded region typically helps to stall the one or more helicases on the adjacent spacer. The presence of the double stranded region(s) is particularly preferred if the method is carried out at a salt concentration of about 100 mM or lower. Each double stranded region is typically at least 10, such as at least 12, nucleotides in length. If the polynucleotide used in the invention is single stranded, a double stranded region may be formed by hybridising a shorter polynucleotide to a region adjacent to a spacer. The shorter polynucleotide is typically formed from the same nucleotides as the polynucleotide, but may be formed from different nucleotides. For instance, the shorter polynucleotide may be formed from LNA.

If linear molecule spacers are used, the polynucleotide is preferably provided with a blocking molecule at the end of each spacer opposite to the end past which the one or more helicases are to be moved. This can help to ensure that the one or more helicases remain stalled on each spacer. It may also help retain the one or more helicases on the polynucleotide in the case that it/they diffuse(s) off in solution. The blocking molecule may be any of the chemical groups discussed below which physically cause the one or more helicases to stall. The blocking molecule may be a double stranded region of polynucleotide.

The one or more spacers preferably comprise one or more chemical groups which physically cause the one or more helicases to stall. The one or more chemical groups are preferably one or more pendant chemical groups. The one or more chemical groups may be attached to one or more nucleobases in the polynucleotide. The one or more chemical groups may be attached to the polynucleotide backbone. Any number of these chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzylcyclooctyne groups.

Different spacers in the polynucleotide may comprise different stalling molecules. For instance, one spacer may comprise one of the linear molecules discussed above and another spacer may comprise one or more chemical groups which physically cause the one or more helicases to stall. A spacer may comprise any of the linear molecules discussed above and one or more chemical groups which physically cause the one or more helicases to stall, such as one or more abasics and a fluorophore.

Suitable spacers can be designed depending on the type of polynucleotide and the conditions under which the method of the invention is carried out. Most helicases bind and move along DNA and so may be stalled using anything that is not DNA. Suitable molecules are discussed above.

The method of the invention is preferably carried out in the presence of free nucleotides and/or the presence of a helicase cofactor. This is discussed in more detail below. In the absence of the transmembrane pore and an applied potential, the one or more spacers are preferably capable of stalling the one or more helicases in the presence of free nucleotides and/or the presence of a helicase cofactor.

If the method of the invention is carried out in the presence of free nucleotides and a helicase cofactor as discussed below (such that the one of more helicases are in the active mode), one or more longer spacers are typically used to ensure that the one or more helicases are stalled on the polynucleotide before they are contacted with the transmembrane pore and a potential is applied. One or more shorter spacers may be used in the absence of free nucleotides and a helicase cofactor (such that the one or more helicases are in the inactive mode).

The salt concentration also affects the ability of the one or more spacers to stall the one or more helicases. In the absence of the transmembrane pore and an applied potential, the one or more spacers are preferably capable of stalling the one or more helicases at a salt concentration of about 100 mM or lower. The higher the salt concentration used in the method of the invention, the shorter the one or more spacers that are typically used and vice versa.

Preferred combinations of features are shown in Table 4 below.

TABLE 4

| Poly-nucleotide | Spacer composition* | Spacer length (i.e. number of *) | Salt [ ] | Free nucleotides? | Helicase cofactor? |
| --- | --- | --- | --- | --- | --- |
| DNA | iSpC3 | 4 | 1M | Yes | Yes |
| DNA | iSp18 | 4 | 100-1000 mM | Yes | Yes |
| DNA | iSp18 | 6 | <100-1000 mM | Yes | Yes |
| DNA | iSp18 | 2 | 1M | Yes | Yes |
| DNA | iSpC3 | 12 | <100-1000 mM | Yes | Yes |
| DNA | iSpC3 | 20 | <100-1000 mM | Yes | Yes |
| DNA | iSp9 | 6 | 100-1000 mM | Yes | Yes |
| DNA | idSp | 4 | 1M | Yes | Yes |

The method may concern moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths in the third column of Table 4 above may be increased 1.5 fold, 2 fold, 2.5 fold or 3 fold.

Membrane

The pore of the invention may be present in a membrane. In the methods of the invention, the polynucleotide is typically contacted with the pore of the invention in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in International Application No. PCT/GB2013/052766 or PCT/GB2013/052767.

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s-1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconionic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In another preferred embodiment, the membrane comprises a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647). If the membrane comprises a solid state layer, the pore is typically present in an amphiphilic membrane or layer contained within the solid state layer, for instance within a hole, well, gap, channel, trench or slit within the solid state layer. The skilled person can prepare suitable solid state/amphiphilic hybrid systems. Suitable systems are disclosed in WO 2009/020682 and WO 2012/005857. Any of the amphiphilic membranes or layers discussed above may be used.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Coupling

The polynucleotide is preferably coupled to the membrane comprising the pore. The method may comprise coupling the polynucleotide to the membrane comprising the pore. The polynucleotide is preferably coupled to the membrane using one or more anchors. The polynucleotide may be coupled to the membrane using any known method.

Each anchor comprises a group which couples (or binds) to the polynucleotide and a group which couples (or binds) to the membrane. Each anchor may covalently couple (or bind) to the polynucleotide and/or the membrane. If a Y adaptor and/or a hairpin loop adaptors are used, the polynucleotide is preferably coupled to the membrane using the adaptor(s).

The polynucleotide may be coupled to the membrane using any number of anchors, such as 2, 3, 4 or more anchors. For instance, a polynucleotide may be coupled to the membrane using two anchors each of which separately couples (or binds) to both the polynucleotide and membrane.

The one or more anchors may comprise the one or more helicases and/or the one or more molecular brakes.

If the membrane is an amphiphilic layer, such as a copolymer membrane or a lipid bilayer, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors.

Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The one or more anchors or one or more linkers may comprise a component that can be cut to broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane or may be used to couple (or bind) to the polynucleotide. This is discussed in more detail below.

Crosslinkage of polynucleotides can be avoided using a "lock and key" arrangement. Only one end of each linker may react together to form a longer linker and the other ends of the linker each react with the polynucleotide or membrane respectively. Such linkers are described in International Application No. PCT/GB10/000132 (published as WO 2010/086602).

The use of a linker is preferred in the sequencing embodiments discussed below. If a polynucleotide is permanently coupled directly to the membrane in the sense that it does not uncouple when interacting with the pore (i.e. does not uncouple in step (b) or (e)), then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore.

For certain applications, such as aptamer detection, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 5 below.

TABLE 5

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPTS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other polynucleotide. The Examples below describes how a polynucleotide can be coupled to a membrane using streptavidin/biotin and streptavidin/desthiobiotin. It may also be possible that anchors may be directly added to polynucleotides using terminal transferase with suitably modified nucleotides (e.g. cholesterol or palmitate).

The one or more anchors preferably couple the polynucleotide to the membrane via hybridisation. Hybridisation in the one or more anchors allows coupling in a transient manner as discussed above. The hybridisation may be present in any part of the one or more anchors, such as between the one or more anchors and the polynucleotide, within the one or more anchors or between the one or more anchors and the membrane. For instance, a linker may comprise two or more polynucleotides, such as 3, 4 or 5 polynucleotides, hybridised together. The one or more anchors may hybridise to the polynucleotide. The one or more anchors may hybridise directly to the polynucleotide or directly to a Y adaptor and/or leader sequence attached to the polynucleotide or directly to a hairpin loop adaptor attached to the polynucleotide (as discussed below). Alternatively, the one or more anchors may be hybridised to one or more, such as 2 or 3, intermediate polynucleotides (or "splints") which are hybridised to the polynucleotide, to a Y adaptor and/or leader sequence attached to the polynucleotide or to a hairpin loop adaptor attached to the polynucleotide (as discussed below).

The one or more anchors may comprise a single stranded or double stranded polynucleotide. One part of the anchor may be ligated to a single stranded or double stranded polynucleotide. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the a double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and E. coli Poly(A) polymerase). By substituting ATP in the reaction for a modified nucleotide triphosphate then anchors, such as a cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalise the polynucleotide. This can be achieved by coupling the one or more anchors, such as a polynucleotide binding protein or a chemical group, to the membrane and allowing the one or more anchors to interact with the polynucleotide or by functionalising the membrane. The one or more anchors may be coupled to the membrane by any of the methods described herein. In particular, the one or more anchors may comprise one or more linkers, such as maleimide functionalised linkers.

In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, E. coli single stranded binding protein, P5 single stranded binding protein, T4 gp32 single stranded binding protein, the TOPO V dsDNA binding region, human histone proteins, E. coli HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the polynucleotide before contacting with the membrane, but the one or more anchors may be contacted with the membrane and subsequently contacted with the polynucleotide.

In another aspect the polynucleotide may be functionalised, using methods described above, so that it can be recognised by a specific binding group. Specifically the polynucleotide may be functionalised with a ligand such as biotin (for binding to streptavidin), amylose (for binding to maltose binding protein or a fusion protein), Ni-NTA (for binding to poly-histidine or poly-histidine tagged proteins) or a peptides (such as an antigen).

According to a preferred embodiment, the one or more anchors may be used to couple a polynucleotide to the membrane when the polynucleotide is attached to a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Double Stranded Polynucleotide

The polynucleotide may be double stranded. If the polynucleotide is double stranded, the method preferably further comprises before the contacting step ligating a bridging moiety, such as a hairpin loop, to one end of the polynucleotide. The two strands of the polynucleotide may then be separated as or before the polynucleotide is contacted with the pore in accordance with the invention. The two strands may be separated as the polynucleotide movement through the pore is controlled by a polynucleotide binding protein, such as a helicase, or molecular brake.

Linking and interrogating both strands on a double stranded construct in this way increases the efficiency and accuracy of characterisation.

The bridging moiety is capable of linking the two strands of the target polynucleotide. The bridging moiety typically covalently links the two strands of the target polynucleotide. The bridging moiety can be anything that is capable of linking the two strands of the target polynucleotide, provided that the bridging moiety does not interfere with movement of the single stranded polynucleotide through the transmembrane pore.

The bridging moiety may be linked to the target polynucleotide by any suitable means known in the art. The bridging moiety may be synthesised separately and chemically attached or enzymatically ligated to the target polynucleotide. Alternatively, the bridging moiety may be generated in the processing of the target polynucleotide.

The bridging moiety is linked to the target polynucleotide at or near one end of the target polynucleotide. The bridging moiety is preferably linked to the target polynucleotide within 10 nucleotides of the end of the target polynucleotide Suitable bridging moieties include, but are not limited to a polymeric linker, a chemical linker, a polynucleotide or a polypeptide. Preferably, the bridging moiety comprises DNA, RNA, modified DNA (such as abasic DNA), RNA, PNA, LNA or PEG. The bridging moiety is more preferably DNA or RNA.

The bridging moiety is most preferably a hairpin loop or a hairpin loop adaptor. Suitable hairpin adaptors can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin adaptor may be ligated to either end of the first and/or second polynucleotide, i.e. the 5' or the 3' end. The hairpin adaptor may be ligated to the first and/or second polynucleotide using any method known in the art. The hairpin adaptor may be ligated using a ligase, such as T4 DNA ligase, E. coli DNA ligase, Taq DNA ligase, Tma DNA ligase and 9° N DNA ligase.

The two strands of the polynucleotide may be separated using any method known in the art. For instance, they may be separated by a polynucleotide binding protein or using conditions which favour dehybridisation (examples of conditions which favour dehybridisation include, but are not limited to, high temperature, high pH and the addition of agents that can disrupt hydrogen bonding or base pairing, such as formamide and urea).

The hairpin adaptor preferably comprises a selectable binding moiety. This allows the first and/or second polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The hairpin adaptor and/or the selectable binding moiety may comprise a region that can be cut, nicked, cleaved or hydrolysed. Such a region can be designed to allow the first and/or second polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The double stranded target polynucleotide preferably comprises a leader sequence at the opposite end of the bridging moiety, such as a hairpin loop or hairpin loop adaptor. Leader sequences are discussed in more detail below.

Round the Corner Sequencing

In a preferred embodiment, a target double stranded polynucleotide is provided with a bridging moiety, such as a hairpin loop or hairpin loop adaptor, at one end and the method comprises contacting the polynucleotide with the pore such that both strands of the polynucleotide move through the pore and taking one or more measurements as the both strands of the polynucleotide move with respect to the pore wherein the measurements are indicative of one or more characteristics of the strands of the polynucleotide and thereby characterising the target double stranded polynucleotide. In another preferred embodiment, a target double stranded polynucleotide is provided with a bridging moiety, such as a hairpin loop or hairpin loop adaptor, at one end and the method comprises contacting the polynucleotide with the pore and exonuclease such that both strands of the polynucleotide are digested to form individual nucleotides. Any of the embodiments discussed above equally apply to this embodiment.

Leader Sequence

Before the contacting step in the strand characterisation/sequencing method, the method preferably comprises attaching to the polynucleotide a leader sequence which preferentially threads into the pore. The leader sequence facilitates the method of the invention. The leader sequence is designed to preferentially thread into the pore and thereby facilitate the movement of polynucleotide through the pore. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

The leader sequence is preferably part of a Y adaptor as defined below.

Double Coupling

The method of the invention may involve double coupling of a double stranded polynucleotide. In a preferred embodiment, the method of the invention comprises:

(a) providing the double stranded polynucleotide with a Y adaptor at one end and a bridging moiety adaptor, such as a hairpin loop adaptor, at the other end, wherein the Y adaptor comprises one or more first anchors for coupling the polynucleotide to the membrane, wherein the bridging moiety adaptor comprises one or more second anchors for coupling the polynucleotide to the membrane and wherein the strength of coupling of the bridging moiety adaptor to the membrane is greater than the strength of coupling of the Y adaptor to the membrane;

(b) contacting the polynucleotide provided in step (a) with a pore the invention such that the polynucleotide moves with respect to, such as through, the pore; and (c) taking one or more measurements as the polynucleotide moves with respect to the pore, wherein the measurements are indicative of one or more characteristics of the polynucleotide, and thereby characterising the target polynucleotide.

This type of method is discussed in detail in the UK Application No. 1406147.7.

The double stranded polynucleotide is provided with a Y adaptor at one end and a bridging moiety adaptor at the other end. The Y adaptor and/or the bridging moiety adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor comprises the one or more first anchors. Anchors are discussed in more detail above.

The Y adaptor preferably comprises a leader sequence which preferentially threads into the pore. This is discussed above.

The bridging moiety adaptor preferably comprises a selectable binding moiety as discussed above. The bridging moiety adaptor and/or the selectable binding moiety may comprise a region that can be cut, nicked, cleaved or hydrolysed as discussed above.

If one or more helicases and one or more molecular brakes are used as discussed above, the Y adaptor preferably comprises the one or more helicases and the bridging moiety adaptor preferably comprises the one or more molecular brakes.

The Y adaptor and/or the bridging moiety adaptor may be ligated to the polynucleotide using any method known in the art. One or both of the adaptors may be ligated using a ligase, such as T4 DNA ligase, E. coli DNA ligase, Taq DNA ligase, Tma DNA ligase and 9° N DNA ligase. Alternatively, the adaptors may be added to the polynucleotide using the methods of the invention discussed below.

In a preferred embodiment, step a) of the method comprises modifying the double stranded polynucleotide so that it comprises the Y adaptor at one end and the bridging moiety adaptor at the other end. Any manner of modification can be used. The method preferably comprises modifying the double stranded polynucleotide in accordance with the invention. This is discussed in more detail below. The methods of modification and characterisation may be combined in any way.

The strength of coupling (or binding) of the bridging moiety adaptor to the membrane is greater than the strength of coupling (or binding) of the Y adaptor to the membrane. This can be measured in any way. A suitable method for measuring the strength of coupling (or binding) is disclosed in the Examples of the UK Application No. 1406147.7.

The strength of coupling (or binding) of the bridging moiety adaptor is preferably at least 1.5 times the strength of coupling (or binding) of the Y adaptor, such as at least twice, at least three times, at least four times, at least five or at least ten times the strength of coupling (or binding) of the anchor adaptor. The affinity constant (Kd) of the bridging moiety adaptor for the membrane is preferably at least 1.5 times the affinity constant of the Y adaptor, such as at least twice, at least three times, at least four times, at least five or at least ten times the strength of coupling of the Y adaptor.

There are several ways in which the bridging moiety adaptor couples (or binds) more strongly to the membrane than the Y adaptor. For instance, the bridging moiety adaptor may comprise more anchors than the Y adaptor. For instance, the bridging moiety adaptor may comprise 2, 3 or more second anchors whereas the Y adaptor may comprise one first anchor.

The strength of coupling (or binding) of the one or more second anchors to the membrane may be greater than the strength of coupling (or binding) of the one or more first anchors to the membrane. The strength of coupling (or binding) of the one or more second anchors to the bridging moiety adaptor may be greater than the strength of coupling (or binding) of the one or more first anchors to the Y adaptor. The one or more first anchors and the one or more second anchors may be attached to their respective adaptors via hybridisation and the strength of hybridisation is greater in the one or more second anchors than in the one or more first anchors. Any combination of these embodiments may also be used in the invention. Strength of coupling (or binding) may be measure using known techniques in the art.

The one or more second anchors preferably comprise one or more groups which couple(s) (or bind(s)) to the membrane with a greater strength than the one or more groups in the one or more first anchors which couple(s) (or bind(s)) to the membrane. In preferred embodiments, the bridging moiety adaptor/one or more second anchors couple (or bind) to the membrane using cholesterol and the Y adaptor/one or more first anchors couple (or bind) to the membrane using palmitate. Cholesterol binds to triblock copolymer membranes and lipid membranes more strongly than palmitate. In an alternative embodiment, the bridging moiety adaptor/one or more second anchors couple (or bind) to the membrane using a mono-acyl species, such as palmitate, and the Y adaptor/one or more first anchors couple (or bind) to the membrane using a diacyl species, such as dipalmitoylphosphatidylcholine.

Adding Hairpin Loops and Leader Sequences

Before provision, a double stranded polynucleotide may be contacted with a MuA transposase and a population of double stranded MuA substrates, wherein a proportion of the substrates in the population are Y adaptors comprising the leader sequence and wherein a proportion of the substrates in the population are hairpin loop adaptors. The transposase fragments the double stranded polynucleotide analyte and ligates MuA substrates to one or both ends of the fragments. This produces a plurality of modified double stranded polynucleotides comprising the leader sequence at one end and the hairpin loop at the other. The modified double stranded polynucleotides may then be investigated using the method of the invention.

Each substrate in the population preferably comprises at least one overhang of universal nucleotides such that the transposase fragments the template polynucleotide and ligates a substrate to one or both ends of the double stranded fragments and thereby produces a plurality of fragment/substrate constructs and wherein the method further comprises ligating the overhangs to the fragments in the constructs and thereby producing a plurality of modified double stranded polynucleotides. Suitable universal nucleotides are discussed above. The overhang is preferably five nucleotides in length.

Alternatively, each substrate in population preferably comprises (i) at least one overhang and (ii) at least one nucleotide in the same strand as the at least one overhang which comprises a nucleoside that is not present in the template polynucleotide such that the transposase fragments the template polynucleotide and ligates a substrate to one or both ends of the double stranded fragments and thereby produces a plurality of fragment/substrate constructs, and wherein the method further comprises (a) removing the overhangs from the constructs by selectively removing the at least one nucleotide and thereby producing a plurality of double stranded constructs comprising single stranded gaps and (b) repairing the single stranded gaps in the constructs and thereby producing a plurality of modified double stranded polynucleotides. The polynucleotide typically comprises the nucleosides deoxyadenosine (dA), deoxyuridine (dU) and/or thymidine (dT), deoxyguanosine (dG) and deoxycytidine (dC). The nucleoside that is not present in the polynucleotide is preferably abasic, adenosine (A), uridine (U), 5-methyluridine (msU), cytidine (C) or guanosine (G) or comprises urea, 5, 6 dihydroxythymine, thymine glycol, 5-hydroxy-5 methylhydanton, uracil glycol, 6-hydroxy-5, 6-dihdrothimine, methyltartronylurea, 7, 8-dihydro-8-oxoguanine (8-oxoguanine), 8-oxoadenine, fapy-guanine, methyfapy-guanine, fapy-adenine, aflatoxin B1-fapy-guanine, 5-hydroxy-cytosine, 5-hydroxy-uracil, 3-methyladenine, 7-methylguanine, 1,N6-ethenoadenine, hypoxanthine, 5-hydroxyuracil, 5-hydroxymethyluracil, 5-formyluracil or a cis-syn-cyclobutane pyrimidine dimer. The at least one nucleotide preferably is 10 nucleotides or fewer from the overhang. The at least one nucleotide is the first nucleotide in the overhang. All of the nucleotides in the overhang preferably comprise a nucleoside that is not present in the template polynucleotide.

These MuA based methods are disclosed in International Application No. PCT/GB2014/052505. They are also discussed in detail in the UK Application No. 1406147.7.

One or more helicases may be attached to the MuA substrate Y adaptors before they are contacted with the double stranded polynucleotide and MuA transposase. Alternatively, one or more helicases may be attached to the MuA substrate Y adaptors before they are contacted with the double stranded polynucleotide and MuA transposase.

One or more molecular brakes may be attached to the MuA substrate hairpin loop adaptors before they are contacted with the double stranded polynucleotide and MuA transposase. Alternatively, one or more molecular brakes may be attached to the MuA substrate hairpin loop adaptors before they are contacted with the double stranded polynucleotide and MuA transposase.

Uncoupling

The method of the invention may involve characterising multiple target polynucleotides and uncoupling of the at least the first target polynucleotide.

In a preferred embodiment, the invention involves characterising two or more target polynucleotides. The method comprises:
(a) providing a first polynucleotide in a first sample;
(b) providing a second polynucleotide in a second sample;
(c) coupling the first polynucleotide in the first sample to a membrane using one or more anchors;
(d) contacting the first polynucleotide with a pore of the invention such that the polynucleotide moves with respect to, such as through, the pore;
(e) taking one or more measurements as the first polynucleotide moves with respect to the pore wherein the measurements are indicative of one or more characteristics of the first polynucleotide and thereby characterising the first polynucleotide;
(f) uncoupling the first polynucleotide from the membrane;
(g) coupling the second polynucleotide in the second sample to the membrane using one or more anchors;
(h) contacting the second polynucleotide with the pore of the invention such that the second polynucleotide moves with respect to, such as through, the pore; and
(i) taking one or more measurements as the second polynucleotide moves with respect to the pore wherein the measurements are indicative of one or more characteristics of the second polynucleotide and thereby characterising the second polynucleotide.

This type of method is discussed in detail in the UK Application No. 1406155.0.

Step (f) (i.e. uncoupling of the first polynucleotide) may be performed before step (g) (i.e. before coupling the second polynucleotide to the membrane). Step (g) may be performed before step (f). If the second polynucleotide is coupled to the membrane before the first polynucleotide is uncoupled, step (f) preferably comprises selectively uncoupling the first polynucleotide from the membrane (i.e. uncoupling the first polynucleotide but not the second polynucleotide from the membrane). A skilled person can design a system in which selective uncoupling is achieved. Steps (f) and (g) may be performed at the same time. This is discussed in more detail below.

In step (f), at least 10% of the first polynucleotide is preferably uncoupled from the membrane. For instance, at least 20%, at least 30%, at least 40%, at least 50%, at least 60%, at least 70%, at least 80%, at least 90% or at least 95% of the first polynucleotide may be uncoupled from the membrane. Preferably, all of the first polynucleotide is uncoupled from the membrane. The amount of the first polynucleotide uncoupled from the membrane can be determined using the pore. This is disclosed in the Examples.

The first polynucleotide and second polynucleotide may be different from one another. Alternatively, the first and second polynucleotides may be different polynucleotides. In such instances, there may be no need to remove at least part of the first sample before adding the second polynucleotide. This is discussed in more detail below. If the method concerns investigating three or more polynucleotides, they may all be different from one another or some of them may be different from one another.

The first polynucleotide and the second polynucleotide may be two instances of the same polynucleotide. The first polynucleotide may be identical to the second polynucleotide. This allows proof reading. If the method concerns investigating three or more polynucleotides, they may all be three or more instances of the same polynucleotide or some of them may be separate instances of the same polynucleotide.

The first sample and second sample may be different from one another. For instance, the first sample may be derived from a human and the second sample may be derived from a virus. If the first and second samples are different from one another, they may contain or be suspected of containing the same first and second polynucleotides. If the method concerns investigating three or more samples, they may all be different from one another or some of them may be different from one another.

The first sample and the second sample are preferably two instances of the same sample. The first sample is preferably identical to the second sample. This allows proof reading. If the method concerns investigating three or more samples, they may all be three or more instances of the same sample or some of them may be separate instances of the same sample.

Any number of polynucleotides can be investigated. For instance, the method of the invention may concern characterising 3, 4, 5, 6, 7, 8, 9, 10, 20, 30, 50, 100 or more polynucleotides. If three or more polynucleotides are investigated using the method of the invention, the second polynucleotide is also uncoupled from the membrane and the requisite number of steps are added for the third polynucleotide. The same is true for four or more polynucleotides.

The method of the invention involves uncoupling the first polynucleotide from the membrane. The method of the invention may involve uncoupling the second polynucleotide from the membrane if three or more polynucleotides are being investigated.

The first polynucleotide can be uncoupled from the membrane using any known method. The first polynucleotide is preferably not uncoupled from the membrane in step (f) using the transmembrane pore. The first polynucleotide is preferably not uncoupled from the membrane using a voltage or an applied potential.

Step (f) preferably comprises uncoupling the first polynucleotide from the membrane by removing the one or more anchors from the membrane. If the anchors are removed, the second polynucleotide is coupled to the membrane using other (or separate) anchors. The anchors used to couple the second polynucleotide may be the same type of anchors used to couple the first polynucleotide or different type of anchors.

Step (f) more preferably comprises contacting the one or more anchors with an agent which has a higher affinity for the one or more anchors than the anchors have for the membrane. A variety of protocols for competitive binding or immunoradiometric assays to determine the specific binding capability of molecules are well known in the art (see for example Maddox et al, J. Exp. Med. 158, 1211-1226, 1993). The agent removes the anchor(s) from the membrane and thereby uncouples the first polynucleotide. The agent is preferably a sugar. Any sugar which binds to the one or more anchors with a higher affinity than the one or more anchors have for the membrane may be used. The sugar may be a cyclodextrin or derivative thereof as discussed below.

If one or more anchors comprise a hydrophobic anchor, such as cholesterol, the agent is preferably a cyclodextrin or a derivative thereof or a lipid. The cyclodextrin or derivative thereof may be any of those disclosed in Eliseev, A. V., and Schneider, H-J. (1994) J. Am. Chem. Soc. 116, 6081-6088. The agent is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD). Any of the lipids disclosed herein may be used.

If an anchor comprise(s) streptavidin, biotin or desthiobiotin, the agent is preferably biotin, desthiobiotin or streptavidin. Both biotin and desthiobiotin bind to streptavidin with a higher affinity than streptavidin binds to the membrane and vice versa. Biotin has a stronger affinity for streptavidin than desthiobiotin. An anchor comprising streptavidin may therefore be removed from the membrane using biotin or streptavidin and vice versa.

If an anchor comprises a protein, the agent is preferably an antibody or fragment thereof which specifically binds to the protein. An antibody specifically binds to a protein if it binds to the protein with preferential or high affinity, but does not bind or binds with only low affinity to other or different proteins. An antibody binds with preferential or high affinity if it binds with a Kd of $1\times10^{-6}$ M or less, more preferably $1\times10^{-7}$ M or less, $5\times10^{-8}$ M or less, more preferably $1\times10^{-8}$ M or less or more preferably $5\times10^{-9}$ M or less. An antibody binds with low affinity if it binds with a Kd of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more. Any method may be used to detect binding or specific binding. Methods of quantitatively measuring the binding of an antibody to a protein are well known in the art. The antibody may be a monoclonal antibody or a polyclonal antibody. Suitable fragments of antibodies include, but are not limited to, Fv, F(ab') and F(ab')$_2$ fragments, as well as single chain antibodies. Furthermore, the antibody or fragment thereof may be a chimeric antibody or fragment thereof, a CDR-grafted antibody or fragment thereof or a humanised antibody or fragment thereof.

Step (f) preferably comprises contacting the one or more anchors with an agent which reduces ability of the one or more anchors to couple to the membrane. For instance, the agent could interfere with the structure and/or hydrophobicity of the one or more anchors and thereby reduce their ability to couple to the membrane. If an anchor comprises cholesterol, the agent is preferably cholesterol dehydrogenase. If an anchor comprises a lipid, the agent is preferably a phospholipase. If an anchor comprises a protein, the agent is preferably a proteinase or urea. Other combination of suitable anchors and agents will be clear to a person skilled in the art.

Step (f) preferably comprises uncoupling the first polynucleotide from the membrane by separating the first polynucleotide from the one or more anchors. This can be done in any manner. For instance, the linker could be cut in an anchor comprising a linker. This embodiment is particularly applicable to anchors which involve linkage via hybridisation. Such anchors are discussed above.

Step (f) more preferably comprises uncoupling the first polynucleotide from the membrane by contacting the first polynucleotide and the one or more anchors with an agent which competes with the first polynucleotide for binding to one or more anchors. Methods for determining and measuring competitive binding are known in the art. The agent is preferably a polynucleotide which competes with the first polynucleotide for hybridisation to the one or more anchors. For instance, if the first polynucleotide is coupled to the membrane using one or more anchors which involve hybridisation, the polynucleotide can be uncoupled by contacting the one or more anchors with a polynucleotide which also hybridises to the site of hybridisation. The polynucleotide agent is typically added at a concentration that is higher than the concentration of the first polynucleotide and one or more anchors. Alternatively, the polynucleotide agent may hybridise more strongly to the one or more anchors than the first polynucleotide.

Step (f) more preferably comprises (i) contacting the first polynucleotide and the one or more anchors with urea, tris(2-carboxyethyl)phosphine (TCEP), dithiothreitol (DTT), streptavidin or biotin, UV light, an enzyme or a binding agent; (ii) heating the first polynucleotide and the one or more anchors; or (iii) altering the pH. Urea, tris(2-carboxyethyl)phosphine (TCEP) or dithiothreitol (DTT) are capable of disrupting anchors and separating the first polynucleotide from the membrane. If an anchor comprises a streptavidin-biotin link, then a streptavidin agent will compete for binding to the biotin. If an anchor comprises a streptavidin-desthiobiotin link, then a biotin agent will compete for binding to the streptavidin. UV light can be used to breakdown photolabile groups. Enzymes and binding agents can be used to cut, breakdown or unravel the anchor. Preferred enzymes include, but are not limited to, an exonuclease, an endonuclease or a helicase. Preferred binding agents include, but are not limited to, an enzyme, an antibody or a fragment thereof or a single-stranded binding protein (SSB). Any of the enzymes discussed below or antibodies discussed above may be used. Heat and pH can be used to disrupt hybridisation and other linkages.

If the first polynucleotide is uncoupled from the membrane by separating the first polynucleotide from the one or more anchors, the one or more anchors will remain in the membrane. Step (g) preferably comprises coupling the second polynucleotide to the membrane using the one or more anchors that was separated from the first polynucleotide. For instance, the second polynucleotide may also be provided with one or more polynucleotides which hybridise(s) to the one or more anchors that remain in the membrane. Alternatively, step (g) preferably comprises coupling the second polynucleotide to the membrane using one or more separate anchors from the ones separated from the first polynucleotide (i.e. one or more other anchors). The one or more separate anchors may be the same type of anchors used to couple the first polynucleotide to the membrane or may be different types of anchors. Step (g) preferably comprises coupling the second polynucleotide to the membrane using one or more different anchors from the one or more anchors separated from the first polynucleotide.

In a preferred embodiment, steps (f) and (g) comprise uncoupling the first polynucleotide from the membrane by contacting the membrane with the second polynucleotide such that the second polynucleotide competes with the first polynucleotide for binding to the one or more anchors and replaces the first polynucleotide. For instance, if the first polynucleotide is coupled to the membrane using one or more anchors which involve hybridisation, the first polynucleotide can be uncoupled by contacting the anchors with the second polynucleotide attached to polynucleotides which also hybridise to the sites of hybridisation in the one or more anchors. The second polynucleotide is typically added at a concentration that is higher than the concentration of the first polynucleotide and the one or more anchors. Alternatively, the second polynucleotide may hybridise more strongly to the one or more anchors than the first polynucleotide.

Removal or Washing

Although the first polynucleotide is uncoupled from the membrane in step (f), it is not necessarily removed or washed away. If the second polynucleotide can be easily distinguished from the first polynucleotide, there is no need to remove the first polynucleotide.

Between steps (f) and (g), the method preferably further comprises removing at least some of the first sample from the membrane. At least 10% of the first sample may be removed, such as at least 20%, at least 30%, at least 40%, at least 50%, at least 60%, at least 70%, at least 80% or at least 90% of the first sample may be removed.

The method more preferably further comprises removing all of the first sample from the membrane. This can be done in any way. For instance, the membrane can be washed with a buffer after the first polynucleotide has been uncoupled. Suitable buffers are discussed below.

Modified Polynucleotides

Before characterisation, a target polynucleotide may be modified by contacting the polynucleotide with a polymerase and a population of free nucleotides under conditions in which the polymerase forms a modified polynucleotide using the target polynucleotide as a template, wherein the polymerase replaces one or more of the nucleotide species in the target polynucleotide with a different nucleotide species when forming the modified polynucleotide. The modified polynucleotide may then be provided with one or more helicases attached to the polynucleotide and one or more molecular brakes attached to the polynucleotide. This type of modification is described in UK Application No. 1403096.9. Any of the polymerases discussed above may be used. The polymerase is preferably Klenow or 9o North.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 9o North. A primer or a 3' hairpin is typically used as the nucleation point for polymerase extension.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the target polynucleotide with different nucleotide species in the modified polynucleotide, the modified polynucleotide contains k-mers which differ from those in the target polynucleotide. The different k-mers in the modified polynucleotide are capable of producing different current measurements from the k-mers in the target polynucleotide and so the modified polynucleotide provides different information from the target polynucleotide. The additional information from the modified polynucleotide can make it easier to characterise the target polynucleotide. In some instances, the modified polynucleotide itself may be easier to characterise. For instance, the modified polynucleotide may be designed to include k-mers with an increased separation or a clear separation between their current measurements or k-mers which have a decreased noise.

The polymerase preferably replaces two or more of the nucleotide species in the target polynucleotide with different nucleotide species when forming the modified polynucleotide. The polymerase may replace each of the two or more nucleotide species in the target polynucleotide with a distinct nucleotide species. The polymerase may replace each of the two or more nucleotide species in the target polynucleotide with the same nucleotide species.

If the target polynucleotide is DNA, the different nucleotide species in the modified typically comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the target polynucleotide is RNA, the different nucleotide species in the modified polynucleotide typically comprises a nucleobase which differs from adenine, guanine, uracil, cytosine or methylcytosine and/or comprises a nucleoside which differs from adenosine, guanosine, uridine, cytidine or methylcytidine. The different nucleotide species may be any of the universal nucleotides discussed above.

The polymerase may replace the one or more nucleotide species with a different nucleotide species which comprises a chemical group or atom absent from the one or more nucleotide species. The chemical group may be a propynyl group, a thio group, an oxo group, a methyl group, a hydroxymethyl group, a formyl group, a carboxy group, a carbonyl group, a benzyl group, a propargyl group or a propargylamine group.

The polymerase may replace the one or more nucleotide species with a different nucleotide species which lacks a chemical group or atom present in the one or more nucleotide species. The polymerase may replace the one or more of the nucleotide species with a different nucleotide species having an altered electronegativity. The different nucleotide species having an altered electronegativity preferably comprises a halogen atom.

The method preferably further comprises selectively removing the nucleobases from the one or more different nucleotides species in the modified polynucleotide.

Analyte Delivery

The target analyte is preferably attached to a microparticle which delivers the analyte towards the membrane. This type of delivery is disclosed in UK Application No. 1418469.1. Any type of microparticle and attachment method may be used.

Other Characterisation Method

In another embodiment, a polynucleotide is characterised by detecting labelled species that are added to the target polynucleotide by a polymerase and then released. The polymerase uses the polynucleotide as a template. Each labelled species is specific for each nucleotide. The polynucleotide is contacted with a pore of the invention, such as a pore of the invention, a polymerase and labelled nucleotides such that phosphate labelled species are sequentially added to the polynucleotide by the polymerase, wherein the phosphate species contain a label specific for each nucleotide. The labelled species may be detected using the pore before they are released from the nucleotides (i.e. as they are added to the target polynucleotide) or after they are released from the nucleotides.

The polymerase may be any of those discussed above. The phosphate labelled species are detected using the pore and thereby characterising the polynucleotide. This type of method is disclosed in European Application No. 13187149.3 (published as EP 2682460). Any of the embodiments discussed above equally apply to this method.

Examples of labelled species include, but are not limited to, polymers, polyethylene glycols, sugars, cyclodextrins, fluorophores, drugs, metabolites, peptides. A non-limiting example of such tags can be found in the work of Kumar et al. Sci Rep. 2012; 2:684. Epub 2012 Sep. 21.

Methods of Forming Sensors

The invention also provides a method of forming a sensor for characterising a target polynucleotide. The method comprises forming a complex between a pore of the invention and a polynucleotide binding protein, such as a helicase or an exonuclease. The complex may be formed by contacting the pore and the protein in the presence of the target polynucleotide and then applying a potential across the pore. The applied potential may be a chemical potential or a voltage potential as described above. Alternatively, the complex may be formed by covalently attaching the pore to the protein. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore of the invention and a helicase. Any of the embodiments discussed above equally apply to this method.

The invention also provides a sensor for characterising a target polynucleotide. The sensor comprises a complex between a pore of the invention and a polynucleotide binding protein. Any of the embodiments discussed above equally apply to the sensor of the invention.

Kits

The present invention also provides a kit for characterising a target polynucleotide. The kit comprises a pore of the invention and the components of a membrane. The membrane is preferably formed from the components. The pore is preferably present in the membrane. The kit may comprise components of any of the membranes disclosed above, such as an amphiphilic layer or a triblock copolymer membrane.

The kit may further comprise a polynucleotide binding protein. Any of the polynucleotide binding proteins discussed above may be used.

The kit may further comprise one or more anchors for coupling the polynucleotide to the membrane.

The kit is preferably for characterising a double stranded polynucleotide and preferably comprises a Y adaptor and a hairpin loop adaptor. The Y adaptor preferably has one or more helicases attached and the hairpin loop adaptor preferably has one or more molecular brakes attached. The Y adaptor preferably comprises one or more first anchors for coupling the polynucleotide to the membrane, the hairpin loop adaptor preferably comprises one or more second anchors for coupling the polynucleotide to the membrane and the strength of coupling of the hairpin loop adaptor to the membrane is preferably greater than the strength of coupling of the Y adaptor to the membrane.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

Apparatus

The invention also provides an apparatus for characterising a target analyte, such as a target polynucleotide. The apparatus comprises a plurality of pores of the invention and a plurality of membranes. The plurality of pores are preferably present in the plurality of membranes. The number of pores and membranes is preferably equal. Preferably, a single pore is present in each membrane.

The apparatus preferably further comprises instructions for carrying out the method of the invention. The apparatus may be any conventional apparatus for analyte analysis, such as an array or a chip. Any of the embodiments discussed above with reference to the methods of the invention are equally applicable to the apparatus of the invention. The apparatus may further comprise any of the features present in the kit of the invention.

The apparatus is preferably set up to carry out the method of the invention.

The apparatus preferably comprises:

a sensor device that is capable of supporting the plurality of pores and membranes and being operable to perform analyte characterisation using the pores and membranes; and at least one port for delivery of the material for performing the characterisation.

Alternatively, the apparatus preferably comprises:

a sensor device that is capable of supporting the plurality of pores and membranes being operable to perform analyte characterisation using the pores and membranes; and at least one reservoir for holding material for performing the characterisation.

The apparatus more preferably comprises:

a sensor device that is capable of supporting the membrane and plurality of pores and membranes and being operable to perform analyte characterising using the pores and membranes;

at least one reservoir for holding material for performing the characterising;

a fluidics system configured to controllably supply material from the at least one reservoir to the sensor device; and one or more containers for receiving respective samples, the fluidics system being configured to supply the samples selectively from one or more containers to the sensor device.

The apparatus may be any of those described in International Application No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

The following Example illustrates the invention.

Example 1

This Example describes the simulations which were run to investigate DNA behaviour within CsgG.

Materials and Methods

Steered molecular dynamics simulations were performed to investigate the magnitude of the energetic barrier of CsgG-Eco and various mutants to DNA translocation. Simulations were performed using the GROMACS package version 4.0.5, with the GROMOS 53a6 forcefield and the SPC water model. The structure of CsgG-Eco (SEQ ID NO: 2) was taken from the protein data bank, accession code 4UV3. In order to make models of the CsgG-Eco mutants, the wild-type protein structure was mutated using PyMOL. The mutants studied were CsgG-Eco-(F56A) (SEQ ID NO: 2 with mutation F56A), CsgG-Eco-(F56A-N55S) (SEQ ID NO: 2 with mutations F56A/N55S) and CsgG-Eco-(F56A-N55S-Y51A) (SEQ ID NO: 2 with mutations F56A/N55S/Y51A).

DNA was then placed into the pores. Two different systems were set up:
  i. A single guanine nucleotide was placed into the pore, just above the constriction region (approximately 5-10 Angstroms above the residue 56 ring)
  ii. A single strand of DNA (ssDNA) was placed along the pore axis, with the 5' end towards the beta-barrel side of the pore. In this set up, the ssDNA was pre-threaded through the entire length of the pore.

The simulation box was then solvated and then energy minimised using the steepest descents algorithm.

Each system was simulated in the NPT ensemble, using the Berendsen thermostat and Berendsen barostat at 300 K. Throughout the simulation, restraints were applied to the backbone of the pore.

In order to pull the DNA through the pore, a pulling force was applied to the phosphorus atom in the single guanine simulations. In the ssDNA simulations the pulling force was applied to the phosphorus atom at the 5' end of the strand. The pulling force was applied at a constant velocity by connecting a spring between the DNA phosphorus atom mentioned above and an imaginary point travelling at a constant velocity parallel to the pore axis. Note that the spring does not have any shape nor does it undergo any hydrodynamic drag. The spring constant was equal to 5 kJmol$^{-1}$ Å$^{-2}$.

Results

Single G Translocation

Figure 3:
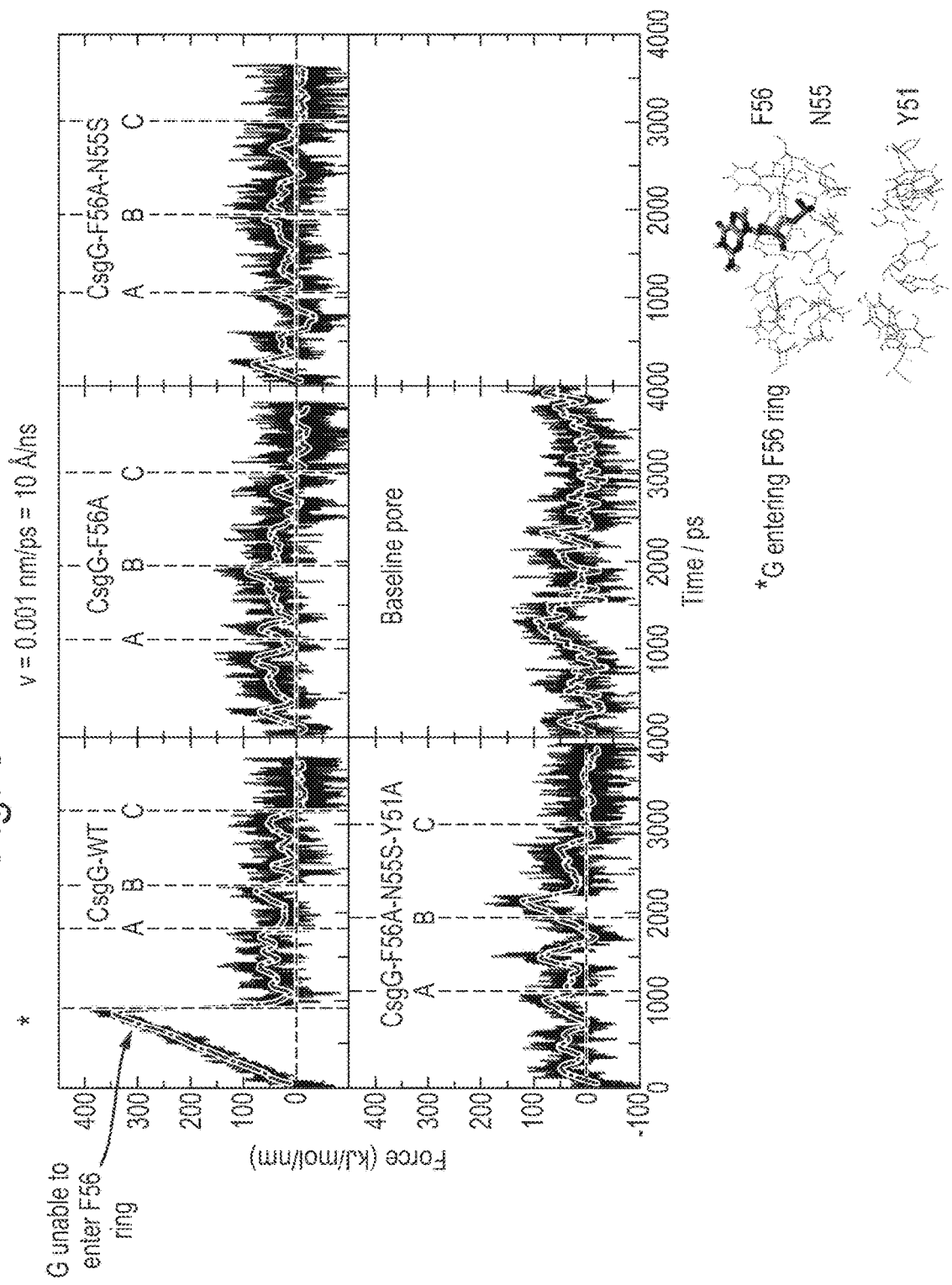
FIG. 3: Illustrates single G translocation at 10 Å/ns. There is a large barrier for entry of guanine into F56 ring in CsgG-Eco. *=G enters F56 ring. A=G stops interacting with 56 ring. B=G stops interacting with 55 ring. C=G stops interacting with 51 ring.

As shown in FIG. 3, a plot of the pulling force versus time shows that there is a large barrier for nucleotide entry into the ring of phenylalanine residues F56 in the wild type CsgG-Eco pore. There was no significant barrier to guanine translocation observed for the CsgG-Eco mutants studied.

ssDNA Translocation

Figure 4:
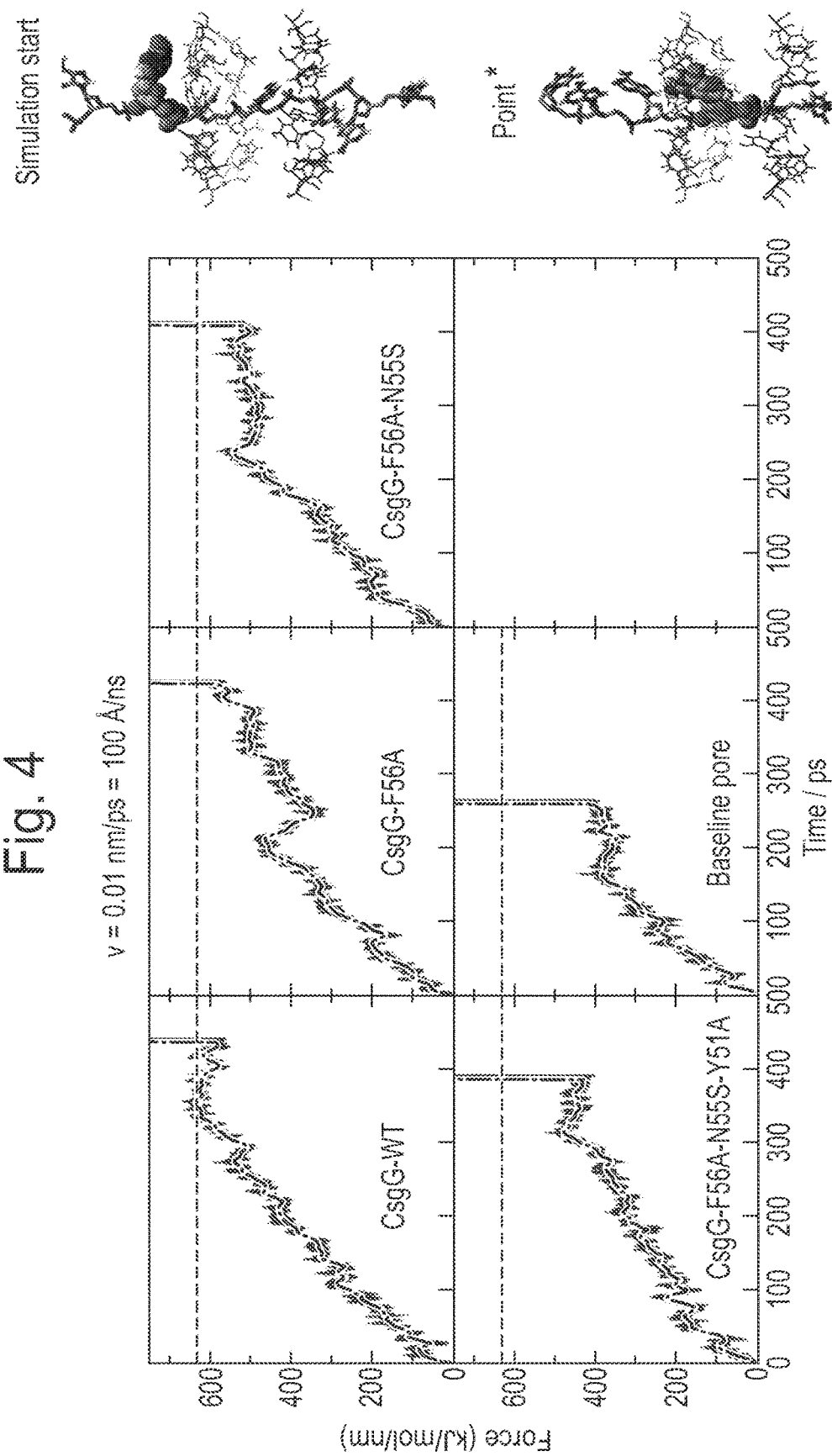
FIG. 4: Illustrates ssDNA translocation at 100 Å/ns. A larger force is required to pull the DNA through the constriction for CsgG-Eco.
Figure 5:
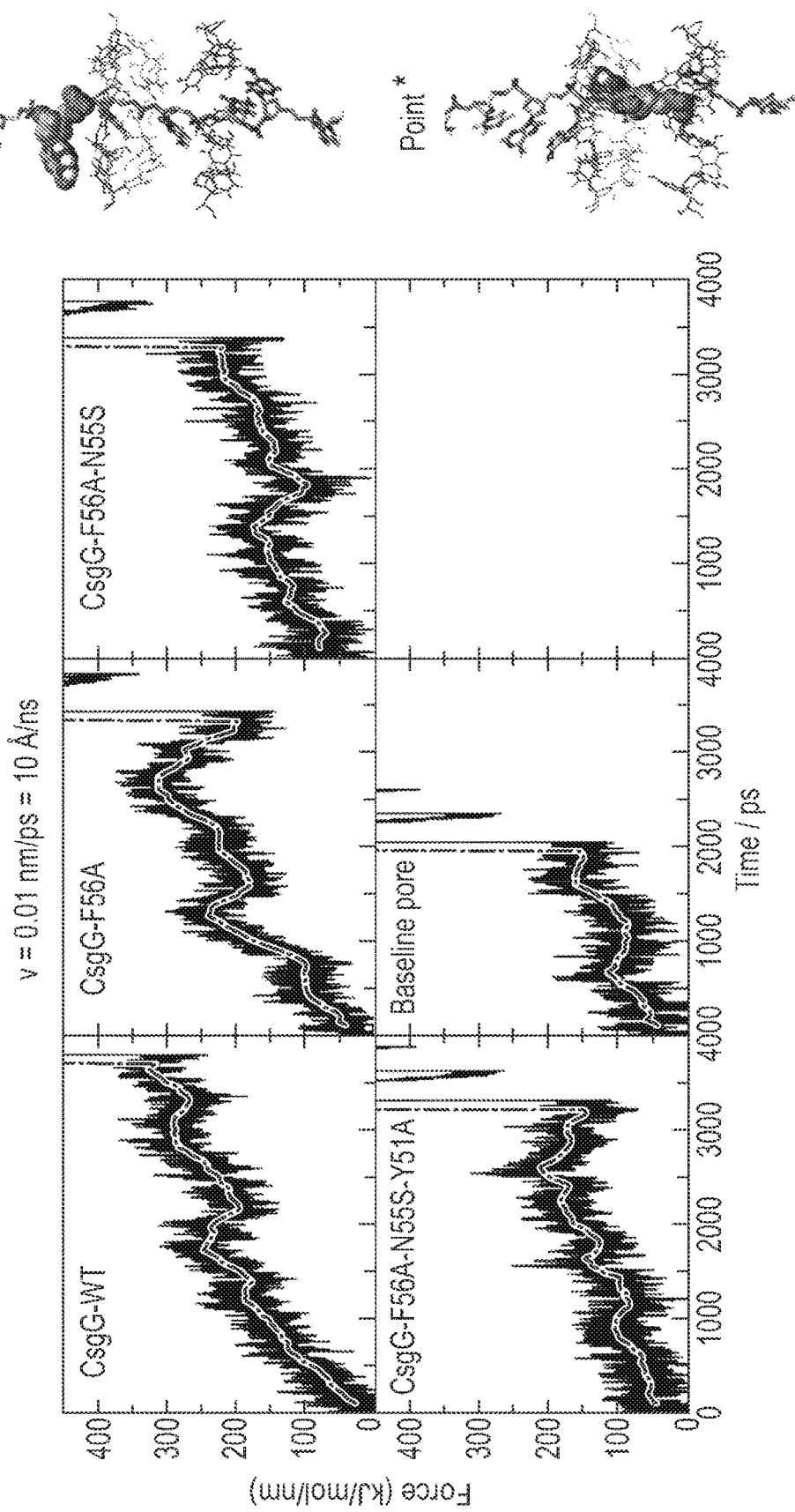
FIG. 5: Illustrates ss DNA translocation at 10 Å/ns. CsgG-F56A-N55S and CsG-F56A-N55S-Y51A mutants both have a lower barrier for ssDNA translocation.

For ssDNA translocation, two simulations were run per pore with each run having a different applied pulling velocity (100 Å/ns and 10 Å/ns). As shown in FIG. 4, which illustrates the faster pulling velocity simulations, the CsgG wild-type pore required the largest pulling force to enable ssDNA translocation. As shown in FIG. 5, which illustrates the slower pulling velocity simulations, both the CsgG-Eco (wild-type, SEQ ID NO: 2) and CsgG-Eco-(F56A) pores required the largest applied force to enable ssDNA translocation. Comparisons between the pulling force required for ssDNA translocation through CsgG and MspA baseline pore, suggest that mutation of the CsgG pore is required to allow a similar level of ssDNA translocation.

Example 2

This Example describes the characterisation of several CsgG mutants.

Materials and Methods

Figure 13:
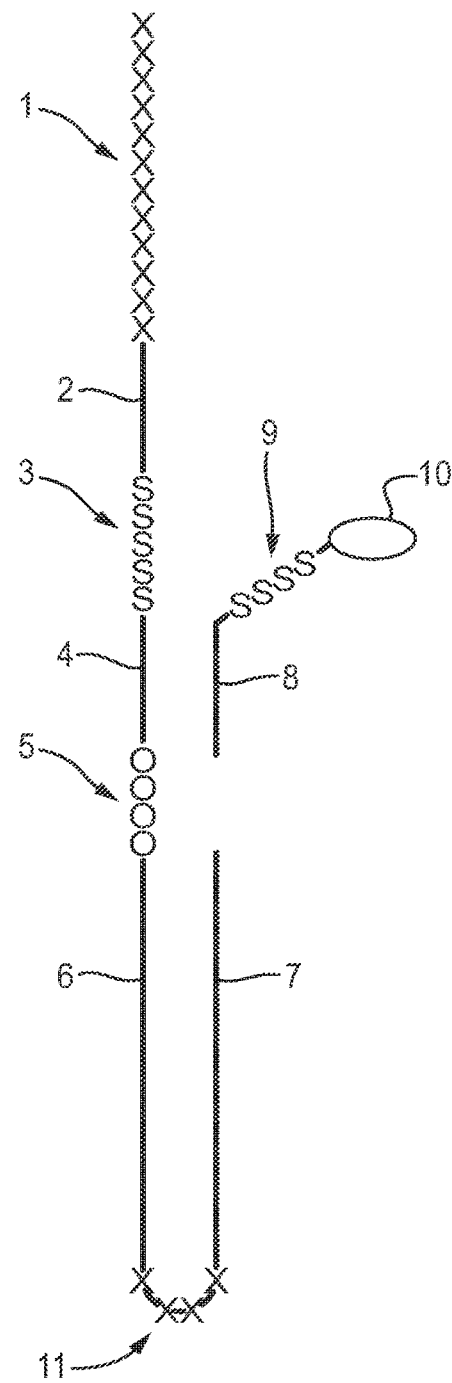
FIG. 13: shows the DNA construct X used in Example 2. The region labelled 1 corresponded to 30 SpC3 spacers. The region labelled 2 corresponded to SEQ ID NO: 42. The region labelled 3 corresponded to four iSp18 spacers. The region labelled 4 corresponded to SEQ ID NO: 43. The section labelled 5 corresponded to four 5-nitroindoles. The region labelled 6 corresponded to SEQ ID NO: 44. The region labelled 7 corresponded to SEQ ID NO: 45. The region labelled 8 corresponded to SEQ ID NO: 46 which had four iSp18 spacers (the region labelled 9) attached at the 3' end of SEQ ID NO: 46. At the opposite end of the iSp18 spacers was a 3' cholesterol tether (labelled 10). The region labelled 11 corresponded to four SpC3 spacers.

Prior to setting up the experiment, DNA construct X (final concentration 0.1 nM, see FIG. 13 for cartoon representation of construct X and description) was pre-incubated at room temperature for five minutes with T4 Dda-E94C/C109A/C136A/A360C (SEQ ID NO: 24 with mutations E94C/C109A/C136A/A360C, final concentration added to the nanopore system 10 nM, which was provided in buffer (151.5 mM KCl, 25 mM potassium phosphate, 5% glycerol, pH 7.0, 1 mM EDTA)). After five minutes, TMAD (100 µM) was added to the pre-mix and the mixture incubated for a further 5 minutes. Finally, MgCl2 (1.5 mM final concentration added to the nanopore system), ATP (1.5 mM final concentration added to the nanopore system), KCl (500 mM final concentration added to the nanopore system) and potassium phosphate buffer (25 mM final concentration added to the nanopore system) were added to the pre-mix.

Electrical measurements were acquired from a variety of single CsgG nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess CsgG nanopores. 150 uL of 500 mM KCl, 25 mM K Phosphate, 1.5 mM MgCl2, 1.5 mM ATP, pH8.0 was then flowed through the system. After 10 minutes a 150 uL of 500 mM KCl, 25 mM potassium phosphate, 1.5 mM MgCl2, 1.5 mM ATP, pH8.0 was flowed through the system and then the enzyme (T4 Dda-E94C/C109A/C136A/A360C, 10 nM final concentration), DNA construct X (0.1 nM final concentration), fuel (MgCl2 1.5 mM final concentration, ATP 1.5 mM final concentration) pre-mix (150 μL total) was then flowed into the single nanopore experimental system. The experiment was run at −120 mV and helicase-controlled DNA movement monitored.

Results

Pores Showing Increased Range (FIGS. 6A-6C to 8A-8C, and 18 to 30)

Figure 6A:
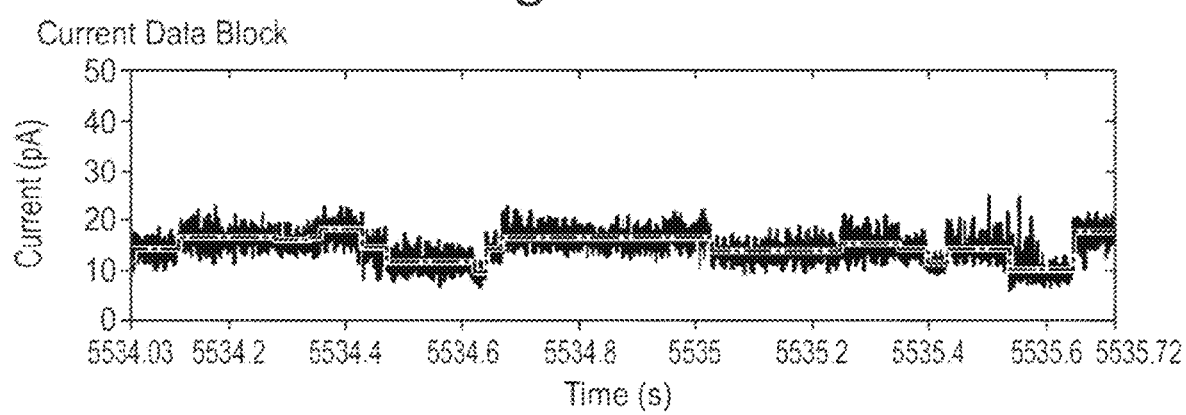
FIGS. 6A-6C, 7A-7C, and 8A-8C: Mutant pores showing increased range compared with wild-type (WT).

CsgG-Eco-(StrepII(C)) (SEQ ID NO: 2 where StrepII(C) is SEQ ID NO: 47 and is attached at the C-terminus) has a range of ~10 pA (see FIG. 6A whereas the CsgG-Eco pore mutants below exhibited an increased current range—

Figure 6B:
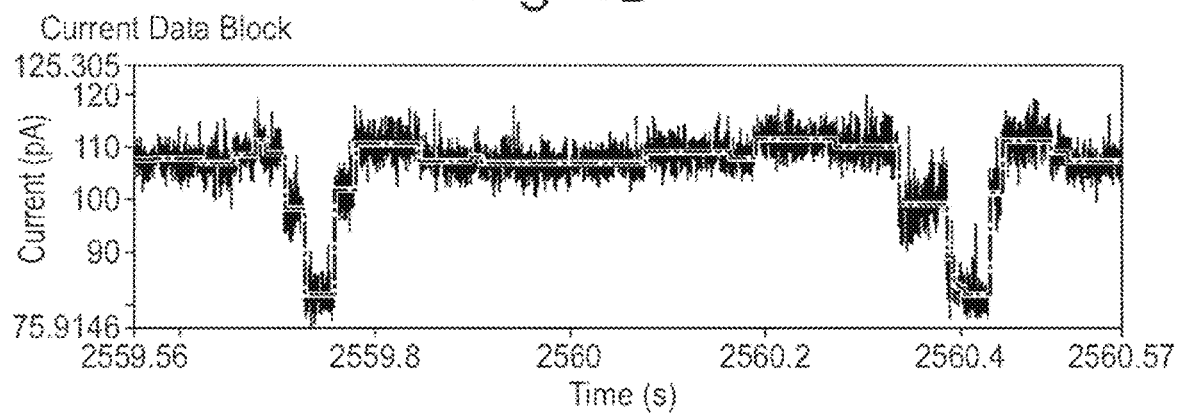

1—CsgG-Eco-(Y51N-F56A-D149N-E185R-E201N-E203N-StrepII(C))9 (SEQ ID NO: 2 with mutations Y51N/F56A/D149N/E185R/E201N/E203N where StrepII(C) is SEQ ID NO: 47 and is attached at the C-terminus) exhibited a range of ~30 pA (See FIG. 6B).

Figure 6C:
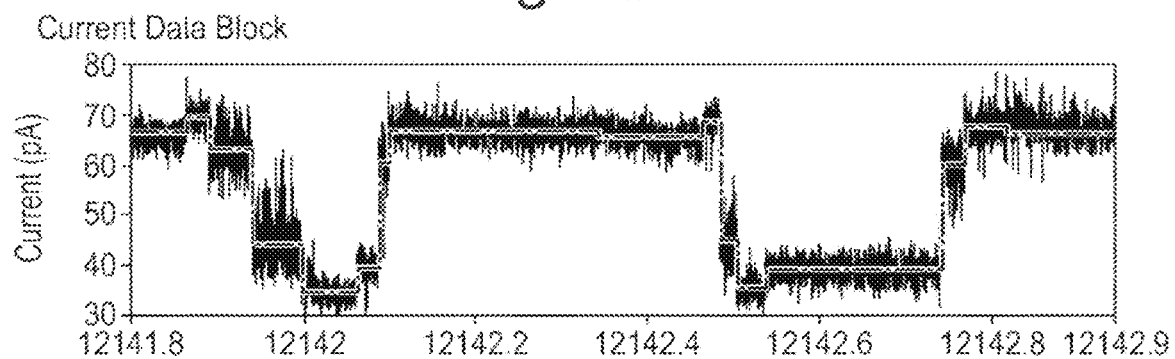

2—CsgG-Eco-(N55A-StrepII(C))9 (SEQ ID NO: 2 with mutation N55A where StrepII(C) is has SEQ ID NO: 47 and is attached at the C-terminus) exhibited a range of ~35 pA (see FIG. 6C).

Figure 7A:
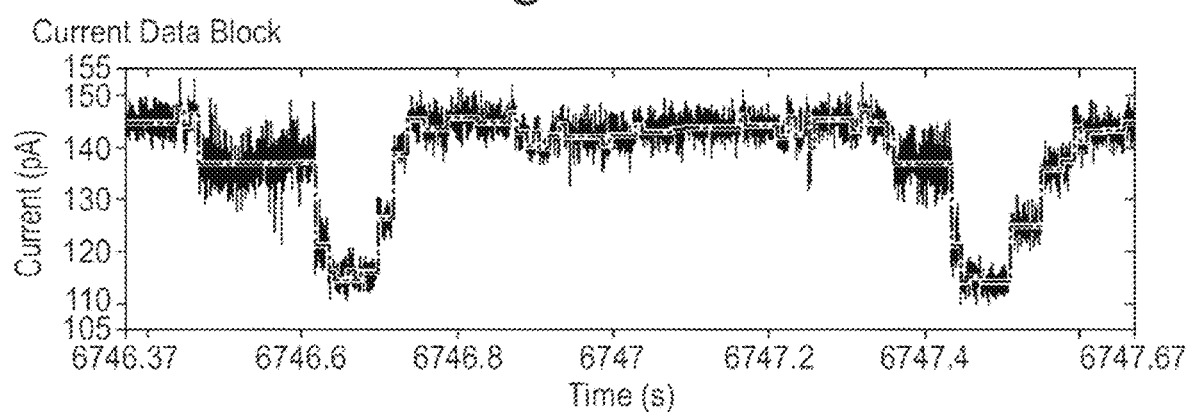

3—CsgG-Eco-(N55S-StrepII(C))9 (SEQ ID NO: 2 with mutations N55S where StrepII(C) is SEQ ID NO: 47 and is attached at the C-terminus) exhibited a range of ~40 pA (see FIG. 7A).

Figure 7B:
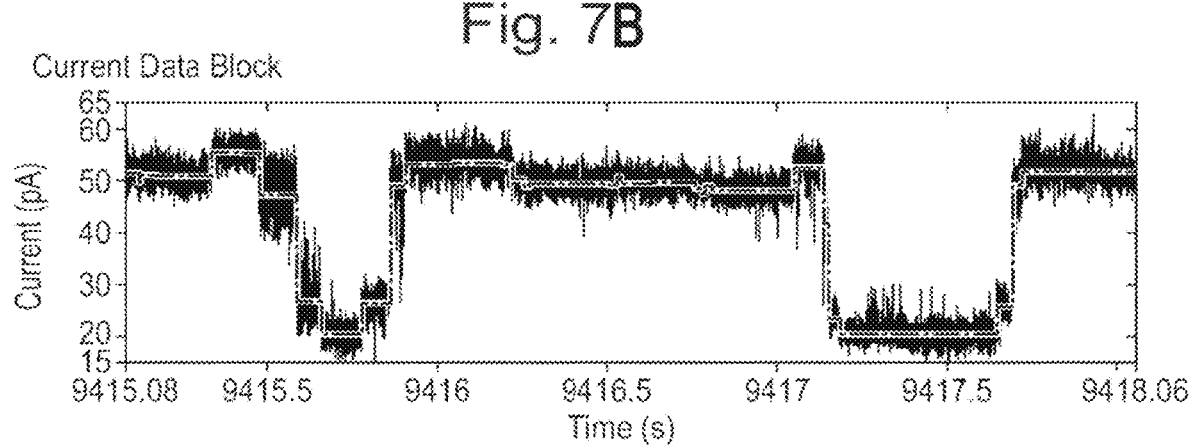

4—CsgG-Eco-(Y51N-StrepII(C))9 (SEQ ID NO: 2 with mutation Y51N where StrepII(C) is SEQ ID NO: 47 and is attached at the C-terminus) exhibited a range of ~40 pA (see FIG. 7B).

Figure 7C:
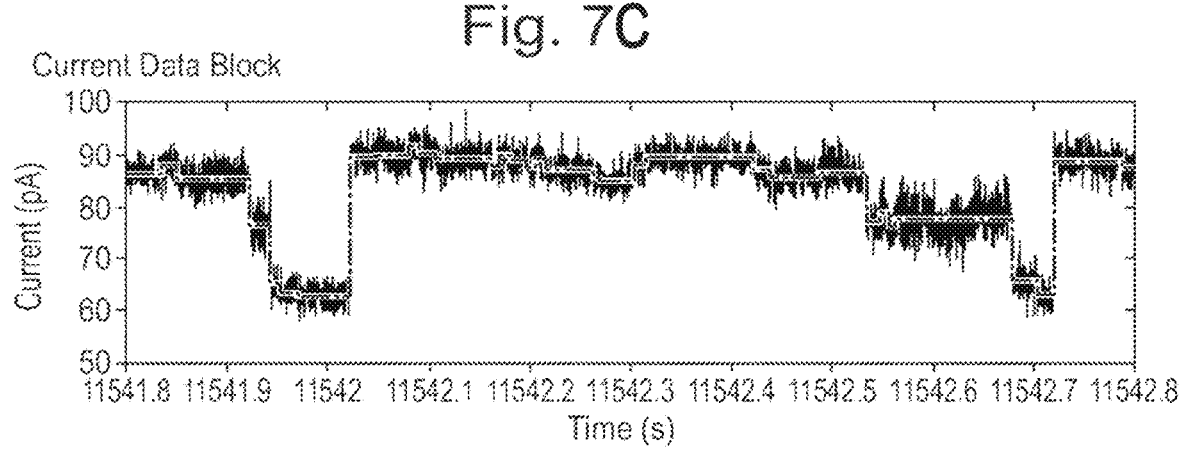

5—CsgG-Eco-(Y51A-F56A-StrepII(C))9 (SEQ ID NO: 2 with mutations Y51A/F56A where StrepII(C) is SEQ ID NO: 47 and is attached at the C-terminus) exhibited a range of ~30 pA (see FIG. 7C).

Figure 8A:
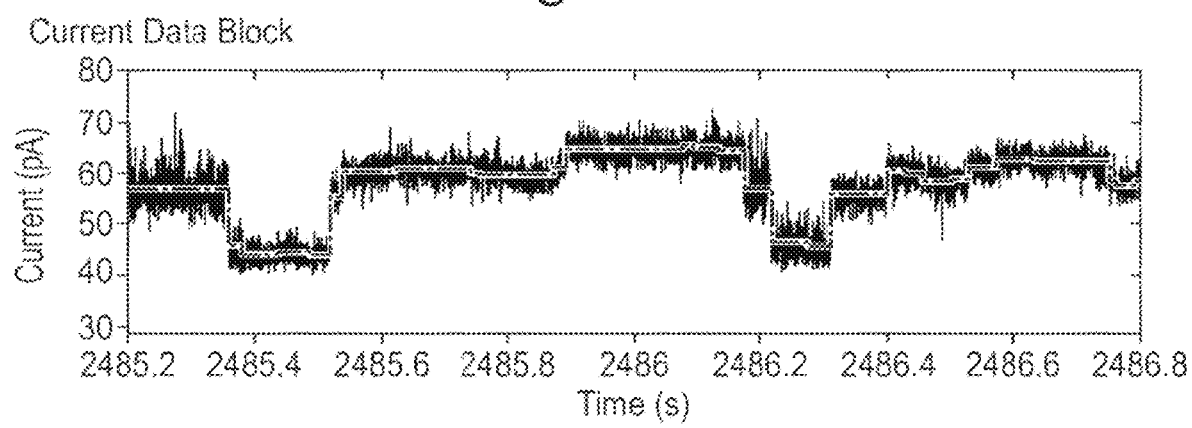

6—CsgG-Eco-(Y51A-F56N-StrepII(C))9 (SEQ ID NO: 2 with mutations Y51A/F56N where StrepII(C) is SEQ ID NO: 47 and is attached at the C-terminus) exhibited a range of ~20 pA (see FIG. 8A).

Figure 8B:
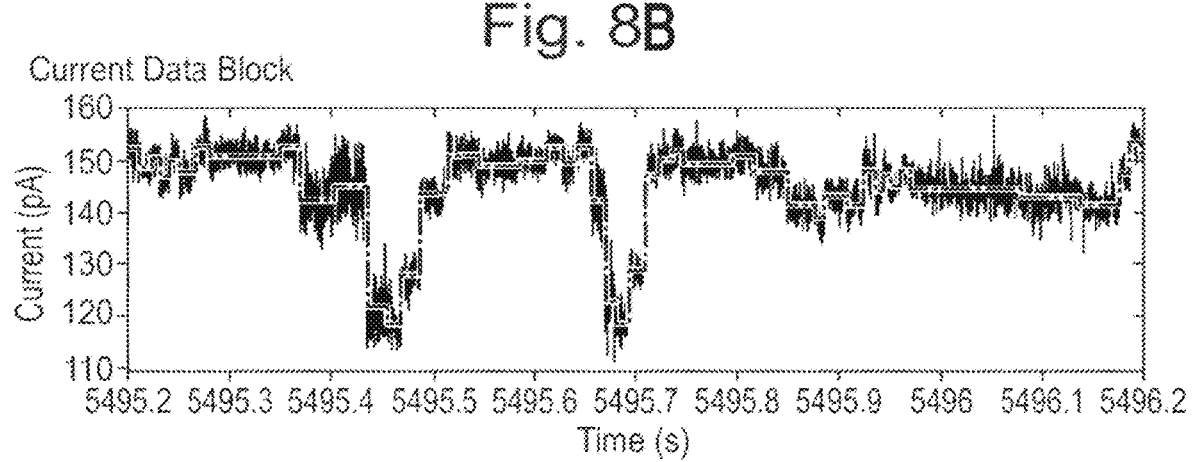

7—CsgG-Eco-(Y51A-N55S-F56A-StrepII(C))9 (SEQ ID NO: 2 with mutations Y51A/N55S/F56A where StrepII(C) is SEQ ID NO: 47 and is attached at the C-terminus) exhibited a range of ~30 pA (see FIG. 8B).

Figure 8C:
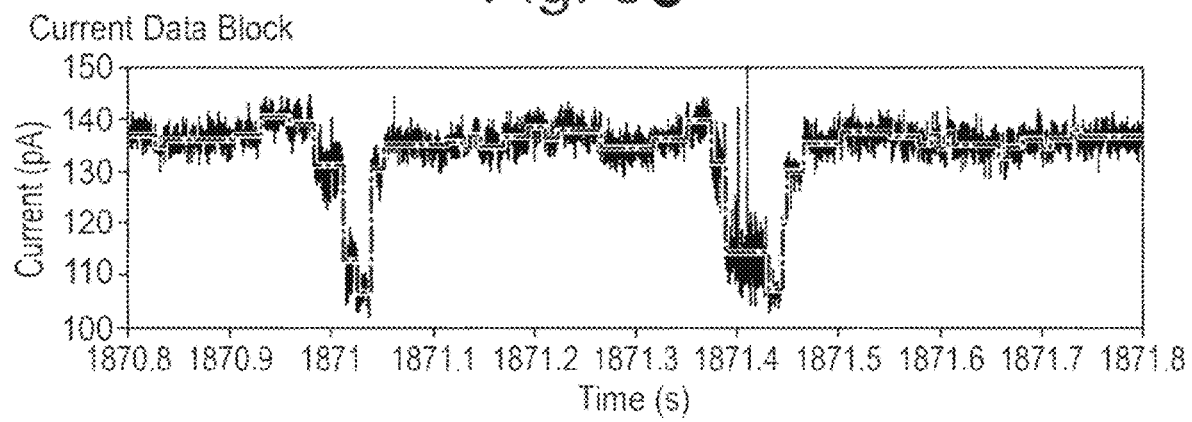

8—CsgG-Eco-(Y51A-N55S-F56N-StrepII(C))9 (SEQ ID NO: 2 with mutations Y51A/N55S/F56N where StrepII(C) is SEQ ID NO: 47 and is attached at the C-terminus) exhibited a range of ~30 pA (see FIG. 8C).

Figure 18:
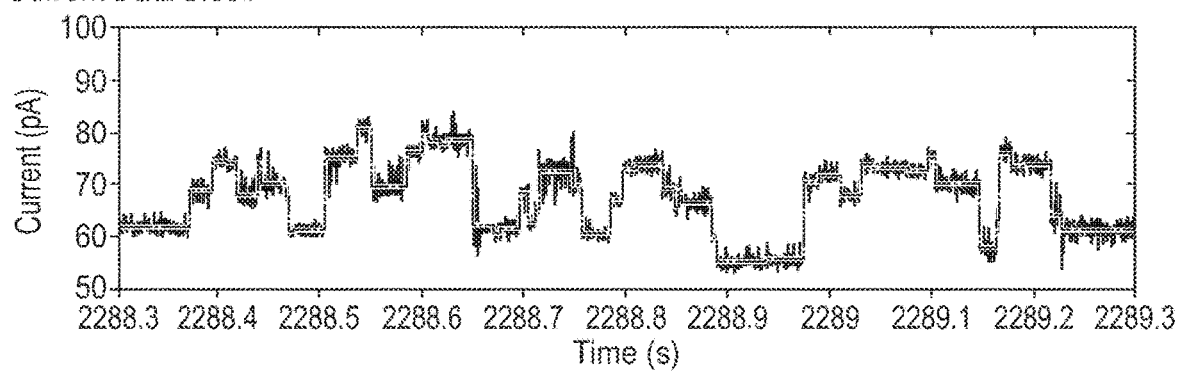
FIGS. 18 to 24: Mutant pores showing increased range compared with wild-type (WT).

13—CsgG-Eco-(F56H-StrepII(C))9 (SEQ ID NO: 2 with mutation F56H where StrepII(C) is SEQ ID NO: 47 and is attached at the C-terminus) exhibited a range of ~35 pA (see FIG. 18).

Figure 19:
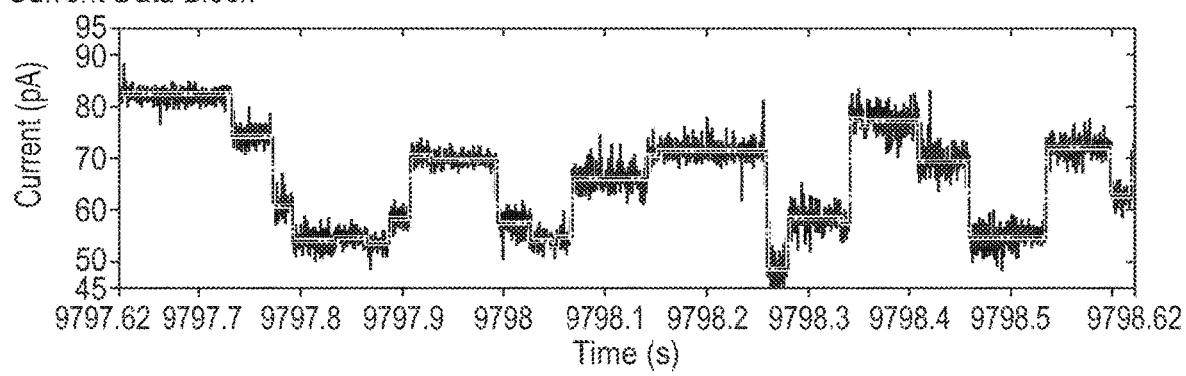

14—CsgG-Eco-(F56Q-StrepII(C))9 (SEQ ID NO: 2 with mutation F56Q where StrepII(C) is SEQ ID NO: 47 and is attached at the C-terminus) exhibited a range of ~40 pA (see FIG. 19).

Figure 20:
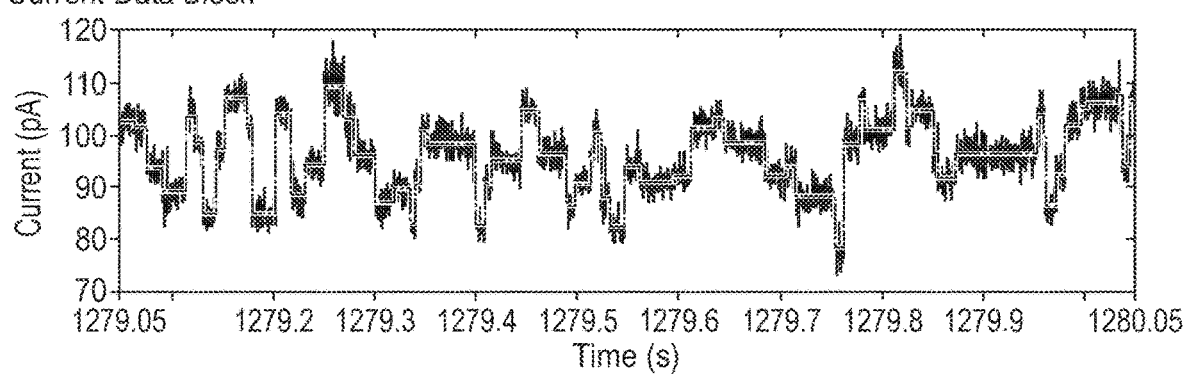

15—CsgG-Eco-(F56T-StrepII(C))9 (SEQ ID NO: 2 with mutation F56T where StrepII(C) is SEQ ID NO: 47 and is attached at the C-terminus) exhibited a range of ~35 pA (see FIG. 20).

Figure 21:
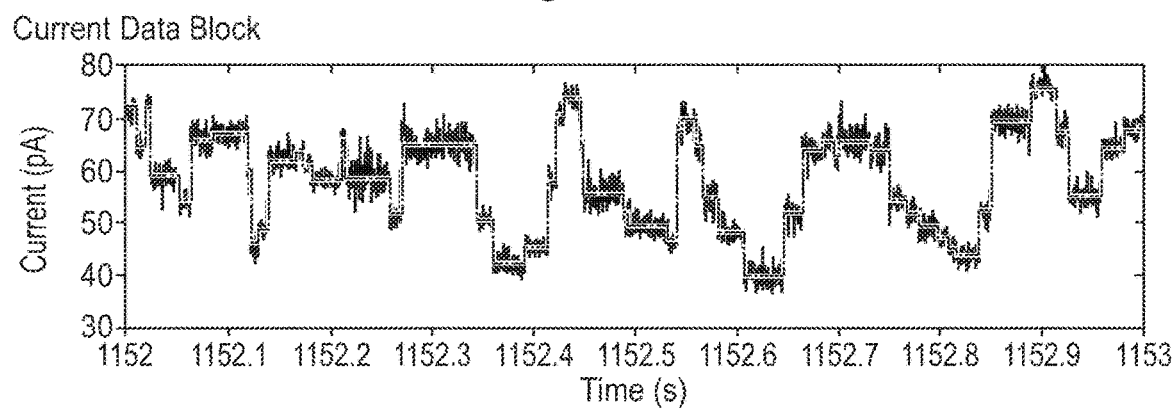

16—CsgG-Eco-(S54P/F56A-StrepII(C))9 (SEQ ID NO: 2 with mutation S54P/F56A where StrepII(C) is SEQ ID NO: 47 and is attached at the C-terminus) exhibited a range of ~35 pA (see FIG. 21).

Figure 22:
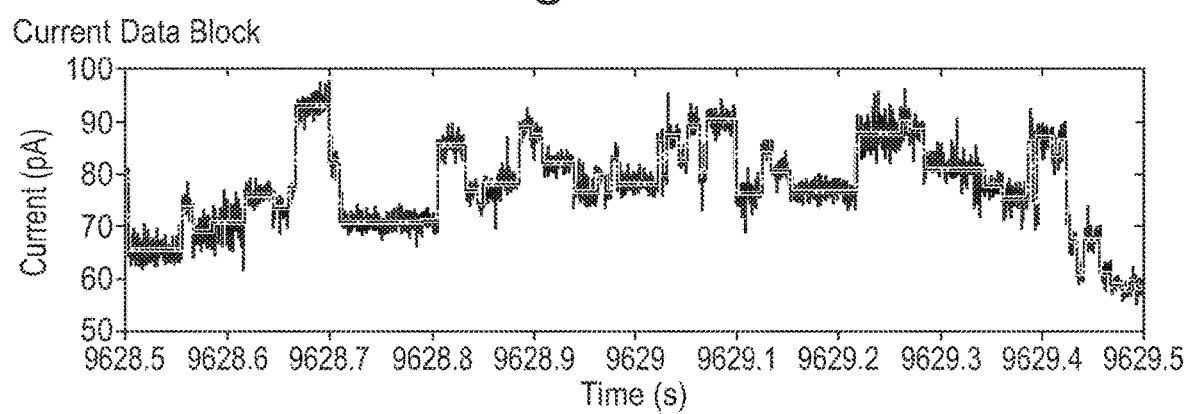

17—CsgG-Eco-(Y51T/F56A-StrepII(C))9 (SEQ ID NO: 2 with mutations Y51T/F56A where StrepII(C) is SEQ ID NO: 47 and is attached at the C-terminus) exhibited a range of ~30 pA (see FIG. 22).

Figure 23:
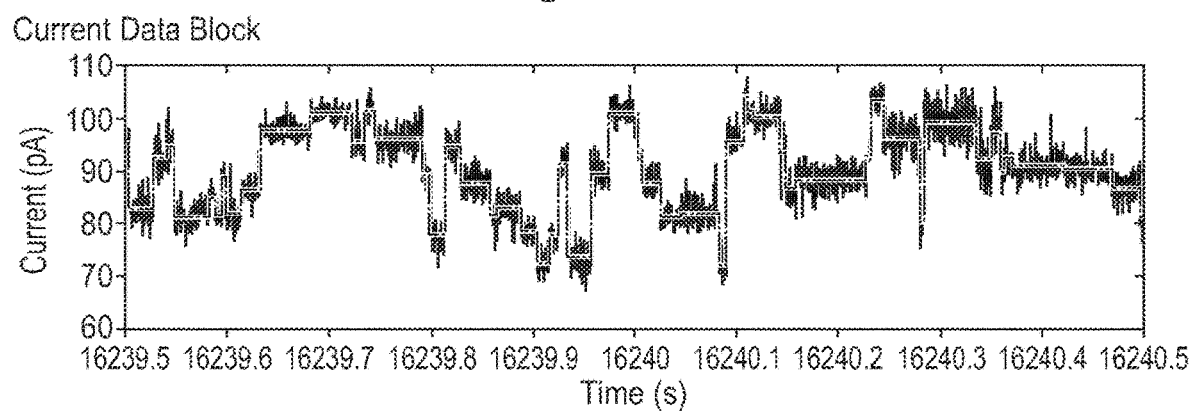

18—CsgG-Eco-(F56P-StrepII(C))9 (SEQ ID NO: 2 with mutation F56P where StrepII(C) is SEQ ID NO: 47 and is attached at the C-terminus) exhibited a range of ~30 pA (see FIG. 23).

Figure 24:
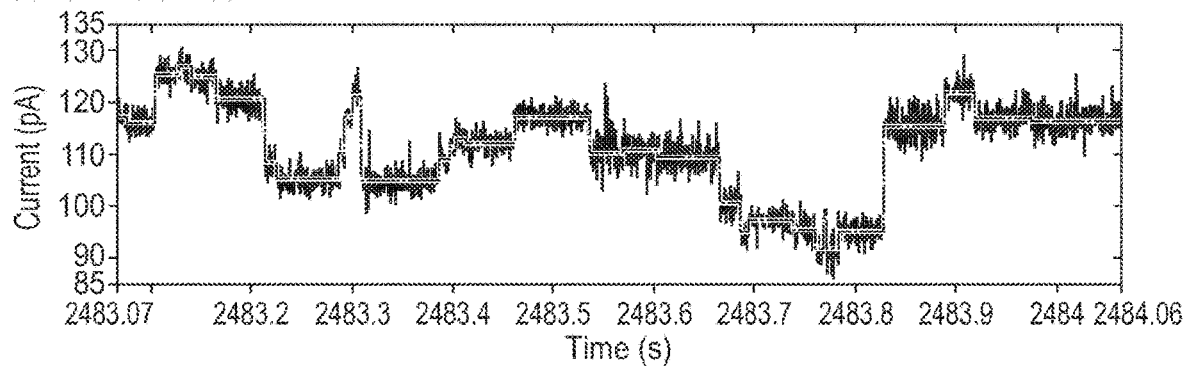

19—CsgG-Eco-(F56A-StrepII(C))9 (SEQ ID NO: 2 with mutation F56A where StrepII(C) is SEQ ID NO: 47 and is attached at the C-terminus) exhibited a range of ~40 pA (see FIG. 24).

Figure 25:
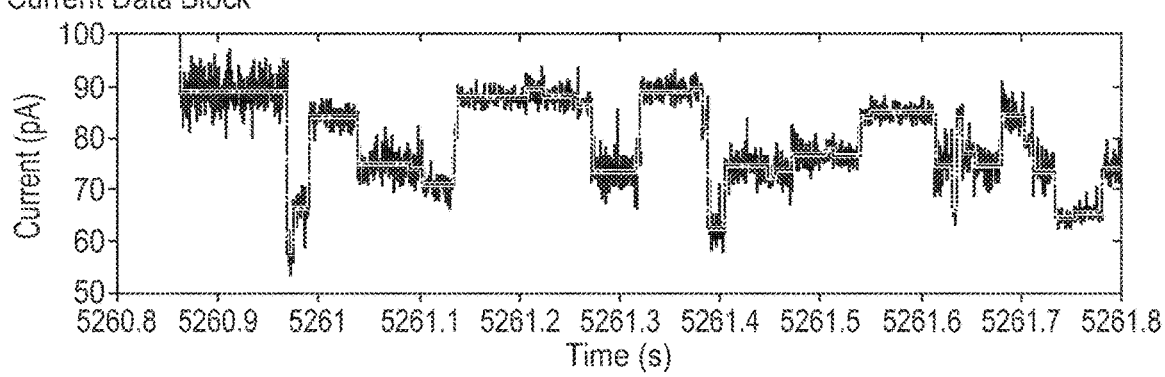
FIGS. 25 to 30: Mutant pores showing increased range compared with wild-type (WT).

20—CsgG-Eco-(Y51T/F56Q-StrepII(C))9 (SEQ ID NO: 2 with mutations Y51T/F56Q where StrepII(C) is SEQ ID NO: 47 and is attached at the C-terminus) exhibited a range of ~30 pA (see FIG. 25).

Figure 26:
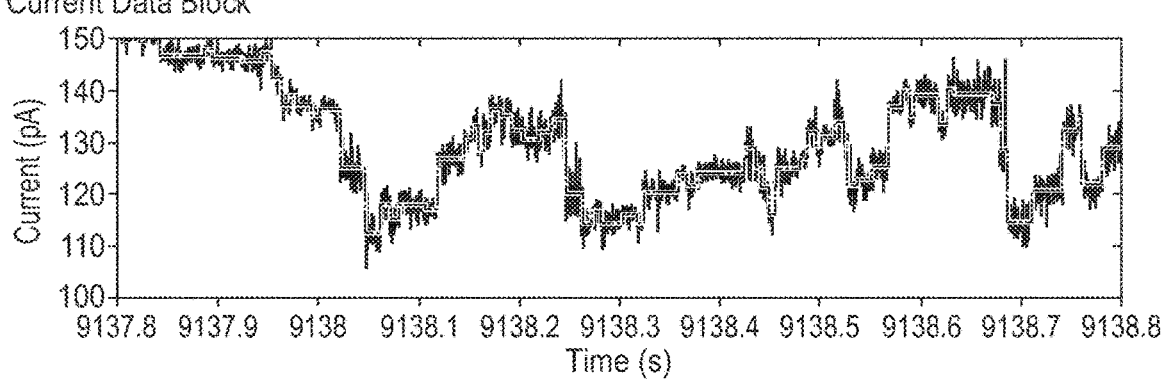

21—CsgG-Eco-(N55S/F56Q-StrepII(C))9 (SEQ ID NO: 2 with mutations N55S/F56Q where StrepII(C) is SEQ ID NO: 47 and is attached at the C-terminus) exhibited a range of ~35 pA (see FIG. 26).

Figure 27:
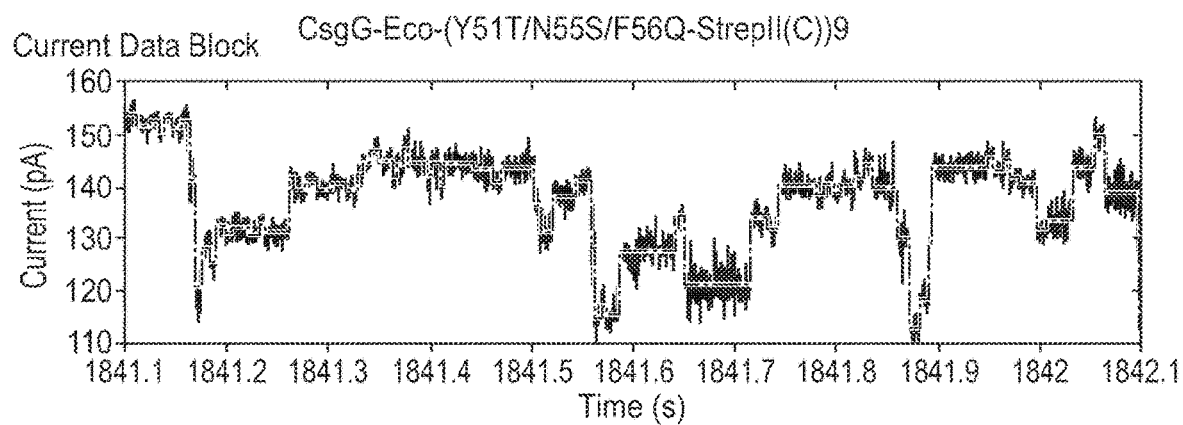

22—CsgG-Eco-(Y51T/N55S/F56Q-StrepII(C))9 (SEQ ID NO: 2 with mutations Y51T/N55S/F56Q where StrepII(C) is SEQ ID NO: 47 and is attached at the C-terminus) exhibited a range of ~35 pA (see FIG. 27).

Figure 28:
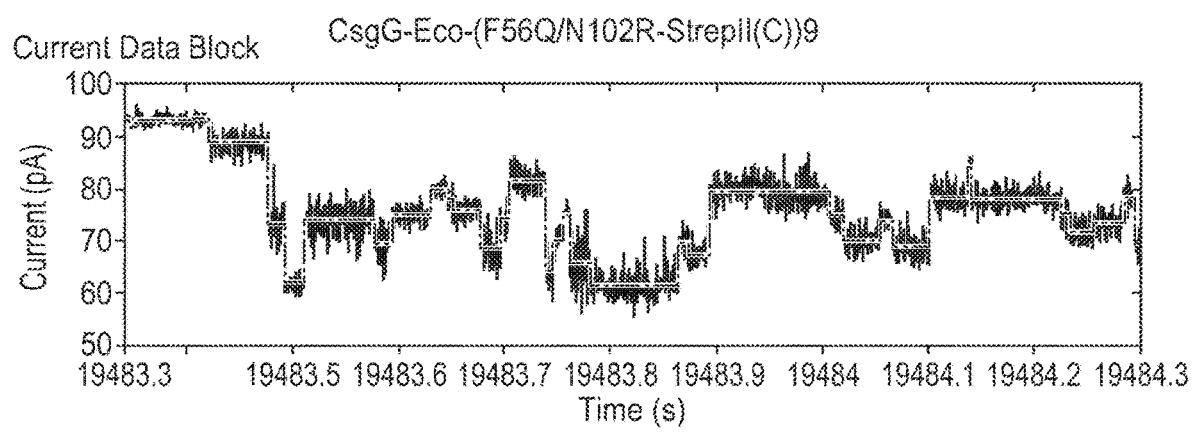

23—CsgG-Eco-(F56Q/N102R-StrepII(C))9 (SEQ ID NO: 2 with mutations F56Q/N102R where StrepII(C) is SEQ ID NO: 47 and is attached at the C-terminus) exhibited a range of ~30 pA (see FIG. 28).

Figure 29:
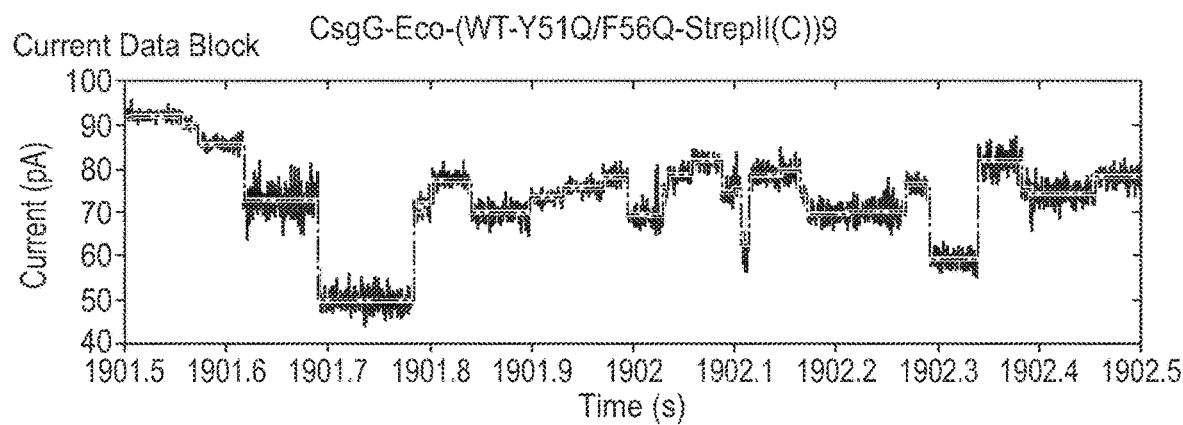

24—CsgG-Eco-(Y51Q/F56Q-StrepII(C))9 (SEQ ID NO: 2 with mutations Y51Q/F56Q where StrepII(C) is SEQ ID NO: 47 and is attached at the C-terminus) exhibited a range of ~40 pA (see FIG. 29).

Figure 30:
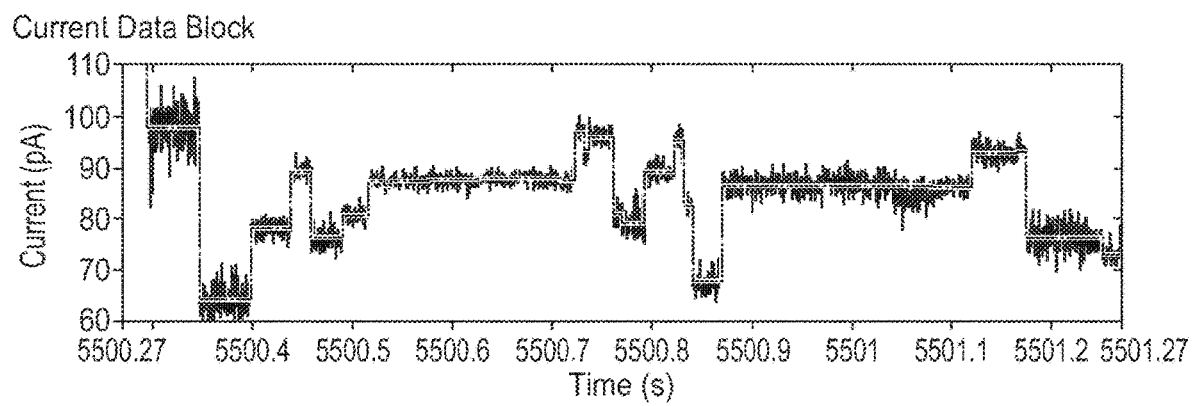

25—CsgG-Eco-(Y51A/F56Q-StrepII(C))9 (SEQ ID NO: 2 with mutations Y51A/F56Q where StrepII(C) is SEQ ID NO: 47 and is attached at the C-terminus) exhibited a range of ~35 pA (see FIG. 30).

Pores Showing Increased Throughput (FIGS. 9A-9C and 10A-10B)

Figure 9A:
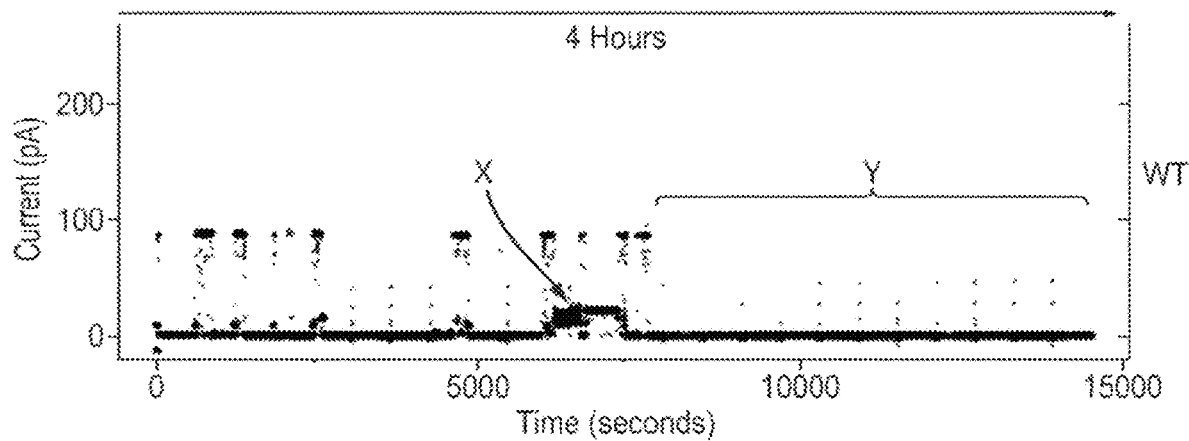
FIGS. 9A-9C and 10A-10B: Mutant pores showing increased throughput compared with wild-type (WT).

As can be seen from FIGS. 9A-9C and 10A-10B, the following mutant pores (9-12 below) exhibited multiple helicase controlled DNA movements (Labelled as X in FIGS. 9A-9C and 10A-10B) per channel in 4 hours, whereas CsgG-Eco-(StrepII(C)) (SEQ ID NO: 2 where StrepII(C) is SEQ ID NO: 47 and is attached at the C-terminus) shown in FIG. 9A frequently exhibited only 1 or 2 helicase controlled DNA movements (labelled as X in FIG. 9A) per channel in 4 hours and instead exhibited prolonged block regions (labelled as Y in FIG. 9A).

Figure 9B:
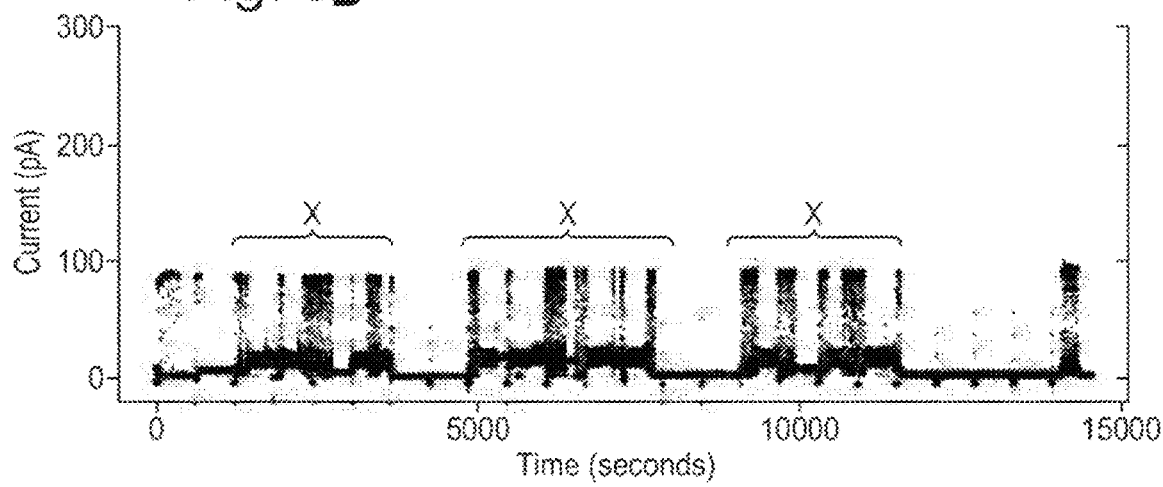

9—CsgG-Eco-(D149N-E185N-E203N-StrepII(C))9 (SEQ ID NO: 2 with mutations D149N/E185N/E203N where StrepII(C) is SEQ ID NO: 47 and is attached at the C-terminus) (FIG. 9B)

Figure 9C:
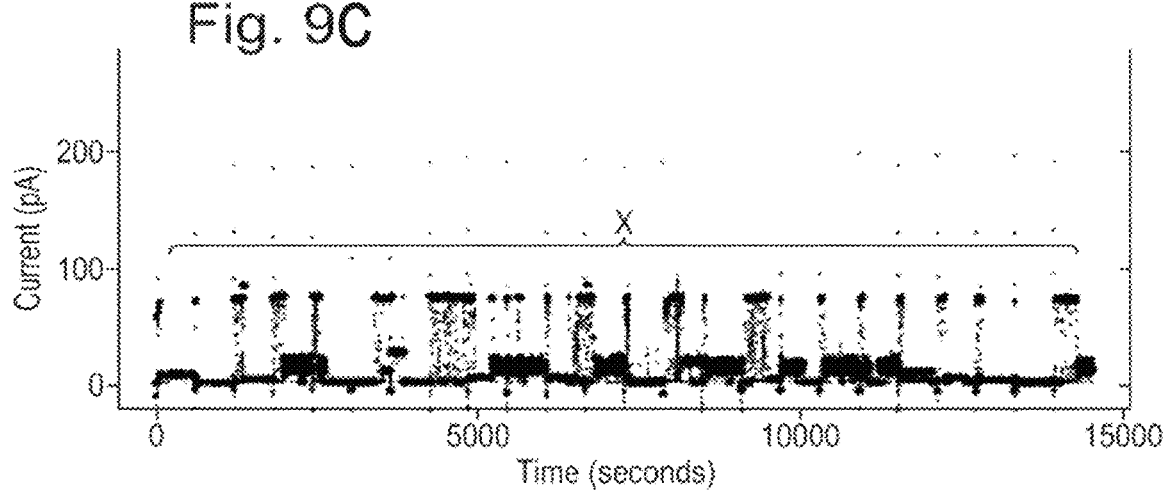

10—CsgG-Eco-(D149N-E185N-E201N-E203N-StrepII(C))9 (SEQ ID NO: 2 with mutations D149N/E185N/E201N/E203N where StrepII(C) is SEQ ID NO: 47 and is attached at the C-terminus) (FIG. 9C)

Figure 10A:
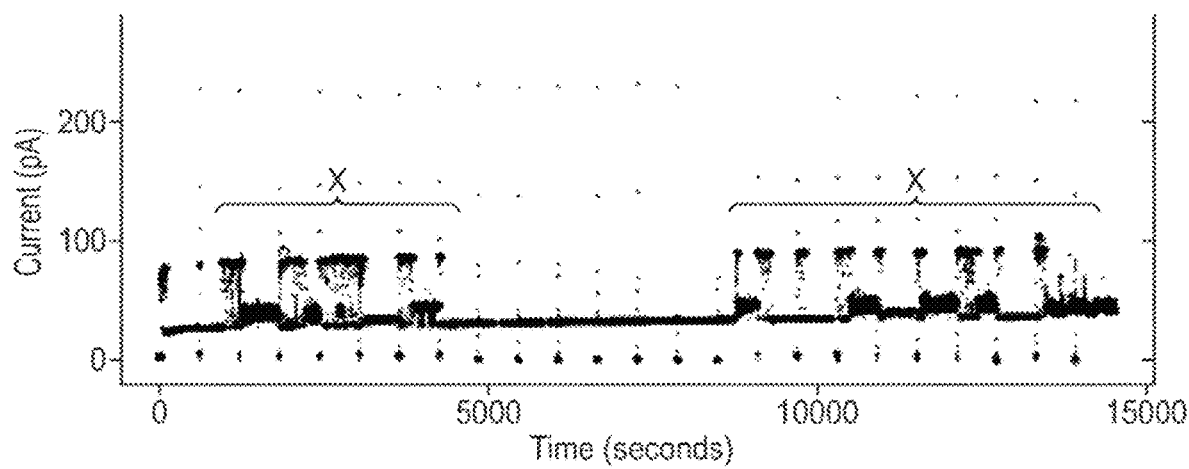

11—CsgG-Eco-(D149N-E185R-D195N-E201N-E203N)-StrepII(C))9 (SEQ ID NO: 2 with mutations D149N/E185R/D195N/E201N/E203N where StrepII(C) is SEQ ID NO: 47 and is attached at the C-terminus) (FIG. 10A)

Figure 10B:
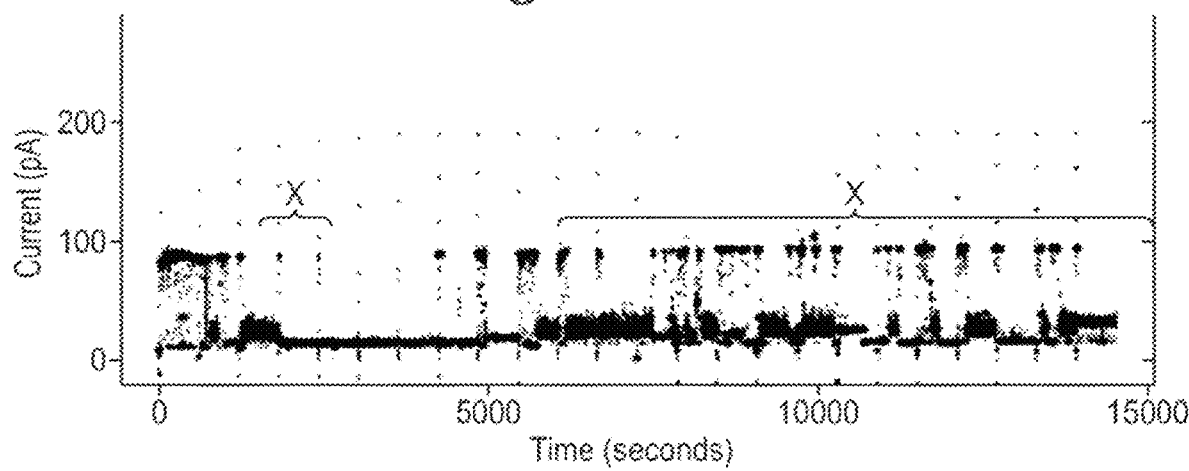

12—CsgG-Eco-(D149N-E185R-D195N-E201R-E203N)-StrepII(C))9 (SEQ ID NO: 2 with mutations D149N/E185R/D195N/E201R/E203N where StrepII(C) is SEQ ID NO: 47 and is attached at the C-terminus) (FIG. 10B)

Figure 11:
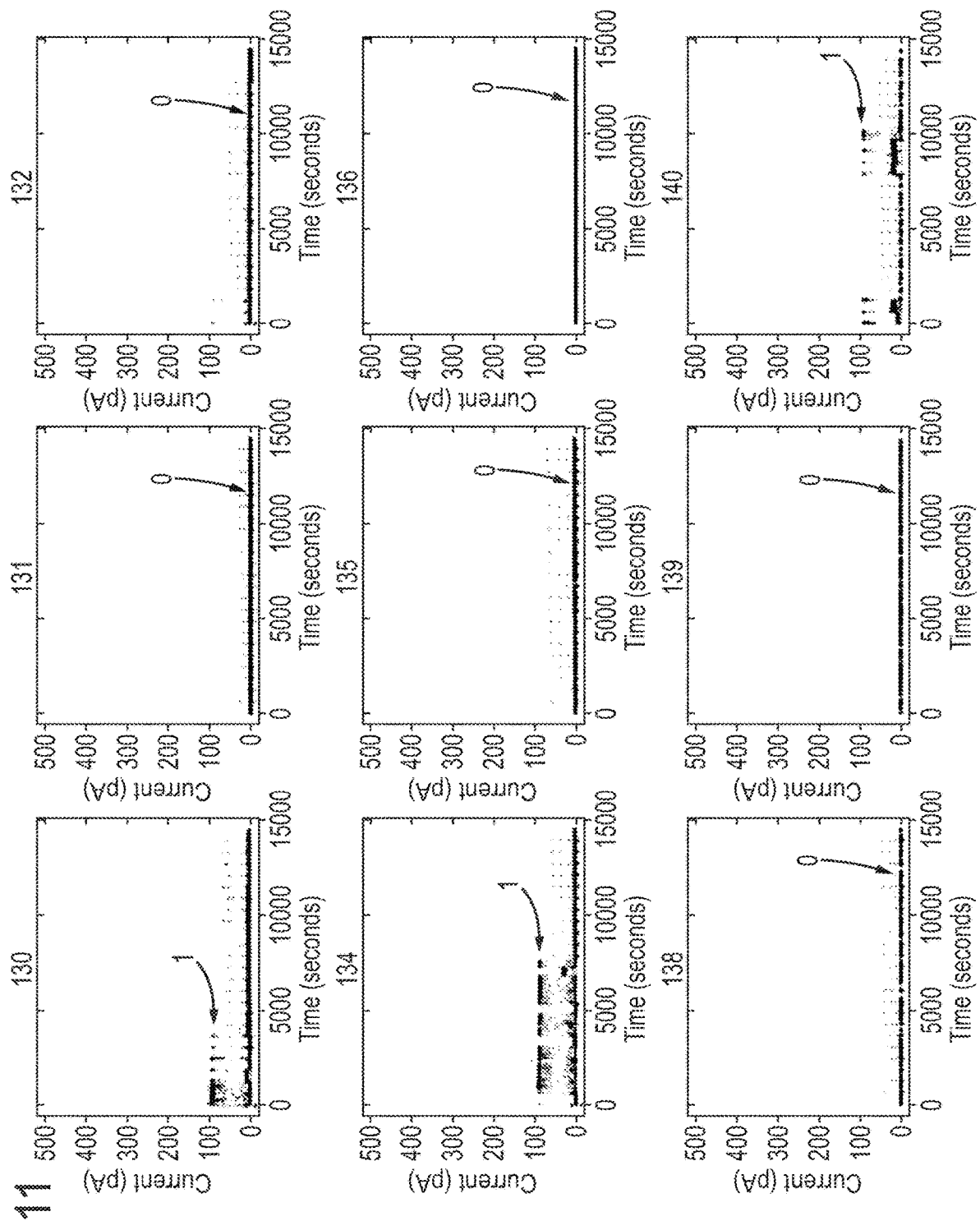
FIGS. 11 and 12: Mutant pore showing increased insertion compared with wild-type (WT).
Figure 12:
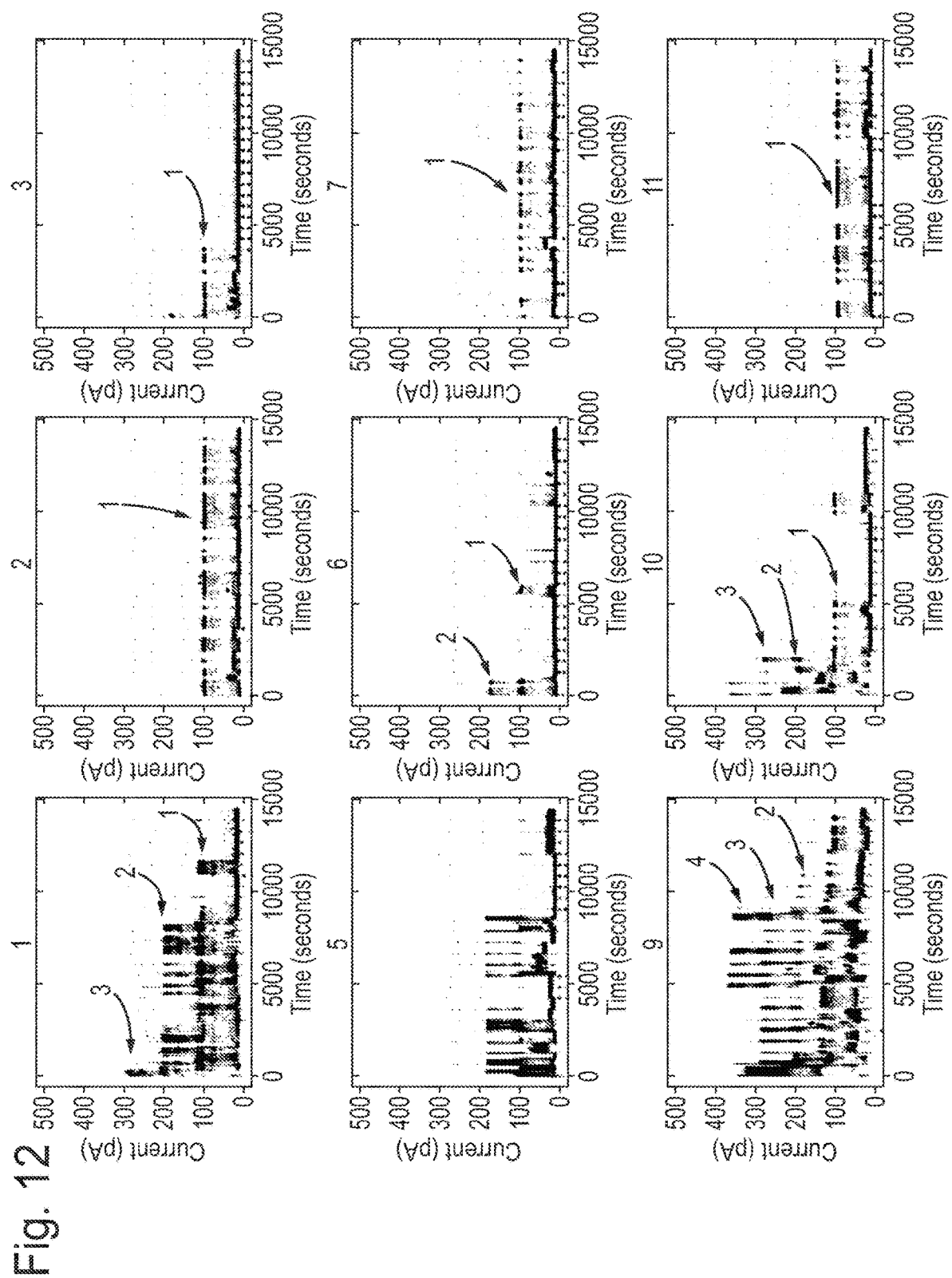

Pore Showing Increased Insertion (FIGS. 11 and 12)

As can be seen by comparing FIGS. 11 and 12, the mutant pore CsgG-Eco-(T150I-StrepII(C))9 (SEQ ID NO: 2 with mutations T150I where StrepII(C) is SEQ ID NO: 47 and is attached at the C-terminus) shown in FIG. 12. was present in the membrane in increased pore numbers (~4-5 fold) compared with the CsgG-Eco-(StrepII(C)) (SEQ ID NO: 2 where StrepII(C) is SEQ ID NO: 47 and is attached at the C-terminus) pore (shown in FIG. 11). Arrows in FIGS. 11 and 12 illustrated the number of CsgG-Eco nanopores which inserted into the block co-polymer in a 4 hour experiment (130-140 in FIG. 11 and 1-11 in FIG. 12 each corresponded to a separate nanopore experiment). For CsgG-Eco-(StrepII (C)) (SEQ ID NO: 2 where StrepII(C) is SEQ ID NO: 47 and is attached at the C-terminus) three experiments showed insertion of one nanopore, whereas for the mutant pore (CsgG-Eco-(T150I-StrepII(C))9) each experiment showed insertion of at least one nanopore and several experiments showed multiple pore insertions.

Example 3

This example described an *E. coli* purification method developed to purify the CsgG pore.
Materials and Methods
DNA encoding the polypeptide Pro-CsgG-Eco-(StrepII (C)) (SEQ ID NO: 2 where StrepII(C) is SEQ ID NO: 47 and is attached at the C-terminus and where Pro is SEQ ID NO: 48 and is attached at the N-terminus) was synthesised in GenScript USA Inc. and cloned into a pT7 vector containing ampicillin resistance gene. Protein expression of the pT7 vector was induced by Isopropyl β-D-1-thiogalactopyranoside (IPTG). The concentration of the DNA solution was adjusted to 400 ng/uL. DNA (1 μl) was used to transform Lemo21(DE3) competent *E. coli* cells (50 μl, NEB, catalogue number C2528H). Prior to transformation, the CsgG gene was knocked out from Lemo21(DE3) cells (Gene Bridges GmbH, Germany). The cells were then plated out on LB agar containing ampicillin (0.1 mg/mL) and incubated for approx 16 hours at 37° C.

Bacterial colonies grown on LB plates, containing ampicillin, incorporated the CsgG plasmid. One such colony was used to inoculate a starter culture of LB media (100 mL) containing carbenicillin (0.1 mg/mL). The starter culture was grown at 37° C. with agitation until OD600 was reached to 1.0-1.2. The starter culture was used to inoculate a fresh 500 mL of LB media containing carbenicillin (0.1 mg/mL) and Rhamnose (500 μM) to an O.D. 600 of 0.1. The culture was grown at 37° C. with agitation until OD600 reached 0.6. The temperature of the culture was then adjusted to 18° C. and induction was initiated by the addition of IPTG (0.2 mM final concentration). Induction was carried out for approximately 18 hours with agitation at 18° C.

Following induction, the culture was pelleted by centrifugation at 6,000 g for 30 minutes. The pellet was resuspended in 50 mM Tris, 300 mM NaCl, containing protease inhibitors (Merck Millipore 539138), benzonase nuclease (Sigma E1014) and 1× bugbuster (Merck Millipore 70921) pH8.0 (approximately 10 mL of buffer per gram of pellet). Suspension was mixed well until it was fully homogeneous, the sample was then transferred to roller mixer at 4° C. for approx 5 hours. Lysate was pelleted by centrifugation at 20,000 g for 45 minutes and the supernatant was filtered through 0.22 μM PES syringe filter. Supernatant which contained CsgG (known as sample 1) was taken forward for purification by column chromatography.

Figure 14:
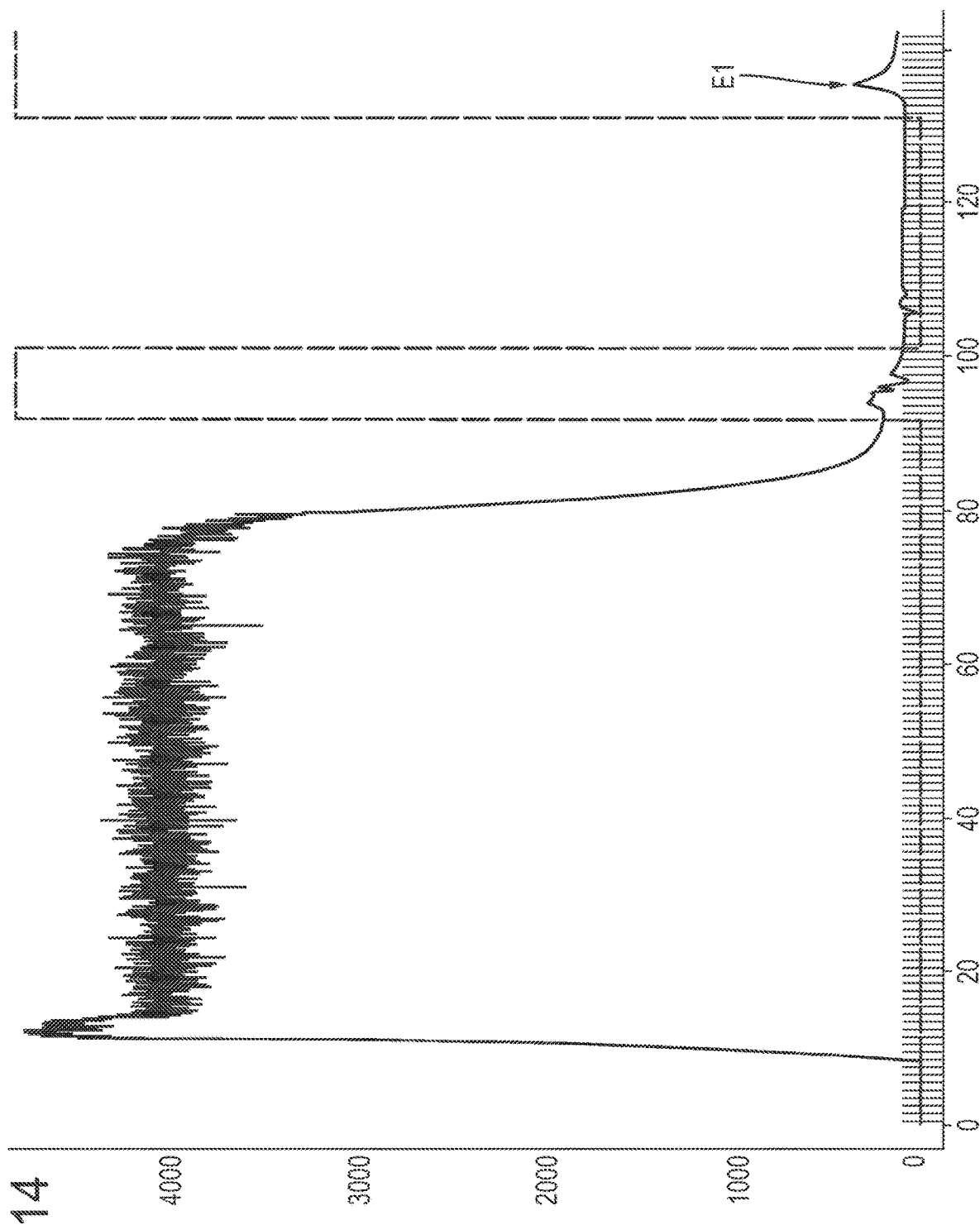
FIG. 14: shows an example chromatography trace of Strep trap (GE Healthcare) purification of CsgG protein (x-axis label=elution volume (mL), Y-axis label=Absorbance (mAu)). The sample was loaded in 25 mM Tris, 150 mM NaCl, 2 mM EDTA, 0.01% DDM and eluted with 10 mM desthiobiotin. The elution peak in which CsgG protein eluted is labelled as E1.
Figure 15:
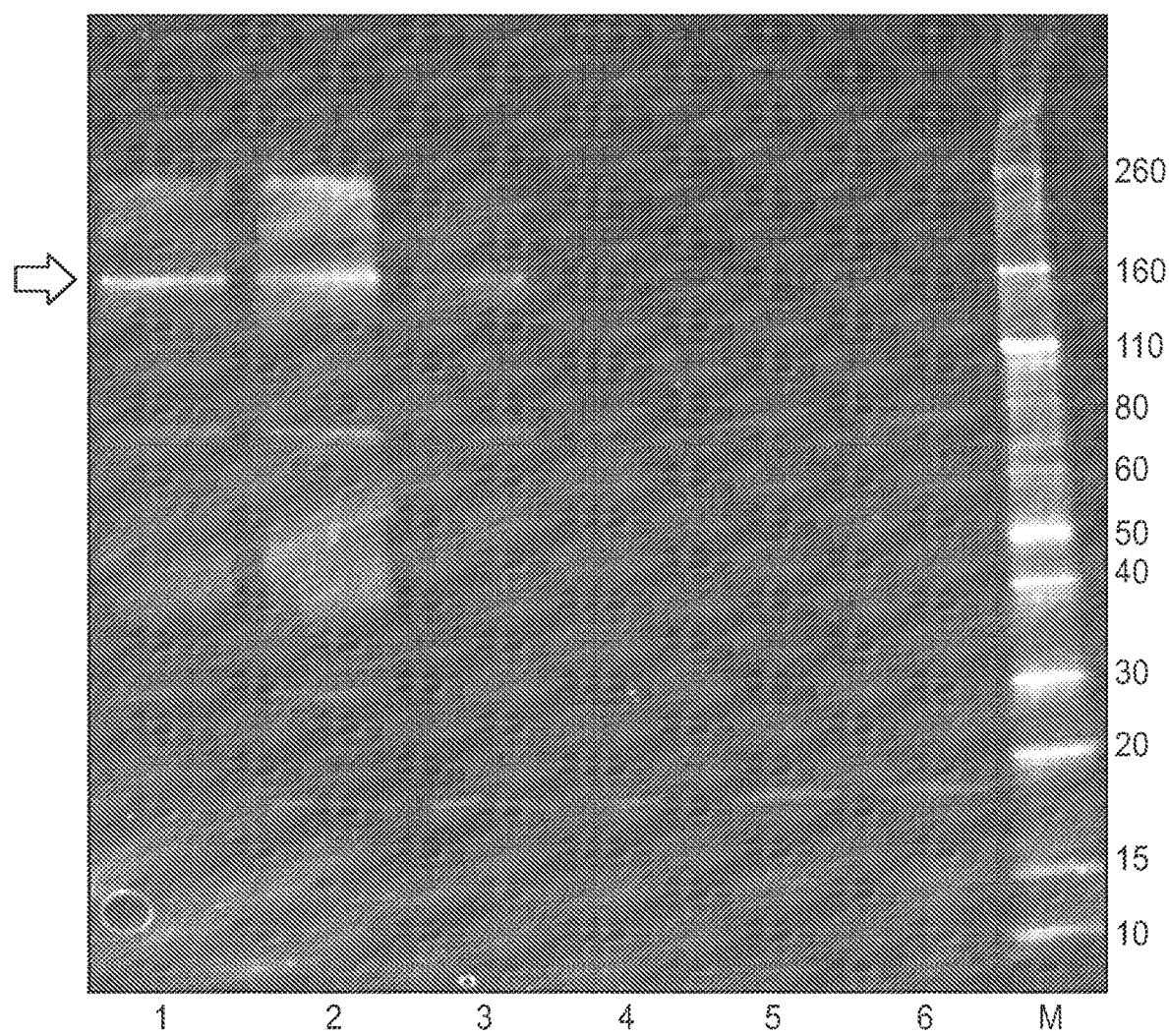
FIG. 15: shows an example of a typical SDS-PAGE visualisation of CsgG protein after the initial strep purification. A 4-20% TGX Gel (Bio Rad) was run at 300 V for 22 minutes in 1×TGS buffer. The gel was stained with Sypro Ruby stain. Lanes 1-3 show the main elution peak (labelled E1 in FIG. 14) which contained CsgG protein as indicated by the arrow. Lanes 4-6 corresponded to elution fractions of the tail of the main elution peak (labelled E1 in FIG. 14) which contained contaminants. M shows the molecular weight marker used which was a Novex Sharp Unstained (unit=kD).

Sample 1 was applied to a 5 mL Strep Trap column (GE Healthcare). The column was washed with 25 mM Tris, 150 mM NaCl, 2 mM EDTA, 0.01% DDM pH8 until a stable baseline of 10 column volumes was maintained. The column was then washed with 25 mM Tris, 2M NaCl, 2 mM EDTA, 0.01% DDM pH8 before being returned to the 150 mM buffer. Elution was carried out with 10 mM desthiobiotin. An example of a chromatography trace of Strep trap (GE Healthcare) purification of a CsgG protein is shown in FIG. 14. The elution peak is labelled E1. FIG. 15 shows an example of a typical SDS-PAGE visualization of CsgG-Eco protein after the initial Strep purification. Lanes 1-3 shows the main elution peak (labelled E1 in FIG. 14) which contained CsgG protein as indicated by the arrow. Lanes 4-6 corresponded to elution fractions of the tail of the main elution peak (labelled E1 in FIG. 14) which contained contaminants.

Figure 16:
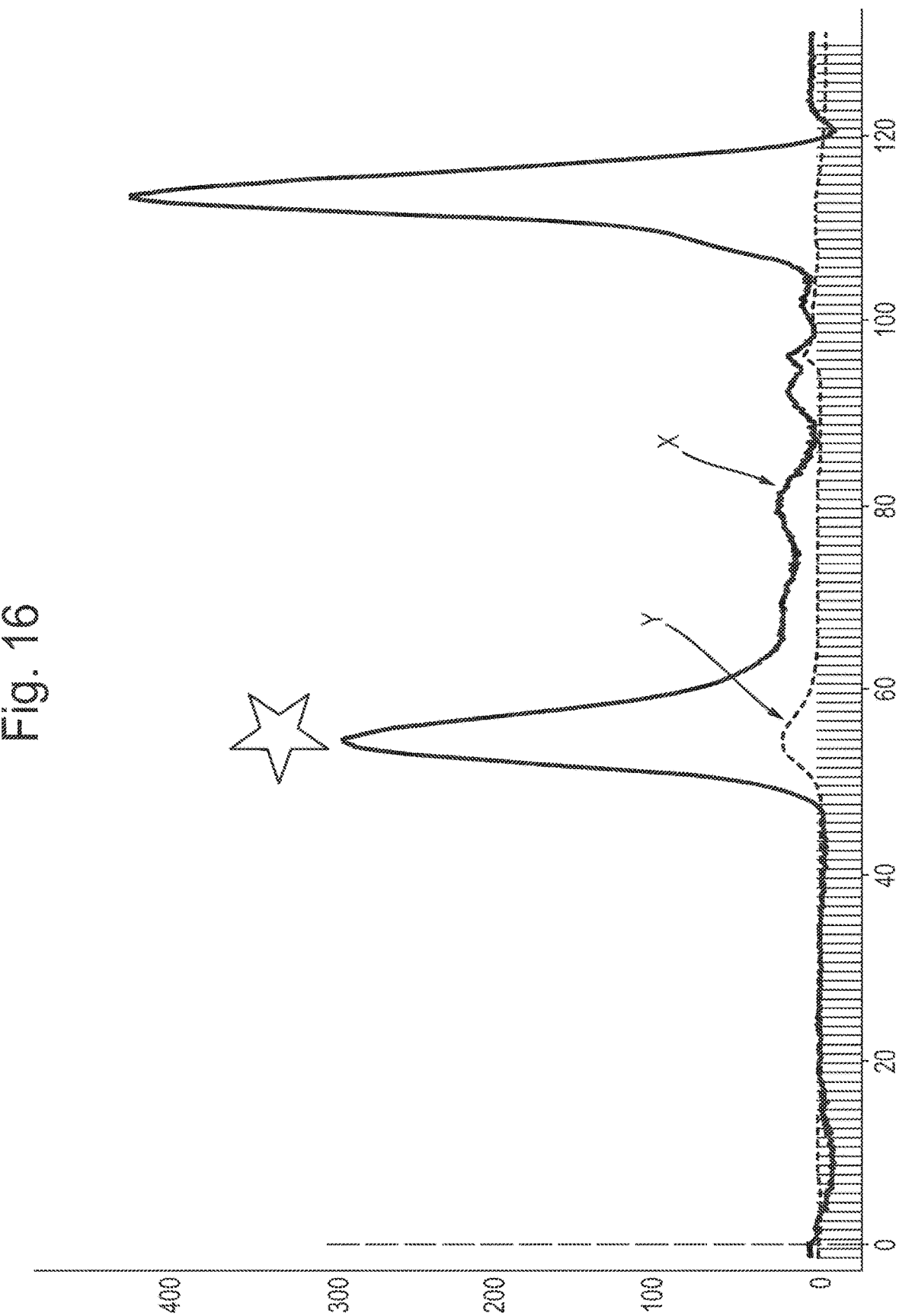
FIG. 16: Shows an example of a size exclusion chromatogram (SEC) of CsgG protein (120 mL S200 GE healthcare, x-axis label=elution volume (mL), y-axis label=absorbance (mAu)). The SEC was carried out after strep purification and heating the protein sample. The running buffer for SEC was 25 mM Tris, 150 mM NaCl, 2 mM EDTA, 0.01% DDM, 0.1% SDS, pH 8.0 and the column was run at 1 mL/minute rate. The trace labelled X shows absorbance at 220 nm and the trace labelled Y shows absorbance at 280 nm. The peak labelled with a star was collected.
Figure 17:
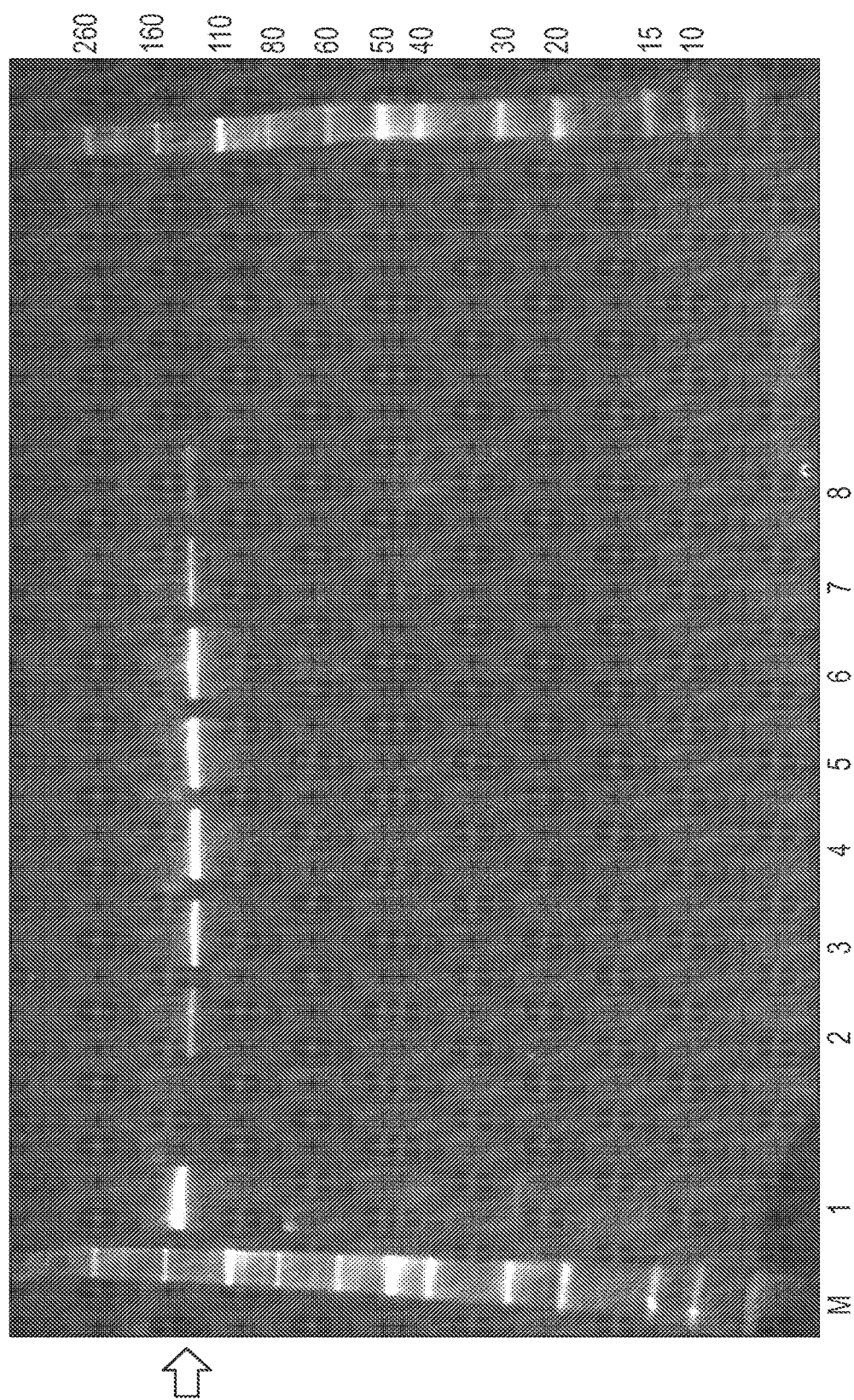
FIG. 17: shows an example of a typical SDS-PAGE visualisation of CsgG protein after SEC. A 4-20% TGX Gel (Bio Rad) was run at 300V for 22 minutes in 1×TGS buffer and the gel was stained with Sypro Ruby stain. Lane 1 shows CsgG protein sample after strep purification and heating but before SEC. Lanes 2-8 show fractions collected across the peak running approximately 48 mL-60 mL of FIG. 16 (mid peak=55 mL) and labelled with a star in FIG. 16. M shows the molecular weight marker used which was a Novex Sharp Unstained (unit=kD). The bar corresponding to the CsgG-Eco pore is indicated by an arrow.

The elution peak was pooled and heated to 65° C. for 15 minutes to remove heat unstable contaminated proteins. The heated solution was subjected to centrifugation at 20,000 g for 10 minutes and the pellet was discarded. The supernatant was subjected to gel filtration on a 120 mL Sephadex S200 column (GE Healthcare) in 25 mM Tris, 150 mM NaCl, 2 mM EDTA, 0.01% DDM, 0.1% SDS pH8. Monitoring was carried out at 220 nM due to low Tryptophan component of protein. The sample was eluted at approximately 55 mL volume (FIG. 16 shows the size exclusion column trace with the 55 mL sample peak labelled with a star). The elution peak was run on a 4-20% TGX (see FIG. 17, Bio Rad) to confirm the presence of the pore of interest CsgG-Eco-(StrepII(C)) (SEQ ID NO: 2 where StrepII(C) is SEQ ID NO: 47 and is attached at the C-terminus). Identified fractions were pooled and concentrated by 50 kD Amicon spin column.

Example 4

This example describes the simulations which were run to investigate the interaction between CsgG-Eco-(Y51T/F56Q)-StrepII(C))9 (SEQ ID NO: 2 with mutations Y51T/F56Q where StrepII(C) is SEQ ID NO: 47 and is attached at the C-terminus pore mutant No. 20) with T4 Dda-(E94C/C109A/C136A/A360C) (SEQ ID NO: 24 with mutations E94C/C109A/C136A/A360C and then (ΔM1)G1G2).
Simulation Methods
Simulations were performed using the GROMACS package version 4.0.5, with the GROMOS 53a6 forcefield and the SPC water model.

The CsgG-Eco-(Y51T/F56Q)-StrepII(C))9 (SEQ ID NO: 2 with mutations Y51T/F56Q where StrepII(C) is SEQ ID NO: 47 and is attached at the C-terminus pore mutant No. 20) model was based on the crystal structures of CsgG found in the protein data bank, accession codes 4UV3 and 4Q79. The relevant mutations were made using PyMOL. The resultant pore model was then energy minimised using the steepest descents algorithm. The T4 Dda-(E94C/C109A/C136A/A360C) (SEQ ID NO: 24 with mutations E94C/C109A/C136A/A360C and then (ΔM1)G1G2) model was based on the Dda1993 structure found in the protein data bank, accession code 3UPU. Again, relevant mutations were made using PyMOL, and the model was energy minimised using the steepest descents algorithm.

Figure 31:
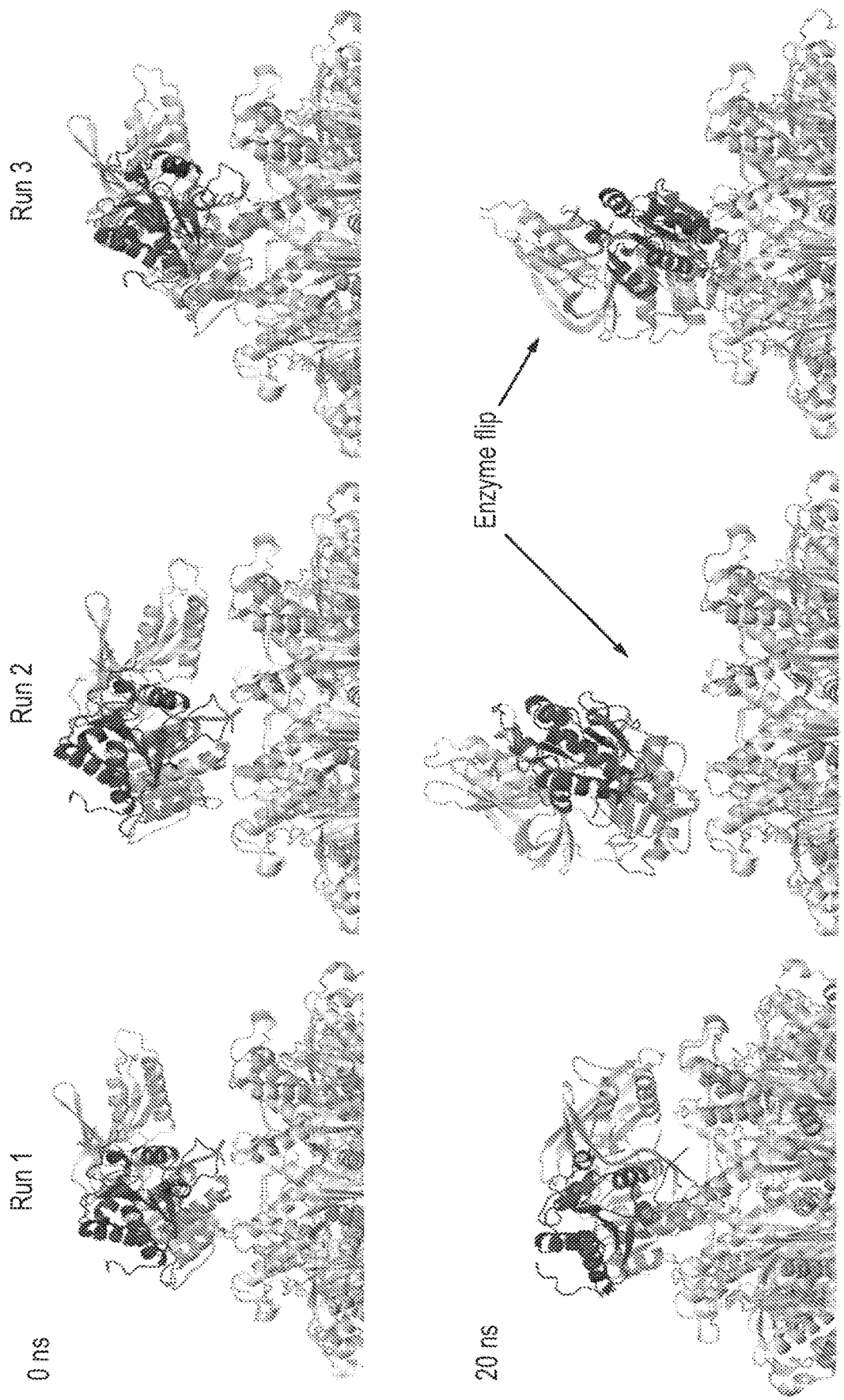
FIG. 31 shows snap shots of the enzyme (T4 Dda-(E94C/C109A/C136A/A360C) (SEQ ID NO: 24 with mutations E94C/C109A/C136A/A360C and then (ΔM1)G1G2)) on top of the pore (CsgG-Eco-(Y51T/F56Q)-StrepII(C))9 (SEQ ID NO: 2 with mutations Y51T/F56Q where StrepII(C) is SEQ ID NO: 47 and is attached at the C-terminus pore mutant No. 20)) taken at 0 and 20 ns during the simulations (Runs 1 to 3).

The T4 Dda-(E94C/C109A/C136A/A360C) (SEQ ID NO: 24 with mutations E94C/C109A/C136A/A360C and then (ΔM1)G1G2) model was then placed above CsgG-Eco-(Y51T/F56Q)-StrepII(C))9 (SEQ ID NO: 2 with mutations Y51T/F56Q where StrepII(C) is SEQ ID NO: 47 and is attached at the C-terminus pore mutant No. 20). Three simulations were performed with a different initial enzyme conformation (Runs 1 to 3 (0 ns), see FIG. 31):

In all enzyme conformations, the enzyme was oriented such that the 5' end of the DNA was pointing towards the pore, and the enzyme was unrestrained throughout the simulation. The pore backbone was restrained and the simulation box was solvated. The system was simulated in the NPT ensemble for 40 ns, using the Berendsen thermostat and Berendsen barostat to 300 K.

Figure 32:
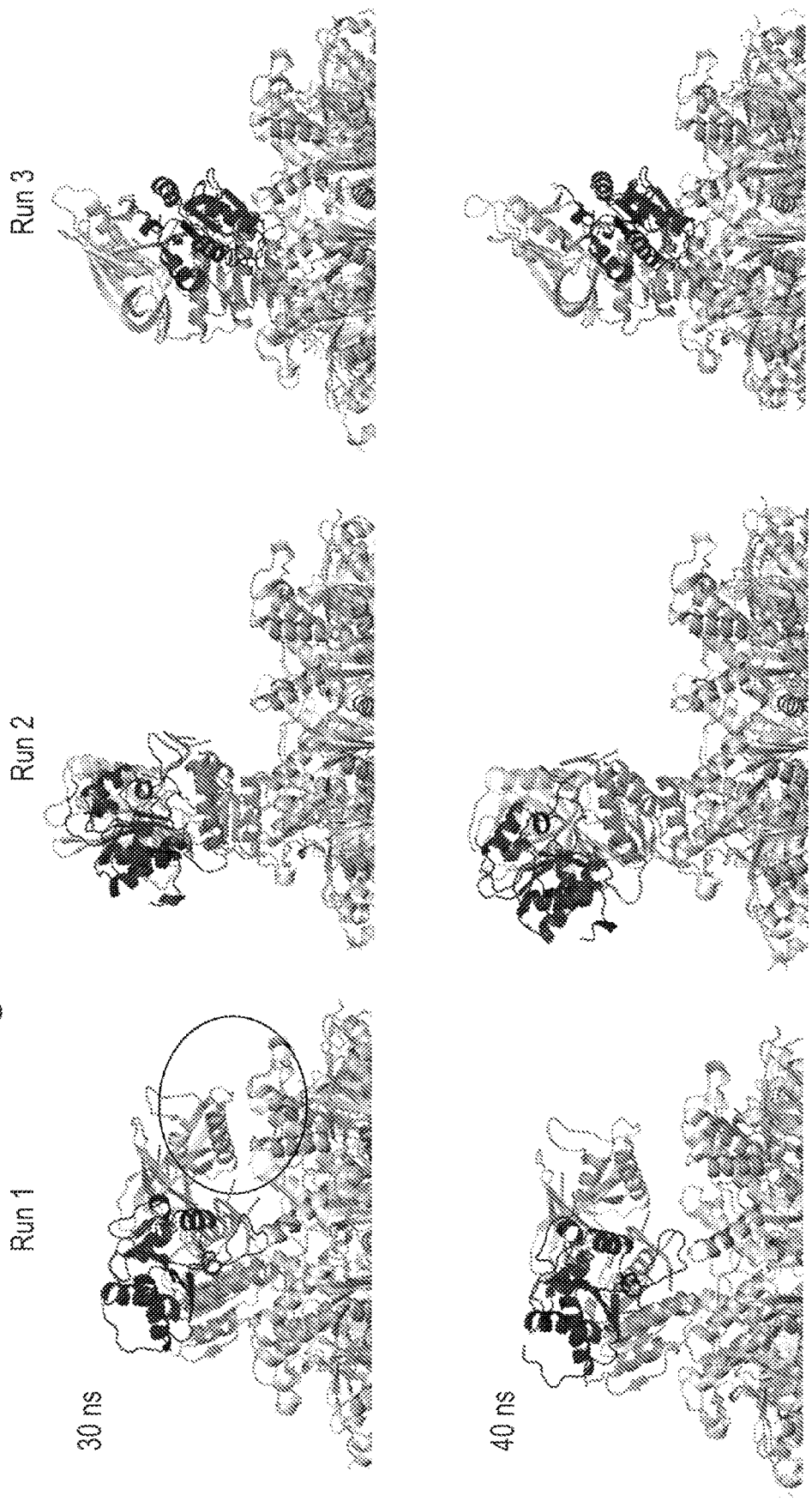
FIG. 32 shows snap shots of the enzyme (T4 Dda-(E94C/C109A/C136A/A360C) (SEQ ID NO: 24 with mutations E94C/C109A/C136A/A360C and then (ΔM1)G1G2)) on top of the pore (CsgG-Eco-(Y51T/F56Q)-StrepII(C))9 (SEQ ID NO: 2 with mutations Y51T/F56Q where StrepII(C) is SEQ ID NO: 47 and is attached at the C-terminus pore mutant No. 20)) taken at 30 and 40 ns during the simulations (Runs 1 to 3).

The contacts between the enzyme and pore were analysed using both GROMACS analysis software and also locally written code. The tables below show the number of contacts observed for both pore and enzyme amino acids. Tables 6-8 shows the amino acid contact points on pore which interact with the amino acid contact points on the enzyme. In two out of the three simulations the enzyme tilts on top of the pore (see run 2 and 3 (20, 30 and 40 ns), FIGS. 31 and 32). Run 1 shows that the enzyme has not tilted and so points that are shown to have high interaction in table 6 can be optimised in order to increase enzyme stability on the pore cap.

TABLE 6 run 1 enzyme and pore contact interactions

| Pore | Enzyme | # contacts |
|---|---|---|
| ASN 102 | ASP 198 | 8200 |
| ASN 102 | TYR 438 | 8130 |
| GLN 100 | ASP 212 | 7369 |
| GLU 101 | TRP 195 | 5979 |
| ARG 97 | TYR 350 | 4873 |
| GLU 101 | LEU 215 | 4851 |
| ASN 102 | TRP 195 | 3988 |
| ARG 97 | TYR 415 | 3798 |
| GLU 101 | TYR 350 | 3759 |
| LEU 113 | ASP 212 | 3718 |
| ASN 102 | LYS 358 | 3124 |
| ARG 97 | GLY 211 | 2765 |
| GLU 101 | CYS 412 | 2715 |
| ARG 97 | GLY 193 | 2708 |
| ASN 102 | ILE 196 | 2342 |
| GLU 101 | TYR 415 | 2268 |
| GLU 101 | ARG 216 | 2158 |
| ARG 110 | THR 213 | 2094 |
| ARG 110 | ASP 212 | 2066 |
| GLY 103 | ARG 216 | 1456 |
| GLU 101 | TYR 318 | 1333 |
| ASN 102 | GLU 347 | 1316 |
| GLU 101 | LYS 194 | 1310 |
| ARG 97 | PRO 411 | 1203 |
| GLU 101 | LYS 358 | 1161 |
| ASN 102 | ARG 216 | 1132 |
| ARG 97 | TRP 195 | 888 |
| LYS 94 | TYR 415 | 793 |
| ASN 102 | PRO 315 | 696 |
| ASN 102 | LYS 247 | 541 |
| GLU 101 | ALA 214 | 449 |
| ASN 102 | ASP 346 | 440 |
| ARG 97 | ALA 214 | 366 |
| ARG 97 | LYS 194 | 336 |
| GLU 101 | ASP 212 | 302 |
| ARG 97 | VAL 439 | 267 |
| ARG 110 | THR 210 | 263 |
| ARG 97 | THR 210 | 259 |
| ARG 97 | GLN 422 | 257 |
| GLU 101 | TYR 409 | 228 |
| ALA 98 | TRP 195 | 207 |
| GLU 101 | LYS 247 | 201 |
| ASN 102 | GLU 317 | 179 |
| ARG 110 | ARG 216 | 147 |
| ARG 97 | ASP 212 | 108 |
| ASN 102 | VAL 314 | 87 |
| GLU 101 | THR 213 | 72 |
| ASN 102 | LYS 255 | 70 |
| VAL 105 | ARG 216 | 69 |
| ASN 102 | LEU 215 | 59 |
| ASN 102 | THR 210 | 55 |
| ILE 111 | ASP 212 | 48 |
| ARG 97 | HIS 414 | 48 |
| THR 104 | ARG 216 | 36 |
| ASN 102 | TYR 197 | 32 |
| GLN 100 | THR 213 | 30 |
| ASN 102 | GLU 361 | 28 |

TABLE 6-continued run 1 enzyme and pore contact interactions

| Pore | Enzyme | # contacts |
|---|---|---|
| ARG 97 | VAL 418 | 28 |
| ALA 98 | TYR 415 | 27 |
| GLU 101 | LEU 354 | 17 |
| GLU 101 | TYR 197 | 16 |
| ASN 102 | GLY 316 | 16 |
| ARG 97 | GLU 361 | 16 |
| ARG 97 | GLU 347 | 14 |
| ILE 107 | ARG 216 | 12 |
| ASN 102 | GLY 208 | 12 |
| ARG 97 | TYR 409 | 11 |
| ARG 97 | LYS 247 | 11 |
| GLU 101 | LYS 364 | 8 |
| ARG 97 | PHE 209 | 7 |
| LYS 94 | GLU 419 | 6 |
| GLU 101 | PRO 411 | 5 |
| GLU 101 | GLU 317 | 5 |
| ASN 102 | ILE 251 | 5 |
| ARG 97 | LEU 354 | 5 |
| LYS 94 | VAL 418 | 3 |
| ASN 102 | ARG 321 | 3 |
| ARG 97 | LYS 243 | 3 |
| LYS 94 | CYS 412 | 2 |
| LEU 113 | THR 210 | 2 |
| GLY 103 | GLU 317 | 2 |
| GLU 101 | LYS 351 | 2 |
| ASN 102 | TYR 318 | 2 |
| ASN 102 | MET 219 | 2 |
| ASN 102 | LYS 194 | 2 |
| ARG 97 | VAL 314 | 2 |
| ARG 97 | LYS 364 | 2 |
| THR 104 | PRO 315 | 1 |
| GLY 103 | THR 213 | 1 |
| GLU 101 | PRO 315 | 1 |

TABLE 7 run 2 enzyme and pore contact interactions

| Pore | Enzyme | # contacts |
|---|---|---|
| GLU 101 | THR 210 | 14155 |
| SER 115 | ASP 202 | 9477 |
| ARG 97 | THR 210 | 9064 |
| ASN 102 | VAL 200 | 5323 |
| THR 104 | ASP 202 | 4476 |
| ASN 102 | ASN 221 | 3422 |
| GLU 101 | PHE 437 | 3171 |
| ARG 97 | ASP 217 | 2698 |
| GLU 101 | ARG 216 | 2198 |
| ARG 97 | GLY 208 | 1730 |
| GLU 101 | LYS 199 | 1710 |
| SER 115 | SER 224 | 1440 |
| ASN 102 | LYS 199 | 1351 |
| ASN 102 | ASP 212 | 1298 |
| ASN 102 | ARG 405 | 1219 |
| GLU 101 | ARG 207 | 1180 |
| ASN 102 | SER 224 | 1150 |
| ASN 102 | LYS 255 | 1114 |
| ARG 97 | ASP 198 | 946 |
| GLU 101 | PHE 209 | 931 |
| ARG 97 | THR 213 | 791 |
| ARG 97 | ARG 216 | 599 |
| ASN 102 | THR 210 | 589 |
| GLN 114 | ASP 202 | 530 |
| ASN 102 | ASP 202 | 492 |
| ARG 97 | ASP 212 | 490 |
| GLY 103 | ARG 405 | 474 |
| THR 104 | SER 224 | 451 |
| GLU 101 | LYS 255 | 429 |
| ASN 102 | ASP 198 | 405 |
| ASN 102 | PHE 209 | 400 |
| ASN 102 | ARG 178 | 316 |
| ARG 110 | GLU 258 | 309 |

TABLE 7-continued run 2 enzyme and pore contact interactions

| Pore | Enzyme | # contacts |
|---|---|---|
| ASN 102 | ASN 180 | 257 |
| GLN 100 | PHE 223 | 256 |
| GLU 101 | TYR 197 | 220 |
| GLN 114 | SER 228 | 212 |
| LEU 113 | PHE 223 | 210 |
| ASN 102 | ILE 225 | 204 |
| GLN 114 | LYS 227 | 194 |
| GLU 101 | GLY 211 | 189 |
| GLU 101 | ASP 212 | 174 |
| LEU 113 | SER 224 | 159 |
| LEU 113 | GLY 203 | 145 |
| ARG 97 | VAL 220 | 134 |
| GLU 101 | THR 213 | 133 |
| THR 104 | SER 228 | 125 |
| ARG 97 | TYR 197 | 123 |
| LYS 94 | ASP 212 | 118 |
| ASN 102 | ARG 216 | 110 |
| ASN 102 | ASN 235 | 108 |
| ASN 102 | GLY 211 | 104 |
| GLU 101 | ARG 405 | 79 |
| GLN 114 | SER 224 | 69 |
| ASN 102 | VAL 220 | 63 |
| LEU 113 | LYS 227 | 49 |
| ASN 102 | VAL 201 | 42 |
| ARG 97 | PHE 209 | 42 |
| GLU 101 | ASN 180 | 40 |
| ARG 97 | TYR 438 | 38 |
| ARG 97 | ARG 207 | 32 |
| ASN 102 | PHE 407 | 28 |
| SER 115 | ASN 221 | 23 |
| ARG 110 | HIS 204 | 22 |
| GLU 101 | PHE 223 | 21 |
| ARG 97 | ASP 189 | 19 |
| ARG 110 | PHE 223 | 16 |
| THR 104 | ILE 225 | 13 |
| GLY 103 | ASN 180 | 11 |
| ARG 97 | LYS 194 | 11 |
| GLU 101 | PHE 407 | 10 |
| ARG 97 | MET 219 | 9 |
| THR 104 | ASN 235 | 8 |
| ARG 110 | ARG 405 | 8 |
| ARG 97 | TRP 195 | 7 |
| ILE 111 | PHE 223 | 6 |
| GLU 101 | GLY 208 | 6 |
| LEU 113 | ASP 202 | 5 |
| GLU 101 | ARG 178 | 5 |
| ASN 102 | THR 213 | 5 |
| ALA 98 | ARG 216 | 5 |
| ASN 102 | ASP 217 | 4 |
| ARG 97 | LYS 199 | 4 |
| THR 104 | LEU 229 | 3 |
| THR 104 | ARG 405 | 3 |
| GLU 101 | VAL 201 | 3 |
| GLU 101 | MET 219 | 3 |
| ARG 110 | ASP 202 | 3 |
| ARG 110 | ARG 207 | 2 |
| THR 104 | VAL 201 | 1 |
| GLY 103 | SER 224 | 1 |
| GLY 103 | LYS 255 | 1 |
| GLY 103 | GLU 258 | 1 |
| GLY 103 | ASN 235 | 1 |
| GLU 101 | ASP 198 | 1 |
| ASN 102 | PHE 437 | 1 |
| ARG 97 | PHE 437 | 1 |
| ARG 110 | LYS 227 | 1 |

TABLE 8 run 3 enzyme and pore contact interactions

| Pore | Enzyme | # contacts |
|---|---|---|
| ARG 97 | THR 174 | 15557 |
| GLN 100 | ASP 5 | 10353 |
| GLU 101 | LYS 177 | 9238 |
| ARG 97 | SER 179 | 6630 |
| LEU 116 | ASP 202 | 6545 |
| GLU 101 | TYR 434 | 6524 |
| SER 115 | ASP 202 | 5693 |
| GLU 101 | HIS 204 | 5457 |
| ARG 97 | GLN 10 | 5106 |
| ARG 93 | ASP 202 | 4646 |
| ARG 93 | GLU 8 | 4446 |
| SER 115 | LYS 11 | 4342 |
| LEU 113 | ASP 5 | 3871 |
| ASN 102 | SER 224 | 3605 |
| GLU 101 | ASN 12 | 3344 |
| GLU 101 | GLN 10 | 3327 |
| ARG 97 | GLU 175 | 3096 |
| GLU 101 | SER 224 | 3028 |
| LEU 116 | GLU 8 | 2936 |
| LYS 94 | ASP 185 | 2708 |
| ARG 97 | ASN 180 | 2700 |
| GLU 101 | PHE 3 | 2500 |
| THR 104 | LYS 11 | 2352 |
| SER 115 | GLU 8 | 2323 |
| ARG 93 | ASN 180 | 1912 |
| ASN 102 | LYS 177 | 1838 |
| LYS 94 | ASP 198 | 1828 |
| ARG 110 | ASP 5 | 1714 |
| ALA 98 | GLY 203 | 1701 |
| ASN 102 | ASN 12 | 1695 |
| GLU 101 | TYR 169 | 1691 |
| ARG 97 | THR 7 | 1593 |
| ARG 110 | ASP 4 | 1404 |
| ARG 97 | ASP 212 | 1381 |
| ASN 102 | HIS 204 | 1226 |
| ASN 102 | ASN 15 | 1173 |
| ARG 97 | VAL 176 | 1096 |
| ALA 98 | HIS 204 | 998 |
| ARG 97 | ASP 202 | 875 |
| ASN 102 | TYR 434 | 850 |
| ALA 98 | ASN 12 | 716 |
| GLU 101 | THR 213 | 702 |
| GLU 101 | ARG 178 | 642 |
| GLU 101 | ASN 221 | 600 |
| ASN 102 | LYS 11 | 588 |
| ARG 97 | ASP 217 | 585 |
| ARG 97 | ARG 207 | 537 |
| GLU 101 | ARG 207 | 525 |
| ARG 97 | PHE 437 | 511 |
| GLU 101 | ARG 216 | 510 |
| ASN 102 | LYS 19 | 482 |
| ARG 97 | HIS 204 | 473 |
| LEU 113 | LYS 11 | 409 |
| ARG 97 | THR 213 | 358 |
| ARG 93 | ASP 212 | 354 |
| ARG 97 | TYR 169 | 316 |
| ARG 97 | GLY 203 | 308 |
| ARG 97 | ASP 435 | 300 |
| GLN 87 | LYS 199 | 249 |
| THR 104 | ASN 15 | 221 |
| ARG 97 | ALA 181 | 220 |
| ASN 102 | LYS 227 | 198 |
| LYS 94 | ARG 178 | 184 |
| ASN 102 | GLU 8 | 183 |
| LEU 113 | LEU 6 | 182 |
| ARG 93 | SER 179 | 179 |
| LEU 90 | ASN 180 | 172 |
| LEU 90 | ASP 202 | 144 |
| ARG 97 | ILE 225 | 138 |
| GLU 101 | ASN 15 | 135 |
| GLU 101 | LYS 19 | 113 |
| LYS 94 | ASN 180 | 109 |
| LYS 94 | GLU 175 | 105 |
| ARG 93 | THR 7 | 81 |
| LYS 94 | ARG 207 | 77 |
| GLN 100 | PHE 3 | 72 |

TABLE 8-continued run 3 enzyme and pore contact interactions

| Pore | Enzyme | # contacts |
|---|---|---|
| ASN 102 | ARG 216 | 66 |
| ARG 97 | LYS 177 | 62 |
| GLU 101 | THR 210 | 59 |
| ARG 97 | ARG 178 | 56 |
| LYS 94 | ASP 212 | 55 |
| ARG 97 | GLU 172 | 53 |
| GLU 101 | VAL 176 | 51 |
| ALA 98 | ARG 207 | 49 |
| ARG 110 | PHE 3 | 48 |
| ALA 98 | ASP 202 | 47 |
| ARG 97 | VAL 200 | 40 |
| ALA 98 | VAL 201 | 36 |
| LYS 94 | THR 210 | 35 |
| ILE 111 | ASP 5 | 32 |
| ARG 97 | ARG 405 | 27 |
| LEU 90 | VAL 200 | 26 |
| ARG 97 | THR 210 | 26 |
| GLY 103 | PHE 3 | 25 |
| GLU 101 | PHE 209 | 25 |
| ARG 97 | ARG 216 | 22 |
| ASN 102 | VAL 220 | 21 |
| LYS 94 | GLY 211 | 19 |
| ARG 97 | PHE 209 | 17 |
| GLU 101 | LYS 227 | 15 |
| GLN 114 | LYS 11 | 15 |
| GLY 103 | LYS 19 | 13 |
| ARG 97 | PHE 3 | 13 |
| GLU 101 | THR 2 | 12 |
| GLU 101 | ILE 225 | 12 |
| ARG 97 | ILE 184 | 12 |
| ALA 98 | GLU 8 | 12 |
| ALA 98 | ARG 178 | 12 |
| ASN 102 | ILE 225 | 11 |
| LYS 94 | LYS 199 | 10 |
| GLU 101 | ARG 433 | 8 |
| ARG 97 | ASN 221 | 8 |
| LYS 94 | VAL 200 | 7 |
| ASN 102 | ASP 202 | 7 |
| ASN 102 | ASN 221 | 7 |
| ARG 97 | LEU 173 | 7 |
| SER 115 | HIS 204 | 6 |
| ASN 102 | GLY 203 | 6 |
| GLU 101 | CYS 171 | 5 |
| ARG 97 | ASN 12 | 5 |
| ASN 102 | PHE 223 | 4 |
| ASN 102 | LYS 166 | 4 |
| ARG 97 | GLY 211 | 4 |
| ARG 97 | GLN 170 | 4 |
| GLU 101 | ARG 405 | 3 |
| ASN 102 | PHE 3 | 3 |
| GLU 101 | GLU 175 | 2 |
| ARG 97 | VAL 220 | 2 |
| ARG 93 | GLY 203 | 2 |
| LYS 94 | THR 174 | 1 |
| LEU 90 | LYS 199 | 1 |
| LEU 116 | ASN 180 | 1 |
| LEU 113 | ASP 212 | 1 |
| LEU 113 | ASP 202 | 1 |
| GLY 103 | ASN 15 | 1 |
| GLU 101 | THR 7 | 1 |
| GLU 101 | PHE 437 | 1 |
| GLN 114 | ASP 202 | 1 |
| ASN 102 | ARG 405 | 1 |
| ARG 97 | TYR 434 | 1 |
| ARG 97 | PRO 182 | 1 |
| ARG 97 | GLY 9 | 1 |
| ARG 97 | GLU 8 | 1 |
| ALA 99 | ASP 202 | 1 |

Example 5

This example describes the simulations which were run to investigate the interaction between a) CsgG-Eco-(Y51A/F56Q)-StrepII(C))9 (SEQ ID NO: 2 with mutations Y51A/F56Q where StrepII(C) is SEQ ID NO: 47 and is attached at the C-terminus pore mutant No. 25) with T4 Dda-(E94C/F98W/C109A/C136A/K194L/A360C) (SEQ ID NO: 24 with mutations E94C/F98W/C109A/C136A/K194L/A360C and then (ΔM1)G1G2) and b) CsgG-Eco-(Y51A/F56Q/R97W)-StrepII(C))9 (SEQ ID NO: 2 with mutations Y51A/F56Q/R97W where StrepII(C) is SEQ ID NO: 47 and is attached at the C-terminus pore mutant No. 26) with T4 Dda-(E94C/F98W/C109A/C136A/K194L/A360C) (SEQ ID NO: 24 with mutations E94C/F98W/C109A/C136A/K194L/A360C and then (ΔM1)G1G2).

Simulation Methods

Simulations were performed as described in Example 4.

The CsgG-Eco-(Y51A/F56Q)-StrepII(C))9 (SEQ ID NO: 2 with mutations Y51A/F56Q where StrepII(C) is SEQ ID NO: 47 and is attached at the C-terminus pore mutant No. 25) and CsgG-Eco-(Y51A/F56Q/R97W)-StrepII(C))9 (SEQ ID NO: 2 with mutations Y51A/F56Q/R97W where StrepII(C) is SEQ ID NO: 47 and is attached at the C-terminus pore mutant No. 26) models were based on the crystal structures of CsgG found in the protein data bank, accession codes 4UV3 and 4Q79. The relevant mutations were made using PyMOL. The resultant pore model was then energy minimised using the steepest descents algorithm.

The T4 Dda-(E94C/F98W/C109A/C136A/K194L/A360C) (SEQ ID NO: 24 with mutations E94C/F98W/C109A/C136A/K194L/A360C and then (ΔM1)G1G2) model was based on the Dda1993 structure found in the protein data bank, accession code 3UPU. Again, relevant mutations were made using PyMOL, and the model was energy minimised using the steepest descents algorithm.

The T4 Dda-(E94C/F98W/C109A/C136A/K194L/A360C) (SEQ ID NO: 24 with mutations E94C/F98W/C109A/C136A/K194L/A360C and then (ΔM1)G1G2) model was then placed above mutant pores 25 and 26.

In the simulations the enzyme was oriented such that the 5' end of the DNA was pointing towards the pore, and the enzyme was unrestrained throughout the simulation. For each of the mutant pores investigated two simulations were run—in the first the pore backbone was restrained and the simulation box was solvated and in the second the pore backbone was restrained except for the cap region and the simulation was box solvated. The system was simulated in the NPT ensemble for 40 ns, using the Berendsen thermostat and Berendsen barostat to 300 K.

The contacts between the enzyme and pore were analysed using both GROMACS analysis software and also locally written code. The tables below show the number of contacts observed for both pore and enzyme amino acids (for mutants 25 and 26 with T4 Dda-(E94C/F98W/C109A/C136A/K194L/A360C)). Tables 9 (pore backbone restrained) and 10 (pore backbone restrained with cap region unrestrained) show the amino acid contact points on pore mutant 25 and the number of contacts that they make with the enzyme (T4 Dda-(E94C/F98W/C109A/C136A/K194L/A360C)). Tables 11 (pore backbone restrained) and 12 (pore backbone restrained with cap region unrestrained) show the amino acid contact points on pore mutant 25 (CsgG-Eco-(Y51A/F56Q)-StrepII(C))9 (SEQ ID NO: 2 with mutations Y51A/F56Q where StrepII(C) is SEQ ID NO: 47 and is attached at the C-terminus) which interact with the amino acid contact points on the enzyme (T4 Dda-(E94C/F98W/C109A/C136A/K194L/A360C)). Tables 13 (pore backbone restrained) and 14 (pore backbone restrained with cap region unrestrained) show the amino acid contact points on pore mutant 26 and the number of contacts that they make with the enzyme (T4 Dda-(E94C/F98W/C109A/C136A/K194L/

Figure 33:
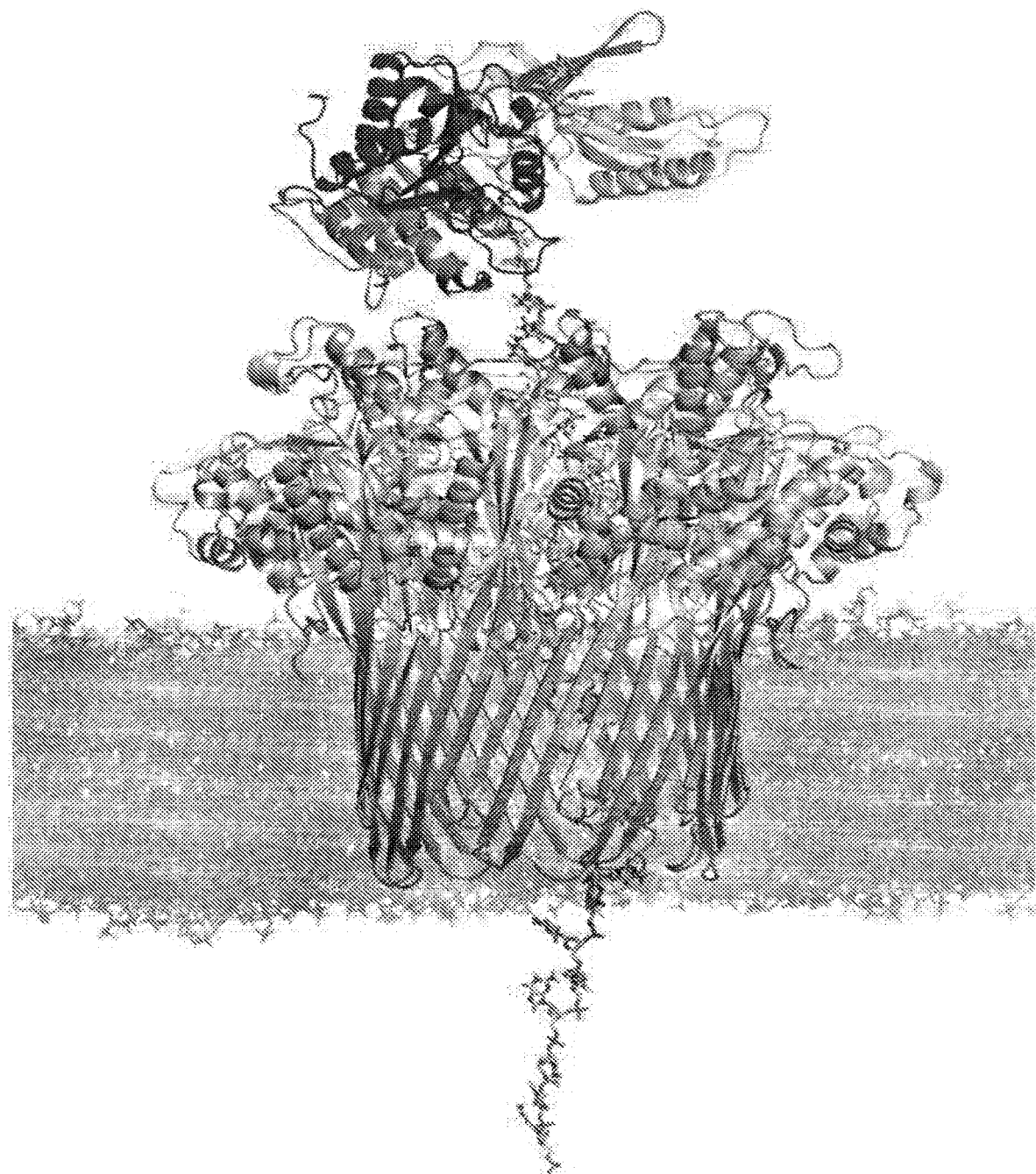
FIG. 33 shows a snap shot of the enzyme (T4 Dda-(E94C/F98W/C109A/C136A/K194L/A360C) (SEQ ID NO: 24 with mutations E94C/F98W/C109A/C136A/K194L/A360C and then (ΔM1)G1G2) on top of the pore CsgG-Eco-(Y51A/F56Q/R97W)-StrepII(C))9 (SEQ ID NO: 2 with mutations Y51A/F56Q/R97W where StrepII(C) is SEQ ID NO: 47 and is attached at the C-terminus pore mutant No. 26) taken during the simulations described in Example 5.

A360C)). Tables 15 (pore backbone restrained) and 16 (pore backbone restrained with cap region unrestrained) show the amino acid contact points on pore mutant 26 (CsgG-Eco-(Y51A/F56Q/R97W)-StrepII(C))9 (SEQ ID NO: 2 with mutations Y51A/F56Q/R97W where StrepII(C) is SEQ ID NO: 47 and is attached at the C-terminus)) which interact with the amino acid contact points on the enzyme (T4 Dda-(E94C/F98W/C109A/C136A/K194L/A360C)). FIG. 33 shows an initial snapshot of pore mutant 26 and T4 Dda-(E94C/F98W/C109A/C136A/K194L/A360C).

TABLE 9

| Amino Acid | Position | Number of Contacts |
|---|---|---|
| GLU | 101 | 26081 |
| ARG | 97 | 12985 |
| GLN | 100 | 6485 |
| ASN | 102 | 4941 |
| LEU | 113 | 3923 |
| LYS | 94 | 3159 |
| ARG | 110 | 2348 |
| GLN | 114 | 617 |
| ILE | 111 | 195 |
| ALA | 98 | 74 |
| ILE | 107 | 67 |
| THR | 104 | 24 |
| PRO | 112 | 21 |
| SER | 115 | 17 |
| GLY | 103 | 17 |
| GLN | 87 | 13 |
| LEU | 90 | 6 |
| ASN | 108 | 3 |

TABLE 10

| Amino Acid | Position | Number of Contacts |
|---|---|---|
| ARG | 97 | 17462 |
| GLU | 101 | 12262 |
| ASN | 102 | 9008 |
| LYS | 94 | 5982 |
| GLN | 100 | 3471 |
| GLY | 103 | 3366 |
| LEU | 113 | 1511 |
| GLN | 87 | 734 |
| THR | 104 | 500 |
| ARG | 110 | 420 |
| ASN | 91 | 273 |
| GLN | 114 | 178 |
| ALA | 98 | 94 |
| ARG | 93 | 44 |
| ILE | 111 | 21 |
| PRO | 112 | 13 |
| LEU | 90 | 13 |
| SER | 115 | 4 |
| VAL | 105 | 2 |
| ALA | 99 | 2 |
| ILE | 95 | 1 |

TABLE 11

| Pore | | Enzyme | | Number of |
|---|---|---|---|---|
| Amino Acid | Position | Amino Acid | Position | Contacts |
| GLU | 101 | TYR | 318 | 7116 |
| GLU | 101 | THR | 210 | 6306 |
| GLN | 100 | ASN | 365 | 4693 |
| GLU | 101 | TRP | 195 | 4608 |
| LEU | 113 | ASN | 367 | 3910 |
| LYS | 94 | ASP | 212 | 2369 |

TABLE 11-continued

| Pore | | Enzyme | | Number of |
|---|---|---|---|---|
| Amino Acid | Position | Amino Acid | Position | Contacts |
| ASN | 102 | LYS | 371 | 2088 |
| GLU | 101 | LYS | 364 | 1903 |
| ARG | 97 | SER | 224 | 1883 |
| ARG | 97 | TYR | 438 | 1764 |
| ARG | 110 | LYS | 368 | 1727 |
| GLU | 101 | LYS | 358 | 1443 |
| GLN | 100 | ASN | 367 | 1390 |
| GLU | 101 | GLN | 422 | 1356 |
| ARG | 97 | TRP | 195 | 1318 |
| ARG | 97 | PHE | 209 | 1095 |
| ARG | 97 | TYR | 318 | 965 |
| ARG | 97 | TYR | 350 | 895 |
| ASN | 102 | LYS | 358 | 833 |
| ARG | 97 | GLU | 361 | 818 |
| AUG | 97 | GLY | 208 | 706 |
| GLU | 101 | GLY | 316 | 697 |
| GLU | 101 | GLU | 317 | 678 |
| ARG | 97 | GLU | 317 | 647 |
| GLN | 114 | ASN | 367 | 617 |
| GLU | 101 | LYS | 371 | 506 |
| ASN | 102 | TRP | 366 | 466 |
| ARG | 97 | THR | 210 | 463 |
| ASN | 102 | ARG | 207 | 457 |
| LYS | 94 | ASP | 217 | 423 |
| GLU | 101 | ARG | 207 | 409 |
| ASN | 102 | GLU | 419 | 405 |
| GLN | 100 | LYS | 368 | 402 |
| GLU | 101 | ARG | 321 | 354 |
| ARG | 110 | GLY | 369 | 332 |
| ARG | 97 | GLN | 422 | 324 |
| ASN | 102 | GLY | 313 | 313 |
| ARG | 97 | ASN | 221 | 306 |
| ARG | 97 | VAL | 439 | 301 |
| ARG | 110 | ASN | 365 | 274 |
| SER | 257 | GLU | 258 | 267 |
| GLU | 101 | LYS | 310 | 217 |
| ILE | 111 | ASN | 367 | 195 |
| ARG | 97 | ASP | 198 | 154 |
| GLU | 101 | SER | 224 | 154 |
| ARG | 97 | VAL | 418 | 145 |
| ARG | 97 | ALA | 157 | 137 |
| GLU | 101 | GLY | 208 | 136 |
| ARG | 97 | GLU | 419 | 135 |
| LYS | 94 | TYR | 415 | 111 |
| ARG | 97 | VAL | 220 | 105 |
| ASN | 102 | PRO | 315 | 104 |
| ASN | 102 | GLU | 93 | 103 |
| ARG | 97 | LYS | 364 | 97 |
| LYS | 94 | TYR | 350 | 94 |
| ARG | 97 | GLU | 154 | 92 |
| ARG | 97 | ALA | 416 | 82 |
| GLU | 101 | PHE | 223 | 76 |
| ILE | 107 | LYS | 368 | 67 |
| ARG | 97 | GLU | 347 | 66 |
| ARG | 97 | TYR | 415 | 60 |
| ASN | 102 | TYR | 197 | 57 |
| LYS | 94 | GLY | 211 | 49 |
| LYS | 94 | THR | 213 | 47 |
| GLU | 101 | ASN | 365 | 46 |
| ARG | 97 | LEU | 354 | 41 |
| LYS | 94 | ARG | 216 | 41 |
| ALA | 98 | TRP | 195 | 37 |
| ASN | 102 | TRP | 195 | 34 |
| ALA | 98 | LYS | 358 | 32 |
| ASN | 102 | LEU | 194 | 27 |
| THR | 104 | TRP | 366 | 24 |
| ARG | 97 | GLY | 211 | 23 |
| PRO | 112 | ASN | 367 | 21 |
| GLU | 101 | PHE | 209 | 21 |
| ASN | 102 | LYS | 364 | 20 |
| LYS | 94 | ALA | 416 | 19 |
| SER | 115 | TRP | 366 | 17 |
| GLY | 103 | LEU | 194 | 17 |
| ARG | 97 | ASP | 212 | 16 |
| GLU | 101 | TYR | 415 | 15 |

TABLE 11-continued

| Pore Amino Acid | Position | Enzyme Amino Acid | Position | Number of Contacts |
|---|---|---|---|---|
| ARG | 110 | GLY | 370 | 15 |
| ARG | 97 | LYS | 351 | 14 |
| ASN | 102 | LYS | 310 | 14 |
| ASN | 102 | GLU | 154 | 14 |
| ARG | 97 | CYS | 360 | 13 |
| ARG | 97 | THR | 156 | 12 |
| GLU | 101 | LEU | 194 | 11 |
| GLN | 87 | ASP | 212 | 9 |
| ARG | 97 | PHE | 308 | 8 |
| GLU | 101 | LEU | 354 | 8 |
| LEU | 113 | TRP | 366 | 7 |
| ARG | 97 | ARG | 321 | 7 |
| GLU | 101 | ALA | 157 | 7 |
| LEU | 113 | ASN | 365 | 6 |
| GLU | 101 | GLY | 193 | 6 |
| ARG | 97 | ASP | 217 | 5 |
| ALA | 98 | THR | 210 | 5 |
| GLN | 87 | ARG | 216 | 4 |
| ARG | 97 | LEU | 319 | 4 |
| ARG | 97 | ASN | 155 | 4 |
| LYS | 94 | VAL | 220 | 4 |
| LEU | 90 | TYR | 415 | 3 |
| LEU | 90 | ASP | 212 | 3 |
| ARG | 97 | PHE | 223 | 3 |
| ARG | 97 | GLY | 193 | 3 |
| ARG | 97 | ALA | 421 | 3 |
| ASN | 108 | LYS | 368 | 3 |
| ASN | 102 | GLY | 316 | 3 |
| GLU | 101 | VAL | 418 | 3 |
| ARG | 97 | ILE | 159 | 2 |
| GLU | 101 | PRO | 315 | 2 |
| SER | 257 | ASP | 260 | 1 |
| ARG | 97 | GLY | 357 | 1 |
| ASN | 102 | THR | 210 | 1 |
| ASN | 102 | ILE | 196 | 1 |
| ASN | 102 | GLU | 317 | 1 |
| GLU | 101 | LYS | 227 | 1 |
| GLU | 101 | GLU | 361 | 1 |
| GLU | 101 | ASN | 221 | 1 |
| LYS | 94 | VAL | 418 | 1 |
| LYS | 94 | GLU | 154 | 1 |

TABLE 12

| Pore Amino Acid | Position | Enzyme Amino Acid | Position | Number of Contacts |
|---|---|---|---|---|
| ARG | 97 | ASN | 365 | 3386 |
| GLU | 101 | GLY | 316 | 2967 |
| GLY | 103 | ASP | 189 | 2773 |
| LYS | 94 | ASP | 212 | 2524 |
| GLU | 101 | GLU | 317 | 2401 |
| ASN | 102 | TYR | 197 | 2377 |
| GLN | 100 | ASN | 365 | 2241 |
| GLU | 101 | LYS | 358 | 2110 |
| ARG | 97 | GLU | 317 | 2031 |
| GLU | 101 | THR | 210 | 2025 |
| ASN | 102 | ASP | 189 | 1985 |
| LYS | 94 | THR | 213 | 1689 |
| LEU | 113 | ASN | 367 | 1509 |
| ARG | 97 | GLU | 361 | 1421 |
| ARG | 97 | TRP | 195 | 1361 |
| ARG | 97 | TYR | 438 | 1315 |
| ARG | 97 | VAL | 439 | 1145 |
| LYS | 94 | ASP | 217 | 957 |
| GLU | 101 | TYR | 318 | 852 |
| GLU | 101 | ASN | 365 | 797 |
| SER | 257 | ASP | 260 | 784 |
| ARG | 97 | GLY | 193 | 744 |
| ARG | 97 | GLU | 419 | 738 |

TABLE 12-continued

| Pore Amino Acid | Position | Enzyme Amino Acid | Position | Number of Contacts |
|---|---|---|---|---|
| ARG | 97 | PHE | 209 | 731 |
| ASN | 102 | ARG | 321 | 719 |
| ASN | 102 | TRP | 195 | 708 |
| ASN | 102 | LYS | 371 | 686 |
| ARG | 97 | GLN | 422 | 637 |
| GLN | 87 | ASP | 212 | 603 |
| ARG | 97 | TYR | 318 | 603 |
| ARG | 97 | ASN | 367 | 575 |
| ARG | 97 | ASP | 198 | 543 |
| GLN | 100 | ASN | 367 | 517 |
| LYS | 94 | TYR | 350 | 470 |
| ARG | 97 | ALA | 157 | 446 |
| ARG | 97 | GLY | 208 | 444 |
| SER | 257 | GLU | 258 | 425 |
| GLU | 101 | LYS | 371 | 407 |
| GLU | 101 | LYS | 364 | 400 |
| ASN | 102 | GLU | 93 | 389 |
| GLN | 100 | LYS | 368 | 383 |
| ARG | 110 | LYS | 368 | 357 |
| ARG | 97 | THR | 210 | 303 |
| ASN | 91 | ARG | 216 | 273 |
| THR | 104 | ASN | 367 | 214 |
| GLY | 103 | TYR | 197 | 204 |
| GLN | 114 | ASN | 367 | 178 |
| GLU | 101 | ARG | 207 | 173 |
| ASN | 102 | TRP | 366 | 171 |
| ASN | 102 | GLY | 369 | 153 |
| ASN | 102 | LEU | 194 | 123 |
| ASN | 102 | GLY | 313 | 120 |
| ARG | 97 | THR | 362 | 100 |
| THR | 104 | TRP | 366 | 99 |
| GLY | 103 | THR | 164 | 97 |
| LYS | 94 | TRP | 195 | 94 |
| GLN | 100 | GLY | 193 | 84 |
| GLY | 103 | LYS | 177 | 81 |
| ASN | 102 | LYS | 166 | 80 |
| ARG | 97 | ILE | 159 | 78 |
| LYS | 94 | ALA | 416 | 76 |
| GLN | 87 | ARG | 216 | 75 |
| ASN | 102 | SER | 306 | 73 |
| ASN | 102 | ARG | 207 | 73 |
| ALA | 98 | TRP | 195 | 68 |
| ARG | 97 | TYR | 158 | 65 |
| ASN | 102 | GLU | 347 | 65 |
| ASN | 102 | GLN | 170 | 65 |
| SER | 257 | LYS | 261 | 62 |
| ARG | 97 | ASN | 192 | 62 |
| GLN | 100 | GLY | 369 | 61 |
| THR | 104 | LYS | 199 | 60 |
| ARG | 97 | LEU | 194 | 57 |
| ASN | 102 | PHE | 163 | 54 |
| ASN | 102 | GLU | 348 | 53 |
| GLY | 103 | GLY | 313 | 53 |
| GLN | 100 | GLU | 419 | 53 |
| ASN | 102 | LYS | 351 | 52 |
| GLN | 87 | THR | 213 | 51 |
| LYS | 94 | GLY | 211 | 49 |
| GLN | 100 | GLN | 423 | 49 |
| THR | 104 | LYS | 166 | 48 |
| GLU | 101 | ARG | 321 | 45 |
| ARG | 97 | PHE | 308 | 44 |
| ARG | 93 | GLU | 419 | 44 |
| ASN | 102 | GLY | 370 | 41 |
| ARG | 110 | GLY | 369 | 41 |
| SER | 257 | THR | 259 | 40 |
| ARG | 97 | GLY | 211 | 40 |
| ARG | 97 | THR | 156 | 39 |
| ASN | 102 | THR | 164 | 39 |
| LYS | 94 | ARG | 216 | 39 |
| ARG | 97 | ARG | 321 | 38 |
| GLY | 103 | LYS | 166 | 35 |
| ASN | 102 | GLY | 208 | 33 |
| GLU | 101 | GLY | 370 | 30 |
| LYS | 94 | GLU | 361 | 28 |
| ASN | 102 | SER | 224 | 27 |

TABLE 12-continued

| Pore Amino Acid | Position | Enzyme Amino Acid | Position | Number of Contacts |
|---|---|---|---|---|
| GLU | 101 | ILE | 159 | 25 |
| THR | 104 | PHE | 308 | 23 |
| THR | 104 | ASN | 365 | 21 |
| ASN | 102 | PRO | 315 | 21 |
| LYS | 94 | GLU | 154 | 21 |
| ILE | 111 | ASN | 367 | 21 |
| ARG | 110 | ILE | 159 | 20 |
| GLY | 103 | ARG | 321 | 20 |
| GLN | 100 | LEU | 194 | 20 |
| ARG | 97 | GLU | 347 | 18 |
| ARG | 97 | ARG | 122 | 16 |
| GLY | 103 | TRP | 366 | 16 |
| GLY | 103 | GLY | 369 | 15 |
| PRO | 112 | ASN | 367 | 13 |
| ALA | 98 | ARG | 216 | 13 |
| ARG | 97 | SER | 345 | 12 |
| ASN | 102 | LYS | 364 | 12 |
| GLN | 100 | GLY | 370 | 12 |
| GLU | 101 | PRO | 315 | 11 |
| GLN | 100 | ILE | 159 | 11 |
| GLN | 100 | GLU | 317 | 11 |
| LEU | 90 | VAL | 418 | 10 |
| ASN | 102 | VAL | 220 | 10 |
| ASN | 102 | LYS | 255 | 10 |
| ALA | 98 | LYS | 358 | 10 |
| THR | 104 | ASN | 180 | 9 |
| GLY | 103 | LEU | 194 | 9 |
| THR | 104 | LYS | 368 | 8 |
| LYS | 94 | TYR | 415 | 8 |
| GLN | 100 | THR | 164 | 8 |
| ARG | 97 | VAL | 418 | 7 |
| ARG | 97 | VAL | 220 | 7 |
| ARG | 97 | TRP | 366 | 7 |
| ASN | 102 | LEU | 319 | 7 |
| GLY | 103 | LYS | 255 | 7 |
| LYS | 94 | ILE | 413 | 7 |
| GLN | 100 | PHE | 163 | 7 |
| THR | 104 | LYS | 255 | 6 |
| THR | 104 | LYS | 177 | 6 |
| LYS | 94 | GLU | 347 | 6 |
| GLN | 100 | ASN | 192 | 6 |
| GLN | 87 | ALA | 416 | 5 |
| ARG | 97 | LYS | 368 | 5 |
| ARG | 97 | ASP | 217 | 5 |
| ASN | 102 | ARG | 216 | 5 |
| LYS | 94 | VAL | 439 | 5 |
| ASN | 102 | VAL | 200 | 4 |
| ASN | 102 | ASN | 365 | 4 |
| GLU | 101 | LYS | 310 | 4 |
| GLU | 101 | GLY | 313 | 4 |
| GLY | 103 | PHE | 223 | 4 |
| LYS | 94 | ASN | 155 | 4 |
| GLN | 100 | LEU | 420 | 4 |
| ARG | 97 | SER | 224 | 3 |
| ARG | 97 | ASP | 417 | 3 |
| ASN | 102 | THR | 362 | 3 |
| SER | 115 | GLU | 419 | 3 |
| GLU | 101 | LEU | 194 | 3 |
| GLU | 101 | GLY | 369 | 3 |
| GLY | 103 | ASN | 192 | 3 |
| LYS | 94 | ASP | 417 | 3 |
| VAL | 105 | LYS | 166 | 2 |
| LEU | 113 | ASN | 365 | 2 |
| LEU | 90 | ASP | 212 | 2 |
| ARG | 97 | TYR | 92 | 2 |
| ARG | 97 | GLU | 154 | 2 |
| ARG | 97 | ARG | 207 | 2 |
| THR | 104 | TYR | 197 | 2 |
| THR | 104 | ASP | 185 | 2 |
| ASN | 102 | PHE | 209 | 2 |
| ASN | 102 | ILE | 159 | 2 |
| GLY | 103 | PHE | 308 | 2 |
| GLY | 103 | LEU | 319 | 2 |
| GLY | 103 | ILE | 159 | 2 |
| ALA | 98 | THR | 210 | 2 |
| ALA | 99 | ILE | 159 | 2 |
| GLN | 100 | THR | 210 | 2 |
| SER | 257 | LYS | 254 | 1 |
| ILE | 95 | ARG | 216 | 1 |
| LEU | 90 | THR | 213 | 1 |
| ARG | 97 | TYR | 304 | 1 |
| ARG | 97 | ASP | 212 | 1 |
| THR | 104 | GLY | 369 | 1 |
| THR | 104 | ASN | 192 | 1 |
| ASN | 102 | VAL | 314 | 1 |
| ASN | 102 | THR | 210 | 1 |
| ASN | 102 | PHE | 223 | 1 |
| ASN | 102 | LYS | 199 | 1 |
| SER | 115 | ASP | 212 | 1 |
| ARG | 110 | GLU | 317 | 1 |
| ARG | 110 | ASN | 365 | 1 |
| GLY | 103 | PRO | 315 | 1 |
| GLY | 103 | ASN | 367 | 1 |
| ALA | 98 | ALA | 157 | 1 |
| LYS | 94 | VAL | 418 | 1 |

TABLE 13

| Amino Acid | Position | Number of Contacts |
|---|---|---|
| GLU | 101 | 18418 |
| TRP | 97 | 12195 |
| ASN | 102 | 5232 |
| GLY | 103 | 212 |
| ALA | 98 | 113 |
| SER | 115 | 89 |
| THR | 104 | 57 |
| LYS | 94 | 52 |
| LEU | 113 | 11 |
| GLN | 100 | 5 |
| ARG | 110 | 5 |
| GLN | 114 | 4 |
| ARG | 93 | 1 |

TABLE 14

| Amino Acid | Position | Number of Contacts |
|---|---|---|
| TRP | 97 | 16770 |
| ASN | 102 | 11609 |
| GLU | 101 | 4947 |
| GLY | 103 | 2211 |
| THR | 104 | 2187 |
| GLN | 100 | 1589 |
| LYS | 94 | 686 |
| ALA | 98 | 289 |
| SER | 115 | 274 |
| ARG | 110 | 251 |
| ARG | 93 | 44 |
| ILE | 95 | 14 |
| LEU | 113 | 5 |
| ASN | 91 | 5 |
| LEU | 116 | 4 |
| VAL | 105 | 1 |
| LEU | 90 | 1 |

TABLE 15

| Pore Amino Acid | Position | Enzyme Amino Acid | Position | Number of Contacts |
|---|---|---|---|---|
| GLU | 101 | TRP | 195 | 5230 |
| TRP | 97 | GLY | 211 | 4360 |
| GLU | 101 | THR | 210 | 3265 |
| GLU | 101 | LYS | 358 | 3046 |
| GLU | 101 | GLN | 422 | 2476 |
| ASN | 102 | ASP | 212 | 1980 |
| TRP | 97 | ARG | 216 | 1707 |
| TRP | 97 | ASN | 365 | 1445 |
| TRP | 97 | GLU | 361 | 944 |
| GLU | 101 | LYS | 368 | 937 |
| TRP | 97 | GLU | 419 | 909 |
| GLU | 101 | ALA | 157 | 906 |
| ASN | 102 | LYS | 368 | 842 |
| GLU | 101 | TYR | 318 | 764 |
| TRP | 97 | THR | 210 | 720 |
| ASN | 102 | TRP | 366 | 626 |
| GLU | 101 | ARG | 216 | 518 |
| TRP | 97 | ASN | 155 | 487 |
| GLU | 101 | LYS | 364 | 482 |
| ASN | 102 | GLU | 361 | 409 |
| ASN | 102 | THR | 210 | 292 |
| GLU | 101 | ASN | 365 | 284 |
| GLU | 101 | GLY | 211 | 261 |
| TRP | 97 | TRP | 366 | 253 |
| ASN | 102 | TRP | 195 | 243 |
| ASN | 102 | ASN | 365 | 239 |
| TRP | 97 | GLN | 422 | 230 |
| TRP | 97 | VAL | 418 | 205 |
| ASN | 102 | LYS | 358 | 204 |
| TRP | 97 | THR | 156 | 195 |
| GLY | 103 | GLY | 193 | 152 |
| TRP | 97 | GLU | 154 | 148 |
| ASN | 102 | THR | 213 | 129 |
| TRP | 97 | ASP | 212 | 128 |
| ALA | 98 | ASP | 212 | 112 |
| TRP | 97 | THR | 213 | 112 |
| TRP | 97 | ALA | 157 | 101 |
| SER | 115 | ASP | 212 | 76 |
| ASN | 102 | LEU | 194 | 75 |
| GLU | 101 | PRO | 315 | 61 |
| ASN | 102 | VAL | 314 | 59 |
| THR | 104 | TRP | 366 | 56 |
| TRP | 97 | TYR | 350 | 48 |
| GLU | 101 | GLY | 193 | 46 |
| TRP | 97 | LYS | 364 | 45 |
| ASN | 102 | PRO | 315 | 45 |
| GLU | 101 | THR | 156 | 38 |
| ASN | 102 | GLU | 317 | 37 |
| GLU | 101 | LEU | 194 | 36 |
| TRP | 97 | PHE | 209 | 32 |
| GLY | 103 | LEU | 194 | 31 |
| TRP | 97 | TYR | 318 | 30 |
| LYS | 94 | GLU | 154 | 30 |
| TRP | 97 | GLY | 193 | 28 |
| TRP | 97 | ALA | 214 | 27 |
| GLU | 101 | GLU | 317 | 25 |
| ASN | 102 | GLU | 154 | 22 |
| TRP | 97 | LEU | 354 | 18 |
| GLY | 103 | TRP | 366 | 14 |
| ALA | 115 | TRP | 366 | 13 |
| TRP | 97 | ASP | 417 | 12 |
| LEU | 113 | TRP | 366 | 11 |
| GLU | 101 | VAL | 418 | 11 |
| ASN | 102 | GLY | 211 | 10 |
| GLU | 101 | ARG | 207 | 10 |
| GLY | 103 | LYS | 368 | 9 |
| GLU | 101 | VAL | 314 | 8 |
| LYS | 94 | VAL | 418 | 8 |
| ASN | 102 | LYS | 166 | 7 |
| GLU | 101 | LYS | 166 | 7 |
| GLY | 103 | ASN | 365 | 6 |
| TRP | 97 | LYS | 358 | 5 |
| ASN | 102 | LYS | 364 | 5 |
| ARG | 110 | ASN | 365 | 5 |
| LYS | 94 | TYR | 350 | 5 |
| GLN | 114 | TRP | 366 | 4 |
| LYS | 94 | ASN | 155 | 4 |
| GLN | 100 | ASN | 365 | 4 |
| ASN | 102 | GLY | 313 | 3 |
| GLU | 101 | ASP | 212 | 3 |
| LYS | 94 | ALA | 416 | 3 |
| ASN | 102 | GLY | 316 | 2 |
| ASN | 102 | ALA | 157 | 2 |
| GLU | 101 | LYS | 126 | 2 |
| ALA | 98 | GLY | 211 | 1 |
| TRP | 97 | VAL | 439 | 1 |
| TRP | 97 | VAL | 314 | 1 |
| TRP | 97 | TRP | 195 | 1 |
| TRP | 97 | GLU | 347 | 1 |
| TRP | 97 | GLU | 317 | 1 |
| TRP | 97 | ARG | 122 | 1 |
| THR | 104 | LYS | 368 | 1 |
| ARG | 93 | TRP | 366 | 1 |
| ASN | 102 | THR | 362 | 1 |
| GLU | 101 | CYS | 360 | 1 |
| GLU | 101 | ARG | 321 | 1 |
| LYS | 94 | HIS | 414 | 1 |
| LYS | 94 | ASP | 417 | 1 |
| GLN | 100 | LYS | 368 | 1 |

TABLE 16

| Pore Amino Acid | Position | Enzyme Amino Acid | Position | Number of Contacts |
|---|---|---|---|---|
| TRP | 97 | GLU | 361 | 3862 |
| TRP | 97 | GLU | 317 | 3269 |
| TRP | 97 | GLU | 154 | 2166 |
| ASN | 102 | GLY | 313 | 2086 |
| ASN | 102 | THR | 210 | 2009 |
| GLU | 101 | TRP | 195 | 1896 |
| ASN | 102 | ASN | 365 | 1656 |
| THR | 104 | GLU | 419 | 1510 |
| TRP | 97 | ASN | 365 | 1488 |
| TRP | 97 | ARG | 216 | 1435 |
| GLN | 100 | ALA | 157 | 1204 |
| GLY | 103 | TRP | 195 | 1191 |
| GLU | 101 | ASN | 365 | 1106 |
| GLU | 101 | LYS | 368 | 1100 |
| ASN | 102 | TRP | 195 | 822 |
| SER | 257 | ASP | 260 | 779 |
| ASN | 102 | GLU | 361 | 738 |
| TRP | 97 | TRP | 195 | 719 |
| TRP | 97 | ASN | 155 | 591 |
| ASN | 102 | ARG | 207 | 535 |
| ASN | 102 | TRP | 366 | 524 |
| GLY | 103 | LYS | 364 | 514 |
| GLU | 101 | THR | 210 | 402 |
| TRP | 97 | THR | 210 | 377 |
| ASN | 102 | GLY | 208 | 371 |
| TRP | 97 | TYR | 318 | 365 |
| TRP | 97 | GLN | 422 | 333 |
| TRP | 97 | PRO | 315 | 316 |
| TRP | 97 | VAL | 220 | 309 |
| THR | 104 | LYS | 368 | 307 |
| TRP | 97 | THR | 156 | 304 |
| ASN | 102 | ALA | 157 | 274 |
| SER | 115 | ASP | 212 | 274 |
| TRP | 97 | GLY | 316 | 266 |
| GLU | 101 | GLN | 422 | 264 |
| GLY | 103 | TYR | 197 | 214 |
| ASN | 102 | ARG | 148 | 203 |
| ASN | 102 | LYS | 368 | 199 |
| ASN | 102 | ASP | 198 | 199 |
| ASN | 102 | LYS | 255 | 192 |

TABLE 16-continued

| Pore Amino Acid | Position | Enzyme Amino Acid | Position | Number of Contacts |
|---|---|---|---|---|
| ASN | 102 | PHE | 308 | 180 |
| TRP | 97 | GLU | 419 | 174 |
| LYS | 94 | GLY | 211 | 174 |
| GLN | 100 | ASN | 155 | 168 |
| ASN | 102 | PHE | 223 | 153 |
| TRP | 97 | LYS | 358 | 152 |
| TRP | 97 | ASP | 198 | 151 |
| ARG | 110 | GLY | 193 | 148 |
| GLN | 100 | GLU | 419 | 144 |
| ASN | 102 | LYS | 364 | 139 |
| ALA | 98 | ALA | 157 | 135 |
| ASN | 102 | ILE | 159 | 122 |
| ALA | 98 | TRP | 195 | 113 |
| THR | 104 | TYR | 197 | 113 |
| TRP | 97 | THR | 362 | 103 |
| GLY | 103 | GLY | 369 | 103 |
| LYS | 94 | THR | 210 | 103 |
| LYS | 94 | ASP | 212 | 89 |
| ASN | 102 | GLU | 154 | 87 |
| ASN | 102 | ILE | 196 | 84 |
| LYS | 94 | TYR | 415 | 84 |
| THR | 104 | GLU | 154 | 77 |
| TRP | 97 | GLY | 193 | 75 |
| ASN | 102 | ARG | 321 | 71 |
| TRP | 97 | VAL | 418 | 69 |
| GLU | 101 | TRP | 366 | 69 |
| THR | 104 | ASP | 198 | 67 |
| THR | 104 | ALA | 157 | 64 |
| GLY | 103 | GLU | 154 | 60 |
| LYS | 94 | GLY | 153 | 60 |
| LYS | 94 | GLU | 154 | 59 |
| TRP | 97 | TRP | 366 | 58 |
| GLU | 101 | ARG | 207 | 56 |
| ARG | 110 | LEU | 194 | 52 |
| ASN | 102 | GLY | 369 | 46 |
| LYS | 94 | GLU | 361 | 46 |
| GLY | 103 | LYS | 368 | 42 |
| ARG | 93 | ASP | 212 | 40 |
| ASN | 102 | GLU | 317 | 39 |
| GLN | 100 | THR | 156 | 34 |
| TRP | 97 | VAL | 314 | 32 |
| ALA | 98 | ASP | 212 | 31 |
| GLY | 103 | ARG | 207 | 31 |
| LYS | 94 | PHE | 209 | 29 |
| TRP | 97 | GLY | 211 | 28 |
| ASN | 102 | ARG | 312 | 28 |
| ARG | 110 | GLY | 313 | 25 |
| TRP | 97 | ARG | 321 | 22 |
| ASN | 102 | VAL | 220 | 22 |
| TRP | 97 | ASP | 417 | 18 |
| THR | 104 | GLY | 369 | 18 |
| ASN | 102 | THR | 164 | 17 |
| LYS | 94 | ARG | 216 | 17 |
| TRP | 97 | GLY | 153 | 16 |
| ASN | 102 | TYR | 158 | 16 |
| GLY | 103 | LEU | 194 | 16 |
| GLU | 101 | ILE | 159 | 15 |
| GLN | 100 | PRO | 315 | 15 |
| ILE | 95 | ASP | 212 | 14 |
| GLY | 103 | TRP | 366 | 14 |
| TRP | 97 | LEU | 194 | 13 |
| GLU | 101 | ARG | 321 | 13 |
| GLN | 100 | LYS | 368 | 13 |
| ASN | 102 | GLY | 153 | 11 |
| ARG | 110 | ASN | 192 | 11 |
| GLN | 100 | TYR | 158 | 10 |
| ASN | 102 | LYS | 145 | 9 |
| GLU | 101 | ARG | 216 | 9 |
| ARG | 110 | PRO | 315 | 8 |
| ALA | 98 | THR | 210 | 7 |
| ASN | 102 | GLY | 211 | 7 |
| ASN | 102 | ARG | 216 | 7 |
| ARG | 110 | LYS | 368 | 7 |
| LYS | 94 | HIS | 414 | 7 |
| LYS | 94 | ALA | 214 | 7 |
| SER | 257 | GLU | 258 | 6 |
| TRP | 97 | LYS | 255 | 6 |
| THR | 104 | ASP | 212 | 6 |
| LYS | 94 | ASP | 417 | 6 |
| ASN | 91 | ASP | 212 | 5 |
| TRP | 97 | THR | 213 | 5 |
| TRP | 97 | LYS | 364 | 5 |
| THR | 104 | TRP | 195 | 5 |
| THR | 104 | PHE | 308 | 5 |
| GLY | 103 | LYS | 255 | 5 |
| GLY | 103 | GLU | 419 | 5 |
| GLY | 103 | ARG | 321 | 5 |
| LEU | 116 | ASP | 212 | 4 |
| THR | 104 | TYR | 438 | 4 |
| THR | 104 | THR | 210 | 4 |
| THR | 104 | ILE | 159 | 4 |
| ARG | 93 | ARG | 216 | 4 |
| GLU | 101 | ALA | 157 | 4 |
| GLY | 103 | ILE | 159 | 4 |
| GLY | 103 | ASP | 198 | 4 |
| LYS | 94 | ASN | 155 | 4 |
| LEU | 113 | ARG | 216 | 3 |
| ASN | 102 | LEU | 319 | 3 |
| GLU | 101 | VAL | 314 | 3 |
| GLU | 101 | GLY | 193 | 3 |
| LEU | 113 | TRP | 366 | 2 |
| ASN | 102 | VAL | 314 | 2 |
| ASN | 102 | TYR | 197 | 2 |
| ASN | 102 | PHE | 209 | 2 |
| ASN | 102 | LEU | 194 | 2 |
| GLU | 101 | THR | 362 | 2 |
| GLU | 101 | GLY | 313 | 2 |
| GLY | 103 | ILE | 196 | 2 |
| ALA | 98 | PRO | 315 | 1 |
| ALA | 98 | GLY | 211 | 1 |
| ALA | 98 | ASN | 155 | 1 |
| VAL | 105 | LYS | 368 | 1 |
| LEU | 90 | ASP | 212 | 1 |
| TRP | 97 | PHE | 223 | 1 |
| TRP | 97 | PHE | 209 | 1 |
| TRP | 97 | ASP | 217 | 1 |
| TRP | 97 | ASP | 212 | 1 |
| THR | 104 | VAL | 200 | 1 |
| THR | 104 | GLY | 370 | 1 |
| THR | 104 | ARG | 207 | 1 |
| ASN | 102 | PRO | 152 | 1 |
| ASN | 102 | LYS | 310 | 1 |
| ASN | 102 | LYS | 227 | 1 |
| ASN | 102 | GLU | 419 | 1 |
| ASN | 102 | ARG | 122 | 1 |
| ASN | 102 | ALA | 311 | 1 |
| GLU | 101 | VAL | 418 | 1 |
| GLU | 101 | PHE | 308 | 1 |
| GLU | 101 | LEU | 194 | 1 |
| GLY | 103 | PHE | 308 | 1 |
| LYS | 94 | VAL | 439 | 1 |
| GLN | 100 | ARG | 122 | 1 |

Example 6

This Example describes the characterisation of several CsgG mutants which show improved characterisation accuracy.

Materials and Methods

The materials and methods that were used in this example are the same as those described above for example 2. The enzyme used to control movement was either Enzyme 1=T4 Dda-E94C/C109A/C136A/A360C (SEQ ID NO: 24 with mutations E94C/C109A/C136A/A360C) or Enzyme 2=T4 Dda-E94C/F98W/C109A/C136A/K194L/A360C (SEQ ID NO: 24 with mutations E94C/F98W/C109A/C136A/K194L/A360C).

The 1D accuracy characterisation measurements were calculated using methods as disclosed in the International Application PCT/GB2012/052343 (published as WO/2013/041878).

Results

The 1D basecall characterisation accuracy for MspA mutant x=MspA-((Del-L74/G75/D118/L119)D56F/E59R/L88N/D90N/D91N/Q126R/D134R/E139K)8 (SEQ ID NO: 50 with mutations D56F/E59R/L88N/D90N/D91N/Q126R/D134R/E139K and deletion of the amino acids L74/G75/D118/L119) with DNA translocation controlled by T4 Dda-E94C/F98W/C109A/C136A/K194L/A360C was 68.7%. All of the mutants tested (see Table 17 below) showed improved 1D basecall characterisation accuracy in comparison to MspA mutant X.

27—CsgG-Eco-(Y51A/F56Q/R97W/R192Q-StrepII(C))9 (SEQ ID NO: 2 with mutations Y51A/F56Q/R97W/R192Q where StrepII(C) is SEQ ID NO: 47 and is attached at the C-terminus)

28—CsgG-Eco-(Y51A/F56Q/R97W/R192D-StrepII(C))9 (SEQ ID NO: 2 with mutations Y51A/F56Q/R97W/R192D where StrepII(C) is SEQ ID NO: 47 and is attached at the C-terminus)

29—CsgG-Eco-(Y51A/F56Q/K135L/T150I/S208V-StrepII(C))9 (SEQ ID NO: 2 with mutations Y51A/F56Q/K135L/T150I/S208V where StrepII(C) is SEQ ID NO: 47 and is attached at the C-terminus)

30—CsgG-Eco-(Y51A/F56Q/T150I/S208V-StrepII(C))9 (SEQ ID NO: 2 with mutations Y51A/F56Q/T150I/S208V where StrepII(C) is SEQ ID NO: 47 and is attached at the C-terminus)

31—CsgG-Eco-(Y51A/F56Q/S208V-StrepII(C))9 (SEQ ID NO: 2 with mutations Y51A/F56Q/S208V where StrepII(C) is SEQ ID NO: 47 and is attached at the C-terminus)

32—CsgG-Eco-(Y51A/F56Q/T150I-StrepII(C))9 (SEQ ID NO: 2 with mutations Y51A/F56Q/T150I where StrepII(C) is SEQ ID NO: 47 and is attached at the C-terminus)

33—CsgG-Eco-(Y51A/F56Q/K135V/T150Y-StrepII(C))9 (SEQ ID NO: 2 with mutations Y51A/F56Q/K135V/T150Y where StrepII(C) is SEQ ID NO: 47 and is attached at the C-terminus)

34—CsgG-Eco-(Y51A/F56Q/K135L-StrepII(C))9 (SEQ ID NO: 2 with mutations Y51A/F56Q/K135L where StrepII(C) is SEQ ID NO: 47 and is attached at the C-terminus)

35—CsgG-Eco-(Y51A/F56Q/R97F/R192D-StrepII(C))9 (SEQ ID NO: 2 with mutations Y51A/F56Q/R97F/R192D where StrepII(C) is SEQ ID NO: 47 and is attached at the C-terminus)

36—CsgG-Eco-(Y51A/F56Q/K135L/T150I-StrepII(C))9 (SEQ ID NO: 2 with mutations Y51A/F56Q/K135L/T150I where StrepII(C) is SEQ ID NO: 47 and is attached at the C-terminus)

37—CsgG-Eco-((Del-D195/Y196/Q197/R198/L199)-Y51A/F56Q-StrepII(C))9 (SEQ ID NO: 2 with mutations Y51A/F56Q where StrepII(C) is SEQ ID NO: 47 and is attached at the C-terminus and deletion of the amino acids D195/Y196/Q197/R198/L199)

38—CsgG-Eco-((Del-R192/F193/I194/D195/Y196/Q197/R198/L199/L200)-Y51A/F56Q-StrepII(C))9 (SEQ ID NO: 2 with mutations Y51A/F56Q where StrepII(C) is SEQ ID NO: 47 and is attached at the C-terminus and deletion of the amino acids R192/F193/I194/D195/Y196/Q197/R198/L199/L200)

39—CsgG-Eco-((Del-Q197/R198/L199/L200)-Y51A/F56Q-StrepII(C))9 (SEQ ID NO: 2 with mutations Y51A/F56Q where StrepII(C) is SEQ ID NO: 47 and is attached at the C-terminus and deletion of the amino acids Q197/R198/L199/L200)

40—CsgG-Eco-((Del-I194/D195/Y196/Q197/R198/L199)-Y51A/F56Q-StrepII(C))9 (SEQ ID NO: 2 with mutations Y51A/F56Q where StrepII(C) is SEQ ID NO: 47 and is attached at the C-terminus and deletion of the amino acids I194/D195/Y196/Q197/R198/L199)

41—CsgG-Eco-((Del-V139/G140/D149/T150/V186/Q187/V204/G205)-Y51A/F56Q-StrepII(C))9 (SEQ ID NO: 2 with mutations Y51A/F56Q where StrepII(C) is SEQ ID NO: 47 and is attached at the C-terminus and deletion of the amino acids V139/G140/D149/T150/V186/Q187/V204/G205)

42—CsgG-Eco-((Del-D195/Y196/Q197/R198/L199/L200)-Y51A/F56Q-StrepII(C))9 (SEQ ID NO: 2 with mutations Y51A/F56Q where StrepII(C) is SEQ ID NO: 47 and is attached at the C-terminus and deletion of the amino acids D195/Y196/Q197/R198/L199/L200)

43—CsgG-Eco-((Del-Y196/Q197/R198/L199/L200/E201)-Y51A/F56Q-StrepII(C))9 (SEQ ID NO: 2 with mutations Y51A/F56Q where StrepII(C) is SEQ ID NO: 47 and is attached at the C-terminus and deletion of the amino acids Y196/Q197/R198/L199/L200/E201)

44—CsgG-Eco-((Del-Q197/R198/L199)-Y51A/F56Q-StrepII(C))9 (SEQ ID NO: 2 with mutations Y51A/F56Q where StrepII(C) is SEQ ID NO: 47 and is attached at the C-terminus and deletion of the amino acids Q197/R198/L199)

45—CsgG-Eco-((Del-F193/I194/D195/Y196/Q197/R198/L199)-Y51A/F56Q-StrepII(C))9 (SEQ ID NO: 2 with mutations Y51A/F56Q where StrepII(C) is SEQ ID NO: 47 and is attached at the C-terminus and deletion of the amino acids F193/I194/D195/Y196/Q197/R198/L199)

46—CsgG-Eco-(Y51A/F56Q/R192T-StrepII(C))9 (SEQ ID NO: 2 with mutations Y51A/F56Q/R192T where StrepII(C) is SEQ ID NO: 47 and is attached at the C-terminus)

47—CsgG-Eco-(Y51A/F56Q/N102S-StrepII(C))9 (SEQ ID NO: 2 with mutations Y51A/F56Q/N102S where StrepII(C) is SEQ ID NO: 47 and is attached at the C-terminus)

48—CsgG-Eco-(Y51A/F56Q/Q42R-StrepII(C))9 (SEQ ID NO: 2 with mutations Y51A/F56Q/Q42R where StrepII(C) is SEQ ID NO: 47 and is attached at the C-terminus)

49—CsgG-Eco-(Y51A/F56Q/R192S-StrepII(C))9 (SEQ ID NO: 2 with mutations Y51A/F56Q/R192S where StrepII(C) is SEQ ID NO: 47 and is attached at the C-terminus)

50—CsgG-Eco-(Y51A/F56Q/G103N-StrepII(C))9 (SEQ ID NO: 2 with mutations Y51A/F56Q/G103N where StrepII(C) is SEQ ID NO: 47 and is attached at the C-terminus)

51—CsgG-Eco-(Y51A/F56Q/R97N/N102R-StrepII(C))9 (SEQ ID NO: 2 with mutations Y51A/F56Q/R97N/N102R where StrepII(C) is SEQ ID NO: 47 and is attached at the C-terminus)

52—CsgG-Eco-(Y51A/F56Q/R97L-StrepII(C))9 (SEQ ID NO: 2 with mutations Y51A/F56Q/R97L where StrepII(C) is SEQ ID NO: 47 and is attached at the C-terminus)

53—CsgG-Eco-(Y51A/F56Q/R192D-StrepII(C))9 (SEQ ID NO: 2 with mutations Y51A/F56Q/R192D where StrepII(C) is SEQ ID NO: 47 and is attached at the C-terminus)

54—CsgG-Eco-(Y51A/F56Q/R97N/N102G-StrepII(C))9 (SEQ ID NO: 2 with mutations Y51A/F56Q/R97N/N102G where StrepII(C) is SEQ ID NO: 47 and is attached at the C-terminus)

55—CsgG-Eco-(Y51A/F56Q/F48S-StrepII(C))9 (SEQ ID NO: 2 with mutations Y51A/F56Q/F48S where StrepII(C) is SEQ ID NO: 47 and is attached at the C-terminus)

56—CsgG-Eco-(Y51A/F56Q/G103S-StrepII(C))9 (SEQ ID NO: 2 with mutations Y51A/F56Q/G103S where StrepII(C) is SEQ ID NO: 47 and is attached at the C-terminus)

57—CsgG-Eco-(Y51A/F56Q/E101L-StrepII(C))9 (SEQ ID NO: 2 with mutations Y51A/F56Q/E101L where StrepII(C) is SEQ ID NO: 47 and is attached at the C-terminus)
58—CsgG-Eco-(Y51A/F56Q/R192Q-StrepII(C))9 (SEQ ID NO: 2 with mutations Y51A/F56Q/R192Q where StrepII(C) is SEQ ID NO: 47 and is attached at the C-terminus)
59—CsgG-Eco-(Y51A/F56Q/K135N/R142N/R192N-StrepII(C))9 (SEQ ID NO: 2 with mutations Y51A/F56Q/K135N/R142N/R192N where StrepII(C) is SEQ ID NO: 47 and is attached at the C-terminus)
60—CsgG-Eco-(Y51A/F56Q/R97N-StrepII(C))9 (SEQ ID NO: 2 with mutations Y51A/F56Q/R97N where StrepII(C) is SEQ ID NO: 47 and is attached at the C-terminus)
61—CsgG-Eco-(Y51A/F56Q/R192N-StrepII(C))9 (SEQ ID NO: 2 with mutations Y51A/F56Q/R192N where StrepII(C) is SEQ ID NO: 47 and is attached at the C-terminus)
62—CsgG-Eco-(Y51A/F56Q/Y130W-StrepII(C))9 (SEQ ID NO: 2 with mutations Y51A/F56Q/Y130W where StrepII(C) is SEQ ID NO: 47 and is attached at the C-terminus)
63—CsgG-Eco-(Y51A/F56Q/E101G-StrepII(C))9 (SEQ ID NO: 2 with mutations Y51A/F56Q/E101G where StrepII(C) is SEQ ID NO: 47 and is attached at the C-terminus)

TABLE 17

| CsgC Mutant No. | Enzyme | 1D Basecall Characterisation Accuracy (%) |
| --- | --- | --- |
| 25 | 2 | 72.6 |
| 26 | 2 | 79.2 |
| 27 | 2 | 81.3 |
| 28 | 2 | 80.2 |
| 29 | 2 | 72.2 |
| 30 | 2 | 74.7 |
| 31 | 2 | 74.5 |
| 32 | 2 | 73.3 |
| 33 | 2 | 73.8 |
| 34 | 2 | 74.3 |
| 35 | 2 | 75.5 |
| 36 | 2 | 73.5 |
| 37 | 2 | 73.4 |
| 38 | 2 | 75.3 |
| 39 | 2 | 72.0 |
| 40 | 2 | 74.5 |
| 41 | 2 | 74.8 |
| 42 | 2 | 71.0 |
| 43 | 2 | 70.9 |
| 44 | 2 | 71.9 |
| 45 | 2 | 73.0 |
| 46 | 1 | 75.0 |
| 47 | 1 | 72.1 |
| 48 | 1 | 75.0 |
| 49 | 1 | 74.8 |
| 50 | 1 | 75.2 |
| 51 | 1 | 73.1 |
| 52 | 1 | 75.4 |
| 53 | 1 | 77.1 |
| 54 | 1 | 75.9 |
| 55 | 1 | 73.7 |
| 56 | 1 | 73.1 |
| 57 | 1 | 73.2 |
| 58 | 1 | 76.8 |
| 59 | 1 | 72.7 |
| 60 | 1 | 76.1 |
| 61 | 1 | 75.0 |
| 62 | 1 | 74.7 |
| 63 | 1 | 73.1 |
| 25 | 1 | 74.8 |
| 26 | 1 | 77.4 |

Example 7

This example compares DNA capture of a number of different mutant nanopores.

Materials and Methods

Electrical measurements were acquired from a variety of single CsgG or MspA nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess nanopores. 150 uL of 500 mM KCl, 25 mM K Phosphate, 1.5 mM MgCl2, 1.5 mM ATP, pH8.0 was then flowed through the system. After 10 minutes a 150 uL of DNA (SEQ ID NO: 51, 200 nM) was then flowed into the single nanopore experimental system. The experiment was run at −120 mV and helicase-controlled DNA movement monitored.

Results

The CsgG mutant CsgG-Eco-(Y51A/F56Q/R97W/E101S/R192D-StrepII(C))9 (SEQ ID NO: 2 with mutations Y51A/F56Q/R97W/E101S/R192D where StrepII(C) is SEQ ID NO: 47 and is attached at the C-terminus) (see FIG. 36) shows a higher rate of capture (e.g. captures DNA polynucleotides more easily) than MspA-((Del-L74/G75/D118/L119)D56F/E59R/L88N/D90N/D91N/Q126R/D134R/E139K)8 (see FIG. 34). Each spike in the current traces corresponds to translocation of the DNA polynucleotide (SEQ ID NO: 51) through the nanopore without being controlled by an enzyme. The 10 second current traces in FIG. 34 show fewer DNA translocations than the 10 second current traces for the CsgG nanopore-CsgG-Eco-(Y51A/F56Q/R97W/E101S/R192D-StrepII(C))9.

The mutation of position E101 to E101S resulted in an increase in the capture rate when compared to a CsgG mutant without the E101S mutation. FIG. 35 shows that the 10 second current traces for CsgG mutant CsgG-Eco-(Y51A/F56Q/R97W/R192D-StrepII(C))9 (SEQ ID NO: 2 with mutations Y51A/F56Q/R97W/R192D where StrepII(C) is SEQ ID NO: 47 and is attached at the C-terminus) exhibited fewer translocations than CsgG-Eco-(Y51A/F56Q/R97W/E101S/R192D-StrepII(C))9. The average number of translocations for CsgG-Eco-(Y51A/F56Q/R97W/R192D-StrepII(C))9 was 7.25 per second (n=12) and the average number of translocations for CsgG-Eco-(Y51A/F56Q/R97W/E101S/R192D-StrepII(C))9 was 18 per second (n=14).

Example 8

This example compares the level of expression of two different CsgG mutant pores.

Materials and Methods

The materials and methods that were used to make the nanopores (A=CsgG-Eco-(Y51A/F56Q/R97W)-StrepII(C))9 (SEQ ID NO: 2 with mutations Y51A/F56Q/R97W where StrepII(C) is SEQ ID NO: 47 and is attached at the C-terminus) and B=CsgG-Eco-(Y51A/F56Q/R97W/R192D)-StrepII(C))9 (SEQ ID NO: 2 with mutations Y51A/F56Q/R97W/R192D where StrepII(C) is SEQ ID NO: 47 and is attached at the C-terminus)) in this example are the same as those described above for example 3.

Results

Figure 37:
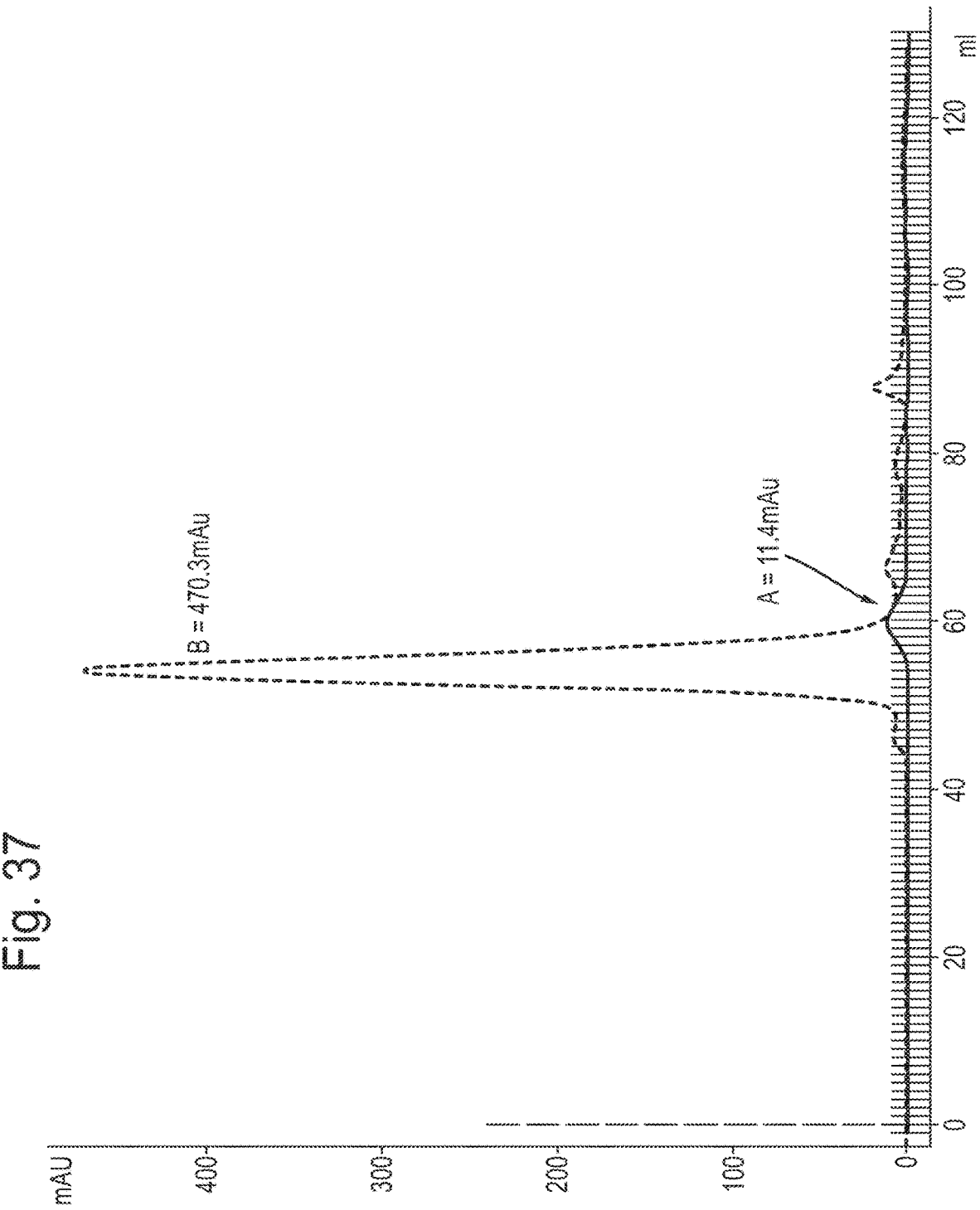
FIG. 37 shows an overlay of two gel filtration chromatograms (120 ml S200 column) of the CsgG mutants pores A) CsgG-Eco-(Y51A/F56Q/R97W)-StrepII(C))9 (SEQ ID NO: 2 with mutations Y51A/F56Q/R97W where StrepII(C) is SEQ ID NO: 47 and is attached at the C-terminus) and B) CsgG-Eco-(Y51A/F56Q/R97W/R192D)-StrepII(C))9 (SEQ ID NO: 2 with mutations Y51A/F56Q/R97W/R192D where StrepII(C) is SEQ ID NO: 47 and is attached at the C-terminus). Absorbance at A280 for CsgG-Eco-(Y51A/F56Q/R97W)-StrepII(C))9 is labelled A and for CsgG-Eco-(Y51A/F56Q/R97W/R192D)-StrepII(C))9 is labelled B. Both constructs were grown in 500 ml cultures. Expression and purification of both proteins were carried out using exactly the same protocol and same volumes were loaded onto the column. Running Buffer was 25 mM Tris, 150 mM NaCl, 2 mM EDTA, 0.01% DDM, 0.1% SDS pH8. The fractional delay with CsgG-Eco-(Y51A/F56Q/R97W)-StrepII(C))9 pore was due to different connection configuration used on AKTA Purifier 10. The difference in the absorbance values indicated the amount of proteins expressed with higher absorbance values indicating higher amounts of expressed protein.
Figure 38:
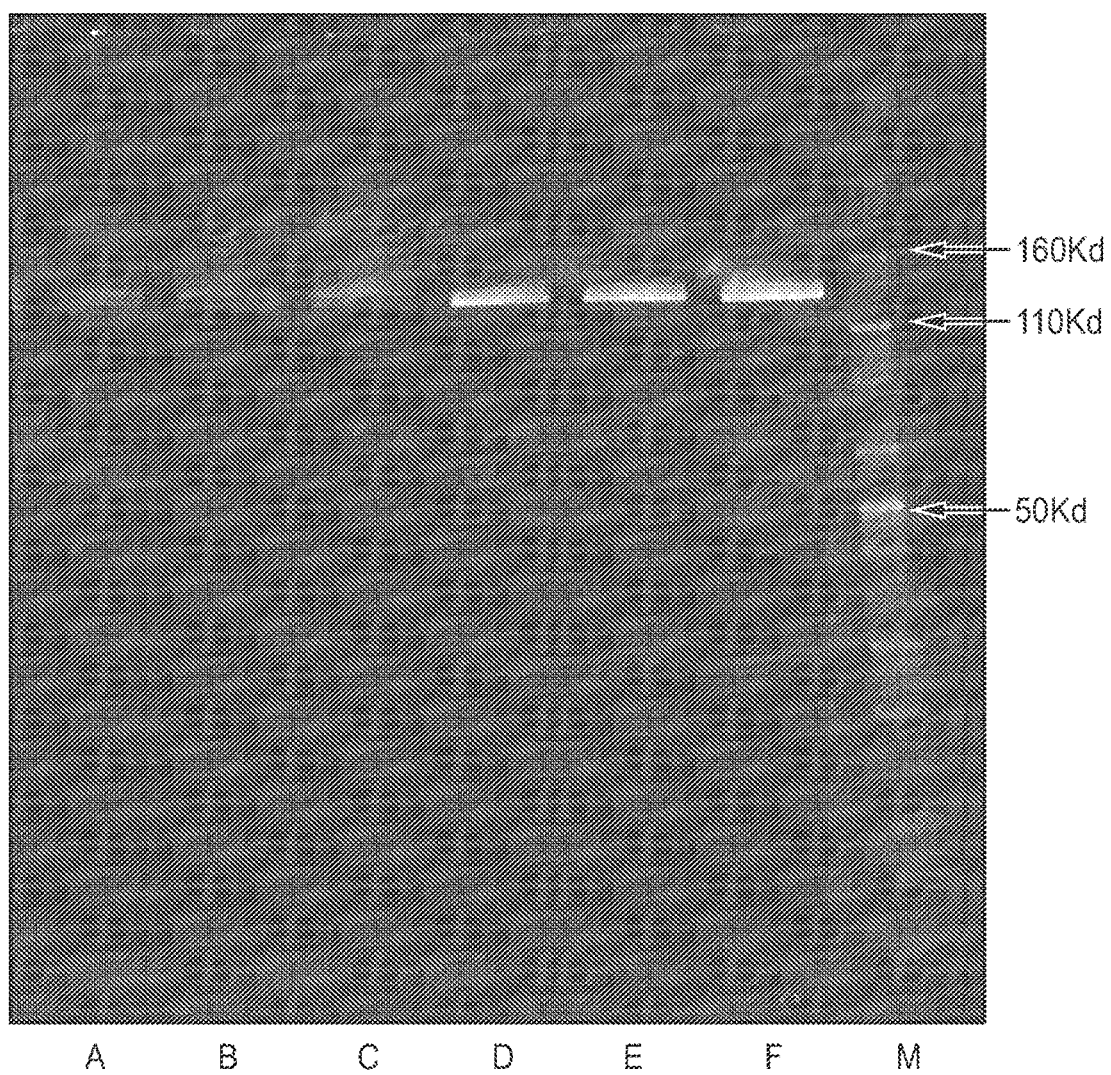
FIG. 38 shows SDS-PAGE analysis of CsgG nanopores. Lanes A-C contained CsgG-Eco-(Y51A/F56Q/R97W)-StrepII(C))9, lanes D-F contained CsgG-Eco-(Y51A/F56Q/R97W/R192D)-StrepII(C))9 and lane M contained the molecular weight marker. The two pores were expressed and purified using exactly the same protocol. The pores were subjected to electrophoresis on a 4-20% TGX gel (Bio rad cat #5671093) in TGS buffer at 300 V for 22 minutes. The gel was visualised with Sypro Ruby stain (Life Technologies cat #S1200). The same volumes from each pore sample were loaded on the gel to compare the amount of proteins obtained after purification—lanes A and D contained 5 uL, lanes B and E contained 10 uL and lanes C and F contained 15 uL.

The two nanopores A=CsgG-Eco-(Y51A/F56Q/R97W)-StrepII(C))9 (SEQ ID NO: 2 with mutations Y51A/F56Q/R97W where StrepII(C) is SEQ ID NO: 47 and is attached at the C-terminus) and B=CsgG-Eco-(Y51A/F56Q/R97W/R192D)-StrepII(C))9 (SEQ ID NO: 2 with mutations Y51A/F56Q/R97W/R192D where StrepII(C) is SEQ ID NO: 47 and is attached at the C-terminus) were expressed and purified using exactly the same protocol and the same volumes of each nanopore were analysed using gel filtration chromatograms (120 mL S200 Column, see FIG. 37) and SDS-PAGE analysis (see FIG. 38). The absorbance value for B (470.3 mAu) was much higher than A (11.4 mAu) which indicated that CsgG-Eco-(Y51A/F56Q/R97W/R192D)-StrepII(C))9 expressed at a much higher level than CsgG-Eco-(Y51A/F56Q/R97W)-StrepII(C))9. The intensity of the bands in FIG. 38 also indicate the expression level of the two pores. Bands A-C (containing CsgG-Eco-(Y51A/F56Q/R97W)-StrepII(C))9) were less intense than bands D-E (containing CsgG-Eco-(Y51A/F56Q/R97W/R192D)-StrepII(C))9). The two methods of analysis both indicated that the addition of R192D mutation greatly increased the observed expression of the CsgG mutant.

Example 9

Figure 43:
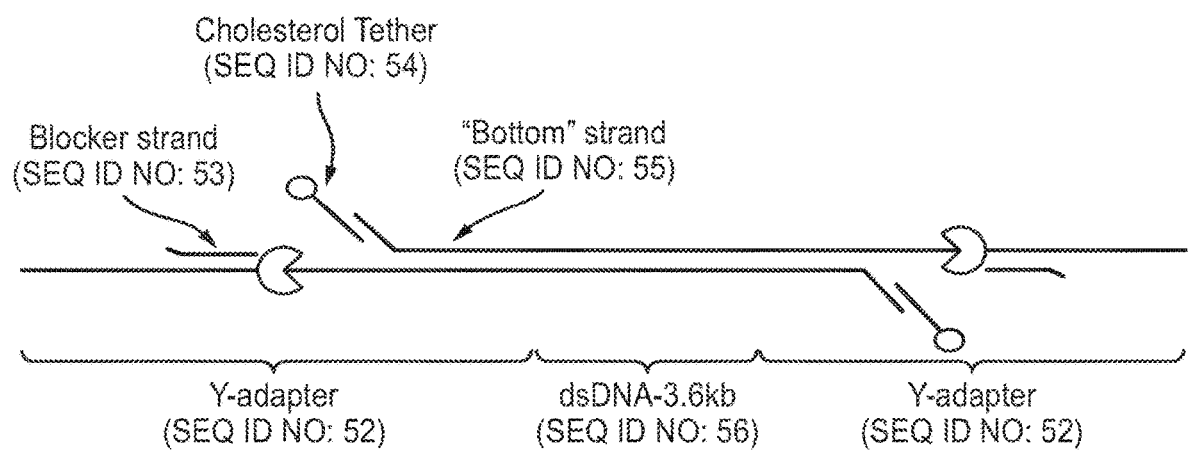
FIG. 43 illustrates the structure of the template strand having an adapter ligated to each end thereof. The adapter has a T4 Dda helicase enzyme prebound thereto. The sequences of the various parts of the adaptor used in the Examples are shown in SEQ ID NOs: 52 to 55.

This Example describes the characterisation of several CsgG mutants which show improved characterisation accuracy.
Materials and Methods
CsG Pores The following 8 CsgG mutant pores were tested. Mutant 28 described in Example X above was used as the baseline pore. The mutations are made in SEQ ID NO: 2 and the purification tag StrepII has the sequence shown in SEQ ID NO: 47.
Baseline pore (mutant 28): CsgG-(WT-Y51A/F56Q/R97W/R192D-StrepII)9
Mutant A: CsgG-(WT-Y51A/F56Q/R97W/R192D-StrepII)9-del(D195-L199)
Mutant B: CsgG-(WT-Y51A/F56Q/R97W/R192D-StrepII)9-del(F193-L199)
Mutant C: CsgG-(WT-Y51A/F56Q/R97W/R192D-StrepII)9-F191T
Mutant D: CsgG-(WT-Y51A/F56Q/R97W/R192D-del(V105-I107)-StrepII)9
Mutant E: CsgG-(WT-Y51A/F56Q/K94Q/R97W/R192D-del(V105-I107)
Mutant F: CsgG-(WT-Y51A/F56Q/R192D-StrepII)9-R93W
Mutant G: CsgG-(WT-Y51A/F56Q/R192D-StrepII)9-R93W-del(D195-L199)
Mutant H: CsgG-(WT-Y51A/F56Q/R192D-StrepII)9-R93Y/R97Y
Nanopore Preparation To prepare a nanopore array chip that contain multiple wells of block co-polymer membrane each with a single CsgG mutant nanopore inserted the following method was used. CsgG mutants expressed in *E. coli* were purified and stored in buffer containing 25 mM Tris, 150 mM NaCl, 2 mM EDTA, 0.01% DDM, 0.1% SDS, 0.1% Brij 58 at pH8. These mutant CsgG pores were diluted to 1 in 1 million using buffer comprising 25 mM Potassium Phosphate, 150 mM Potassium Ferrocyanide (II), 150 mM Potassium Ferricyanide (III) at pH 8.0 and added to chips to obtain single pores in each of the wells. After pore insertion, the array chip was washed with 1 mL buffer comprising 25 mM Potassium Phosphate, 150 mM Potassium Ferrocyanide (II), 150 mM Potassium Ferricyanide (III) at pH 8.0 to remove excess pores. After a few minutes, each chip was flushed twice with 500 mL of sequencing mix containing 470 mM KCl, 25 mM HEPES, 11 mM ATP and 10 mM MgCl2.
DNA Sample Preparation DNA sample was prepared for sequencing using the following method. 1 µg of DNA analyte was incubated with the 40 nM of adapter mix containing a T4 Dda helicase enzyme prebound to the adapter and blunt TA ligase for 10 minutes (available from https://store.nanoporetech.com/). The structure of the adapter is shown in FIG. 43 and the sequences contained in the adapter are set out in SEQ ID NOs: 52 to 55. The ligation mixture was then purified to remove unligated free adapter using Spri purification. The final ligated mixture was eluted in 25 µL elution buffer containing 40 mM CAPS at pH10, 40 mM KCl and 400 nM cholesterol tether. For each chip, 12 µl of DNA-adapter ligated mix was mixed with the sequencing mix (final volume of 150 µL) and added to chip for sequencing. The experiment was then run for 6 hours at 160 mV.

Figure 39:
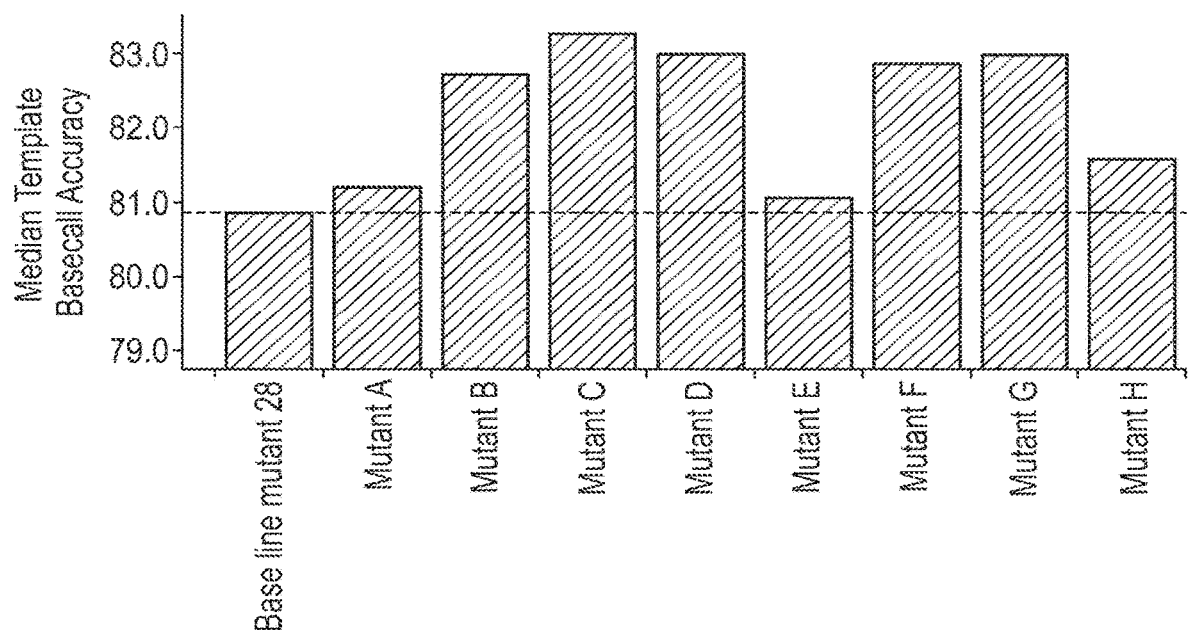
FIG. 39 shows the basecall accuracy of eight CsgG mutant pores compared to the basecall accuracy of a baseline pore, mutant 28 (CsgG-(WT-Y51A/F56Q/R97W/R192D-StrepII)9). The deletion of D195-L199 (Mutant A), F193-L199 (Mutant B) or V105-I107 (Mutant D), or the substitution of F191T (Mutant C) results in a further improvement in accuracy in addition to the improvement in accuracy resulting from the R97W and R192D substitutions in mutant 28. The effect on basecall accuracy of deleting V105-I107 was also tested in a mutant pore containing an additional K94Q mutation (Mutant E) and an improvement in accuracy compared to baseline mutant 28 was still observed. Introducing a R93W mutation (Mutant F) or both R93Y and R97W mutations (Mutant H) instead of a R97W mutation (baseline mutant 28) increased the basecall accuracy. Deleting D195-L199 in addition to R93W (Mutant G) resulted in an enhancement of basecall accuracy.

The 1D accuracy characterisation measurements were calculated using methods as disclosed in WO2013/041878.
Measuring Template Speed The template speed was measured by the following method. The basecall of each squiggle was aligned to the reference sequence. The number of bases that spanned the alignment (alignment end position subtracted from the alignment start position) was divided by the time between the event that corresponded to the end of the alignment and by the event that corresponded to the start of the alignment.
Results
Basecall Accuracy As shown in FIG. 39, all 8 CsgG mutant pores were found to have an improved basecall accuracy compared to the baseline pore, mutant 28 (CsgG-(WT-Y51A/F56Q/R97W/R192D-StrepII)9) described in Example 6. As shown in Table 17, mutant 28 showed the highest basecall accuracy (80.2%) of all the CsgG mutants tested in Example 6, in which mutant 25 (CsgG-(WT-Y51A/F56Q-StrepII)9) described in Example 5 was the baseline mutant. Therefore the deletion of D195-L199, of F193-L199 or V105-I107, or the substitution of F191T results in a further improvement in accuracy in addition to the improvement in accuracy resulting from the R97W and R192D substitutions in mutant 28.

The deletion of D195-L199, of F193-L199 or V105-I107, or the substitution of F191T, would each also be expected to improve accuracy in the presence of other mutations in the CsgG sequence or in the absence of the R97W, R192D, Y51A and/or F56Q mutations. For example, mutant E, which contains the mutation K94Q in addition to the del (V105-I107) mutation has an improved accuracy compared to mutant 28, as does the del(V105-I107)-containing mutant G which does not contain the R97W substitution, but instead contains a R93W substitution.

Figure 40A:
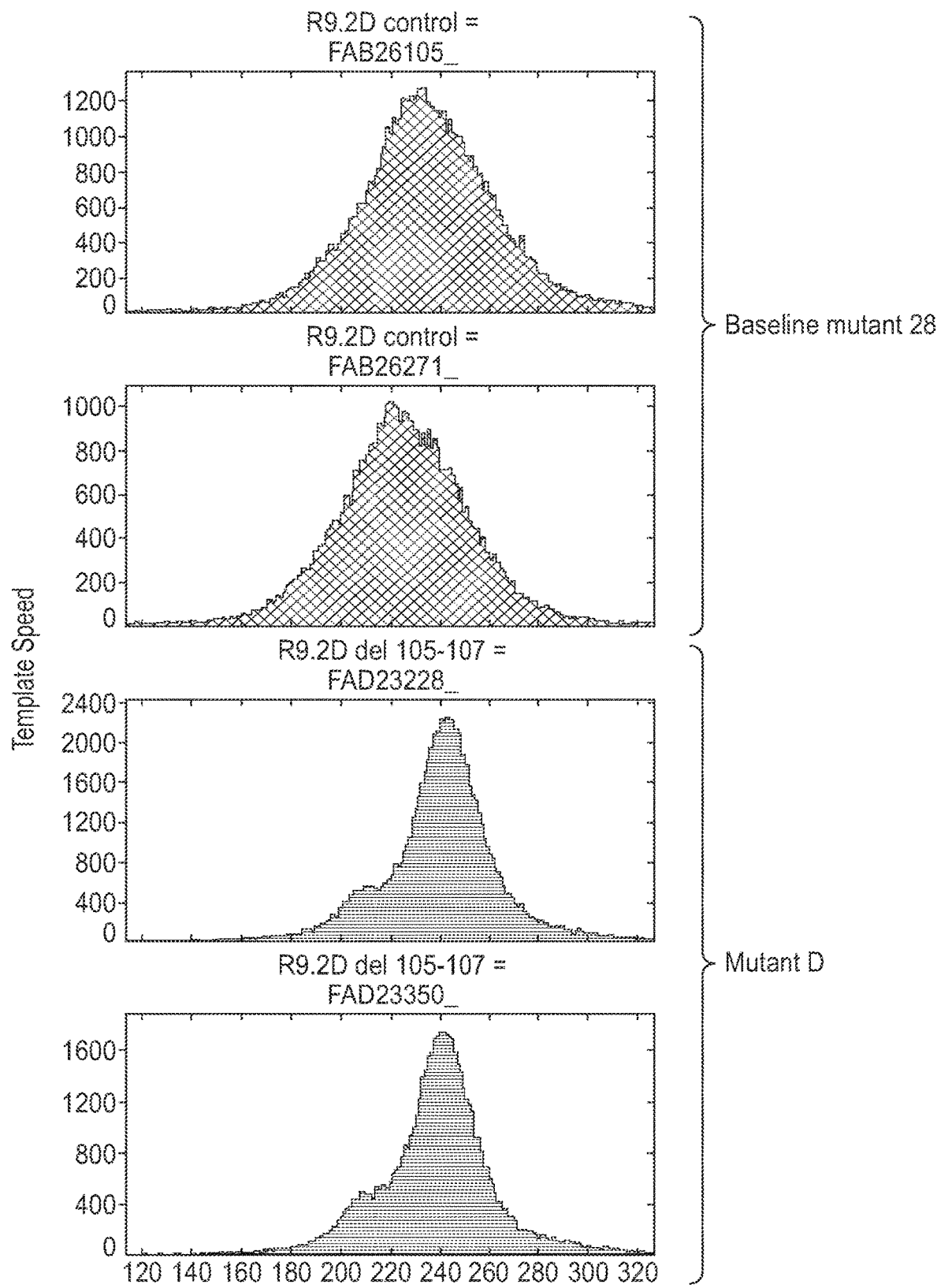
FIG. 40A-40B show the template speed distribution (A) and the template accuracy distribution (B) of the baseline mutant 28 CsgG-(WT-Y51A/F56Q/R97W/R192D-StrepII)9 and Mutant D which comprises an additional deletion of V105-I107. A template DNA was prepared and passed through the mutant pores as described in the Examples. The template speed and accuracy were determined as described in the Examples.

Table 17 in Example 26 shows that mutant 26, which contains the R97W substitution has almost as good a basecall accuracy (79.2%) as mutant 28 (80.2%). This suggests that the R97W mutation underlies the increased basecall accuracy. In this Example, two mutants which do not contain the R97W mutation (and also do not contain the R192D mutation), but instead contain a R93W substitution (mutant F) or both a R93Y substitution and a R97Y substitution (mutant H) were tested and found to have a higher basecall accuracy than mutant 28. This shows that R93W and R93Y/R97Y substitutions can be used to improve the basecall accuracy of CsgG nanopores.
Template Speed and Template Accuracy As shown in FIG. 40A, mutant D (CsgG-(WT-Y51A/F56Q/R97W/R192D-del(V105-I107)-StrepII)9) has a tightened distribution of speed population as compared to the baseline mutant 28 CsgG-(WT-Y51A/F56Q/R97W/R192D-StrepII)9.

Figure 40B:
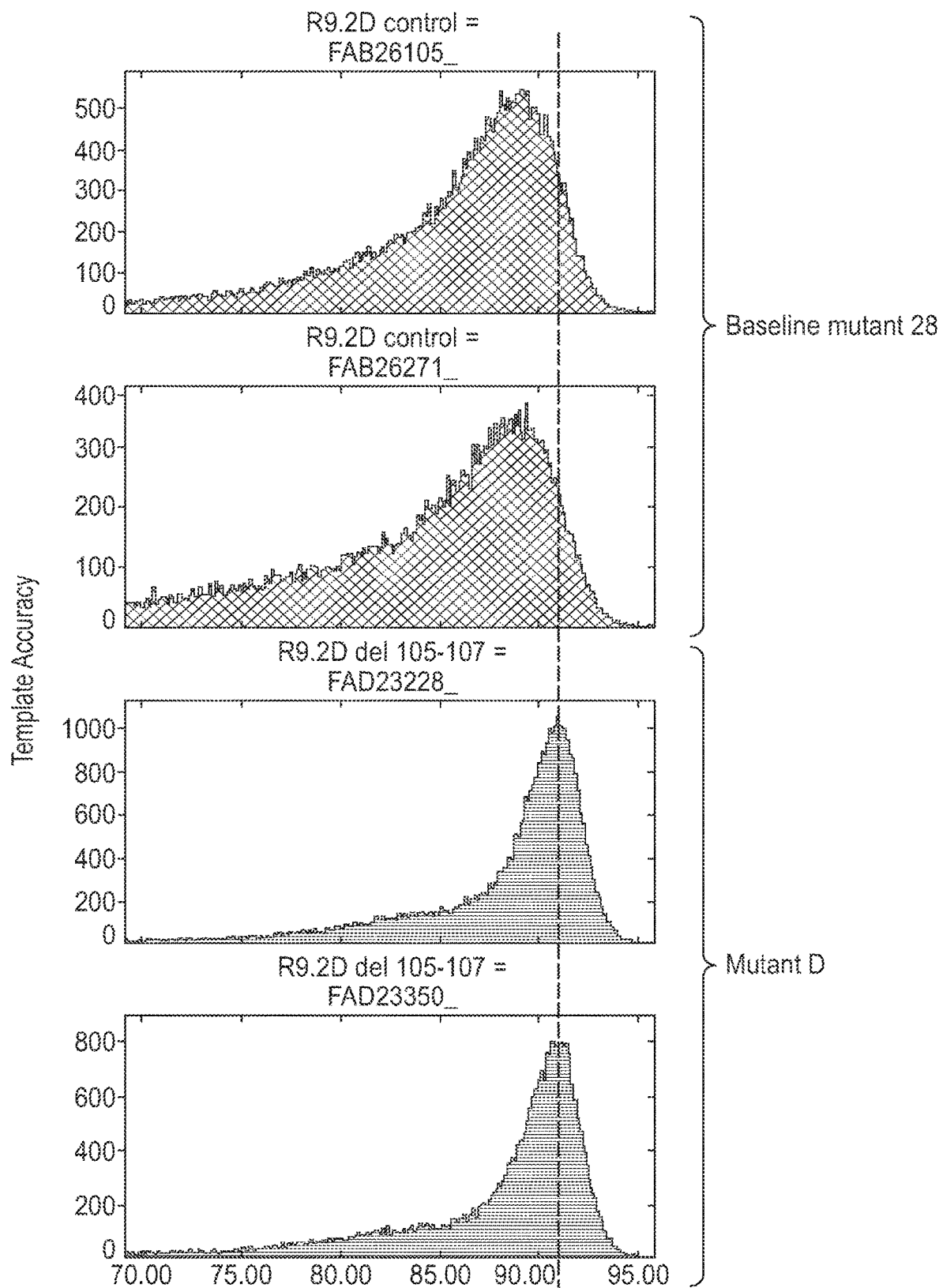

FIG. 40B shows that mutant D (CsgG-(WT-Y51A/F56Q/R97W/R192D-del(V105-I107)-StrepII)9) has tightened distribution of template accuracy as compared to the baseline mutant 28 CsgG-(WT-Y51A/F56Q/R97W/R192D-StrepII)9.

It is an advantage to have a tightened speed and accuracy distribution since there is less variation in the data. Also, the median accuracy of the data will increase by reducing the amount of lower accuracy data generated. Thus, deleting the amino acids from V105 to I107 of a CsgG nanopore can be used to produce a CsgG nanopore with improved properties for characterising polynucleotides.

Example 10

Figure 41:
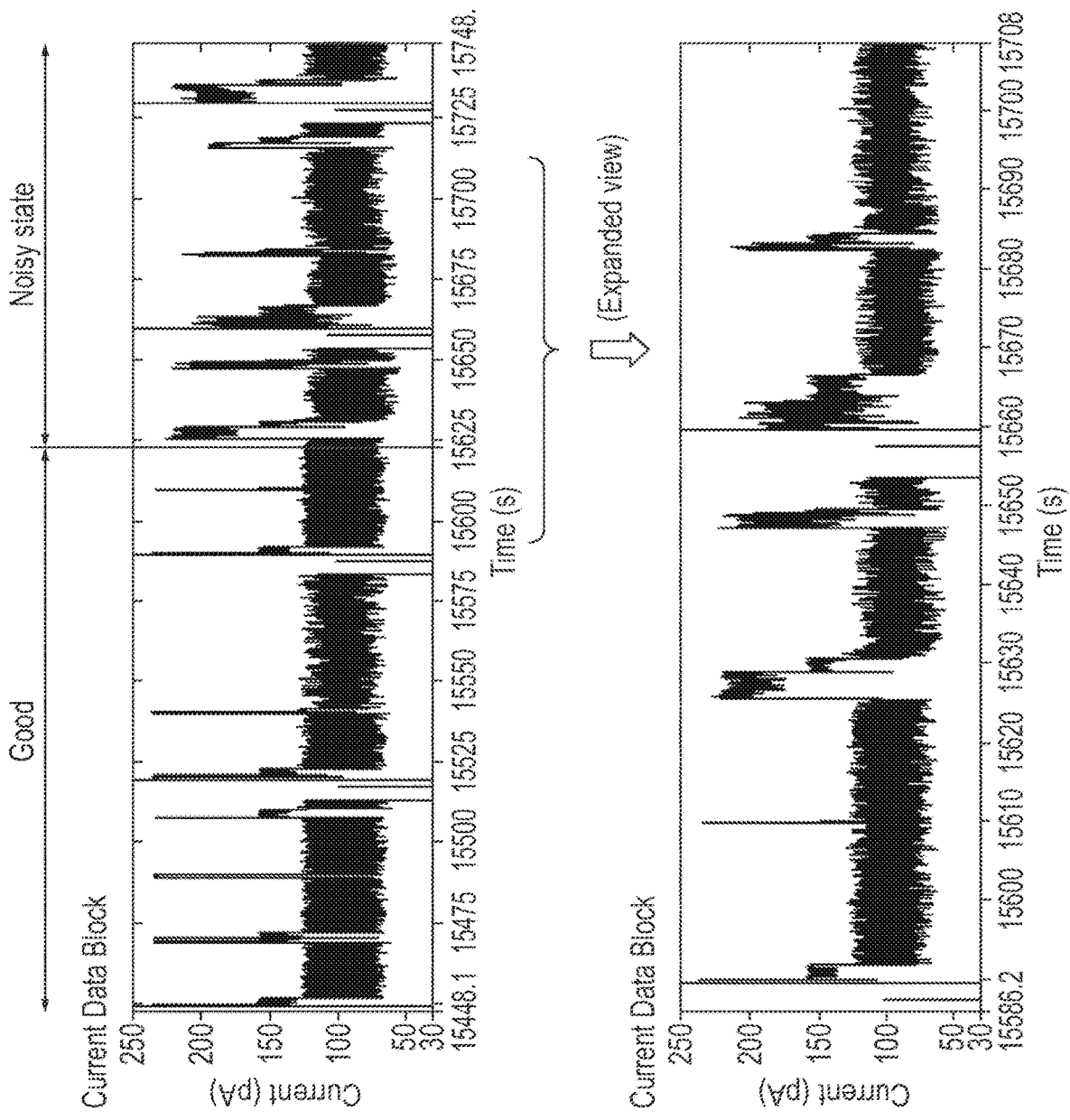
FIG. 41 displays an example "squiggle" that shows the "noisy" pore error mode exhibited by baseline mutant 28 CsgG-(WT-Y51A/F56Q/R97W/R192D-StrepII)9. The top panel of FIG. 41 shows the difference in flow of current through the pore during the "good" and "noisy" pore states. The bottom panel of FIG. 41 shows an expanded view of the transition from "good" state to "noisy" state.

This Example describes the characterisation of CsgG mutants which show a reduction in noisy pore signal.
Materials and Methods
CsG Pores The following CsgG mutant pores were tested. Mutant 28 described in Example X above was used as the baseline pore. The mutations are made in SEQ ID NO: 2 and the purification tag StrepII has the sequence shown in SEQ ID NO: 47.
Baseline pore (mutant 28): CsgG-(WT-Y51A/F56Q/R97W/R192D-StrepII)9
Mutant I: CsgG-(WT-Y51A/F56Q/R97W/R192D-StrepII)9-K94N.
Mutant J: CsgG-(WT-Y51A/F56Q/R97W/R192D-StrepII)9-K94Q.
Nanopore Preparation Chips containing multiple wells of block co-polymer membrane each with a single CsgG mutant nanopore inserted were prepared as described in Example 9.
DNA Sample Preparation DNA sample was prepared for sequencing using the method described in Example 9.
Determining Time Spent in Noisy Pore State The percentage of time spent in a noisy pore state was calculated as follows. The event detected signal within each channel was split up into non-overlapping short windows. For each window the mean average of the current levels and the dispersion of the current levels was calculated. The values obtained were then passed to a classifier which returned a label denoting whether the window contained a noisy signal. The classifier was trained to detect noisy signals by providing it with pre-labelled data.
Results
Noisy Pore State FIG. 41 displays an example "squiggle" that shows the "noisy" pore error mode exhibited by baseline mutant 28 CsgG-(WT-Y51A/F56Q/R97W/R192D-StrepII)9. The top panel of FIG. 41 shows the difference in flow of current through the pore during the "good" and "noisy" pore states. The bottom panel of FIG. 41 shows an expanded view of the transition from "good" state to "noisy" state.

Figure 42:
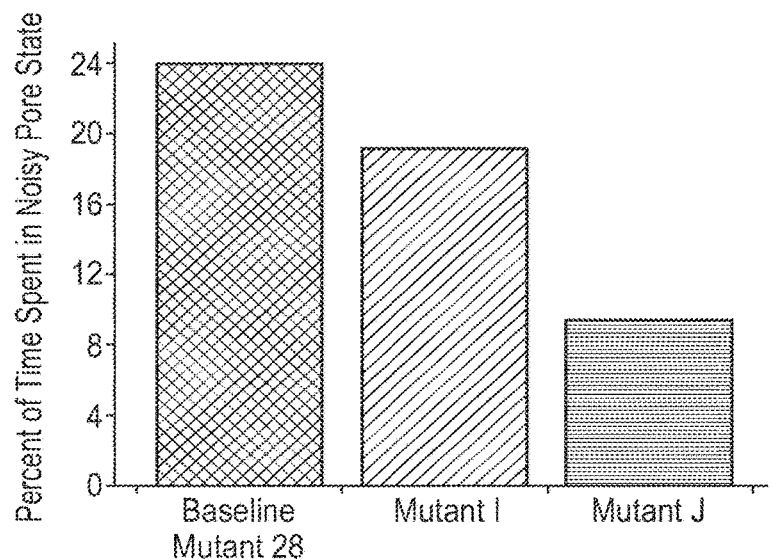
FIG. 42 shows the reduction in noisy pore state of mutant pores having the same sequence as the baseline mutant 28, which contains Y51A/F56Q/R97W/R192D mutations, with an additional K94N mutation (Mutant I) or an additional K94Q mutation (Mutant J) when compared to baseline mutant 28, averaged over at least 5 runs.

FIG. 42 shows the reduction in noisy pore state of mutant pores I and J when compared to baseline mutant 28, averaged over at least 5 runs.

The percentage of time spent in noise pore state by both Mutant J and Mutant I is significantly reduced compared to the baseline. Mutants I and J differ from the mutant 28 used as a baseline at just one residue. Both mutant I and mutant J contain a substitution of K94. Mutant I contains a K94N mutation and mutant II contains a K94Q mutation. Therefore substitution of K94 in a CsgG nanopore, particularly substitution with N or Q, can be used to produce a CsgG nanopore with improved properties for characterizing polynucleotides.

Example 11

This Example describes the characterisation of several CsgG mutants which show increased capture activity.
Materials and Methods
CsG Pores The following CsgG mutant pores were tested. Mutant E described in Example 9 above was used as the baseline pore. The mutations are made in SEQ ID NO: 2 and the purification tag StrepII has the sequence shown in SEQ ID NO: 47.
Baseline (mutant E): CsgG-(WT-Y51A/F56Q/K94Q/R97W/R192D-del(V105-I107)).
Mutant K: CsgG-(WT-Y51A/F56Q/K94Q/R97W/R192D-del(V105-I107)-Q42K
Mutant L: CsgG-(WT-Y51A/F56Q/K94Q/R97W/R192D-del(V105-I107)-E44N
Mutant M: CsgG-(WT-Y51A/F56Q/K94Q/R97W/R192D-del(V105-I107)-E44Q
Mutant N: CsgG-(WT-Y51A/F56Q/K94Q/R97W/R192D-del(V105-I107)-L90R
Mutant O: CsgG-(WT-Y51A/F56Q/K94Q/R97W/R192D-del(V105-I107)-N91R
Mutant P: CsgG-(WT-Y51A/F56Q/K94Q/R97W/R192D-del(V105-I107)-I95R
Mutant Q: CsgG-(WT-Y51A/F56Q/K94Q/R97W/R192D-del(V105-I107)-A99R
Mutant R: CsgG-(WT-Y51A/F56Q/K94Q/R97W/R192D-del(V105-I107)-E101H
Mutant S: CsgG-(WT-Y51A/F56Q/K94Q/R97W/R192D-del(V105-I107)-E101K
Mutant T: CsgG-(WT-Y51A/F56Q/K94Q/R97W/R192D-del(V105-I107)-E101N
Mutant U: CsgG-(WT-Y51A/F56Q/K94Q/R97W/R192D-del(V105-I107)-E101Q
Mutant V: CsgG-(WT-Y51A/F56Q/K94Q/R97W/R192D-del(V105-I107)-E101T
Mutant W: CsgG-(WT-Y51A/F56Q/K94Q/R97W/R192D-del(V105-I107)-Q114K
Nanopore Preparation To prepare nanopore array chips that contain multiple wells of block co-polymer membrane each with a single CsgG mutant nanopore inserted the following method was used. CsgG mutants expressed in E. coli were purified and stored in buffer containing 25 mM Tris, 150 mM NaCl, 2 mM EDTA, 0.01% DDM, 0.1% SDS, 0.1% Brij 58 at pH8. These mutant CsgG pores were diluted to 1 in 1 million using buffer comprising 25 mM Potassium Phosphate, 150 mM Potassium Ferrocyanide (II), 150 mM Potassium Ferricyanide (III) at pH 8.0 and added to the chips to obtain single pores in each of the wells. After pore insertion, the chips were washed with 1 mL buffer comprising 25 mM Potassium Phosphate, 150 mM Potassium Ferrocyanide (II), 150 mM Potassium Ferricyanide (III) at pH 8.0 to remove excess pores. 1 mL of solution containing 240 nM TBA analyte in 25 mM Potassium Phosphate, 150 mM Potassium Ferrocyanide (II), 150 mM Potassium Ferricyanide (III) at pH 8.0 was flushed into the chip.
Determining Capture Ability The ability of a mutant pore to capture DNA analyte is then assessed by its ability to capture Thrombin Binding Aptamer (TBA) (SEQ ID NO: 51). The experiment was run at 180 mV. In order to measure TBA capture by a pore, the median time between TBA events was calculated.

Results

As shown in FIG. 44, the median time between TBA events for 13 mutants was significantly reduced compared to the baseline, indicating that all 13 mutants display increased capture rates of template DNA.

Each of the 13 mutants had a single amino acid substitution compared to the baseline pore. The particular substitutions were: Q42K, E44N, E44Q, L90R, N91R, I95R, A99R, E101H, E101K, E101N, E101Q, E101T and Q114K. All of these mutations involve the substitution of a negatively charged amino acid with an uncharged amino acid or a positively charged amino acid, or of an uncharged amino acid with a positively charged amino acid. Therefore, it can be concluded that substitution of the amino acid at one or more of positions Q42, E44, E44, L90, N91, I95, A99, E101 and Q114 with amino acids that remove the negative charge and/or increase the positive charge at these positions results in increased capture of a polynucleotide.

Sequence Alignment of the Various CsgG Homologues

FIGS. 45A-45C show the sequence alignment between the twenty-one CsgG homologues as detailed above. A multiple sequence alignment was performed on SEQ ID NO: 2, SEQ ID NO: 3, SEQ ID NO: 4, SEQ ID NO: 5, SEQ ID NO: 6, SEQ ID NO: 7, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40 and SEQ ID NO: 41.

Praline software, a multiple sequence alignment toolbox that integrates homology-extended and secondary structure information was used to perform the alignment http://www.ibi.vu.nl/programs/pralinewww/, see also Simossis VA1, Heringa J.; Nucleic Acids Res. 2005 Jul. 1; 33(Web Server issue):W289-94. The alignment was scored using the BLOSUM62 residue exchange matrix. For details of this method, see for example Henikoff S, Henikoff J G; Proc. Natl. Acad. Sci. USA Vol. 89, pp. 10915-10919, November 1992. Gap opening and extension penalties of 12 and 1 were used respectively. Secondary structure prediction using PSIPRED was used to guide the alignment. For details of this method, see for example Jones D. T.; J Mol Biol. 1999 Sep. 17; 292(2):195-202. The above methods used to align the sequences are exemplary and other methods of sequence alignment known in the art may be used.

With reference to the sequence alignments of FIGS. 45A-45C, each section of sequence alignment the conservation at each position is indicated by a histogram and a score. Numbers 0-9 on the scale indicate increasing conservation, columns with mutations which result in similar properties of that amino being conserved are marked with a plus ('+') and the star symbol ('*') indicates 100% sequence identity at that position. It can be seen from the conservation values of the sequence alignment that many of the residues show very high or even perfect sequence identity indicating that these 21 homologues are closely related.

FIGS. 46A-46C show the same relative sequence alignments as FIGS. 45A-45C with predicted alpha helical secondary structure regions additionally shaded in grey. FIGS. 47A-47C show the same relative sequence alignments as FIGS. 45A-45C with predicted beta sheet secondary structure regions additionally shaded in grey. FIGS. 46A-46C and F47A-47C show that the regions of predicted alpha helices and beta sheets of these homologues, important secondary structures for CsgG nanopores are highly conserved.

The multiple sequence alignment strongly suggests the sequences are related; not only is there a high degree of conservation along the alignment, but the predicted secondary structural elements are also aligned.

The sequence alignments in FIGS. 45A-45C, 46A-46C and 47A-47C may be used as a reference to show the relative positions that align with each other. Thus amino-acid residues identified with respect to SEQ ID NO 2 and the corresponding amino-acid residues in other CsgG homologues can be identified. For ease of identification, residues R97 and R192 have been located with an asterisk. It can be seen from the table that for example R192 of SEQ ID NO: 2 corresponds to residue R191 of SEQ ID NO: 32 and residue K177 of SEQ ID NO: 37.

As will be readily appreciated with reference to FIGS. 45A-45C, 46A-46C and 47A-47C, the CsgG monomers are highly conserved. Furthermore, from knowledge of the mutations in relation to SEQ ID NO: 2 it is possible to determine the equivalent positions for mutations of CsgG monomers other than that of SEQ ID NO: 2.

Thus reference to a mutant CsgG monomer comprising a variant of the sequence as shown in SEQ ID NO: 2 and specific amino-acid mutations thereof as set out in the claims and elsewhere in the specification also encompasses a mutant CsgG monomer comprising a variant of the sequence as shown in SEQ ID NO: 3, SEQ ID NO: 4, SEQ ID NO: 5, SEQ ID NO: 6, SEQ ID NO: 7, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40 and SEQ ID NO: 41 and corresponding amino-acid mutations thereof. Likewise reference to a construct, pore or method involving the use of a pore relating to a mutant CsgG monomer comprising a variant of the sequence as shown in SEQ ID NO: 2 and specific amino-acid mutations thereof as set out in the claims and elsewhere in the specification also encompasses a construct, pore or method relating to a mutant CsgG monomer comprising a variant of the sequence according the above disclosed SEQ ID NOS and corresponding amino-acid mutations thereof. If will further be appreciated that the invention extends to other variant CsgG monomers not expressly identified in the specification that show highly conserved regions.

SEQUENCE LISTING

```
<160> NUMBER OF SEQ ID NOS: 56

<210> SEQ ID NO 1
<211> LENGTH: 786
<212> TYPE: DNA
<213> ORGANISM: Escherichia coli

<400> SEQUENCE: 1
```

```
tgtctgaccg caccgccgaa agaagcggca cgtccgaccc tgatgccgcg tgcacagtct      60
tataaagatc tgacccatct gccggctccg acgggcaaaa ttttttgttag cgtctataac    120
atccaggacg aaaccggtca atttaaaccg tacccggcga gtaatttctc cacggccgtt    180
ccgcagagtg caaccgctat gctggtcacg gcactgaaag attcccgttg gttcattccg    240
ctggaacgcc agggcctgca aaacctgctg aatgaacgta aaattatccg cgcagctcag    300
gaaaacggta ccgtggccat taacaatcgt attccgctgc aaagcctgac cgccgcaaac    360
atcatggttg aaggctctat catcggttac gaatcaaacg tcaaatcggg cggtgtgggc    420
gcacgttatt ttggcattgg tgctgatacc cagtaccaac tggaccagat cgcagttaac    480
ctgcgcgtgg ttaatgtcag caccggcgaa attctgagct ctgtgaatac cagcaaaacg    540
atcctgtctt acgaagtgca ggctggtgtt tttcgtttca ttgattatca acgcctgctg    600
gaaggcgaag tcggttacac ctcaaacgaa ccggtgatgc tgtgtctgat gtcggcgatt    660
gaaacgggtg ttatttttcct gatcaatgat ggcatcgacc gtggtctgtg ggatctgcag    720
aacaaagccg aacgtcaaaa tgacattctg gtgaaatacc gccacatgag tgttccgccg    780
gaatcc                                                                 786
```

<210> SEQ ID NO 2
<211> LENGTH: 262
<212> TYPE: PRT
<213> ORGANISM: Escherichia coli

<400> SEQUENCE: 2

```
Cys Leu Thr Ala Pro Pro Lys Glu Ala Ala Arg Pro Thr Leu Met Pro
1               5                   10                  15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
            100                 105                 110

Leu Gln Ser Leu Thr Ala Ala Asn Ile Met Val Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Val Gly Tyr Thr Ser
        195                 200                 205

Asn Glu Pro Val Met Leu Cys Leu Met Ser Ala Ile Glu Thr Gly Val
    210                 215                 220
```

```
Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
            260
```

<210> SEQ ID NO 3
<211> LENGTH: 248
<212> TYPE: PRT
<213> ORGANISM: Citrobacter koseri

<400> SEQUENCE: 3

```
Met Pro Arg Ala Gln Ser Tyr Lys Asp Leu Thr His Leu Pro Met Pro
1               5                   10                  15

Thr Gly Lys Ile Phe Val Ser Val Tyr Asn Ile Gln Asp Glu Thr Gly
                20                  25                  30

Gln Phe Lys Pro Tyr Pro Ala Ser Asn Phe Ser Thr Ala Val Pro Gln
            35                  40                  45

Ser Ala Thr Ala Met Leu Val Thr Ala Leu Lys Asp Ser Arg Trp Phe
    50                  55                  60

Ile Pro Leu Glu Arg Gln Gly Leu Gln Asn Leu Asn Glu Arg Lys
65                  70                  75                  80

Ile Ile Arg Ala Ala Gln Glu Asn Gly Thr Val Ala Ile Asn Asn Arg
                85                  90                  95

Ile Pro Leu Gln Ser Leu Thr Ala Ala Asn Ile Met Val Glu Gly Ser
            100                 105                 110

Ile Ile Gly Tyr Glu Ser Asn Val Lys Ser Gly Gly Val Gly Ala Arg
        115                 120                 125

Tyr Phe Gly Ile Gly Ala Asp Thr Gln Tyr Gln Leu Asp Gln Ile Ala
130                 135                 140

Val Asn Leu Arg Val Val Asn Val Ser Thr Gly Glu Ile Leu Ser Ser
145                 150                 155                 160

Val Asn Thr Ser Lys Thr Ile Leu Ser Tyr Glu Val Gln Ala Gly Val
                165                 170                 175

Phe Arg Phe Ile Asp Tyr Gln Arg Leu Leu Glu Gly Glu Ile Gly Tyr
            180                 185                 190

Thr Ser Asn Glu Pro Val Met Leu Cys Leu Met Ser Ala Ile Glu Thr
        195                 200                 205

Gly Val Ile Phe Leu Ile Asn Asp Gly Ile Asp Arg Gly Leu Trp Asp
210                 215                 220

Leu Gln Asn Lys Ala Glu Arg Gln Asn Asp Ile Leu Val Lys Tyr Arg
225                 230                 235                 240

His Met Ser Val Pro Pro Glu Ser
                245
```

<210> SEQ ID NO 4
<211> LENGTH: 223
<212> TYPE: PRT
<213> ORGANISM: Salmonella enterica

<400> SEQUENCE: 4

```
Cys Leu Thr Ala Pro Pro Lys Gln Ala Ala Lys Pro Thr Leu Met Pro
1               5                   10                  15

Arg Ala Gln Ser Tyr Lys Asp Leu Thr His Leu Pro Ala Pro Thr Gly
                20                  25                  30
```

-continued

```
Lys Ile Phe Val Ser Val Tyr Asn Ile Gln Asp Glu Thr Gly Gln Phe
             35                  40                  45

Lys Pro Tyr Pro Ala Ser Asn Phe Ser Thr Ala Val Pro Gln Ser Ala
 50                  55                  60

Thr Ala Met Leu Val Thr Ala Leu Lys Asp Ser Arg Trp Phe Ile Pro
 65                  70                  75                  80

Leu Glu Arg Gln Gly Leu Gln Asn Leu Leu Asn Glu Arg Lys Ile Ile
                 85                  90                  95

Arg Ala Ala Gln Glu Asn Gly Thr Val Ala Met Asn Asn Arg Ile Pro
                100                 105                 110

Leu Gln Ser Leu Thr Ala Ala Asn Ile Met Val Glu Gly Ser Ile Ile
                115                 120                 125

Gly Tyr Glu Ser Asn Val Lys Ser Gly Gly Val Gly Ala Arg Tyr Phe
130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
                180                 185                 190

Phe Ile Asp Tyr Gln Arg Leu Leu Glu Gly Glu Ile Gly Tyr Thr Ser
                195                 200                 205

Asn Glu Pro Val Met Leu Cys Leu Met Ser Ala Ile Glu Thr Gly
                210                 215                 220

<210> SEQ ID NO 5
<211> LENGTH: 262
<212> TYPE: PRT
<213> ORGANISM: Citrobacter amalonaticus

<400> SEQUENCE: 5

Cys Leu Thr Ala Pro Pro Lys Glu Ala Ala Lys Pro Thr Leu Met Pro
 1               5                  10                  15

Arg Ala Gln Ser Tyr Lys Asp Leu Thr His Leu Pro Ile Pro Thr Gly
             20                  25                  30

Lys Ile Phe Val Ser Val Tyr Asn Ile Gln Asp Glu Thr Gly Gln Phe
             35                  40                  45

Lys Pro Tyr Pro Ala Ser Asn Phe Ser Thr Ala Val Pro Gln Ser Ala
 50                  55                  60

Thr Ala Met Leu Val Thr Ala Leu Lys Asp Ser Arg Trp Phe Val Pro
 65                  70                  75                  80

Leu Glu Arg Gln Gly Leu Gln Asn Leu Leu Asn Glu Arg Lys Ile Ile
                 85                  90                  95

Arg Ala Ala Gln Glu Asn Gly Thr Val Ala Ile Asn Asn Arg Ile Pro
                100                 105                 110

Leu Gln Ser Leu Thr Ala Ala Asn Ile Met Val Glu Gly Ser Ile Ile
                115                 120                 125

Gly Tyr Glu Ser Asn Val Lys Ser Gly Gly Val Gly Ala Arg Tyr Phe
130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
                180                 185                 190
```

```
Phe Ile Asp Tyr Gln Arg Leu Leu Glu Gly Glu Ile Gly Tyr Thr Ser
            195                 200                 205

Asn Glu Pro Val Met Leu Cys Leu Met Ser Ala Ile Glu Thr Gly Val
        210                 215                 220

Ile Phe Leu Ile Asn Asp Gly Ile Asp Arg Gly Leu Trp Asp Leu Gln
225                 230                 235                 240

Asn Lys Ala Asp Arg Gln Asn Asp Ile Leu Val Lys Tyr Arg His Met
                245                 250                 255

Ser Val Pro Pro Glu Ser
            260

<210> SEQ ID NO 6
<211> LENGTH: 262
<212> TYPE: PRT
<213> ORGANISM: Citrobacter rodentium

<400> SEQUENCE: 6

Cys Leu Thr Thr Pro Pro Lys Glu Ala Ala Lys Pro Thr Leu Met Pro
1               5                   10                  15

Arg Ala Gln Ser Tyr Lys Asp Leu Thr His Leu Pro Val Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
            100                 105                 110

Leu Pro Ser Leu Thr Ala Ala Asn Ile Met Val Glu Gly Ser Ile Ile
        115                 120                 125

Gly Tyr Glu Ser Asn Val Lys Ser Gly Gly Ala Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Ile Gly Tyr Thr Ser
        195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Asp Arg Gln Asn Asp Ile Leu Val Lys Tyr Arg Gln Met
                245                 250                 255

Ser Val Pro Pro Glu Ser
            260

<210> SEQ ID NO 7
<211> LENGTH: 262
<212> TYPE: PRT
```

<213> ORGANISM: Enterobacter asburiae

<400> SEQUENCE: 7

```
Cys Leu Thr Ala Pro Pro Lys Glu Ala Ala Lys Pro Thr Leu Met Pro
1               5                   10                  15

Arg Ala Gln Ser Tyr Arg Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser His Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Asn Asn Asn Arg Met Pro
            100                 105                 110

Leu Gln Ser Leu Ala Ala Ala Asn Val Met Ile Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Val Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Ile Gly Tyr Thr Ser
        195                 200                 205

Asn Glu Pro Val Met Met Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Asp Ala Gln Asn Pro Val Leu Val Lys Tyr Arg Asp Met
                245                 250                 255

Ser Val Pro Pro Glu Ser
            260
```

<210> SEQ ID NO 8
<211> LENGTH: 1830
<212> TYPE: DNA
<213> ORGANISM: Bacteriophage phi-29

<400> SEQUENCE: 8

```
atgaaacaca tgccgcgtaa aatgtatagc tgcgcgtttg aaaccacgac caaagtggaa      60
gattgtcgcg tttgggccta tggctacatg aacatcgaag atcattctga atacaaaatc    120
ggtaacagtc tggatgaatt tatggcatgg gtgctgaaag ttcaggcgga tctgtacttc    180
cacaacctga atttgatgg cgcattcatt atcaactggc tggaacgtaa tggctttaaa    240
tggagcgcgg atggtctgcc gaacacgtat aataccatta tctctcgtat gggccagtgg    300
tatatgattg atatctgcct gggctacaaa ggtaaacgca aaattcatac cgtgatctat    360
gatagcctga aaaactgcc gtttccggtg aagaaaattg cgaaagattt caaactgacg    420
gttctgaaag gcgatattga ttatcacaaa gaacgtccgg ttggttacaa aatcaccccg    480
```

```
gaagaatacg catacatcaa aaacgatatc cagatcatcg cagaagcgct gctgattcag    540
tttaaacagg gcctggatcg catgaccgcg ggcagtgata gcctgaaagg tttcaaagat    600
atcatcacga ccaaaaaatt caaaaagtg ttcccgacgc tgagcctggg tctggataaa     660
gaagttcgtt atgcctaccg cggcggtttt acctggctga cgatcgtttt caagaaaaaa    720
gaaattggcg agggtatggt gtttgatgtt aatagtctgt atccggcaca gatgtacagc    780
cgcctgctgc cgtatggcga accgatcgtg ttcgagggta atatgtttg ggatgaagat     840
tacccgctgc atattcagca catccgttgt gaatttgaac tgaaagaagg ctatattccg    900
accattcaga tcaaacgtag tcgcttctat aagggtaacg aatacctgaa agctctggc    960
ggtgaaatcg cggatctgtg gctgagtaac gtggatctgg aactgatgaa agaacactac   1020
gatctgtaca cgttgaata catcagcggc ctgaaattta agccacgac cggtctgttc    1080
aaagatttca tcgataaatg gacctacatc aaaacgacct ctgaaggcgc gattaaacag   1140
ctggccaaac tgatgctgaa cagcctgtat ggcaaattcg cctctaatcc ggatgtgacc   1200
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccggatgtg attaaagata tcgttgatcc gaaaaaactg   1440
ggttattggg cccacgaaag tacgtttaaa cgtgcaaaat acctgcgcca gaaaacctac   1500
atccaggata tctacatgaa agaagtggat ggcaaactgg ttgaaggttc tccggatgat   1560
tacaccgata tcaaattcag tgtgaaatgc gccggcatga cggataaaat caaaaaagaa   1620
gtgaccttcg aaaacttcaa agttggtttc agccgcaaaa tgaaaccgaa accggtgcag   1680
gttccgggcg gtgtggttct ggtggatgat acgtttacca ttaaatctgg cggtagtgcg   1740
tggagccatc cgcagttcga aaaaggcggt ggctctggtg gcggttctgg cggtagtgcc   1800
tggagccacc cgcagtttga aaataataa                                     1830
```

<210> SEQ ID NO 9
<211> LENGTH: 608
<212> TYPE: PRT
<213> ORGANISM: Bacteriophage phi-29

<400> SEQUENCE: 9

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
```

```
            130                 135                 140
Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
            165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Lys Lys Phe Lys
            195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
            245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
            275                 280                 285

Arg Cys Glu Phe Glu Leu Lys Glu Gly Tyr Ile Pro Thr Ile Gln Ile
            290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
                500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560
```

Val Pro Gly Gly Val Val Leu Val Asp Asp Thr Phe Thr Ile Lys Ser
            565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
            595                 600                 605

<210> SEQ ID NO 10
<211> LENGTH: 1390
<212> TYPE: DNA
<213> ORGANISM: Escherichia coli

<400> SEQUENCE: 10

| | | | | | |
|---|---|---|---|---|---|
| atgatgaacg | atggcaaaca | gcagagcacc | ttcctgtttc | atgattatga | aaccttcggt | 60 |
| acccatccgg | ccctggatcg | tccggcgcag | tttgcggcca | ttcgcaccga | tagcgaattc | 120 |
| aatgtgattg | gcgaaccgga | agtgttttat | tgcaaaccgg | ccgatgatta | tctgccgcag | 180 |
| ccgggtgcgg | tgctgattac | cggtattacc | ccgcaggaag | cgcgcgcgaa | aggtgaaaac | 240 |
| gaagcggcgt | tgccgcgcg | cattcatagc | ctgtttaccg | tgccgaaaac | ctgcattctg | 300 |
| ggctataaca | atgtgcgctt | cgatgatgaa | gttacccgta | atatctttta | tcgtaacttt | 360 |
| tatgatccgt | atgcgtggag | ctggcagcat | gataacagcc | gttgggatct | gctggatgtg | 420 |
| atgcgcgcgt | gctatgcgct | cgcccggaa | ggcattaatt | ggccggaaaa | cgatgatggc | 480 |
| ctgccgagct | ttcgtctgga | acatctgacc | aaagccaacg | gcattgaaca | tagcaatgcc | 540 |
| catgatgcga | tggccgatgt | ttatgcgacc | attgcgatgg | cgaaactggt | taaaacccgt | 600 |
| cagccgcgcc | tgtttgatta | tctgtttacc | caccgtaaca | acacaaaact | gatggcgctg | 660 |
| attgatgttc | cgcagatgaa | accgctggtg | catgtgagcg | catgtttgg | cgcctggcgc | 720 |
| ggcaacacca | gctgggtggc | cccgctggcc | tggcacccgg | aaaatcgtaa | cgccgtgatt | 780 |
| atggttgatc | tggccggtga | tattagcccg | ctgctggaac | tggatagcga | taccctgcgt | 840 |
| gaacgcctgt | ataccgccaa | aaccgatctg | gcgataatg | ccgccgtgcc | ggtgaaactg | 900 |
| gttcacatta | caaatgccc | ggtgctggcc | caggcgaaca | ccctgcgccc | ggaagatgcg | 960 |
| gatcgtctgg | gtattaatcg | ccagcattgt | ctggataatc | tgaaaatcct | gcgtgaaaac | 1020 |
| ccgcaggtgc | gtgaaaaagt | ggtggcgatc | ttcgcggaag | cggaaccgtt | cacccccgagc | 1080 |
| gataacgtgg | atgcgcagct | gtataacggc | ttctttagcg | atgccgatcg | cgcggcgatg | 1140 |
| aaaatcgttc | tggaaaccga | accgcgcaat | ctgccggcgc | tggatattac | ctttgttgat | 1200 |
| aaacgtattg | aaaaactgct | gtttaattat | cgtgcgcgca | attttccggg | taccctggat | 1260 |
| tatgccgaac | agcagcgttg | gctggaacat | cgtcgtcagg | ttttcacccc | ggaatttctg | 1320 |
| cagggttatg | cggatgaact | gcagatgctg | gttcagcagt | atgccgatga | taaagaaaaa | 1380 |
| gtggcgctgc | | | | | | 1390 |

<210> SEQ ID NO 11
<211> LENGTH: 485
<212> TYPE: PRT
<213> ORGANISM: Escherichia coli

<400> SEQUENCE: 11

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

```
Ala Ile Arg Thr Asp Ser Glu Phe Asn Val Ile Gly Glu Pro Glu Val
         35                  40                  45

Phe Tyr Cys Lys Pro Ala Asp Asp Tyr Leu Pro Gln Pro Gly Ala Val
 50                  55                  60

Leu Ile Thr Gly Ile Thr Pro Gln Glu Ala Arg Ala Lys Gly Glu Asn
 65                  70                  75                  80

Glu Ala Ala Phe Ala Ala Arg Ile His Ser Leu Phe Thr Val Pro Lys
                 85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
            115                 120                 125

Gln His Asp Asn Ser Arg Trp Asp Leu Leu Asp Val Met Arg Ala Cys
        130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
            195                 200                 205

Phe Thr His Arg Asn Lys His Lys Leu Met Ala Leu Ile Asp Val Pro
        210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
        290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445
```

Met Leu Val Gln Gln Tyr Ala Asp Asp Lys Glu Lys Val Ala Leu Leu
                450                 455                 460
Lys Ala Leu Trp Gln Tyr Ala Glu Glu Ile Val Ser Gly Ser Gly His
465                 470                 475                 480
His His His His His
            485

<210> SEQ ID NO 12
<211> LENGTH: 804
<212> TYPE: DNA
<213> ORGANISM: Escherichia coli

<400> SEQUENCE: 12
atgaaatttg tctcttttaa tatcaacggc ctgcgcgcca gacctcacca gcttgaagcc      60
atcgtcgaaa agcaccaacc ggatgtgatt ggcctgcagg agacaaaagt tcatgacgat     120
atgtttccgc tcgaagaggt ggcgaagctc ggctacaacg tgttttatca cgggcagaaa     180
ggccattatg gcgtggcgct gctgaccaaa gagacgccga ttgccgtgcg tcgcggcttt     240
cccggtgacg acgaagaggc gcagcggcgg attattatgg cggaaatccc ctcactgctg     300
ggtaatgtca ccgtgatcaa cggttacttc cgcagggtg aaagccgcga ccatccgata     360
aaattcccgg caaaagcgca gttttatcag aatctgcaaa actacctgga aaccgaactc     420
aaacgtgata tccggtact gattatgggc gatatgaata tcagccctac agatctggat     480
atcggcattg gcgaagaaaa ccgtaagcgc tggctgcgta ccggtaaatg ctcttttcctg     540 ccggaagagc gcgaatggat ggacaggctg atgagctggg ggttggtcga taccttccgc     600
catgcgaatc cgcaaacagc agatcgtttc tcatggtttg attaccgctc aaaaggtttt     660
gacgataacc gtggtctgcg catcgacctg ctgctcgcca gccaaccgct ggcagaatgt     720
tgcgtagaaa ccggcatcga ctatgaaatc cgcagcatgg aaaaaccgtc cgatcacgcc     780
cccgtctggg cgaccttccg ccgc                                            804

<210> SEQ ID NO 13
<211> LENGTH: 268
<212> TYPE: PRT
<213> ORGANISM: Escherichia coli

<400> SEQUENCE: 13

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

```
Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
            165                 170                 175

Cys Ser Phe Leu Pro Glu Glu Arg Glu Trp Met Asp Arg Leu Met Ser
        180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
        260                 265
```

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat tcgtgttcac     120
ggcgactatg atgcggatgg cctgaccggc accgcgatcc tggttcgtgg tctggccgcc     180
ctgggtgcgg atgttcatcc gtttatcccg caccgcctgg aagaaggcta tggtgtcctg     240
atggaacgcg tcccggaaca tctggaagcc tcggacctgt ttctgaccgt tgactgcggc     300
attaccaacc atgcggaact cgcgaactg ctggaaaatg cgtggaagt cattgttacc      360
gatcatcata cgccgggcaa aacgccgccg ccgggtctgg tcgtgcatcc ggcgctgacg     420
ccggatctga agaaaaaacc gaccggcgca ggcgtggcgt ttctgctgct gtgggcactg     480
catgaacgcc tgggcctgcc gccgccgctg gaatacgcgg acctggcagc cgttggcacc     540
attgccgacg ttgccccgct gtgggggttgg aatcgtgcac tggtgaaaga aggtctggca     600
cgcatcccgg cttcatcttg ggtgggcctg cgtctgctgg ctgaagccgt gggctatacc     660
ggcaaagcgg tcgaagtcgc tttccgcatc gcgccgcgca tcaatgcggc ttcccgcctg     720
ggcgaagcgg aaaaagccct gcgcctgctg ctgacggatg atgcggcaga agctcaggcg     780
ctggtcggcg aactgcaccg tctgaacgcc gtcgtcaga ccctggaaga agcgatgctg      840
cgcaaactgc tgccgcaggc cgacccggaa gcgaaagcca tcgttctgct ggaccccgaa     900
ggccatccgg tgttatggg tattgtggcc tctcgcatcc tggaagcgac cctgcgcccg     960
gtctttctgg tgcccaggg caaaggcacc gtgcgttcgc tggctccgat ttccgccgtc    1020
gaagcactgc gcagcgcgga agatctgctg ctgcgttatg tggtcataa agaagcggcg    1080
ggtttcgcaa tggatgaagc gctgtttccg gcgttcaaag cacgcgttga agcgtatgcc    1140
gcacgtttcc cggatccggt tcgtgaagtg cactgctgg atctgctgcc ggaaccgggc    1200
ctgctgccgc aggtgttccg tgaactggca ctgctggaac cgtatggtga aggtaacccg    1260
gaaccgctgt cctg                                                      1275
```

<210> SEQ ID NO 15

```
<211> LENGTH: 425
<212> TYPE: PRT
<213> ORGANISM: Thermus thermophilus

<400> SEQUENCE: 15
```

| | | | | | | | | | | | | | | |
|---|---|---|---|---|---|---|---|---|---|---|---|---|---|---|
| Met | Phe | Arg | Arg | Lys | Glu | Asp | Leu | Asp | Pro | Pro | Leu | Ala | Leu | Leu | Pro
| 1 | | | | 5 | | | | | 10 | | | | | 15 |

| Leu | Lys | Gly | Leu | Arg | Glu | Ala | Ala | Leu | Leu | Glu | Glu | Ala | Leu | Arg |
|---|---|---|---|---|---|---|---|---|---|---|---|---|---|---|
| | | | 20 | | | | | 25 | | | | | 30 | |

| Gln | Gly | Lys | Arg | Ile | Arg | Val | His | Gly | Asp | Tyr | Asp | Ala | Asp | Gly | Leu |
|---|---|---|---|---|---|---|---|---|---|---|---|---|---|---|---|
| | | 35 | | | | | 40 | | | | | 45 | | | |

| Thr | Gly | Thr | Ala | Ile | Leu | Val | Arg | Gly | Leu | Ala | Ala | Leu | Gly | Ala | Asp |
|---|---|---|---|---|---|---|---|---|---|---|---|---|---|---|---|
| | 50 | | | | | 55 | | | | | 60 | | | | |

| Val | His | Pro | Phe | Ile | Pro | His | Arg | Leu | Glu | Glu | Gly | Tyr | Gly | Val | Leu |
|---|---|---|---|---|---|---|---|---|---|---|---|---|---|---|---|
| 65 | | | | | 70 | | | | | 75 | | | | | 80 |

| Met | Glu | Arg | Val | Pro | Glu | His | Leu | Glu | Ala | Ser | Asp | Leu | Phe | Leu | Thr |
|---|---|---|---|---|---|---|---|---|---|---|---|---|---|---|---|
| | | | | 85 | | | | | 90 | | | | | 95 | |

| Val | Asp | Cys | Gly | Ile | Thr | Asn | His | Ala | Glu | Leu | Arg | Glu | Leu | Leu | Glu |
|---|---|---|---|---|---|---|---|---|---|---|---|---|---|---|---|
| | | | 100 | | | | | 105 | | | | | 110 | | |

| Asn | Gly | Val | Glu | Val | Ile | Val | Thr | Asp | His | His | Thr | Pro | Gly | Lys | Thr |
|---|---|---|---|---|---|---|---|---|---|---|---|---|---|---|---|
| | | 115 | | | | | 120 | | | | | 125 | | | |

| Pro | Pro | Pro | Gly | Leu | Val | Val | His | Pro | Ala | Leu | Thr | Pro | Asp | Leu | Lys |
|---|---|---|---|---|---|---|---|---|---|---|---|---|---|---|---|
| | 130 | | | | | 135 | | | | | 140 | | | | |

| Glu | Lys | Pro | Thr | Gly | Ala | Gly | Val | Ala | Phe | Leu | Leu | Leu | Trp | Ala | Leu |
|---|---|---|---|---|---|---|---|---|---|---|---|---|---|---|---|
| 145 | | | | | 150 | | | | | 155 | | | | | 160 |

| His | Glu | Arg | Leu | Gly | Leu | Pro | Pro | Leu | Glu | Tyr | Ala | Asp | Leu | Ala |
|---|---|---|---|---|---|---|---|---|---|---|---|---|---|---|
| | | | | 165 | | | | | 170 | | | | | 175 |

| Ala | Val | Gly | Thr | Ile | Ala | Asp | Val | Ala | Pro | Leu | Trp | Gly | Trp | Asn | Arg |
|---|---|---|---|---|---|---|---|---|---|---|---|---|---|---|---|
| | | | 180 | | | | | 185 | | | | | 190 | | |

| Ala | Leu | Val | Lys | Glu | Gly | Leu | Ala | Arg | Ile | Pro | Ala | Ser | Ser | Trp | Val |
|---|---|---|---|---|---|---|---|---|---|---|---|---|---|---|---|
| | | 195 | | | | | 200 | | | | | 205 | | | |

| Gly | Leu | Arg | Leu | Leu | Ala | Glu | Ala | Val | Gly | Tyr | Thr | Gly | Lys | Ala | Val |
|---|---|---|---|---|---|---|---|---|---|---|---|---|---|---|---|
| | 210 | | | | | 215 | | | | | 220 | | | | |

| Glu | Val | Ala | Phe | Arg | Ile | Ala | Pro | Arg | Ile | Asn | Ala | Ala | Ser | Arg | Leu |
|---|---|---|---|---|---|---|---|---|---|---|---|---|---|---|---|
| 225 | | | | | 230 | | | | | 235 | | | | | 240 |

| Gly | Glu | Ala | Glu | Lys | Ala | Leu | Arg | Leu | Leu | Leu | Thr | Asp | Asp | Ala | Ala |
|---|---|---|---|---|---|---|---|---|---|---|---|---|---|---|---|
| | | | | 245 | | | | | 250 | | | | | 255 | |

| Glu | Ala | Gln | Ala | Leu | Val | Gly | Glu | Leu | His | Arg | Leu | Asn | Ala | Arg | Arg |
|---|---|---|---|---|---|---|---|---|---|---|---|---|---|---|---|
| | | | 260 | | | | | 265 | | | | | 270 | | |

| Gln | Thr | Leu | Glu | Glu | Ala | Met | Leu | Arg | Lys | Leu | Leu | Pro | Gln | Ala | Asp |
|---|---|---|---|---|---|---|---|---|---|---|---|---|---|---|---|
| | | 275 | | | | | 280 | | | | | 285 | | | |

| Pro | Glu | Ala | Lys | Ala | Ile | Val | Leu | Leu | Asp | Pro | Glu | Gly | His | Pro | Gly |
|---|---|---|---|---|---|---|---|---|---|---|---|---|---|---|---|
| | 290 | | | | | 295 | | | | | 300 | | | | |

| Val | Met | Gly | Ile | Val | Ala | Ser | Arg | Ile | Leu | Glu | Ala | Thr | Leu | Arg | Pro |
|---|---|---|---|---|---|---|---|---|---|---|---|---|---|---|---|
| 305 | | | | | 310 | | | | | 315 | | | | | 320 |

| Val | Phe | Leu | Val | Ala | Gln | Gly | Lys | Gly | Thr | Val | Arg | Ser | Leu | Ala | Pro |
|---|---|---|---|---|---|---|---|---|---|---|---|---|---|---|---|
| | | | | 325 | | | | | 330 | | | | | 335 | |

| Ile | Ser | Ala | Val | Glu | Ala | Leu | Arg | Ser | Ala | Glu | Asp | Leu | Leu | Leu | Arg |
|---|---|---|---|---|---|---|---|---|---|---|---|---|---|---|---|
| | | | 340 | | | | | 345 | | | | | 350 | | |

| Tyr | Gly | Gly | His | Lys | Glu | Ala | Ala | Gly | Phe | Ala | Met | Asp | Glu | Ala | Leu |
|---|---|---|---|---|---|---|---|---|---|---|---|---|---|---|---|
| | | 355 | | | | | 360 | | | | | 365 | | | |

| Phe | Pro | Ala | Phe | Lys | Ala | Arg | Val | Glu | Ala | Tyr | Ala | Ala | Arg | Phe | Pro |
|---|---|---|---|---|---|---|---|---|---|---|---|---|---|---|---|
| | 370 | | | | | 375 | | | | | 380 | | | | |

| Asp | Pro | Val | Arg | Glu | Val | Ala | Leu | Leu | Asp | Leu | Leu | Pro | Glu | Pro | Gly |
|---|---|---|---|---|---|---|---|---|---|---|---|---|---|---|---|

```
                385               390                395                400
Leu Leu Pro Gln Val Phe Arg Glu Leu Ala Leu Leu Glu Pro Tyr Gly
                    405                 410                415
Glu Gly Asn Pro Glu Pro Leu Phe Leu
                420                 425

<210> SEQ ID NO 16
<211> LENGTH: 738
<212> TYPE: DNA
<213> ORGANISM: Bacteriophage lambda

<400> SEQUENCE: 16
tccggaagcg gctctggtag tggttctggc atgacaccgg acattatcct gcagcgtacc      60
gggatcgatg tgagagctgt cgaacagggg gatgatgcgt ggcacaaatt acggctcggc     120
gtcatcaccg cttcagaagt tcacaacgtg atagcaaaac cccgctccgg aaagaagtgg     180
cctgacatga aaatgtccta cttccacacc ctgcttgctg aggtttgcac cggtgtggct     240
ccggaagtta acgctaaagc actggcctgg ggaaaacagt acgagaacga cgccagaacc     300
ctgtttgaat tcacttccgg cgtgaatgtt actgaatccc cgatcatcta tcgcgacgaa     360
agtatgcgta ccgcctgctc tcccgatggt ttatgcagtg acggcaacgg ccttgaactg     420 aaaatgcccgt ttacctcccg ggatttcatg aagttccggc tcggtggttt cgaggccata     480
aagtcagctt acatggccca ggtgcagtac agcatgtggg tgacgcgaaa aaatgcctgg     540
tactttgcca actatgaccc gcgtatgaag cgtgaaggcc tgcattatgt cgtgattgag     600
cgggatgaaa agtacatggc gagttttgac gagatcgtgc cggagttcat cgaaaaaatg     660
gacgaggcac tggctgaaat tggttttgta tttggggagc aatggcgatc tggctctggt     720
tccggcagcg gttccgga                                                   738

<210> SEQ ID NO 17
<211> LENGTH: 226
<212> TYPE: PRT
<213> ORGANISM: Bacteriophage lambda

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
        50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
                100                 105                 110

Arg Thr Ala Cys Ser Pro Asp Gly Leu Cys Ser Asp Gly Asn Gly Leu
            115                 120                 125

Glu Leu Lys Cys Pro Phe Thr Ser Arg Asp Phe Met Lys Phe Arg Leu
        130                 135                 140

Gly Gly Phe Glu Ala Ile Lys Ser Ala Tyr Met Ala Gln Val Gln Tyr
145                 150                 155                 160
```

```
Ser Met Trp Val Thr Arg Lys Asn Ala Trp Tyr Phe Ala Asn Tyr Asp
                165                 170                 175

Pro Arg Met Lys Arg Glu Gly Leu His Tyr Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
```

```
              290                 295                 300
Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
                340                 345                 350

Arg Ser Tyr Arg Arg Phe Asp Ser Asn Phe Gly Met Gln Pro Ile Pro
                355                 360                 365

Val Leu Glu Tyr Lys Gln Met Ala Gly Arg Ala Gly Arg Pro His Leu
                370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
                420                 425                 430

Ile Val Asn Gly Phe Ala Ser Thr Arg Gln Glu Leu Phe Asp Phe Phe
                435                 440                 445

Gly Ala Thr Phe Phe Ala Tyr Gln Gln Asp Lys Trp Met Leu Glu Glu
                450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
                500                 505                 510

Ser Lys Ile Val Asp Gly Phe Lys Asp Ile Gly Lys Ser Thr Gly Gly
                515                 520                 525

Asn Met Gly Ser Leu Glu Asp Asp Lys Gly Asp Ile Thr Val Thr
                530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
                580                 585                 590

Asp Tyr Glu Trp Phe Met Gly Glu Val Lys Thr Ala Met Leu Leu Glu
                595                 600                 605

Glu Trp Val Thr Glu Val Ser Ala Glu Asp Ile Thr Arg His Phe Asn
610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
                660                 665                 670

Asp Leu Met Glu Leu Val Gly Ile Arg Gly Val Gly Arg Val Arg Ala
                675                 680                 685

Arg Lys Leu Tyr Asn Ala Gly Phe Val Ser Val Ala Lys Leu Lys Gly
                690                 695                 700

Ala Asp Ile Ser Val Leu Ser Lys Leu Val Gly Pro Lys Val Ala Tyr
705                 710                 715                 720
```

-continued

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile

```
                    325                 330                 335
Arg Leu Leu Ala Ser Thr Pro Thr Leu Ala Ala Gly Val Asn Leu Pro
                340                 345                 350

Ala Arg Arg Val Val Ile Ser Ser Val Met Arg Tyr Asn Ser Ser Ser
            355                 360                 365

Gly Met Ser Glu Pro Ile Ser Ile Leu Glu Tyr Lys Gln Leu Cys Gly
        370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Glu Ser Gly Asp Val His Arg Met Val
        595                 600                 605

Glu Ser Ser Gly Trp Leu Leu Arg Cys Ile Trp Glu Ile Ser Lys His
    610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Leu Phe Arg Gly Gly Ile Lys
            660                 665                 670

Gly Pro Gly Asp Leu Ala Ala Val Pro Val Glu Arg Leu Ser Arg Val
        675                 680                 685

Glu Gly Ile Gly Ala Thr Leu Ala Asn Asn Ile Lys Ser Gln Leu Arg
    690                 695                 700

Lys Gly Gly
705

<210> SEQ ID NO 20
<211> LENGTH: 720
<212> TYPE: PRT
<213> ORGANISM: Thermococcus gammatolerans
```

```
<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
    370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
```

```
            405                 410                 415
Ser Gln Val Leu Ala Leu Ile Thr Asn Phe Gly Ile Arg Ser Phe Pro
        420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
        450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
        500                 505                 510

Pro Phe Gly Ile Phe Gln Leu Ile Ala Ser Thr Pro Asp Met Ala Thr
        515                 520                 525

Leu Thr Ala Arg Arg Arg Glu Met Glu Asp Tyr Leu Asp Leu Ala Tyr
        530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Gly Ala Arg Ile Tyr Glu Thr Tyr Ser
        580                 585                 590

Ile Asp Pro Gly Asp Leu Tyr Arg Leu Leu Glu Leu Ala Asp Trp Leu
        595                 600                 605

Met Tyr Ser Leu Ile Glu Leu Tyr Lys Leu Phe Glu Pro Lys Glu Glu
        610                 615                 620

Ile Leu Asn Tyr Leu Arg Asp Leu His Leu Arg Leu His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
        660                 665                 670

Ala Asn Ala Lys Pro Ala Glu Leu Leu Ala Val Glu Gly Ile Gly Ala
        675                 680                 685

Lys Ile Leu Asp Gly Ile Tyr Arg His Leu Gly Ile Glu Lys Arg Val
        690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60
```

```
Ala Ala Gly Gly Lys Cys Leu Tyr Ile Val Pro Leu Arg Ala Leu Ala
 65                  70                  75                  80

Ser Glu Lys Tyr Asp Glu Phe Ser Lys Lys Gly Val Ile Arg Val Gly
                 85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Arg Arg Asn Ala Glu Gly
                245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
        275                 280                 285

Asn Val Leu Ala Asp Cys Val Glu Arg Gly Ala Ala Phe His His Ala
    290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
    370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
```

485                 490                 495
Cys Thr Ala Arg Leu Ile Leu Asp Ser Leu Lys Ser Cys Lys Thr Pro
                500                 505                 510

Thr Leu Ile Gly Leu Leu His Val Ile Cys Val Ser Pro Asp Met Gln
            515                 520                 525

Arg Leu Tyr Leu Lys Ala Ala Asp Thr Gln Leu Leu Arg Thr Phe Leu
        530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
    690                 695                 700

Ser Asp Asp Asp Tyr Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
        755                 760                 765

Ser Glu Lys Glu Asn Ser Ser Asp Lys Thr Glu Glu Ile Pro Asp
    770                 775                 780

Thr Gln Lys Ile Arg Gly Gln Ser Ser Trp Glu Asp Phe Gly Cys
785                 790                 795

<210> SEQ ID NO 22
<211> LENGTH: 1756
<212> TYPE: PRT
<213> ORGANISM: Escherichia coli

<400> SEQUENCE: 22

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

```
Asp Leu Ser Arg Met Gln Asp Gly Ser Asn Lys His Arg Pro Gly Tyr
 65                  70                  75                  80

Asp Leu Thr Phe Ser Ala Pro Lys Ser Val Ser Met Met Ala Met Leu
                 85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
        355                 360                 365

Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
```

-continued

```
                485                 490                 495
Met Ala Phe Thr Pro Gly Ser Thr Val Ile Val Asp Gln Gly Glu Lys
                500                 505                 510

Leu Ser Leu Lys Glu Thr Leu Thr Leu Leu Asp Gly Ala Ala Arg His
            515                 520                 525

Asn Val Gln Val Leu Ile Thr Asp Ser Gly Gln Arg Thr Gly Thr Gly
        530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Pro Gly Arg
            740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910
```

-continued

Lys Arg Gly Asp Leu Leu Tyr Val Asp Val Ala Lys Gly Tyr Gly Thr
            915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr Gln Phe Arg Ala Val Met Ser Ala
            995                 1000                1005

Val Asn Met Leu Pro Ala Ser Glu Arg Pro Arg Val Val Gly Leu
    1010                1015                1020

Gly Pro Thr His Arg Ala Val Gly Glu Met Arg Ser Ala Gly Val
    1025                1030                1035

Asp Ala Gln Thr Leu Ala Ser Phe Leu His Asp Thr Gln Leu Gln
    1040                1045                1050

Gln Arg Ser Gly Glu Thr Pro Asp Phe Ser Asn Thr Leu Phe Leu
    1055                1060                1065

Leu Asp Glu Ser Ser Met Val Gly Asn Thr Glu Met Ala Arg Ala
    1070                1075                1080

Tyr Ala Leu Ile Ala Ala Gly Gly Gly Arg Ala Val Ala Ser Gly
    1085                1090                1095

Asp Thr Asp Gln Leu Gln Ala Ile Ala Pro Gly Gln Ser Phe Arg
    1100                1105                1110

Leu Gln Gln Thr Arg Ser Ala Ala Asp Val Val Ile Met Lys Glu
    1115                1120                1125

Ile Val Arg Gln Thr Pro Glu Leu Arg Glu Ala Val Tyr Ser Leu
    1130                1135                1140

Ile Asn Arg Asp Val Glu Arg Ala Leu Ser Gly Leu Glu Ser Val
    1145                1150                1155

Lys Pro Ser Gln Val Pro Arg Leu Glu Gly Ala Trp Ala Pro Glu
    1160                1165                1170

His Ser Val Thr Glu Phe Ser His Ser Gln Glu Ala Lys Leu Ala
    1175                1180                1185

Glu Ala Gln Gln Lys Ala Met Leu Lys Gly Glu Ala Phe Pro Asp
    1190                1195                1200

Ile Pro Met Thr Leu Tyr Glu Ala Ile Val Arg Asp Tyr Thr Gly
    1205                1210                1215

Arg Thr Pro Glu Ala Arg Glu Gln Thr Leu Ile Val Thr His Leu
    1220                1225                1230

Asn Glu Asp Arg Arg Val Leu Asn Ser Met Ile His Asp Ala Arg
    1235                1240                1245

Glu Lys Ala Gly Glu Leu Gly Lys Glu Gln Val Met Val Pro Val
    1250                1255                1260

Leu Asn Thr Ala Asn Ile Arg Asp Gly Glu Leu Arg Arg Leu Ser
    1265                1270                1275

Thr Trp Glu Lys Asn Pro Asp Ala Leu Ala Leu Val Asp Asn Val
    1280                1285                1290

Tyr His Arg Ile Ala Gly Ile Ser Lys Asp Asp Gly Leu Ile Thr
    1295                1300                1305

```
Leu Gln Asp Ala Glu Gly Asn Thr Arg Leu Ile Ser Pro Arg Glu
1310                1315                1320

Ala Val Ala Glu Gly Val Thr Leu Tyr Thr Pro Asp Lys Ile Arg
1325                1330                1335

Val Gly Thr Gly Asp Arg Met Arg Phe Thr Lys Ser Asp Arg Glu
1340                1345                1350

Arg Gly Tyr Val Ala Asn Ser Val Trp Thr Val Thr Ala Val Ser
1355                1360                1365

Gly Asp Ser Val Thr Leu Ser Asp Gly Gln Gln Thr Arg Val Ile
1370                1375                1380

Arg Pro Gly Gln Glu Arg Ala Glu Gln His Ile Asp Leu Ala Tyr
1385                1390                1395

Ala Ile Thr Ala His Gly Ala Gln Gly Ala Ser Glu Thr Phe Ala
1400                1405                1410

Ile Ala Leu Glu Gly Thr Glu Gly Asn Arg Lys Leu Met Ala Gly
1415                1420                1425

Phe Glu Ser Ala Tyr Val Ala Leu Ser Arg Met Lys Gln His Val
1430                1435                1440

Gln Val Tyr Thr Asp Asn Arg Gln Gly Trp Thr Asp Ala Ile Asn
1445                1450                1455

Asn Ala Val Gln Lys Gly Thr Ala His Asp Val Leu Glu Pro Lys
1460                1465                1470

Pro Asp Arg Glu Val Met Asn Ala Gln Arg Leu Phe Ser Thr Ala
1475                1480                1485

Arg Glu Leu Arg Asp Val Ala Ala Gly Arg Ala Val Leu Arg Gln
1490                1495                1500

Ala Gly Leu Ala Gly Gly Asp Ser Pro Ala Arg Phe Ile Ala Pro
1505                1510                1515

Gly Arg Lys Tyr Pro Gln Pro Tyr Val Ala Leu Pro Ala Phe Asp
1520                1525                1530

Arg Asn Gly Lys Ser Ala Gly Ile Trp Leu Asn Pro Leu Thr Thr
1535                1540                1545

Asp Asp Gly Asn Gly Leu Arg Gly Phe Ser Gly Glu Gly Arg Val
1550                1555                1560

Lys Gly Ser Gly Asp Ala Gln Phe Val Ala Leu Gln Gly Ser Arg
1565                1570                1575

Asn Gly Glu Ser Leu Leu Ala Asp Asn Met Gln Asp Gly Val Arg
1580                1585                1590

Ile Ala Arg Asp Asn Pro Asp Ser Gly Val Val Arg Ile Ala
1595                1600                1605

Gly Glu Gly Arg Pro Trp Asn Pro Gly Ala Ile Thr Gly Gly Arg
1610                1615                1620

Val Trp Gly Asp Ile Pro Asp Asn Ser Val Gln Pro Gly Ala Gly
1625                1630                1635

Asn Gly Glu Pro Val Thr Ala Glu Val Leu Ala Gln Arg Gln Ala
1640                1645                1650

Glu Glu Ala Ile Arg Arg Glu Thr Glu Arg Arg Ala Asp Glu Ile
1655                1660                1665

Val Arg Lys Met Ala Glu Asn Lys Pro Asp Leu Pro Asp Gly Lys
1670                1675                1680

Thr Glu Leu Ala Val Arg Asp Ile Ala Gly Gln Glu Arg Asp Arg
1685                1690                1695

Ser Ala Ile Ser Glu Arg Glu Thr Ala Leu Pro Glu Ser Val Leu
```

```
                    1700                1705                1710

Arg Glu  Ser Gln Arg Glu Arg  Glu Ala Val Arg Glu  Val Ala Arg
        1715                1720                1725

Glu Asn  Leu Leu Gln Glu Arg  Leu Gln Gln Met Glu  Arg Asp Met
        1730                1735                1740

Val Arg  Asp Leu Gln Lys Glu  Lys Thr Leu Gly Gly  Asp
        1745                1750                1755

<210> SEQ ID NO 23
<211> LENGTH: 726
<212> TYPE: PRT
<213> ORGANISM: Methanococcoides burtonii

<400> SEQUENCE: 23

Met Ser Asp Lys Pro Ala Phe Met Lys Tyr Phe Thr Gln Ser Ser Cys
 1               5                  10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
                100                 105                 110

Cys Ser Val Lys Arg Glu Asn Thr Phe Glu Leu Met Glu Thr Glu Arg
            115                 120                 125

Glu Ile Tyr Leu Lys Arg Gln Glu Leu Asn Ser Ala Arg Asp Ser Tyr
        130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
    290                 295                 300

His Asn Leu Phe Asn Ile Phe Leu Glu Val Ile Ser Asp Thr Tyr Asn
305                 310                 315                 320
```

-continued

```
Ser Arg Phe Lys Phe Gly Glu Arg Glu Arg Val Arg Lys Asn Trp Tyr
            325                 330                 335
Asp Ile Arg Ile Ser Asp Pro Tyr Glu Arg Asn Asp Ile Val Arg Gly
            340                 345                 350
Lys Phe Leu Arg Gln Ala Lys Gly Asp Phe Gly Glu Lys Asp Asp Ile
            355                 360                 365
Gln Ile Leu Leu Ser Glu Ala Ser Glu Leu Gly Ala Lys Leu Asp Glu
            370                 375                 380
Thr Tyr Arg Asp Gln Tyr Lys Lys Gly Leu Ser Ser Val Met Lys Arg
385                 390                 395                 400
Ser His Ile Arg Tyr Val Ala Asp Phe Met Ser Ala Tyr Ile Glu Leu
            405                 410                 415
Ser His Asn Leu Asn Tyr Tyr Pro Ile Leu Asn Val Arg Arg Asp Met
            420                 425                 430
Asn Asp Glu Ile Tyr Gly Arg Val Glu Leu Phe Thr Cys Ile Pro Lys
            435                 440                 445
Asn Val Thr Glu Pro Leu Phe Asn Ser Leu Phe Ser Val Ile Leu Met
            450                 455                 460
Ser Ala Thr Leu His Pro Phe Glu Met Val Lys Lys Thr Leu Gly Ile
465                 470                 475                 480
Thr Arg Asp Thr Cys Glu Met Ser Tyr Gly Thr Ser Phe Pro Glu Glu
            485                 490                 495
Lys Arg Leu Ser Ile Ala Val Ser Ile Pro Pro Leu Phe Ala Lys Asn
            500                 505                 510
Arg Asp Asp Arg His Val Thr Glu Leu Leu Glu Gln Val Leu Leu Asp
            515                 520                 525
Ser Ile Glu Asn Ser Lys Gly Asn Val Ile Leu Phe Phe Gln Ser Ala
            530                 535                 540
Phe Glu Ala Lys Arg Tyr Tyr Ser Lys Ile Glu Pro Leu Val Asn Val
545                 550                 555                 560
Pro Val Phe Leu Asp Glu Val Gly Ile Ser Ser Gln Asp Val Arg Glu
            565                 570                 575
Glu Phe Phe Ser Ile Gly Glu Glu Asn Gly Lys Ala Val Leu Leu Ser
            580                 585                 590
Tyr Leu Trp Gly Thr Leu Ser Glu Gly Ile Asp Tyr Arg Asp Gly Arg
            595                 600                 605
Gly Arg Thr Val Ile Ile Gly Val Gly Tyr Pro Ala Leu Asn Asp
            610                 615                 620
Arg Met Asn Ala Val Glu Ser Ala Tyr Asp His Val Phe Gly Tyr Gly
625                 630                 635                 640
Ala Gly Trp Glu Phe Ala Ile Gln Val Pro Thr Ile Arg Lys Ile Arg
            645                 650                 655
Gln Ala Met Gly Arg Val Val Arg Ser Pro Thr Asp Tyr Gly Ala Arg
            660                 665                 670
Ile Leu Leu Asp Gly Arg Phe Leu Thr Asp Ser Lys Lys Arg Phe Gly
            675                 680                 685
Lys Phe Ser Val Phe Glu Val Phe Pro Pro Ala Glu Arg Ser Glu Phe
            690                 695                 700
Val Asp Val Asp Pro Glu Lys Val Lys Tyr Ser Leu Met Asn Phe Phe
705                 710                 715                 720
Met Asp Asn Asp Glu Gln
            725
```

```
<210> SEQ ID NO 24
<211> LENGTH: 439
<212> TYPE: PRT
<213> ORGANISM: Dickeya dadantii

<400> SEQUENCE: 24

Met Thr Phe Asp Asp Leu Thr Glu Gly Gln Lys Asn Ala Phe Asn Ile
1               5                   10                  15

Val Met Lys Ala Ile Lys Glu Lys Lys His Val Thr Ile Asn Gly
            20                  25                  30

Pro Ala Gly Thr Gly Lys Thr Thr Leu Thr Lys Phe Ile Ile Glu Ala
            35                  40                  45

Leu Ile Ser Thr Gly Glu Thr Gly Ile Ile Leu Ala Ala Pro Thr His
        50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
            115                 120                 125

Leu Ser Thr Ile Pro Pro Trp Cys Thr Ile Gly Ile Gly Asp Asn
        130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Asp Gly His Gly Val Arg Gly
            195                 200                 205

Phe Thr Gly Asp Thr Ala Leu Arg Asp Phe Met Val Asn Tyr Phe Ser
        210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Glu Ala Glu Tyr
            290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
370                 375                 380
```

```
Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
            405                 410                 415

Asp Val Glu Leu Ala Gln Gln Leu Leu Tyr Val Gly Val Thr Arg Gly
        420                 425                 430

Arg Tyr Asp Val Phe Tyr Val
        435

<210> SEQ ID NO 25
<211> LENGTH: 970
<212> TYPE: PRT
<213> ORGANISM: Unknown
<220> FEATURE:
<223> OTHER INFORMATION: Synthetic polypeptide

<400> SEQUENCE: 25

Met Leu Ser Val Ala Asn Val Arg Ser Pro Ser Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300
```

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
            325                 330                 335

Gln Asp Arg Gln Thr Ile Ala Ala Gln Ala Val Ala Ser Ala Val
            340                 345                 350

Arg His Leu Ser Gln Arg Glu Ala Ala Phe Glu Arg Thr Ala Leu Tyr
            355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
            405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ser Val Gln Ala Ala Ala Leu
            435                 440                 445

Thr Gly Gln Gly Phe Arg Leu Asn Glu Gly Gln Leu Ala Ala Ala Arg
450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
    515                 520                 525

Phe Leu Gly Gly Trp Asn Lys Leu Leu Asp Asp Pro Gly Asn Val Ala
530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
    595                 600                 605

Arg Ala Gly Ile Ala Arg Ala Glu Met Ala Thr Asn Leu Arg Ala Arg
610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
            645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
    675                 680                 685

Ala Val Asn Ala Ala Val Gln Gln Gly Leu Leu Ala Ser Arg Glu Ile
690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu

```
                    725                 730                 735
Glu Val Ser Arg Lys Gln Gln Ala Leu Gly Leu Phe Ile Gly Glu Tyr
                740                 745                 750
Arg Val Ile Gly Gln Asp Arg Lys Gly Lys Leu Val Glu Val Glu Asp
                755                 760                 765
Lys Arg Gly Lys Arg Phe Arg Phe Asp Pro Ala Arg Ile Arg Ala Gly
                770                 775                 780
Lys Gly Asp Asp Asn Leu Thr Leu Leu Glu Pro Arg Lys Leu Glu Ile
785                 790                 795                 800
His Glu Gly Asp Arg Ile Arg Trp Thr Arg Asn Asp His Arg Arg Gly
                805                 810                 815
Leu Phe Asn Ala Asp Gln Ala Arg Val Val Glu Ile Ala Asn Gly Lys
                820                 825                 830
Val Thr Phe Glu Thr Ser Lys Gly Asp Leu Val Glu Leu Lys Lys Asp
                835                 840                 845
Asp Pro Met Leu Lys Arg Ile Asp Leu Ala Tyr Ala Leu Asn Val His
                850                 855                 860
Met Ala Gln Gly Leu Thr Ser Asp Arg Gly Ile Ala Val Met Asp Ser
865                 870                 875                 880
Arg Glu Arg Asn Leu Ser Asn Gln Lys Thr Phe Leu Val Thr Val Thr
                885                 890                 895
Arg Leu Arg Asp His Leu Thr Leu Val Val Asp Ser Asp Lys Leu
                900                 905                 910
Gly Ala Ala Val Ala Arg Asn Lys Gly Glu Lys Ala Ser Ala Ile Glu
                915                 920                 925
Val Thr Gly Ser Val Lys Pro Thr Ala Thr Lys Gly Ser Gly Val Asp
                930                 935                 940
Gln Pro Lys Ser Val Glu Ala Asn Lys Ala Lys Glu Leu Thr Arg
945                 950                 955                 960
Ser Lys Ser Lys Thr Leu Asp Phe Gly Ile
                965                 970

<210> SEQ ID NO 26
<211> LENGTH: 262
<212> TYPE: PRT
<213> ORGANISM: yokenella regensburgei

<400> SEQUENCE: 26

Cys Leu Thr Ala Pro Lys Glu Ala Ala Lys Pro Thr Leu Met Pro
1               5                   10                  15
Arg Ala Gln Ser Tyr Arg Asp Leu Thr His Leu Pro Leu Pro Ser Gly
                20                  25                  30
Lys Val Phe Val Ser Val Tyr Asn Ile Gln Asp Glu Thr Gly Gln Phe
                35                  40                  45
Lys Pro Tyr Pro Ala Ser Asn Phe Ser Thr Ala Val Pro Gln Ser Ala
                50                  55                  60
Thr Ala Met Leu Val Thr Ala Leu Lys Asp Ser Arg Trp Phe Val Pro
65                  70                  75                  80
Leu Glu Arg Gln Gly Leu Gln Asn Leu Leu Asn Glu Arg Lys Ile Ile
                85                  90                  95
Arg Ala Ala Gln Glu Asn Gly Thr Val Ala Asp Asn Arg Ile Pro
                100                 105                 110
Leu Gln Ser Leu Thr Ala Ala Asn Val Met Ile Glu Gly Ser Ile Ile
                115                 120                 125
```

```
Gly Tyr Glu Ser Asn Val Lys Ser Gly Gly Val Gly Ala Arg Tyr Phe
        130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Val Leu Ser Ser Val Asn
                    165                 170                 175

Thr Ser Lys Thr Ile Leu Ser Tyr Glu Val Gln Ala Gly Val Phe Arg
                180                 185                 190

Phe Val Asp Tyr Gln Arg Leu Leu Glu Gly Glu Ile Gly Tyr Thr Ser
            195                 200                 205

Asn Glu Pro Val Met Leu Cys Leu Met Ser Ala Ile Glu Thr Gly Val
        210                 215                 220

Ile Tyr Leu Ile Asn Asp Gly Ile Glu Arg Gly Leu Trp Asp Leu Gln
225                 230                 235                 240

Gln Lys Ala Asp Val Asp Asn Pro Ile Leu Ala Arg Tyr Arg Asn Met
                245                 250                 255

Ser Ala Pro Pro Glu Ser
            260

<210> SEQ ID NO 27
<211> LENGTH: 262
<212> T

Asn Lys Gly Asp Ala Lys Asn Thr Ile Leu Ala Lys Tyr Arg Ser Met
            245                 250                 255

Ala Val Pro Pro Glu Ser
            260

<210> SEQ ID NO 28
<211> LENGTH: 262
<212> TYPE: PRT
<213> ORGANISM: rahnella aquatilis

<400> SEQUENCE: 28

Cys Leu Thr Ala Ala Pro Lys Glu Ala Ala Arg Pro Thr Leu Leu Pro
1               5                   10                  15

Arg Ala Pro Ser Tyr Thr Asp Leu Thr His Leu Pro Ser Pro Gln Gly
            20                  25                  30

Arg Ile Phe Val Ser Val Tyr Asn Ile Gln Asp Glu Thr Gly Gln Phe
        35                  40                  45

Lys Pro Tyr Pro Ala Cys Asn Phe Ser Thr Ala Val Pro Gln Ser Ala
    50                  55                  60

Thr Ala Met Leu Val Ser Ala Leu Lys Asp Ser Lys Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Ser Val Ala Ile Asn Asn Gln Arg Pro
            100                 105                 110

Leu Ser Ser Leu Val Ala Ala Asn Ile Leu Ile Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Ser Thr Gln Tyr Gln Leu Asp Gln Ile Ala Val Asn
145                 150                 155                 160

Leu Arg Ala Val Asp Val Asn Thr Gly Glu Val Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Leu Gly Tyr Thr Thr
        195                 200                 205

Asn Glu Pro Val Met Leu Cys Leu Met Ser Ala Ile Glu Ser Gly Val
    210                 215                 220

Ile Tyr Leu Val Asn Asp Gly Ile Glu Arg Asn Leu Trp Gln Leu Gln
225                 230                 235                 240

Asn Pro Ser Glu Ile Asn Ser Pro Ile Leu Gln Arg Tyr Lys Asn Asn
                245                 250                 255

Ile Val Pro Ala Glu Ser
            260

<210> SEQ ID NO 29
<211> LENGTH: 259
<212> TYPE: PRT
<213> ORGANISM: kluyvera ascobata

<400> SEQUENCE: 29

Cys Ile Thr Ser Pro Pro Lys Gln Ala Ala Lys Pro Thr Leu Leu Pro
1               5                   10                  15

Arg Ser Gln Ser Tyr Gln Asp Leu Thr His Leu Pro Glu Pro Gln Gly
            20                  25                  30

```
Arg Leu Phe Val Ser Val Tyr Asn Ile Ser Asp Glu Thr Gly Gln Phe
            35                  40                  45

Lys Pro Tyr Pro Ala Ser Asn Phe Ser Thr Ser Val Pro Gln Ser Ala
 50                  55                  60

Thr Ala Met Leu Val Ser Ala Leu Lys Asp Ser Asn Trp Phe Ile Pro
 65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Val Asn Asn Arg Thr Gln
            100                 105                 110

Leu Pro Ser Leu Val Ala Ala Asn Ile Leu Ile Glu Gly Ser Ile Ile
            115                 120                 125

Gly Tyr Glu Ser Asn Val Lys Ser Gly Gly Ala Gly Ala Arg Tyr Phe
130                 135                 140

Gly Ile Gly Ala Ser Thr Gln Tyr Gln Leu Asp Gln Ile Ala Val Asn
145                 150                 155                 160

Leu Arg Val Val Asn Val Ser Thr Gly Glu Val Leu Ser Ser Val Asn
                165                 170                 175

Thr Ser Lys Thr Ile Leu Ser Tyr Glu Phe Gln Ala Gly Val Phe Arg
            180                 185                 190

Tyr Ile Asp Tyr Gln Arg Leu Leu Glu Gly Glu Val Gly Tyr Thr Val
            195                 200                 205

Asn Glu Pro Val Met Leu Cys Leu Met Ser Ala Ile Glu Thr Gly Val
210                 215                 220

Ile Tyr Leu Val Asn Asp Gly Ile Ser Arg Asn Leu Trp Gln Leu Lys
225                 230                 235                 240

Asn Ala Ser Asp Ile Asn Ser Pro Val Leu Glu Lys Tyr Lys Ser Ile
                245                 250                 255

Ile Val Pro

<210> SEQ ID NO 30
<211> LENGTH: 259
<212> TYPE: PRT
<213> ORGANISM: hafnia alvei

<400> SEQUENCE: 30

Cys Leu Thr Ala Pro Pro Lys Gln Ala Ala Lys Pro Thr Leu Met Pro
 1               5                  10                  15

Arg Ala Gln Ser Tyr Gln Asp Leu Thr His Leu Pro Glu Pro Ala Gly
            20                  25                  30

Lys Leu Phe Val Ser Val Tyr Asn Ile Gln Asp Glu Thr Gly Gln Phe
            35                  40                  45

Lys Pro Tyr Pro Ala Ser Asn Phe Ser Thr Ala Val Pro Gln Ser Ala
 50                  55                  60

Thr Ala Met Leu Val Ser Ala Leu Lys Asp Ser Gly Trp Phe Ile Pro
 65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Ala Ala Val Asn Asn Gln His Gln
            100                 105                 110

Leu Ser Ser Leu Val Ala Ala Asn Val Leu Val Glu Gly Ser Ile Ile
            115                 120                 125

Gly Tyr Glu Ser Asn Val Lys Ser Gly Gly Ala Gly Ala Arg Phe Phe
130                 135                 140
```

```
Gly Ile Gly Ala Ser Thr Gln Tyr Gln Leu Asp Gln Ile Ala Val Asn
145                 150                 155                 160

Leu Arg Val Val Asp Val Asn Thr Gly Gln Val Leu Ser Ser Val Asn
                165                 170                 175

Thr Ser Lys Thr Ile Leu Ser Tyr Glu Val Gln Ala Gly Val Phe Arg
            180                 185                 190

Tyr Ile Asp Tyr Gln Arg Leu Leu Glu Gly Glu Ile Gly Tyr Thr Thr
            195                 200                 205

Asn Glu Pro Val Met Leu Cys Val Met Ser Ala Ile Glu Thr Gly Val
            210                 215                 220

Ile Tyr Leu Val Asn Asp Gly Ile Asn Arg Asn Leu Trp Thr Leu Lys
225                 230                 235                 240

Asn Pro Gln Asp Ala Lys Ser Ser Val Leu Glu Arg Tyr Lys Ser Thr
                245                 250                 255

Ile Val Pro

<210> SEQ ID NO 31
<211> LENGTH: 255
<212> TYPE: PRT
<213> ORGANISM: Unknown
<220> FEATURE:
<223> OTHER INFORMATION: Enterobacteriaceae bacterium

<400> SEQUENCE: 31

Cys Ile Thr Thr Pro Pro Gln Glu Ala Ala Lys Pro Thr Leu Leu Pro
1               5                   10                  15

Arg Asp Ala Thr Tyr Lys Asp Leu Val Ser Leu Pro Gln Pro Arg Gly
                20                  25                  30

Lys Ile Tyr Val Ala Val Tyr Asn Ile Gln Asp Glu Thr Gly Gln Phe
            35                  40                  45

Gln Pro Tyr Pro Ala Ser Asn Phe Ser Thr Ser Val Pro Gln Ser Ala
        50                  55                  60

Thr Ala Met Leu Val Ser Ser Leu Lys Asp Ser Arg Trp Phe Val Pro
65                  70                  75                  80

Leu Glu Arg Gln Gly Leu Asn Asn Leu Leu Asn Glu Arg Lys Ile Ile
                85                  90                  95

Arg Ala Ala Gln Gln Asn Gly Thr Val Gly Asp Asn Asn Ala Ser Pro
            100                 105                 110

Leu Pro Ser Leu Tyr Ser Ala Asn Val Ile Val Glu Gly Ser Ile Ile
        115                 120                 125

Gly Tyr Ala Ser Asn Val Lys Thr Gly Gly Phe Gly Ala Arg Tyr Phe
130                 135                 140

Gly Ile Gly Gly Ser Thr Gln Tyr Gln Leu Asp Gln Val Ala Val Asn
145                 150                 155                 160

Leu Arg Ile Val Asn Val His Thr Gly Glu Val Leu Ser Ser Val Asn
                165                 170                 175

Thr Ser Lys Thr Ile Leu Ser Tyr Glu Ile Gln Ala Gly Val Phe Arg
            180                 185                 190

Phe Ile Asp Tyr Gln Arg Leu Leu Glu Gly Glu Ala Gly Phe Thr Thr
            195                 200                 205

Asn Glu Pro Val Met Thr Cys Leu Met Ser Ala Ile Glu Glu Gly Val
            210                 215                 220

Ile His Leu Ile Asn Asp Gly Ile Asn Lys Lys Leu Trp Ala Leu Ser
225                 230                 235                 240
```

```
Asn Ala Ala Asp Ile Asn Ser Glu Val Leu Thr Arg Tyr Arg Lys
                245                 250                 255
```

<210> SEQ ID NO 32
<211> LENGTH: 258
<212> TYPE: PRT
<213> ORGANISM: plesiomonas shigelloides

<400> SEQUENCE: 32

```
Ile Thr Glu Val Pro Lys Glu Ala Ala Lys Pro Thr Leu Met Pro Arg
1               5                   10                  15

Ala Ser Thr Tyr Lys Asp Leu Val Ala Leu Pro Lys Pro Asn Gly Lys
            20                  25                  30

Ile Ile Val Ser Val Tyr Ser Val Gln Asp Glu Thr Gly Gln Phe Lys
        35                  40                  45

Pro Leu Pro Ala Ser Asn Phe Ser Thr Ala Val Pro Gln Ser Gly Asn
    50                  55                  60

Ala Met Leu Thr Ser Ala Leu Lys Asp Ser Gly Trp Phe Val Pro Leu
65                  70                  75                  80

Glu Arg Glu Gly Leu Gln Asn Leu Leu Asn Glu Arg Lys Ile Ile Arg
                85                  90                  95

Ala Ala Gln Glu Asn Gly Thr Val Ala Ala Asn Asn Gln Gln Pro Leu
            100                 105                 110

Pro Ser Leu Leu Ser Ala Asn Val Val Ile Glu Gly Ala Ile Ile Gly
        115                 120                 125

Tyr Asp Ser Asp Ile Lys Thr Gly Gly Ala Gly Ala Arg Tyr Phe Gly
    130                 135                 140

Ile Gly Ala Asp Gly Lys Tyr Arg Val Asp Gln Val Ala Val Asn Leu
145                 150                 155                 160

Arg Ala Val Asp Val Arg Thr Gly Glu Val Leu Leu Ser Val Asn Thr
                165                 170                 175

Ser Lys Thr Ile Leu Ser Ser Glu Leu Ser Ala Gly Val Phe Arg Phe
            180                 185                 190

Ile Glu Tyr Gln Arg Leu Leu Glu Leu Glu Ala Gly Tyr Thr Thr Asn
        195                 200                 205

Glu Pro Val Met Met Cys Met Met Ser Ala Leu Glu Ala Gly Val Ala
    210                 215                 220

His Leu Ile Val Glu Gly Ile Arg Gln Asn Leu Trp Ser Leu Gln Asn
225                 230                 235                 240

Pro Ser Asp Ile Asn Asn Pro Ile Ile Gln Arg Tyr Met Lys Glu Asp
                245                 250                 255

Val Pro
```

<210> SEQ ID NO 33
<211> LENGTH: 248
<212> TYPE: PRT
<213> ORGANISM: Vibrio fischeri

<400> SEQUENCE: 33

```
Pro Glu Thr Ser Glu Ser Pro Thr Leu Met Gln Arg Gly Ala Asn Tyr
1               5                   10                  15

Ile Asp Leu Ile Ser Leu Pro Lys Pro Gln Gly Lys Ile Phe Val Ser
            20                  25                  30

Val Tyr Asp Phe Arg Asp Gln Thr Gly Gln Tyr Lys Pro Gln Pro Asn
        35                  40                  45

Ser Asn Phe Ser Thr Ala Val Pro Gln Gly Gly Thr Ala Leu Leu Thr
```

```
            50                  55                  60
Met Ala Leu Leu Asp Ser Glu Trp Phe Tyr Pro Leu Glu Arg Gln Gly
 65                  70                  75                  80

Leu Gln Asn Leu Leu Thr Glu Arg Lys Ile Ile Arg Ala Ala Gln Lys
                 85                  90                  95

Lys Gln Glu Ser Ile Ser Asn His Gly Ser Thr Leu Pro Ser Leu Leu
                100                 105                 110

Ser Ala Asn Val Met Ile Glu Gly Ile Val Ala Tyr Asp Ser Asn
                115                 120                 125

Ile Lys Thr Gly Gly Ala Gly Ala Arg Tyr Leu Gly Ile Gly Gly Ser
                130                 135                 140

Gly Gln Tyr Arg Ala Asp Gln Val Thr Val Asn Ile Arg Ala Val Asp
145                 150                 155                 160

Val Arg Ser Gly Lys Ile Leu Thr Ser Val Thr Thr Ser Lys Thr Ile
                165                 170                 175

Leu Ser Tyr Glu Val Ser Ala Gly Ala Phe Arg Phe Val Asp Tyr Lys
                180                 185                 190

Glu Leu Leu Glu Val Glu Leu Gly Tyr Thr Asn Asn Glu Pro Val Asn
                195                 200                 205

Ile Ala Leu Met Ser Ala Ile Asp Ser Ala Val Ile His Leu Ile Val
                210                 215                 220

Lys Gly Val Gln Gln Gly Leu Trp Arg Pro Ala Asn Leu Asp Thr Arg
225                 230                 235                 240

Asn Asn Pro Ile Phe Lys Lys Tyr
                245

<210> SEQ ID NO 34
<211> LENGTH: 248
<212> TYPE: PRT
<213> ORGANISM: Aliivibrio logei

<400> SEQUENCE: 34

Pro Asp Ala Ser Glu Ser Pro Thr Leu Met Gln Arg Gly Ala Thr Tyr
 1               5                  10                  15

Leu Asp Leu Ile Ser Leu Pro Lys Pro Gln Gly Lys Ile Tyr Val Ser
                20                  25                  30

Val Tyr Asp Phe Arg Asp Gln Thr Gly Gln Tyr Lys Pro Gln Pro Asn
                35                  40                  45

Ser Asn Phe Ser Thr Ala Val Pro Gln Gly Gly Thr Ala Leu Leu Thr
 50                  55                  60

Met Ala Leu Leu Asp Ser Glu Trp Phe Tyr Pro Leu Glu Arg Gln Gly
 65                  70                  75                  80

Leu Gln Asn Leu Leu Thr Glu Arg Lys Ile Ile Arg Ala Ala Gln Lys
                 85                  90                  95

Lys Gln Glu Ser Ile Ser Asn His Gly Ser Thr Leu Pro Ser Leu Leu
                100                 105                 110

Ser Ala Asn Val Met Ile Glu Gly Ile Val Ala Tyr Asp Ser Asn
                115                 120                 125

Ile Lys Thr Gly Gly Ala Gly Ala Arg Tyr Leu Gly Ile Gly Gly Ser
                130                 135                 140

Gly Gln Tyr Arg Ala Asp Gln Val Thr Val Asn Ile Arg Ala Val Asp
145                 150                 155                 160

Val Arg Ser Gly Lys Ile Leu Thr Ser Val Thr Thr Ser Lys Thr Ile
                165                 170                 175
```

```
Leu Ser Tyr Glu Leu Ser Ala Gly Ala Phe Arg Phe Val Asp Tyr Lys
            180                 185                 190

Glu Leu Leu Glu Val Glu Leu Gly Tyr Thr Asn Asn Glu Pro Val Asn
        195                 200                 205

Ile Ala Leu Met Ser Ala Ile Asp Ser Ala Val Ile His Leu Ile Val
    210                 215                 220

Lys Gly Ile Glu Glu Gly Leu Trp Arg Pro Glu Asn Gln Asn Gly Lys
225                 230                 235                 240

Glu Asn Pro Ile Phe Arg Lys Tyr
                245
```

<210> SEQ ID NO 35
<211> LENGTH: 254
<212> TYPE: PRT
<213> ORGANISM: Photobacterium sp

<400> SEQUENCE: 35

```
Pro Glu Thr Ser Lys Glu Pro Thr Leu Met Ala Arg Gly Thr Ala Tyr
1               5                   10                  15

Gln Asp Leu Val Ser Leu Pro Leu Pro Lys Gly Lys Val Tyr Val Ser
            20                  25                  30

Val Tyr Asp Phe Arg Asp Gln Thr Gly Gln Tyr Lys Pro Gln Pro Asn
        35                  40                  45

Ser Asn Phe Ser Thr Ala Val Pro Gln Gly Ala Ala Leu Leu Thr
    50                  55                  60

Thr Ala Leu Leu Asp Ser Arg Trp Phe Met Pro Leu Glu Arg Glu Gly
65                  70                  75                  80

Leu Gln Asn Leu Leu Thr Glu Arg Lys Ile Ile Arg Ala Ala Gln Lys
                85                  90                  95

Lys Asp Glu Ile Pro Thr Asn His Gly Val His Leu Pro Ser Leu Ala
            100                 105                 110

Ser Ala Asn Ile Met Val Glu Gly Gly Ile Val Ala Tyr Asp Thr Asn
        115                 120                 125

Ile Gln Thr Gly Gly Ala Gly Ala Arg Tyr Leu Gly Val Gly Ala Ser
    130                 135                 140

Gly Gln Tyr Arg Thr Asp Gln Val Thr Val Asn Ile Arg Ala Val Asp
145                 150                 155                 160

Val Arg Thr Gly Arg Ile Leu Leu Ser Val Thr Thr Ser Lys Thr Ile
                165                 170                 175

Leu Ser Lys Glu Leu Gln Thr Gly Val Phe Lys Phe Asp Tyr Lys
            180                 185                 190

Asp Leu Leu Glu Ala Glu Leu Gly Tyr Thr Thr Asn Glu Pro Val Asn
        195                 200                 205

Leu Ala Val Met Ser Ala Ile Asp Ala Ala Val Val His Val Ile Val
    210                 215                 220

Asp Gly Ile Lys Thr Gly Leu Trp Glu Pro Leu Arg Gly Glu Asp Leu
225                 230                 235                 240

Gln His Pro Ile Ile Gln Glu Tyr Met Asn Arg Ser Lys Pro
                245                 250
```

<210> SEQ ID NO 36
<211> LENGTH: 261
<212> TYPE: PRT
<213> ORGANISM: Aeromonas veronii

<400> SEQUENCE: 36

Cys Ala Thr His Ile Gly Ser Pro Val Ala Asp Glu Lys Ala Thr Leu
1               5                   10                  15

Met Pro Arg Ser Val Ser Tyr Lys Glu Leu Ile Ser Leu Pro Lys Pro
            20                  25                  30

Lys Gly Lys Ile Val Ala Ala Val Tyr Asp Phe Arg Asp Gln Thr Gly
        35                  40                  45

Gln Tyr Leu Pro Ala Pro Ala Ser Asn Phe Ser Thr Ala Val Thr Gln
    50                  55                  60

Gly Gly Val Ala Met Leu Ser Thr Ala Leu Trp Asp Ser Gln Trp Phe
65                  70                  75                  80

Val Pro Leu Glu Arg Glu Gly Leu Gln Asn Leu Leu Thr Glu Arg Lys
                85                  90                  95

Ile Val Arg Ala Ala Gln Asn Lys Pro Asn Val Pro Gly Asn Asn Ala
            100                 105                 110

Asn Gln Leu Pro Ser Leu Val Ala Ala Asn Ile Leu Ile Glu Gly Gly
        115                 120                 125

Ile Val Ala Tyr Asp Ser Asn Val Arg Thr Gly Gly Ala Gly Ala Lys
    130                 135                 140

Tyr Phe Gly Ile Gly Ala Ser Gly Glu Tyr Arg Val Asp Gln Val Thr
145                 150                 155                 160

Val Asn Leu Arg Ala Val Asp Ile Arg Ser Gly Arg Ile Leu Asn Ser
                165                 170                 175

Val Thr Thr Ser Lys Thr Val Met Ser Gln Val Gln Ala Gly Val
            180                 185                 190

Phe Arg Phe Val Glu Tyr Lys Arg Leu Leu Glu Ala Glu Ala Gly Phe
        195                 200                 205

Ser Thr Asn Glu Pro Val Gln Met Cys Val Met Ser Ala Ile Glu Ser
    210                 215                 220

Gly Val Ile Arg Leu Ile Ala Asn Gly Val Arg Asp Asn Leu Trp Gln
225                 230                 235                 240

Leu Ala Asp Gln Arg Asp Ile Asp Asn Pro Ile Leu Gln Glu Tyr Leu
                245                 250                 255

Gln Asp Asn Ala Pro
            260

<210> SEQ ID NO 37
<211> LENGTH: 239
<212> TYPE: PRT
<213> ORGANISM: Shewanella sp.

<400> SEQUENCE: 37

Ala Ser Ser Ser Leu Met Pro Lys Gly Glu Ser Tyr Tyr Asp Leu Ile
1               5                   10                  15

Asn Leu Pro Ala Pro Gln Gly Val Met Leu Ala Ala Val Tyr Asp Phe
            20                  25                  30

Arg Asp Gln Thr Gly Gln Tyr Lys Pro Ile Pro Ser Ser Asn Phe Ser
        35                  40                  45

Thr Ala Val Pro Gln Ser Gly Thr Ala Phe Leu Ala Gln Ala Leu Asn
    50                  55                  60

Asp Ser Ser Trp Phe Ile Pro Val Glu Arg Glu Gly Leu Gln Asn Leu
65                  70                  75                  80

Leu Thr Glu Arg Lys Ile Val Arg Ala Gly Leu Lys Gly Asp Ala Asn
                85                  90                  95

Lys Leu Pro Gln Leu Asn Ser Ala Gln Ile Leu Met Glu Gly Gly Ile
            100                 105                 110

```
Val Ala Tyr Asp Thr Asn Val Arg Thr Gly Ala Gly Ala Arg Tyr
            115                 120                 125

Leu Gly Ile Gly Ala Ala Thr Gln Phe Arg Val Asp Thr Val Thr Val
        130                 135                 140

Asn Leu Arg Ala Val Asp Ile Arg Thr Gly Arg Leu Leu Ser Ser Val
145                 150                 155                 160

Thr Thr Thr Lys Ser Ile Leu Ser Lys Glu Ile Thr Ala Gly Val Phe
                165                 170                 175

Lys Phe Ile Asp Ala Gln Glu Leu Leu Glu Ser Glu Leu Gly Tyr Thr
                180                 185                 190

Ser Asn Glu Pro Val Ser Leu Cys Val Ala Ser Ala Ile Glu Ser Ala
            195                 200                 205

Val Val His Met Ile Ala Asp Gly Ile Trp Lys Gly Ala Trp Asn Leu
            210                 215                 220

Ala Asp Gln Ala Ser Gly Leu Arg Ser Pro Val Leu Gln Lys Tyr
225                 230                 235

<210> SEQ ID NO 38
<211> LENGTH: 233
<212> TYPE: PRT
<213> ORGANISM: Pseudomonas putida

<400> SEQUENCE: 38

Gln Asp Ser Glu Thr Pro Thr Leu Thr Pro Arg Ala Ser Thr Tyr Tyr
1               5                   10                  15

Asp Leu Ile Asn Met Pro Arg Pro Lys Gly Arg Leu Met Ala Val Val
                20                  25                  30

Tyr Gly Phe Arg Asp Gln Thr Gly Gln Tyr Lys Pro Thr Pro Ala Ser
            35                  40                  45

Ser Phe Ser Thr Ser Val Thr Gln Gly Ala Ala Ser Met Leu Met Asp
        50                  55                  60

Ala Leu Ser Ala Ser Gly Trp Phe Val Val Leu Glu Arg Glu Gly Leu
65                  70                  75                  80

Gln Asn Leu Leu Thr Glu Arg Lys Ile Ile Arg Ala Ser Gln Lys Lys
                85                  90                  95

Pro Asp Val Ala Glu Asn Ile Met Gly Glu Leu Pro Pro Leu Gln Ala
            100                 105                 110

Ala Asn Leu Met Leu Glu Gly Ile Ile Ala Tyr Asp Thr Asn Val
            115                 120                 125

Arg Ser Gly Gly Glu Gly Ala Arg Tyr Leu Gly Ile Asp Ile Ser Arg
        130                 135                 140

Glu Tyr Arg Val Asp Gln Val Thr Val Asn Leu Arg Ala Val Asp Val
145                 150                 155                 160

Arg Thr Gly Gln Val Leu Ala Asn Val Met Thr Ser Lys Thr Ile Tyr
                165                 170                 175

Ser Val Gly Arg Ser Ala Gly Val Phe Lys Phe Ile Glu Phe Lys Lys
            180                 185                 190

Leu Leu Glu Ala Glu Val Gly Tyr Thr Thr Asn Glu Pro Ala Gln Leu
        195                 200                 205

Cys Val Leu Ser Ala Ile Glu Ser Ala Val Gly His Leu Leu Ala Gln
            210                 215                 220

Gly Ile Glu Gln Arg Leu Trp Gln Val
225                 230
```

<210> SEQ ID NO 39
<211> LENGTH: 234
<212> TYPE: PRT
<213> ORGANISM: Shewanella violacea

<400> SEQUENCE: 39

Met Pro Lys Ser Asp Thr Tyr Tyr Asp Leu Ile Gly Leu Pro His Pro
1               5                   10                  15

Gln Gly Ser Met Leu Ala Ala Val Tyr Asp Phe Arg Asp Gln Thr Gly
            20                  25                  30

Gln Tyr Lys Ala Ile Pro Ser Ser Asn Phe Ser Thr Ala Val Pro Gln
        35                  40                  45

Ser Gly Thr Ala Phe Leu Ala Gln Ala Leu Asn Asp Ser Ser Trp Phe
    50                  55                  60

Val Pro Val Glu Arg Glu Gly Leu Gln Asn Leu Leu Thr Glu Arg Lys
65                  70                  75                  80

Ile Val Arg Ala Gly Leu Lys Gly Glu Ala Asn Gln Leu Pro Gln Leu
                85                  90                  95

Ser Ser Ala Gln Ile Leu Met Glu Gly Gly Ile Val Ala Tyr Asp Thr
            100                 105                 110

Asn Ile Lys Thr Gly Gly Ala Gly Ala Arg Tyr Leu Gly Ile Gly Val
        115                 120                 125

Asn Ser Lys Phe Arg Val Asp Thr Val Thr Val Asn Leu Arg Ala Val
    130                 135                 140

Asp Ile Arg Thr Gly Arg Leu Leu Ser Ser Val Thr Thr Lys Ser
145                 150                 155                 160

Ile Leu Ser Lys Glu Val Ser Ala Gly Val Phe Lys Phe Ile Asp Ala
                165                 170                 175

Gln Asp Leu Leu Glu Ser Glu Leu Gly Tyr Thr Ser Asn Glu Pro Val
            180                 185                 190

Ser Leu Cys Val Ala Gln Ala Ile Glu Ser Ala Val Val His Met Ile
        195                 200                 205

Ala Asp Gly Ile Trp Lys Arg Ala Trp Asn Leu Ala Asp Thr Ala Ser
    210                 215                 220

Gly Leu Asn Asn Pro Val Leu Gln Lys Tyr
225                 230

<210> SEQ ID NO 40
<211> LENGTH: 245
<212> TYPE: PRT
<213> ORGANISM: Marinobacterium jannaschii

<400> SEQUENCE: 40

Leu Thr Arg Arg Met Ser Thr Tyr Gln Asp Leu Ile Asp Met Pro Ala
1               5                   10                  15

Pro Arg Gly Lys Ile Val Thr Ala Val Tyr Ser Phe Arg Asp Gln Ser
            20                  25                  30

Gly Gln Tyr Lys Pro Ala Pro Ser Ser Ser Phe Ser Thr Ala Val Thr
        35                  40                  45

Gln Gly Ala Ala Ala Met Leu Val Asn Val Leu Asn Asp Ser Gly Trp
    50                  55                  60

Phe Ile Pro Leu Glu Arg Glu Gly Leu Gln Asn Ile Leu Thr Glu Arg
65                  70                  75                  80

Lys Ile Ile Arg Ala Ala Leu Lys Lys Asp Asn Val Pro Val Asn Asn
                85                  90                  95

Ser Ala Gly Leu Pro Ser Leu Leu Ala Ala Asn Ile Met Leu Glu Gly

```
                100                 105                 110
Gly Ile Val Gly Tyr Asp Ser Asn Ile His Thr Gly Gly Ala Gly Ala
            115                 120                 125

Arg Tyr Phe Gly Ile Gly Ala Ser Glu Lys Tyr Arg Val Asp Glu Val
        130                 135                 140

Thr Val Asn Leu Arg Ala Ile Asp Ile Arg Thr Gly Arg Ile Leu His
145                 150                 155                 160

Ser Val Leu Thr Ser Lys Lys Ile Leu Ser Arg Glu Ile Arg Ser Asp
                165                 170                 175

Val Tyr Arg Phe Ile Glu Phe Lys His Leu Leu Glu Met Glu Ala Gly
            180                 185                 190

Ile Thr Thr Asn Asp Pro Ala Gln Leu Cys Val Leu Ser Ala Ile Glu
        195                 200                 205

Ser Ala Val Ala His Leu Ile Val Asp Gly Val Ile Lys Lys Ser Trp
210                 215                 220

Ser Leu Ala Asp Pro Asn Glu Leu Asn Ser Pro Val Ile Gln Ala Tyr
225                 230                 235                 240

Gln Gln Gln Arg Ile
                245

<210> SEQ ID NO 41
<211> LENGTH: 234
<212> TYPE: PRT
<213> ORGANISM: Chryseobacterium oranimense

<400> SEQUENCE: 41

Pro Ser Asp Pro Glu Arg Ser Thr Met Gly Glu Leu Thr Pro Ser Thr
1               5                   10                  15

Ala Glu Leu Arg Asn Leu Pro Leu Pro Asn Glu Lys Ile Val Ile Gly
            20                  25                  30

Val Tyr Lys Phe Arg Asp Gln Thr Gly Gln Tyr Lys Pro Ser Glu Asn
        35                  40                  45

Gly Asn Asn Trp Ser Thr Ala Val Pro Gln Gly Thr Thr Thr Ile Leu
    50                  55                  60

Ile Lys Ala Leu Glu Asp Ser Arg Trp Phe Ile Pro Ile Glu Arg Glu
65                  70                  75                  80

Asn Ile Ala Asn Leu Leu Asn Glu Arg Gln Ile Ile Arg Ser Thr Arg
                85                  90                  95

Gln Glu Tyr Met Lys Asp Ala Asp Lys Asn Ser Gln Ser Leu Pro Pro
                100                 105                 110

Leu Leu Tyr Ala Gly Ile Leu Leu Glu Gly Gly Val Ile Ser Tyr Asp
            115                 120                 125

Ser Asn Thr Met Thr Gly Gly Phe Gly Ala Arg Tyr Phe Gly Ile Gly
        130                 135                 140

Ala Ser Thr Gln Tyr Arg Gln Asp Arg Ile Thr Ile Tyr Leu Arg Ala
145                 150                 155                 160

Val Ser Thr Leu Asn Gly Glu Ile Leu Lys Thr Val Tyr Thr Ser Lys
                165                 170                 175

Thr Ile Leu Ser Thr Ser Val Asn Gly Ser Phe Phe Arg Tyr Ile Asp
            180                 185                 190

Thr Glu Arg Leu Leu Glu Ala Glu Val Gly Leu Thr Gln Asn Glu Pro
        195                 200                 205

Val Gln Leu Ala Val Thr Glu Ala Ile Glu Lys Ala Val Arg Ser Leu
    210                 215                 220
```

Ile Ile Glu Gly Thr Arg Asp Lys Ile Trp
225                 230

<210> SEQ ID NO 42
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 42
tttttttttt tt                                                                12

<210> SEQ ID NO 43
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 43
ggttgtttct gttggtgctg atattgc                                                27

<210> SEQ ID NO 44
<211> LENGTH: 3635
<212> TYPE: DNA
<213> ORGANISM: Artificial Sequence
<220> FEATURE:
<223> OTHER INFORMATION: Synthetic polynucleotide

<400> SEQUENCE: 44
gccatcagat tgtgtttgtt agtcgctgcc atcagattgt gtttgttagt cgcttttttt           60
ttttggaatt ttttttttgg aattttttttt ttgcgctaac aacctcctgc cgttttgccc         120
gtgcatatcg gtcacgaaca atctgattta ctaaacacag tagcctggat ttgttctatc         180
agtaatcgac cttattccta attaaataga gcaaatcccc ttattggggg taagacatga         240
agatgccaga aaaacatgac ctgttggccg ccattctcgc ggcaaaggaa caaggcatcg         300
gggcaatcct tgcgtttgca atggcgtacc ttcgcggcag atataatggc ggtgcgttta         360
caaaaacagt aatcgacgca acgatgtgcg ccattatcgc ctagttcatt cgtgaccttc         420
tcgacttcgc cggactaagt agcaatctcg cttatataac gagcgtgttt atcggctaca         480
tcggtactga ctcgattggt tcgcttatca aacgcttcgc tgctaaaaaa gccggagtag         540
aagatggtag aaatcaataa tcaacgtaag gcgttcctcg atatgctggc gtggtcggag         600
ggaactgata acggacgtca gaaaaccaga aatcatggtt atgacgtcat tgtaggcgga         660
gagctattta ctgattactc cgatcaccct cgcaaacttg tcacgctaaa cccaaaactc         720
aaatcaacag gcgccggacg ctaccagctt ctttcccgtt ggtgggatgc ctaccgcaag         780
cagcttggcc tgaaagactt ctctccgaaa agtcaggacg ctgtggcatt gcagcagatt         840
aaggagcgtg gcgctttacc tatgattgat cgtggtgata tccgtcaggc aatcgaccgt         900
tgcagcaata tctgggcttc actgccgggc gctggttatg gtcagttcga gcataaggct         960
gacagcctga ttgcaaaatt caaagaagcg ggcggaacgg tcagagagat tgatgtatga        1020
gcagagtcac cgcgattatc tccgctctgg ttatctgcat catcgtctgc ctgtcatggg        1080
ctgttaatca ttaccgtgat aacgccatta cctacaaagc ccagcgcgac aaaaatgcca        1140
gagaactgaa gctggcgaac gcggcaatta ctgacatgca gatgcgtcag cgtgatgttg        1200
ctgcgctcga tgcaaaatac acgaaggagt tagctgatgc taaagctgaa aatgatgctc        1260

-continued

```
tgcgtgatga tgttgccgct ggtcgtcgtc ggttgcacat caaagcagtc tgtcagtcag    1320
tgcgtgaagc caccaccgcc tccggcgtgg ataatgcagc ctcccccccga ctggcagaca    1380 ccgctgaacg ggattatttc accctcagag agaggctgat cactatgcaa aaacaactgg    1440
aaggaaccca gaagtatatt aatgagcagt gcagatagag ttgcccatat cgatgggcaa    1500
ctcatgcaat tattgtgagc aatacacacg cgcttccagc ggagtataaa tgcctaaagt    1560
aataaaaccg agcaatccat ttacgaatgt ttgctgggtt tctgttttaa caacattttc    1620
tgcgccgcca caaattttgg ctgcatcgac agttttcttc tgcccaattc cagaaacgaa    1680
gaaatgatgg gtgatggttt cctttggtgc tactgctgcc ggtttgtttt gaacagtaaa    1740
cgtctgttga gcacatcctg taataagcag ggccagcgca gtagcgagta gcattttttt    1800
catggtgtta ttcccgatgc ttttgaagt tcgcagaatc gtatgtgtag aaaattaaac    1860
aaaccctaaa caatgagttg aaatttcata ttgttaatat ttattaatgt atgtcaggtg    1920
cgatgaatcg tcattgtatt cccggattaa ctatgtccac agccctgacg gggaacttct    1980
ctgcgggagt gtccgggaat aattaaaacg atgcacacag ggtttagcgc gtacacgtat    2040
tgcattatgc caacgccccg gtgctgacac ggaagaaacc ggacgttatg atttagcgtg    2100
gaaagatttg tgtagtgttc tgaatgctct cagtaaatag taatgaatta tcaaaggtat    2160
agtaatatct tttatgttca tggatatttg taacccatcg gaaaactcct gctttagcaa    2220
gattttccct gtattgctga atgtgatttt ctcttgattt caacctatca taggacgttt    2280
ctataagatg cgtgtttctt gagaatttaa catttacaac ctttttaagt cctttatta    2340 acacggtgtt atcgttttct aacacgatgt gaatattatc tgtggctaga tagtaaatat    2400
aatgtgagac gttgtgacgt tttagttcag aataaaacaa ttcacagtct aaatcttttc    2460
gcacttgatc gaatatttct ttaaaaatgg caacctgagc cattggtaaa accttccatg    2520
tgatacgagg gcgcgtagtt tgcattatcg ttttatcgt ttcaatctgg tctgacctcc    2580
ttgtgttttg ttgatgattt atgtcaaata ttaggaatgt tttcacttaa tagtattggt    2640
tgcgtaacaa agtgcggtcc tgctggcatt ctggagggaa atacaaccga cagatgtatg    2700
taaggccaac gtgctcaaat cttcatacag aaagatttga agtaatattt taaccgctag    2760
atgaagagca agcgcatgga gcgacaaaat gaataaagaa caatctgctg atgatccctc    2820
cgtggatctg attcgtgtaa aaaatatgct taatagcacc attttctatga gttaccctga    2880 tgttgtaatt gcatgtatag aacataaggt gtctctggaa gcattcagag caattgaggc    2940
agcgttggtg aagcacgata ataatatgaa ggattattcc ctggtggttg actgatcacc    3000
ataactgcta atcattcaaa ctatttagtc tgtgacagag ccaacacgca gtctgtcact    3060
gtcaggaaag tggtaaaact gcaactcaat tactgcaatg ccctcgtaat taagtgaatt    3120
tacaatatcg tcctgttcgg agggaagaac gcgggatgtt cattcttcat cacttttaat    3180
tgatgtatat gctctctttt ctgacgttag tctccgacgg caggcttcaa tgacccaggc    3240
tgagaaattc ccggaccctt tttgctcaag agcgatgtta atttgttcaa tcatttggtt    3300
aggaaagcgg atgttgcggg ttgttgttct gcgggttctg ttcttcgttg acatgaggtt    3360
gccccgtatt cagtgtcgct gatttgtatt gtctgaagtt gtttttacgt taagttgatg    3420
cagatcaatt aatacgatac ctgcgtcata attgattatt tgacgtggtt tgatggcctc    3480
cacgcacgtt gtgatatgta gatgataatc attatcactt tacgggtcct ttccggtgaa    3540
aaaaaaggta ccaaaaaaaa catcgtcgtg agtagtgaac cgtaagccgt tctgtttatg    3600
tttcttggac actgattgac acggtttagt agaac                               3635
```

<210> SEQ ID NO 45
<211> LENGTH: 3636
<212> TYPE: DNA
<213> ORGANISM: Artificial Sequence
<220> FEATURE:
<223> OTHER INFORMATION: Synthetic polynucleotide

<400> SEQUENCE: 45

```
ttttttttt  tttttttttt  ttttttttca  agaaacataa  acagaacgtg  cttacggttc     60
actactcacg  acgatgtttt  ttttggtacc  tttttttca   ccggaaagga  cccgtaaagt    120
gataatgatt  atcatctaca  tatcacaacg  tgcgtggagg  ccatcaaacc  acgtcaaata    180
atcaattatg  acgcaggtat  cgtattaatt  gatctgcatc  aacttaacgt  aaaaacaact    240
tcagacaata  caaatcagcg  acactgaata  cggggcaacc  tcatgtcaac  gaagaacaga    300
acccgcagaa  caacaacccg  caacatccgc  tttcctaacc  aaatgattga  acaaattaac    360
atcgctcttg  agcaaaaagg  gtccgggaat  ttctcagcct  gggtcattga  agcctgccgt    420
cggagactaa  cgtcagaaaa  gagagcatat  acatcaatta  aaagtgatga  agaatgaaca    480
tcccgcgttc  ttccctccga  acaggacgat  attgtaaatt  cacttaatta  cgagggcatt    540
gcagtaattg  agttgcagtt  ttaccacttt  cctgacagtg  acagactgcg  tgttggctct    600
gtcacagact  aaatagtttg  aatgattagc  agttatggtg  atcagtcaac  caccagggaa    660
taatccttca  tattattatc  gtgcttcacc  aacgctgcct  caattgctct  gaatgcttcc    720
agagacacct  tatgttctat  acatgcaatt  acaacatcag  ggtaactcat  agaaatggtg    780
ctattaagca  tatttttac   acgaatcaga  tccacggagg  gatcatcagc  agattgttct    840
ttattcattt  tgtcgctcca  tgcgcttgct  cttcatctag  cggttaaaat  attacttcaa    900
atctttctgt  atgaagattt  gagcacgttg  gccttacata  catctgtcgg  ttgtatttcc    960
ctccagaatg  ccagcaggac  cgcactttgt  tacgcaacca  atactattaa  gtgaaaacat   1020
tcctaatatt  tgacataaat  catcaacaaa  acacaaggag  gtcagaccag  attgaaacga   1080
taaaaacgat  aatgcaaact  acgcgccctc  gtatcacatg  gaaggtttta  ccaatggctc   1140
aggttgccat  ttttaaagaa  atattcgatc  aagtgcgaaa  agatttagac  tgtgaattgt   1200
tttattctga  actaaaacgt  cacaacgtct  cacattatat  ttactatcta  gccacagata   1260
atattcacat  cgtgttagaa  aacgataaca  ccgtgttaat  aaaaggactt  aaaaaggttg   1320
taaatgttaa  attctcaaga  aacacgcatc  ttatagaaac  gtcctatgat  aggttgaaat   1380
caagagaaat  cacatttcag  caatacaggg  aaaatcttgc  taaagcagga  gttttccgat   1440
gggttacaaa  tatccatgaa  cataaaagat  attactatac  ctttgataat  tcattactat   1500
ttactgagag  cattcagaac  actacacaaa  tctttccacg  ctaaatcata  acgtccggtt   1560
tcttccgtgt  cagcaccggg  gcgttggcat  aatgcaatac  gtgtacgcgc  taaaccctgt   1620
gtgcatcgtt  ttaattattc  ccggacactc  ccgcagagaa  gttccccgtc  agggctgtgg   1680
acatagttaa  tccgggaata  caatgacgat  tcatcgcacc  tgacatacat  taataaatat   1740
taacaatatg  aaatttcaac  tcattgttta  gggtttgttt  aatttttctac  acatacgatt   1800
ctgcgaactt  caaaaagcat  cggaataac   accatgaaaa  aaatgctact  cgctactgcg   1860
ctggccctgc  ttattacagg  atgtgctcaa  cagacgttta  ctgttcaaaa  caaaccggca   1920
gcagtagcac  caaaggaaac  catcaccat   catttcttcg  tttctggaat  tgggcagaag   1980
aaaactgtcg  atgcagccaa  aatttgtggc  ggcgcagaaa  atgttgttaa  aacagaaacc   2040
```

-continued

```
cagcaaacat tcgtaaatgg attgctcggt tttattactt taggcattta tactccgctg    2100
gaagcgcgtg tgtattgctc acaataattg catgagttgc ccatcgatat gggcaactct    2160
atctgcactg ctcattaata tacttctggg ttccttccag ttgtttttgc atagtgatca    2220
gcctctctct gagggtgaaa taatcccgtt cagcggtgtc tgccagtcgg ggggaggctg    2280
cattatccac gccggaggcg gtggtggctt cacgcactga ctgacagact gctttgatgt    2340
gcaaccgacg acgaccagcg gcaacatcat cacgcagagc atcattttca gctttagcat    2400
cagctaactc cttcgtgtat tttgcatcga gcgcagcaac atcacgctga cgcatctgca    2460
tgtcagtaat tgccgcgttc gccagcttca gttctctggc attttgtcg cgctgggctt     2520 tgtaggtaat ggcgttatca cggtaatgat taacagccca tgacaggcag acgatgatgc    2580
agataaccag agcggagata tcgcggtga ctctgctcat acatcaatct ctctgaccgt     2640
tccgcccgct tctttgaatt tgcaatcag gctgtcagcc ttatgctcga actgaccata    2700
accagcgccc ggcagtgaag cccagatatt gctgcaacgg tcgattgcct gacggatatc    2760
accacgatca atcataggta aagcgccacg ctccttaatc tgctgcaatg ccacagcgtc    2820 ctgactttc ggagagaagt ctttcaggcc aagctgcttg cggtaggcat cccaccaacg     2880
ggaaagaagc tggtagcgtc cggcgcctgt tgatttgagt tttgggttta gcgtgacaag    2940
tttgcgaggg tgatcggagt aatcagtaaa tagctctccg cctacaatga cgtcataacc    3000
atgatttctg gttttctgac gtccgttatc agttccctcc gaccacgcca gcatatcgag    3060
gaacgcctta cgttgattat tgatttctac catcttctac tccggctttt ttagcagcga    3120
agcgtttgat aagcgaacca atcgagtcag taccgatgta gccgataaac acgctcgtta    3180
tataagcgag attgctactt agtccggcga agtcgagaag gtcacgaatg aactaggcga    3240
taatggcgca catcgttgcg tcgattactg ttttgtaaa cgcaccgcca ttatatctgc     3300
cgcgaaggta cgccattgca aacgcaagga ttgccccgat gccttgttcc tttgccgcga    3360
gaatggcggc caacaggtca tgtttttctg gcatcttcat gtcttacccc caataagggg    3420
atttgctcta tttaattagg aataaggtcg attactgata gaacaaatcc aggctactgt    3480
gtttagtaat cagatttgtt cgtgaccgat atgcacgggc aaaacggcag gaggttgtta    3540
gcgcaaaaaa aaaattccaa aaaaaaaatt ccaaaaaaaa aaagcgacta acaaacacaa    3600
tctgatggca gcgactaaca acacaatct gatggc                               3636
```

<210> SEQ ID NO 46
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 46

```
gcaatatcag caccaacaga aacaacct                                          28
```

<210> SEQ ID NO 47
<211> LENGTH: 10
<212> TYPE: PRT
<213> ORGANISM: Artificial Sequence
<220> FEATURE:
<223> OTHER INFORMATION: StrepII (C)

<400> SEQUENCE: 47

```
Ser Ala Trp Ser His Pro Gln Phe Glu Lys
1               5                   10
```

<210> SEQ ID NO 48
<211> LENGTH: 15
<212> TYPE: PRT
<213> ORGANISM: Artificial Sequence
<220> FEATURE:
<223> OTHER INFORMATION: Pro

<400> SEQUENCE: 48

Met Gln Arg Leu Phe Leu Leu Val Ala Val Met Leu Leu Ser Gly
1               5                   10                  15

<210> SEQ ID NO 49
<211> LENGTH: 558
<212> TYPE: DNA
<213> ORGANISM: Mycobacterium smegmatis

<400> SEQUENCE: 49
atgggcctgg ataacgaact tagcctggtg gacggccaag atcgcacgct gacggtgcaa      60
caatgggata ccttcctgaa tggtgtgttt ccgctggatc gtaaccgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc gatgacggtg atattaccgc accgccgttt     300
ggcctgaaca gcgtgattac gccgaacctg tttccgggtg ttagcatctc tgccgatctg     360
ggcaacggtc cgggcattca agaagtggca acctttagtg tggacgtttc cggcgctgaa     420
ggcggtgtcg cggtgtctaa tgcccacggt accgttacgg gcgcggccgg cggtgtcctg     480
ctgcgtccgt tcgcgcgcct gattgcgagc accggcgact ctgttacgac ctatggcgaa     540
ccgtggaata tgaactaa                                                    558

<210> SEQ ID NO 50
<211> LENGTH: 184
<212> TYPE: PRT
<213> ORGANISM: Mycobacterium smegmatis

<400> SEQUENCE: 50

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Ala Glu Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
            165                 170                 175

Tyr Gly Glu Pro Trp Asn Met Asn
        180

<210> SEQ ID NO 51
<211> LENGTH: 35
<212> TYPE: DNA
<213> ORGANISM: Artificial Sequence
<220> FEATURE:
<223> OTHER INFORMATION: Thrombin Binding Aptamer

<400> SEQUENCE: 51
tttttttttt tttttttttt ggttggtgtg gttgg                          35

<210> SEQ ID NO 52
<211> LENGTH: 95
<212> TYPE: DNA
<213> ORGANISM: Artificial Sequence
<220> FEATURE:
<223> OTHER INFORMATION: Y Adaptor Top Strand
<220> FEATURE:
<221> NAME/KEY: C3 Spacer
<222> LOCATION: (1)..(30)
<223> OTHER INFORMATION: C3 Spacer phosphoramidite (Integrated DNA
      technologies: 5SpC3)
<220> FEATURE:
<221> NAME/KEY: misc_feature
<222> LOCATION: (1)..(30)
<223> OTHER INFORMATION: n is a, c, g, or t
<220> FEATURE:
<221> NAME/KEY: misc_feature
<222> LOCATION: (64)..(67)
<223> OTHER INFORMATION: n is a, c, g, or t
<220> FEATURE:
<221> NAME/KEY: 18 Spacer
<222> LOCATION: (80)..(83)
<223> OTHER INFORMATION: 18-atom hexa-ethyleneglycol spacer (Integrated
      DNA technologies: iSp18)

<400> SEQUENCE: 52
nnnnnnnnnn nnnnnnnnnn nnnnnnnnnn ggcgtctgct tgggtgttta acctttttt   60 tttnnnnaat gtacttcgtt cagttacgta ttgct                            95

<210> SEQ ID NO 53
<211> LENGTH: 25
<212> TYPE: DNA
<213> ORGANISM: Artificial Sequence
<220> FEATURE:
<223> OTHER INFORMATION: Y Adaptor Blocker Strand

<400> SEQUENCE: 53
ttccgcagac gaacccacaa attgg                                      25

<210> SEQ ID NO 54
<211> LENGTH: 15
<212> TYPE: DNA
<213> ORGANISM: Artificial Sequence
<220> FEATURE:
<223> OTHER INFORMATION: Y Adaptor Cholesterol Tether
<220> FEATURE:
<221> NAME/KEY: 5' Cholesterol tag
<222> LOCATION: (1)..(1)

<400> SEQUENCE: 54
ttgaccgctc gcctc                                                 15

<210> SEQ ID NO 55

```
<211> LENGTH: 45
<212> TYPE: DNA
<213> ORGANISM: Artificial Sequence
<220> FEATURE:
<223> OTHER INFORMATION: Y Adaptor Bottom Strand
<220> FEATURE:
<221> NAME/KEY: misc_feature
<222> LOCATION: (45)..(45)
<223> OTHER INFORMATION: 5 Phos

<400> SEQUENCE: 55
aactggcgag cggagttttt acatgaagca agtcaatgca taacg              45

<210> SEQ ID NO 56
<211> LENGTH: 3561
<212> TYPE: DNA
<213> ORGANISM: Artificial Sequence
<220> FEATURE:
<223> OTHER INFORMATION: 3.6kb target sequence

<400> SEQUENCE: 56
gccatcagat tgtgtttgtt agtcgctttt ttttttggaa attttttttt tggaattttt      60
tttttgcgct aacaacctcc tgccgttttg cccgtgcata tcggtcacga acaaatctga    120
ttactaaaca cagtagcctg gatttgttct atcagtaatc gaccttattc ctaattaaat    180
agagcaaatc cccttattgg gggtaagaca tgaagatgcc agaaaaacat gacctgttgg    240
ccgccattct cgcggcaaag gaacaaggca tcggggcaat ccttgcgttt gcaatggcgt    300
accttcgcgg cagatataat ggcggtgcgt ttacaaaaac agtaatcgac gcaacgatgt    360
gcgccattat cgcctagttc attcgtgacc ttctcgactt cgccggacta agtagcaatc    420
tcgcttatat aacgagcgtg tttatcggct acatcggtac tgactcgatt ggttcgctta    480
tcaaacgctt cgctgctaaa aaagccggag tagaagatgg tagaaatcaa taatcaacgt    540
aaggcgttcc tcgatatgct ggcgtggtcg gagggaactg ataacggacg tcagaaaacc    600
agaaatcatg gttatgacgt cattgtaggc ggagagctat ttactgatta ctccgatcac    660
cctcgcaaac ttgtcacgct aaacccaaaa ctcaaatcaa caggcgccgg acgctaccag    720 cttcttttccc gttggtggga tgcctaccgc aagcagcttg gcctgaaaga cttctctccg    780
aaaagtcagg acgctgtggc attgcagcag attaaggagc gtggcgcttt acctatgatt    840
gatcgtggtg atatccgtca ggcaatcgac cgttgcagca atatctgggc ttcactgccg    900
ggcgctggtt atggtcagtt cgagcataag gctgacagcc tgattgcaaa attcaaagaa    960
gcgggcggaa cggtcagaga gattgatgta tgagcagagt caccgcgatt atctccgctc   1020
tggttatctg catcatcgtc tgcctgtcat gggctgttaa tcattaccgt gataacgcca   1080
ttacctacaa agcccagcgc gacaaaaatg ccagagaact gaagctggcg aacgcggcaa   1140
ttactgacat gcagatgcgt cagcgtgatg ttgctgcgct cgatgcaaaa tacacgaagg   1200
agttagctga tgctaaagct gaaaatgatg ctctgcgtga tgatgttgcc gctggtcgtc   1260
gtcggttgca catcaaagca gtctgtcagt cagtgcgtga agccaccacc gcctccggcg   1320
tggataatgc agcctccccc cgactggcag acaccgctga acgggattat ttcaccctca   1380
gagagaggct gatcactatg caaaaacaac tggaaggaac ccagaagtat attaatgagc   1440
agtgcagata gagttgccca tatcgatggg caactcatgc aattattgtg agcaatacac   1500
acgcgcttcc agcggagtat aaatgcctaa agtaataaaa ccgagcaatc catttacgaa   1560
tgtttgctgg gttctgtgtt taacaacatt ttctgcgccg ccacaaattt tggctgcatc   1620
gacagttttc ttctgcccaa ttccagaaac gaagaaatga tgggtgatgg tttcctttgg   1680
```

```
tgctactgct gccggtttgt tttgaacagt aaacgtctgt tgagcacatc ctgtaataag    1740
cagggccagc gcagtagcga gtagcatttt tttcatggtg ttattcccga tgcttttga     1800 agttcgcaga atcgtatgtg tagaaaatta aacaaaccct aaacaatgag ttgaaatttc    1860
atattgttaa tatttattaa tgtatgtcag gtgcgatgaa tcgtcattgt attcccggat    1920
taactatgtc cacagccctg acggggaact tctctgcggg agtgtccggg aataattaaa    1980
acgatgcaca cagggtttag cgcgtacacg tattgcatta tgccaacgcc ccggtgctga    2040
cacggaagaa accggacgtt atgatttagc gtggaaagat tgtgtagtg ttctgaatgc     2100 tctcagtaaa tagtaatgaa ttatcaaagg tatagtaata tcttttatgt tcatggatat    2160
ttgtaaccca tcggaaaact cctgctttag caagattttc cctgtattgc tgaaatgtga    2220
tttctcttga tttcaaccta tcataggacg tttctataag atgcgtgttt cttgagaatt    2280
taacatttac aaccttttta agtccttta ttaacacggt gttatcgttt tctaacacga     2340
tgtgaatatt atctgtggct agatagtaaa tataatgtga gacgttgtga cgttttagtt    2400
cagaataaaa caattcacag tctaaatctt ttcgcacttg atcgaatatt tctttaaaaa    2460
tggcaacctg agccattggt aaaaccttcc atgtgatacg agggcgcgta gtttgcatta    2520
tcgtttttat cgtttcaatc tggtctgacc tccttgtgtt ttgttgatga tttatgtcaa    2580
atattaggaa tgttttcact taatagtatt ggttgcgtaa caaagtgcgg tcctgctggc    2640
attctggagg gaaatacaac cgacagatgt atgtaaggcc aacgtgctca aatcttcata    2700
cagaaagatt tgaagtaata ttttaaccgc tagatgaaga gcaagcgcat ggagcgacaa    2760
aatgaataaa gaacaatctg ctgatgatcc ctccgtggat ctgattcgtg taaaaaatat    2820
gcttaatagc accatttcta tgagttaccc tgatgttgta attgcatgta tagaacataa    2880
ggtgtctctg gaagcattca gagcaattga ggcagcgttg gtgaagcacg ataataaat    2940 gaaggattat tccctggtgg ttgactgatc accataactg ctaatcattc aaactattta    3000
gtctgtgaca gagccaacac gcagtctgtc actgtcagga aagtggtaaa actgcaactc    3060
aattactgca atgccctcgt aattaagtga atttacaata tcgtcctgtt cggagggaag    3120
aacgcgggat gttcattctt catcactttt aattgatgta tatgctctct tttctgacgt    3180
tagtctccga cggcaggctt caatgaccca ggctgagaaa ttcccggacc cttttgctc     3240 aagagcgatg ttaatttgtt caatcatttg gttaggaaag cggatgttgc gggttgttgt    3300
tctgcgggtt ctgttcttcg ttgacatgag gttgccccgt attcagtgtc gctgatttgt    3360
attgtctgaa gttgtttta cgttaagttg atgcagatca attaatacga tacctgcgtc     3420
ataattgatt atttgacgtg gtttgatggc ctccacgcac gttgtgatat gtagatgata    3480
atcattatca ctttacgggt cctttccggt gaaaaaaag gtaccaaaaa aaacatcgtc     3540
gtgagtagtg aaccgtaagc a                                              3561
```

The invention claimed is:

1. A mutant CsgG monomer comprising a variant of the sequence shown in SEQ ID NO: 2 which
   (a) comprises:
   R97W;
   R93W;
   R93Y and R97Y; or
   F191T; and/or
   (b) consisting of deletion of V105, A106 and I107; and/or
   (c) comprises deletion of one or more of positions R192, F193, I194, D195, Y196, Q197, R198, L199, L200 and E201.

2. The mutant CsgG monomer according to claim 1, wherein the variant comprises R97W.

3. The mutant CsgG monomer according to claim 1, which comprises deletion of F193, I194, D195, Y196, Q197, R198 and L199 or deletion of D195, Y196, Q197, R198 and L199.

4. The mutant CsgG monomer according to claim 1, wherein the variant comprises one or more of the following: (i) one or more mutations at the following positions N40, D43, E44, S54, S57, Q62, R97, E101, E124, E131, R142, T150 and R192; (ii) mutations at Y51/N55, Y51/F56, N55/F56 or Y51/N55/F56; (iii) Q42R or Q42K; (iv) K49R or K94Q; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; (xi) deletion of one or more of the following positions F48, K49, P50, Y51, P52, A53, S54, N55, F56 and S57; and (xii) one or more mutations at the following positions L90, N91, I95, A99, Q114.

5. The mutant CsgG monomer according to claim 1, wherein the variant comprises (a) a mutation at Y51 and/or F56, and/or (b) a mutation at R192, and/or (c) a mutation at T150.

6. The mutant CsgG monomer according to claim 5, wherein the mutation at Y51 is Y51A, and/or the mutation at F56 is F56Q, and/or the mutation at R192 is R192D.

7. The mutant CsgG monomer according to claim 1, wherein
   (a) the variant comprises one or more of the following substitutions N40R, N40K, D43N, D43Q, D43R, D43K, E44N, E44Q, E44R, E44K, S54P, S57P, Q62R, Q62K, R97N, R97G, R97L, E101N, E101Q, E101R, E101K, E101F, E101Y, E101W, E101T, E124N, E124Q, E124R, E124K, E124F, E124Y, E124W, E131D, R142E, R142N, T150I, R192E and R192N;
   (b) the variant comprises in (ii) F56N/N55Q, F56N/N55R, F56N/N55K, F56N/N55S, F56N/N55G, F56N/N55A, F56N/N55T, F56Q/N55Q, F56Q/N55R, F56Q/N55K, F56Q/N55S, F56Q/N55G, F56Q/N55A, F56Q/N55T, F56R/N55Q, F56R/N55R, F56R/N55K, F56R/N55S, F56R/N55G, F56R/N55A, F56R/N55T, F56S/N55Q, F56S/N55R, F56S/N55K, F56S/N55S, F56S/N55G, F56S/N55A, F56S/N55T, F56G/N55Q, F56G/N55R, F56G/N55K, F56G/N55S, F56G/N55G, F56G/N55A, F56G/N55T, F56A/N55Q, F56A/N55R, F56A/N55K, F56A/N55S, F56A/N55G, F56A/N55A, F56A/N55T, F56K/N55Q, F56K/N55R, F56K/N55K, F56K/N55S, F56K/N55G, F56K/N55A, F56K/N55T, F56N/Y51L, F56N/Y51V, F56N/Y51A, F56N/Y51N, F56N/Y51Q, F56N/Y51S, F56N/Y51G, F56Q/Y51L, F56Q/Y51V, F56Q/Y51A, F56Q/Y51N, F56Q/Y51Q, F56Q/Y51S, F56Q/Y51G, F56R/Y51L, F56R/Y51V, F56R/Y51A, F56R/Y51N, F56R/Y51Q, F56R/Y51S, F56R/Y51G, F56S/Y51L, F56S/Y51V, F56S/Y51A, F56S/Y51N, F56S/Y51Q, F56S/Y51S, F56S/Y51G, F56G/Y51L, F56G/Y51V, F56G/Y51A, F56G/Y51N, F56G/Y51Q, F56G/Y51S, F56G/Y51G, F56A/Y51L, F56A/Y51V, F56A/Y51A, F56A/Y51N, F56A/Y51Q, F56A/Y51S, F56A/Y51G, F56K/Y51L, F56K/Y51V, F56K/Y51A, F56K/Y51N, F56K/Y51Q, F56K/Y51S, F56K/Y51G, N55Q/Y51L, N55Q/Y51V, N55Q/Y51A, N55Q/Y51N, N55Q/Y51Q, N55Q/Y51S, N55Q/Y51G, N55R/Y51L, N55R/Y51V, N55R/Y51A, N55R/Y51N, N55R/Y51Q, N55R/Y51S, N55R/Y51G, N55K/Y51L, N55K/Y51V, N55K/Y51A, N55K/Y51N, N55K/Y51Q, N55K/Y51S, N55K/Y51G, N55S/Y51L, N55S/Y51V, N55S/Y51A, N55S/Y51N, N55S/Y51Q, N55S/Y51S, N55S/Y51G, N55G/Y51L, N55G/Y51V, N55G/Y51A, N55G/Y51N, N55G/Y51Q, N55G/Y51S, N55G/Y51G, N55A/Y51L, N55A/Y51V, N55A/Y51A, N55A/Y51N, N55A/Y51Q, N55A/Y51S, N55A/Y51G, N55T/Y51L, N55T/Y51V, N55T/Y51A, N55T/Y51N, N55T/Y51Q, N55T/Y51S, N55T/Y51G, F56N/N55Q/Y51L, F56N/N55Q/Y51V, F56N/N55Q/Y51A, F56N/N55Q/Y51N, F56N/N55Q/Y51Q, F56N/N55Q/Y51S, F56N/N55Q/Y51G, F56N/N55R/Y51L, F56N/N55R/Y51V, F56N/N55R/Y51A, F56N/N55R/Y51N, F56N/N55R/Y51Q, F56N/N55R/Y51S, F56N/N55R/Y51G, F56N/N55K/Y51L, F56N/N55K/Y51V, F56N/N55K/Y51A, F56N/N55K/Y51N, F56N/N55K/Y51Q, F56N/N55K/Y51S, F56N/N55K/Y51G, F56N/N55S/Y51L, F56N/N55S/Y51V, F56N/N55S/Y51A, F56N/N55S/Y51N, F56N/N55S/Y51Q, F56N/N55S/Y51S, F56N/N55S/Y51G, F56N/N55G/Y51L, F56N/N55G/Y51V, F56N/N55G/Y51A, F56N/N55G/Y51N, F56N/N55G/Y51Q, F56N/N55G/Y51S, F56N/N55G/Y51G, F56N/N55A/Y51L, F56N/N55A/Y51V, F56N/N55A/Y51A, F56N/N55A/Y51N, F56N/N55A/Y51Q, F56N/N55A/Y51S, F56N/N55A/Y51G, F56N/N55T/Y51L, F56N/N55T/Y51V, F56N/N55T/Y51A, F56N/N55T/Y51N, F56N/N55T/Y51Q, F56N/N55T/Y51S, F56N/N55T/Y51G, F56Q/N55Q/Y51L, F56Q/N55Q/Y51V, F56Q/N55Q/Y51A, F56Q/N55Q/Y51N, F56Q/N55Q/Y51Q, F56Q/N55Q/Y51S, F56Q/N55Q/Y51G, F56Q/N55R/Y51L, F56Q/N55R/Y51V, F56Q/N55R/Y51A, F56Q/N55R/Y51N, F56Q/N55R/Y51Q, F56Q/N55R/Y51S, F56Q/N55R/Y51G, F56Q/N55K/Y51L, F56Q/N55K/Y51V, F56Q/N55K/Y51A, F56Q/N55K/Y51N, F56Q/N55K/Y51Q, F56Q/N55K/Y51S, F56Q/N55K/Y51G, F56Q/N55S/Y51L, F56Q/N55S/Y51V, F56Q/N55S/Y51A, F56Q/N55S/Y51N, F56Q/N55S/Y51Q, F56Q/N55S/Y51S, F56Q/N55S/Y51G, F56Q/N55G/Y51L, F56Q/N55G/Y51V, F56Q/N55G/Y51A, F56Q/N55G/Y51N, F56Q/N55G/Y51Q, F56Q/N55G/Y51S, F56Q/N55G/Y51G, F56Q/N55A/Y51L, F56Q/N55A/Y51V, F56Q/N55A/Y51A, F56Q/N55A/Y51N, F56Q/N55A/Y51Q, F56Q/N55A/Y51S, F56Q/N55A/Y51G, F56Q/N55T/Y51L, F56Q/N55T/Y51V, F56Q/N55T/Y51A, F56Q/N55T/Y51N, F56Q/N55T/Y51Q, F56Q/N55T/Y51S, F56Q/N55T/Y51G, F56R/N55Q/Y51L, F56R/N55Q/Y51V, F56R/N55Q/Y51A, F56R/N55Q/Y51N, F56R/N55Q/Y51Q, F56R/N55Q/Y51S, F56R/N55Q/Y51G, F56R/N55R/Y51L, F56R/N55R/Y51V, F56R/N55R/Y51A, F56R/N55R/Y51N, F56R/N55R/Y51Q, F56R/N55R/Y51S, F56R/N55R/Y51G, F56R/N55K/Y51L, F56R/N55K/Y51V, F56R/N55K/Y51A, F56R/N55K/Y51N, F56R/N55K/Y51Q, F56R/N55K/Y51S, F56R/N55K/Y51G, F56R/N55S/Y51L, F56R/N55S/Y51V, F56R/N55S/Y51A, F56R/N55S/Y51N, F56R/N55S/Y51Q, F56R/N55S/Y51S, F56R/N55S/Y51G, F56R/N55G/Y51L, F56R/N55G/Y51V, F56R/N55G/Y51A, F56R/N55G/

Y51N, F56R/N55G/Y51Q, F56R/N55G/Y51S, F56R/ N55G/Y51G, F56R/N55A/Y51L, F56R/N55A/Y51V, F56R/N55A/Y51A, F56R/N55A/Y51N, F56R/N55A/ Y51Q, F56R/N55A/Y51S, F56R/N55A/Y51G, F56R/ N55T/Y51L, F56R/N55T/Y51V, F56R/N55T/Y51A, F56R/N55T/Y51N, F56R/N55T/Y51Q, F56R/N55T/ Y51S, F56R/N55T/Y51G, F56S/N55Q/Y51L, F56S/ N55Q/Y51V, F56S/N55Q/Y51A, F56S/N55Q/Y51N, F56S/N55Q/Y51Q, F56S/N55Q/Y51S, F56S/N55Q/ Y51G, F56S/N55R/Y51L, F56S/N55R/Y51V, F56S/ N55R/Y51A, F56S/N55R/Y51N, F56S/N55R/Y51Q, F56S/N55R/Y51S, F56S/N55R/Y51G, F56S/N55K/ Y51L, F56S/N55K/Y51V, F56S/N55K/Y51A, F56S/ N55K/Y51N, F56S/N55K/Y51Q, F56S/N55K/Y51S, F56S/N55K/Y51G, F56S/N55S/Y51L, F56S/N55S/ Y51V, F56S/N55S/Y51A, F56S/N55S/Y51N, F56S/ N55S/Y51Q, F56S/N55S/Y51S, F56S/N55S/Y51G, F56S/N55G/Y51L, F56S/N55G/Y51V, F56S/N55G/ Y51A, F56S/N55G/Y51N, F56S/N55G/Y51Q, F56S/ N55G/Y51S, F56S/N55G/Y51G, F56S/N55A/Y51L, F56S/N55A/Y51V, F56S/N55A/Y51A, F56S/N55A/ Y51N, F56S/N55A/Y51Q, F56S/N55A/Y51S, F56S/ N55A/Y51G, F56S/N55T/Y51L, F56S/N55T/Y51V, F56S/N55T/Y51A, F56S/N55T/Y51N, F56S/N55T/ Y51Q, F56S/N55T/Y51S, F56S/N55T/Y51G, F56G/ N55Q/Y51L, F56G/N55Q/Y51V, F56G/N55Q/Y51A, F56G/N55Q/Y51N, F56G/N55Q/Y51Q, F56G/N55Q/ Y51S, F56G/N55Q/Y51G, F56G/N55R/Y51L, F56G/ N55R/Y51V, F56G/N55R/Y51A, F56G/N55R/Y51N, F56G/N55R/Y51Q, F56G/N55R/Y51S, F56G/N55R/ Y51G, F56G/N55K/Y51L, F56G/N55K/Y51V, F56G/ N55K/Y51A, F56G/N55K/Y51N, F56G/N55K/Y51Q, F56G/N55K/Y51S, F56G/N55K/Y51G, F56G/N55S/ Y51L, F56G/N55S/Y51V, F56G/N55S/Y51A, F56G/ N55S/Y51N, F56G/N55S/Y51Q, F56G/N55S/Y51S, F56G/N55S/Y51G, F56G/N55G/Y51L, F56G/N55G/ Y51V, F56G/N55G/Y51A, F56G/N55G/Y51N, F56G/ N55G/Y51Q, F56G/N55G/Y51S, F56G/N55G/Y51G, F56G/N55A/Y51L, F56G/N55A/Y51V, F56G/N55A/ Y51A, F56G/N55A/Y51N, F56G/N55A/Y51Q, F56G/ N55A/Y51S, F56G/N55A/Y51G, F56G/N55T/Y51L, F56G/N55T/Y51V, F56G/N55T/Y51A, F56G/N55T/ Y51N, F56G/N55T/Y51Q, F56G/N55T/Y51S, F56G/ N55T/Y51G, F56A/N55Q/Y51L, F56A/N55Q/Y51V, F56A/N55Q/Y51A, F56A/N55Q/Y51N, F56A/N55Q/ Y51Q, F56A/N55Q/Y51S, F56A/N55Q/Y51G, F56A/ N55R/Y51L, F56A/N55R/Y51V, F56A/N55R/Y51A, F56A/N55R/Y51N, F56A/N55R/Y51Q, F56A/N55R/ Y51S, F56A/N55R/Y51G, F56A/N55K/Y51L, F56A/ N55K/Y51V, F56A/N55K/Y51A, F56A/N55K/Y51N, F56A/N55K/Y51Q, F56A/N55K/Y51S, F56A/N55K/ Y51G, F56A/N55S/Y51L, F56A/N55S/Y51V, F56A/ N55S/Y51A, F56A/N55S/Y51N, F56A/N55S/Y51Q, F56A/N55S/Y51S, F56A/N55S/Y51G, F56A/N55G/ Y51L, F56A/N55G/Y51V, F56A/N55G/Y51A, F56A/ N55G/Y51N, F56A/N55G/Y51Q, F56A/N55G/Y51S, F56A/N55G/Y51G, F56A/N55A/Y51L, F56A/N55A/ Y51V, F56A/N55A/Y51A, F56A/N55A/Y51N, F56A/ N55A/Y51Q, F56A/N55A/Y51S, F56A/N55A/Y51G, F56A/N55T/Y51L, F56A/N55T/Y51V, F56A/N55T/ Y51A, F56A/N55T/Y51N, F56A/N55T/Y51Q, F56A/ N55T/Y51S, F56A/N55T/Y51G, F56K/N55Q/Y51L, F56K/N55Q/Y51V, F56K/N55Q/Y51A, F56K/N55Q/ Y51N, F56K/N55Q/Y51Q, F56K/N55Q/Y51S, F56K/ N55Q/Y51G, F56K/N55R/Y51L, F56K/N55R/Y51V, F56K/N55R/Y51A, F56K/N55R/Y51N, F56K/N55R/ Y51Q, F56K/N55R/Y51S, F56K/N55R/Y51G, F56K/ N55K/Y51L, F56K/N55K/Y51V, F56K/N55K/Y51A, F56K/N55K/Y51N, F56K/N55K/Y51Q, F56K/N55K/ Y51S, F56K/N55K/Y51G, F56K/N55S/Y51L, F56K/ N55S/Y51V, F56K/N55S/Y51A, F56K/N55S/Y51N, F56K/N55S/Y51Q, F56K/N55S/Y51S, F56K/N55S/ Y51G, F56K/N55G/Y51L, F56K/N55G/Y51V, F56K/ N55G/Y51A, F56K/N55G/Y51N, F56K/N55G/Y51Q, F56K/N55G/Y51S, F56K/N55G/Y51G, F56K/N55A/ Y51L, F56K/N55A/Y51V, F56K/N55A/Y51A, F56K/ N55A/Y51N, F56K/N55A/Y51Q, F56K/N55A/Y51S, F56K/N55A/Y51G, F56K/N55T/Y51L, F56K/N55T/ Y51V, F56K/N55T/Y51A, F56K/N55T/Y51N, F56K/ N55T/Y51Q,F56K/N55T/Y51S, F56K/N55T/Y51G, F56E/N55R, F56E/N55K, F56D/N55R, F56D/N55K, F56R/N55E, F56R/N55D, F56K/N55E or F56K/ N55D;

(c) the variant comprises deletion of Y51/P52, Y51/P52/ A53, P50 to P52, P50 to A53, K49 to Y51, K49 to A53 and replacement with a single proline (P), K49 to S54 and replacement with a single P, Y51 to A53, Y51 to S54, N55/F56, N55 to S57, N55/F56 and replacement with a single P, N55/F56 and replacement with a single glycine (G), N55/F56 and replacement with a single alanine (A), N55/F56 and replacement with a single P and Y51N, N55/F56 and replacement with a single P and Y51Q, N55/F56 and replacement with a single P and Y51S, N55/F56 and replacement with a single G and Y51N, N55/F56 and replacement with a single G and Y51Q, N55/F56 and replacement with a single G and Y51S, N55/F56 and replacement with a single A and Y51N, N55/F56 and replacement with a single A/Y51Q or N55/F56 and replacement with a single A and Y51S; and/or (d) the variant comprises one or more of L90R or L90K, N91R or N91K, I95R or I95K, A99R or A99K, Q114K or Q114R.

8. The mutant CsgG monomer according to claim 1, wherein the variant comprises D195N/E203N, D195Q/ E203N, D195N/E203Q, D195Q/E203Q, E201N/E203N, E201Q/E203N, E201N/E203Q, E201Q/E203Q, E185N/ E203Q, E185Q/E203Q, E185N/E203N, E185Q/E203N, D195N/E201N/E203N, D195Q/E201N/E203N, D195N/ E201Q/E203N, D195N/E201N/E203Q, D195Q/E201Q/ E203N, D195Q/E201N/E203Q, D195N/E201Q/E203Q, D195Q/E201Q/E203Q, D149N/E201N, D149Q/E201N, D149N/E201Q, D149Q/E201Q, D149N/E201N/D195N, D149Q/E201N/D195N, D149N/E201Q/D195N, D149N/ E201N/D195Q, D149Q/E201Q/D195N, D149Q/E201N/ D195Q, D149N/E201Q/D195Q, D149Q/E201Q/D195Q, D149N/E203N, D149Q/E203N, D149N/E203Q, D149Q/ E203Q, D149N/E185N/E201N, D149Q/E185N/E201N, D149N/E185Q/E201N, D149N/E185N/E201Q, D149Q/ E185Q/E201N, D149Q/E185N/E201Q, D149N/E185Q/ E201Q, D149Q/E185Q/E201Q, D149N/E185N/E203N, D149Q/E185N/E203N, D149N/E185Q/E203N, D149N/ E185N/E203Q, D149Q/E185Q/E203N, D149Q/E185N/ E203Q, D149N/E185Q/E203Q, D149Q/E185Q/E203Q, D149N/E185N/E201N/E203N, D149Q/E185N/E201N/ E203N, D149N/E185Q/E201N/E203N, D149N/E185N/ E201Q/E203N, D149N/E185N/E201N/E203Q, D149Q/ E185Q/E201N/E203N, D149Q/E185N/E201Q/E203N, D149Q/E185N/E201N/E203N, D149N/E185Q/E201Q/ E203N, D149N/E185Q/E201N/E203Q, D149N/E185N/ E201Q/E203Q, D149Q/E185Q/E201Q/E203Q, D149Q/ E185Q/E201N/E203Q, D149Q/E185Q/E201Q/E203Q, D149N/E185Q/E201Q/E203Q, D149Q/E185Q/E201Q/ E203N, D149N/E185N/D195N/E201N/E203N, D149Q/

E185N/D195N/E201N/E203N, D149N/E185Q/D195N/E201N/E203N, D149N/E185N/D195Q/E201N/E203N, D149N/E185N/D195N/E201Q/E203N, D149N/E185N/D195N/E201N/E203Q, D149Q/E185Q/D195N/E201N/E203N, D149Q/E185N/D195Q/E201N/E203N, D149Q/E185N/D195N/E201Q/E203N, D149Q/E185N/D195N/E201N/E203Q, D149N/E185Q/D195Q/E201N/E203N, D149N/E185Q/D195N/E201Q/E203N, D149N/E185Q/D195N/E201N/E203Q, D149N/E185N/D195Q/E201Q/E203N, D149N/E185N/D195Q/E201N/E203Q, D149N/E185N/D195N/E201Q/E203Q, D149Q/E185Q/D195Q/E201N/E203N, D149Q/E185Q/D195N/E201Q/E203N, D149Q/E185Q/D195N/E201N/E203Q, D149Q/E185N/D195Q/E201Q/E203N, D149Q/E185N/D195Q/E201N/E203Q, D149Q/E185N/D195N/E201Q/E203Q, D149N/E185Q/D195Q/E201Q/E203N, D149N/E185Q/D195Q/E201N/E203Q, D149N/E185Q/D195N/E201Q/E203Q, D149N/E185N/D195Q/E201Q/E203Q, D149Q/E185Q/D195Q/E201Q/E203N, D149Q/E185Q/D195Q/E201N/E203Q, D149Q/E185Q/D195N/E201Q/E203Q, D149Q/E185N/D195Q/E201Q/E203Q, D149N/E185Q/D195Q/E201Q/E203Q, D149Q/E185Q/D195Q/E201Q/E203Q, D149N/E185R/E201N/E203N, D149Q/E185R/E201N/E203N, D149N/E185R/E201Q/E203N, D149N/E185R/E201N/E203Q, D149Q/E185R/E201Q/E203N, D149Q/E185R/E201N/E203Q, D149N/E185R/E201Q/E203Q, D149Q/E185R/E201Q/E203Q, D149R/E185N/E201N/E203N, D149R/E185Q/E201N/E203N, D149R/E185N/E201Q/E203N, D149R/E185N/E201N/E203Q, D149R/E185Q/E201Q/E203N, D149R/E185Q/E201N/E203Q, D149R/E185N/E201Q/E203Q, D149R/E185Q/E201Q/E203Q, D149R/E185N/D195N/E201N/E203N, D149R/E185Q/D195N/E201N/E203N, D149R/E185N/D195Q/E201N/E203N, D149R/E185N/D195N/E201Q/E203N, D149R/E185N/D195N/E201N/E203Q, D149R/E185Q/D195Q/E201N/E203N, D149R/E185Q/D195N/E201Q/E203N, D149R/E185Q/D195N/E201N/E203Q, D149R/E185N/D195Q/E201Q/E203N, D149R/E185N/D195Q/E201N/E203Q, D149R/E185N/D195N/E201Q/E203Q, D149R/E185Q/D195Q/E201Q/E203N, D149R/E185Q/D195Q/E201N/E203Q, D149R/E185Q/D195N/E201Q/E203Q, D149R/E185N/D195Q/E201Q/E203Q, D149R/E185Q/D195Q/E201Q/E203Q, D149N/E185R/D195N/E201N/E203N, D149Q/E185R/D195N/E201N/E203N, D149N/E185R/D195Q/E201N/E203N, D149N/E185R/D195N/E201Q/E203N, D149N/E185R/D195N/E201N/E203Q, D149Q/E185R/D195Q/E201N/E203N, D149Q/E185R/D195N/E201Q/E203N, D149Q/E185R/D195N/E201N/E203Q, D149N/E185R/D195Q/E201Q/E203N, D149N/E185R/D195Q/E201N/E203Q, D149N/E185R/D195N/E201Q/E203Q, D149Q/E185R/D195Q/E201Q/E203N, D149Q/E185R/D195Q/E201N/E203Q, D149Q/E185R/D195N/E201Q/E203Q, D149N/E185R/D195Q/E201Q/E203Q, D149Q/E185R/D195Q/E201Q/E203Q, D149N/E185R/D195N/E201R/E203N, D149Q/E185R/D195N/E201R/E203N, D149N/E185R/D195Q/E201R/E203N, D149N/E185R/D195N/E201R/E203Q, D149Q/E185R/D195Q/E201R/E203N, D149Q/E185R/D195N/E201R/E203Q, D149N/E185R/D195Q/E201R/E203Q, D149Q/E185R/D195Q/E201R/E203Q, E131D/K49R, E101N/N102F, E101N/N102Y, E101N/N102W, E101F/N102F, E101F/N102Y, E101F/N102W, E101Y/N102F, E101Y/N102Y, E101Y/N102W, E101W/N102F, E101W/N102Y, E101W/N102W, E101N/N102R, E101F/N102R, E101Y/N102R or E101W/N102F.

9. An apparatus comprising a mutant CsgG monomer comprising a variant of the sequence shown in SEQ ID NO: 2 which comprises
(a) R97W;
R93W;
R93Y and R97Y; or
F191T; and/or
(b) deletion of V105, A106 and I107; and/or
(c) deletion of one or more of positions R192, F193, I194, D195, Y196, Q197, R198, L199, L200 and E201.

10. The apparatus according to claim 9, wherein the variant comprises R97W.

11. The apparatus according to claim 9, wherein the variant comprises deletion of F193, I194, D195, Y196, Q197, R198 and L199 or deletion of D195, Y196, Q197, R198 and L199.

12. The apparatus according to claim 9, wherein the variant comprises one or more of the following: (i) one or more mutations at the following positions N40, D43, E44, S54, S57, Q62, R97, E101, E124, E131, R142, T150 and R192; (ii) mutations at Y51/N55, Y51/F56, N55/F56 or Y51/N55/F56; (iii) Q42R or Q42K; (iv) K49R or K94Q; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; (xi) deletion of one or more of the following positions F48, K49, P50, Y51, P52, A53, S54, N55, F56 and S57; and (xii) one or more mutations at the following positions L90, N91, I95, A99, Q114.

13. The apparatus according to claim 9, wherein the variant comprises (a) a mutation at Y51 and/or F56, and/or (b) a mutation at R192, and/or (c) a mutation at T150.

14. The apparatus according to claim 13, wherein the mutation at Y51 is Y51A, and/or the mutation at F56 is F56Q, and/or the mutation at R192 is R192D.

15. The apparatus according to claim 9, wherein
(a) the variant comprises one or more of the following substitutions N40R, N40K, D43N, D43Q, D43R, D43K, E44N, E44Q, E44R, E44K, S54P, S57P, Q62R, Q62K, R97N, R97G, R97L, E101N, E101Q, E101R, E101K, E101F, E101Y, E101W, E101T, E124N, E124Q, E124R, E124K, E124F, E124Y, E124W, E131D, R142E, R142N, T150I, R192E and R192N;
(b) the variant comprises in (ii) F56N/N55Q, F56N/N55R, F56N/N55K, F56N/N55S, F56N/N55G, F56N/N55A, F56N/N55T, F56Q/N55Q, F56Q/N55R, F56Q/N55K, F56Q/N55S, F56Q/N55G, F56Q/N55A, F56Q/N55T, F56R/N55Q, F56R/N55R, F56R/N55K, F56R/N55S, F56R/N55G, F56R/N55A, F56R/N55T, F56S/N55Q, F56S/N55R, F56S/N55K, F56S/N55S, F56S/N55G, F56S/N55A, F56S/N55T, F56G/N55Q, F56G/N55R, F56G/N55K, F56G/N55S, F56G/N55G, F56G/N55A, F56G/N55T, F56A/N55Q, F56A/N55R, F56A/N55K, F56A/N55S, F56A/N55G, F56A/N55A, F56A/N55T, F56K/N55Q, F56K/N55R, F56K/N55K, F56K/N55S, F56K/N55G, F56K/N55A, F56K/N55T, F56N/Y51L, F56N/Y51V, F56N/Y51A, F56N/Y51N, F56N/Y51Q, F56N/Y51S, F56N/Y51G, F56Q/Y51L, F56Q/Y51V, F56Q/Y51A, F56Q/Y51N, F56Q/Y51Q, F56Q/Y51S, F56Q/Y51G, F56R/Y51L, F56R/Y51V, F56R/Y51A, F56R/Y51N, F56R/Y51Q, F56R/Y51S, F56R/Y51G, F56S/Y51L, F56S/Y51V, F56S/Y51A, F56S/Y51N, F56S/Y51Q, F56S/Y51S, F56S/Y51G, F56G/Y51L, F56G/Y51V, F56G/Y51A, F56G/Y51N, F56G/Y51Q, F56G/Y51S, F56G/Y51G, F56A/Y51L, F56A/Y51V, F56A/Y51A, F56A/Y51N, F56A/Y51Q, F56A/Y51S, F56A/Y51G, F56K/Y51L, F56K/Y51V, F56K/

Y51A, F56K/Y51N, F56K/Y51Q, F56K/Y51S, F56K/
Y51G, N55Q/Y51L, N55Q/Y51V, N55Q/Y51A,
N55Q/Y51N, N55Q/Y51Q, N55Q/Y51S, N55Q/
Y51G, N55R/Y51L, N55R/Y51V, N55R/Y51A, N55R/
Y51N, N55R/Y51Q, N55R/Y51S, N55R/Y51G,
N55K/Y51L, N55K/Y51V, N55K/Y51A, N55K/
Y51N, N55K/Y51Q, N55K/Y51S, N55K/Y51G,
N55S/Y51L, N55S/Y51V, N55S/Y51A, N55S/Y51N,
N55S/Y51Q, N55S/Y51S, N55S/Y51G, N55G/Y51L,
N55G/Y51V, N55G/Y51A, N55G/Y51N, N55G/
Y51Q, N55G/Y51S, N55G/Y51G, N55A/Y51L,
N55A/Y51V, N55A/Y51A, N55A/Y51N, N55A/
Y51Q, N55A/Y51S, N55A/Y51G, N55T/Y51L, N55T/
Y51V, N55T/Y51A, N55T/Y51N, N55T/Y51Q, N55T/
Y51S, N55T/Y51G, F56N/N55Q/Y51L, F56N/N55Q/
Y51V, F56N/N55Q/Y51A, F56N/N55Q/Y51N, F56N/
N55Q/Y51Q, F56N/N55Q/Y51S, F56N/N55Q/Y51G,
F56N/N55R/Y51L, F56N/N55R/Y51V, F56N/N55R/
Y51A, F56N/N55R/Y51N, F56N/N55R/Y51Q, F56N/
N55R/Y51S, F56N/N55R/Y51G, F56N/N55K/Y51L,
F56N/N55K/Y51V, F56N/N55K/Y51A, F56N/N55K/
Y51N, F56N/N55K/Y51Q, F56N/N55K/Y51S, F56N/
N55K/Y51G, F56N/N55S/Y51L, F56N/N55S/Y51V,
F56N/N55S/Y51A, F56N/N55S/Y51N, F56N/N55S/
Y51Q, F56N/N55S/Y51S, F56N/N55S/Y51G, F56N/
N55G/Y51L, F56N/N55G/Y51V, F56N/N55G/Y51A,
F56N/N55G/Y51N, F56N/N55G/Y51Q, F56N/N55G/
Y51S, F56N/N55G/Y51G, F56N/N55A/Y51L, F56N/
N55A/Y51V, F56N/N55A/Y51A, F56N/N55A/Y51N,
F56N/N55A/Y51Q, F56N/N55A/Y51S, F56N/N55A/
Y51G, F56N/N55T/Y51L, F56N/N55T/Y51V, F56N/
N55T/Y51A, F56N/N55T/Y51N, F56N/N55T/Y51Q,
F56N/N55T/Y51S, F56N/N55T/Y51G, F56Q/N55Q/
Y51L, F56Q/N55Q/Y51V, F56Q/N55Q/Y51A, F56Q/
N55Q/Y51N, F56Q/N55Q/Y51Q, F56Q/N55Q/Y51S,
F56Q/N55Q/Y51G, F56Q/N55R/Y51L, F56Q/N55R/
Y51V, F56Q/N55R/Y51A, F56Q/N55R/Y51N, F56Q/
N55R/Y51Q, F56Q/N55R/Y51S, F56Q/N55R/Y51G,
F56Q/N55K/Y51L, F56Q/N55K/Y51V, F56Q/N55K/
Y51A, F56Q/N55K/Y51N, F56Q/N55K/Y51Q, F56Q/
N55K/Y51S, F56Q/N55K/Y51G, F56Q/N55S/Y51L,
F56Q/N55S/Y51V, F56Q/N55S/Y51A, F56Q/N55S/
Y51N, F56Q/N55S/Y51Q, F56Q/N55S/Y51S, F56Q/
N55S/Y51G, F56Q/N55G/Y51L, F56Q/N55G/Y51V,
F56Q/N55G/Y51A, F56Q/N55G/Y51N, F56Q/N55G/
Y51Q, F56Q/N55G/Y51S, F56Q/N55G/Y51G, F56Q/
N55A/Y51L, F56Q/N55A/Y51V, F56Q/N55A/Y51A,
F56Q/N55A/Y51N, F56Q/N55A/Y51Q, F56Q/N55A/
Y51S, F56Q/N55A/Y51G, F56Q/N55T/Y51L, F56Q/
N55T/Y51V, F56Q/N55T/Y51A, F56Q/N55T/Y51N,
F56Q/N55T/Y51Q, F56Q/N55T/Y51S, F56Q/N55T/
Y51G, F56R/N55Q/Y51L, F56R/N55Q/Y51V, F56R/
N55Q/Y51A, F56R/N55Q/Y51N, F56R/N55Q/Y51Q,
F56R/N55Q/Y51S, F56R/N55Q/Y51G, F56R/N55R/
Y51L, F56R/N55R/Y51V, F56R/N55R/Y51A, F56R/
N55R/Y51N, F56R/N55R/Y51Q, F56R/N55R/Y51S,
F56R/N55R/Y51G, F56R/N55K/Y51L, F56R/N55K/
Y51V, F56R/N55K/Y51A, F56R/N55K/Y51N, F56R/
N55K/Y51Q, F56R/N55K/Y51S, F56R/N55K/Y51G,
F56R/N55S/Y51L, F56R/N55S/Y51V, F56R/N55S/
Y51A, F56R/N55S/Y51N, F56R/N55S/Y51Q, F56R/
N55S/Y51S, F56R/N55S/Y51G, F56R/N55G/Y51L,
F56R/N55G/Y51V, F56R/N55G/Y51A, F56R/N55G/
Y51N, F56R/N55G/Y51Q, F56R/N55G/Y51S, F56R/
N55G/Y51G, F56R/N55A/Y51L, F56R/N55A/Y51V,
F56R/N55A/Y51A, F56R/N55A/Y51N, F56R/N55A/
Y51Q, F56R/N55A/Y51S, F56R/N55A/Y51G, F56R/
N55T/Y51L, F56R/N55T/Y51V, F56R/N55T/Y51A,
F56R/N55T/Y51N, F56R/N55T/Y51Q, F56R/N55T/
Y51S, F56R/N55T/Y51G, F56S/N55Q/Y51L, F56S/
N55Q/Y51V, F56S/N55Q/Y51A, F56S/N55Q/Y51N,
F56S/N55Q/Y51Q, F56S/N55Q/Y51S, F56S/N55Q/
Y51G, F56S/N55R/Y51L, F56S/N55R/Y51V, F56S/
N55R/Y51A, F56S/N55R/Y51N, F56S/N55R/Y51Q,
F56S/N55R/Y51S, F56S/N55R/Y51G, F56S/N55K/
Y51L, F56S/N55K/Y51V, F56S/N55K/Y51A, F56S/
N55K/Y51N, F56S/N55K/Y51Q, F56S/N55K/Y51S,
F56S/N55K/Y51G, F56S/N55S/Y51L, F56S/N55S/
Y51V, F56S/N55S/Y51A, F56S/N55S/Y51N, F56S/
N55S/Y51Q, F56S/N55S/Y51S, F56S/N55S/Y51G,
F56S/N55G/Y51L, F56S/N55G/Y51V, F56S/N55G/
Y51A, F56S/N55G/Y51N, F56S/N55G/Y51Q, F56S/
N55G/Y51S, F56S/N55G/Y51G, F56S/N55A/Y51L,
F56S/N55A/Y51V, F56S/N55A/Y51A, F56S/N55A/
Y51N, F56S/N55A/Y51Q, F56S/N55A/Y51S, F56S/
N55A/Y51G, F56S/N55T/Y51L, F56S/N55T/Y51V,
F56S/N55T/Y51A, F56S/N55T/Y51N, F56S/N55T/
Y51Q, F56S/N55T/Y51S, F56S/N55T/Y51G, F56G/
N55Q/Y51L, F56G/N55Q/Y51V, F56G/N55Q/Y51A,
F56G/N55Q/Y51N, F56G/N55Q/Y51Q, F56G/N55Q/
Y51S, F56G/N55Q/Y51G, F56G/N55R/Y51L, F56G/
N55R/Y51V, F56G/N55R/Y51A, F56G/N55R/Y51N,
F56G/N55R/Y51Q, F56G/N55R/Y51S, F56G/N55R/
Y51G, F56G/N55K/Y51L, F56G/N55K/Y51V, F56G/
N55K/Y51A, F56G/N55K/Y51N, F56G/N55K/Y51Q,
F56G/N55K/Y51S, F56G/N55K/Y51G, F56G/N55S/
Y51L, F56G/N55S/Y51V, F56G/N55S/Y51A, F56G/
N55S/Y51N, F56G/N55S/Y51Q, F56G/N55S/Y51S,
F56G/N55S/Y51G, F56G/N55G/Y51L, F56G/N55G/
Y51V, F56G/N55G/Y51A, F56G/N55G/Y51N, F56G/
N55G/Y51Q, F56G/N55G/Y51S, F56G/N55G/Y51G,
F56G/N55A/Y51L, F56G/N55A/Y51V, F56G/N55A/
Y51A, F56G/N55A/Y51N, F56G/N55A/Y51Q, F56G/N55A/Y51S, F56G/N55A/Y51G, F56G/N55T/Y51L, F56G/N55T/Y51V, F56G/N55T/Y51A, F56G/N55T/Y51N, F56G/N55T/Y51Q, F56G/N55T/Y51S, F56G/N55T/Y51G, F56A/N55Q/Y51L, F56A/N55Q/Y51V, F56A/N55Q/Y51A, F56A/N55Q/Y51N, F56A/N55Q/Y51Q, F56A/N55Q/Y51S, F56A/N55Q/Y51G, F56A/N55R/Y51L, F56A/N55R/Y51V, F56A/N55R/Y51A, F56A/N55R/Y51N, F56A/N55R/Y51Q, F56A/N55R/Y51S, F56A/N55R/Y51G, F56A/N55K/Y51L, F56A/N55K/Y51V, F56A/N55K/Y51A, F56A/N55K/Y51N, F56A/N55K/Y51Q, F56A/N55K/Y51S, F56A/N55K/Y51G, F56A/N55S/Y51L, F56A/N55S/Y51V, F56A/N55S/Y51A, F56A/N55S/Y51N, F56A/N55S/Y51Q, F56A/N55S/Y51S, F56A/N55S/Y51G, F56A/N55G/Y51L, F56A/N55G/Y51V, F56A/N55G/Y51A, F56A/N55G/Y51N, F56A/N55G/Y51Q, F56A/N55G/Y51S, F56A/N55G/Y51G, F56A/N55A/Y51L, F56A/N55A/Y51V, F56A/N55A/Y51A, F56A/N55A/Y51N, F56A/N55A/Y51Q, F56A/N55A/Y51S, F56A/N55A/Y51G, F56A/N55T/Y51L, F56A/N55T/Y51V, F56A/N55T/Y51A, F56A/N55T/Y51N, F56A/N55T/Y51Q, F56A/N55T/Y51S, F56A/N55T/Y51G, F56K/N55Q/Y51L, F56K/N55Q/Y51V, F56K/N55Q/Y51A, F56K/N55Q/Y51N, F56K/N55Q/Y51Q, F56K/N55Q/Y51S, F56K/N55Q/Y51G, F56K/N55R/Y51L, F56K/N55R/Y51V, F56K/N55R/Y51A, F56K/N55R/Y51N, F56K/N55R/Y51Q, F56K/N55R/Y51S, F56K/N55R/Y51G, F56K/N55K/Y51L, F56K/N55K/Y51V, F56K/N55K/Y51A, F56K/N55K/Y51N, F56K/N55K/Y51Q, F56K/N55K/Y51S, F56K/N55K/Y51G, F56K/N55S/Y51L, F56K/N55S/Y51V, F56K/N55S/Y51A, F56K/N55S/Y51N,

F56K/N55S/Y51Q, F56K/N55S/Y51S, F56K/N55S/ Y51G, F56K/N55G/Y51L, F56K/N55G/Y51V, F56K/ N55G/Y51A, F56K/N55G/Y51N, F56K/N55G/Y51Q, F56K/N55G/Y51S, F56K/N55G/Y51G, F56K/N55A/ Y51L, F56K/N55A/Y51V, F56K/N55A/Y51A, F56K/ N55A/Y51N, F56K/N55A/Y51Q, F56K/N55A/Y51S, F56K/N55A/Y51G, F56K/N55T/Y51L, F56K/N55T/ Y51V, F56K/N55T/Y51A, F56K/N55T/Y51N, F56K/ N55T/Y51Q,F56K/N55T/Y51S, F56K/N55T/Y51G, F56E/N55R, F56E/N55K, F56D/N55R, F56D/N55K, F56R/N55E, F56R/N55D, F56K/N55E or F56K/ N55D;

(c) the variant comprises deletion of Y51/P52, Y51/P52/ A53, P50 to P52, P50 to A53, K49 to Y51, K49 to A53 and replacement with a single proline (P), K49 to S54 and replacement with a single P, Y51 to A53, Y51 to S54, N55/F56, N55 to S57, N55/F56 and replacement with a single P, N55/F56 and replacement with a single glycine (G), N55/F56 and replacement with a single alanine (A), N55/F56 and replacement with a single P and Y51N, N55/F56 and replacement with a single P and Y51Q, N55/F56 and replacement with a single P and Y51S, N55/F56 and replacement with a single G and Y51N, N55/F56 and replacement with a single G and Y51Q, N55/F56 and replacement with a single G and Y51S, N55/F56 and replacement with a single A and Y51N, N55/F56 and replacement with a single A/Y51Q or N55/F56 and replacement with a single A and Y51S; and/or (d) the variant comprises one or more of L90R or L90K, N91R or N91K, I95R or I95K, A99R or A99K, Q114K or Q114R.

16. The apparatus according to claim 9, wherein the variant comprises D195N/E203N, D195Q/E203N, D195N/ E203Q, D195Q/E203Q, E201N/E203N, E201Q/E203N, E201N/E203Q, E201Q/E203Q, E185N/E203Q, E185Q/ E203Q, E185N/E203N, E185Q/E203N, D195N/E201N/ E203N, D195Q/E201N/E203N, D195N/E201Q/E203N, D195N/E201N/E203Q, D195Q/E201Q/E203N, D195Q/ E201N/E203Q, D195N/E201Q/E203Q, D195Q/E201Q/ E203Q, D149N/E201N, D149Q/E201N, D149N/E201Q, D149Q/E201Q, D149N/E201N/D195N, D149Q/E201N/ D195N, D149N/E201Q/D195N, D149N/E201N/D195Q, D149Q/E201Q/D195N, D149Q/E201N/D195Q, D149N/ E201Q/D195Q, D149Q/E201Q/D195Q, D149N/E203N, D149Q/E203N, D149N/E203Q, D149Q/E203Q, D149N/ E185N/E201N, D149Q/E185N/E201N, D149N/E185Q/ E201N, D149N/E185N/E201Q, D149Q/E185Q/E201N, D149Q/E185N/E201Q, D149N/E185Q/E201Q, D149Q/ E185Q/E201Q, D149N/E185N/E203N, D149Q/E185N/ E203N, D149N/E185N/E203Q, D149N/E185N/E203Q, D149Q/E185Q/E203N, D149Q/E185N/E203Q, D149N/ E185Q/E203Q, D149Q/E185Q/E203Q, D149N/E185N/ E201N/E203N, D149Q/E185N/E201N/E203N, D149N/ E185Q/E201N/E203N, D149N/E185N/E201Q/E203N, D149N/E185N/E201N/E203Q, D149Q/E185Q/E201N/ E203N, D149Q/E185N/E201Q/E203N, D149Q/E185N/ E201N/E203Q, D149N/E185Q/E201Q/E203N, D149N/ E185Q/E201N/E203Q, D149N/E185N/E201Q/E203Q, D149Q/E185Q/E201Q/E203Q, D149Q/E185Q/E201N/ E203Q, D149Q/E185Q/E201Q/E203N, D149N/E185Q/ E201Q/E203Q, D149Q/E185Q/E201Q/E203Q, D149N/ E185N/D195N/E201N/E203N, D149Q/E185N/D195N/ E201N/E203N, D149N/E185Q/D195N/E201N/E203N, D149N/E185N/D195Q/E201N/E203N, D149N/E185N/ D195N/E201Q/E203N, D149N/E185N/D195N/E201N/ E203Q, D149Q/E185Q/D195N/E201N/E203N, D149Q/ E185N/D195Q/E201N/E203N, D149Q/E185N/D195N/ E201Q/E203N, D149Q/E185N/D195N/E201N/E203Q, D149N/E185Q/D195Q/E201N/E203N, D149N/E185Q/ D195N/E201Q/E203Q, D149Q/E185Q/D195Q/E201Q/ E203N, D149Q/E185Q/D195Q/E201N/E203Q, D149Q/ E185Q/D195N/E201Q/E203Q, D149Q/E185N/D195Q/ E201Q/E203Q, D149N/E185Q/D195Q/E201Q/E203Q, D149Q/E185Q/D195Q/E201Q/E203Q, D149N/E185R/ E201N/E203N, D149Q/E185R/E201N/E203N, D149N/ E185R/E201Q/E203N, D149N/E185R/E201N/E203Q, D149Q/E185R/E201Q/E203N, D149Q/E185R/E201N/ E203Q, D149N/E185R/E201Q/E203Q, D149Q/E185R/ E201Q/E203Q, D149R/E185N/E201N/E203N, D149R/ E185Q/E201N/E203N, D149R/E185N/E201Q/E203N, D149R/E185N/E201N/E203Q, D149R/E185Q/E201Q/ E203N, D149R/E185Q/E201N/E203Q, D149R/E185N/ E201Q/E203Q, D149R/E185Q/E201Q/E203Q, D149R/ E185N/D195N/E201N/E203N, D149R/E185Q/D195N/ E201N/E203N, D149R/E185N/D195Q/E201N/E203N, D149R/E185N/D195N/E201Q/E203N, D149R/E185Q/ D195N/E201N/E203Q, D149R/E185Q/D195Q/E201N/ E203N, D149R/E185Q/D195N/E201Q/E203N, D149R/ E185Q/D195N/E201N/E203Q, D149R/E185N/D195Q/ E201Q/E203N, D149R/E185N/D195N/E201Q/E203Q, D149R/E185N/D195Q/E201Q/E203Q, D149R/E185Q/ D195Q/E201Q/E203N, D149R/E185Q/D195N/E201N/ E203Q, D149R/E185Q/D195N/E201Q/E203Q, D149R/ E185N/D195Q/E201Q/E203Q, D149R/E185Q/D195Q/ E201Q/E203Q, D149N/E185R/D195N/E201N/E203N, D149Q/E185R/D195N/E201N/E203N, D149N/E185R/ D195Q/E201N/E203N, D149N/E185R/D195N/E201Q/ E203N, D149N/E185R/D195N/E201N/E203Q, D149Q/ E185R/D195Q/E201N/E203N, D149Q/E185R/D195N/ E201Q/E203N, D149Q/E185R/D195N/E201N/E203Q, D149N/E185R/D195Q/E201Q/E203N, D149N/E185R/ D195Q/E201N/E203Q, D149N/E185R/D195N/E201Q/ E203Q, D149Q/E185R/D195Q/E201Q/E203N, D149Q/ E185R/D195Q/E201N/E203Q, D149Q/E185R/D195N/ E201Q/E203Q, D149N/E185R/D195Q/E201Q/E203Q, D149Q/E185R/D195Q/E201Q/E203Q, D149N/E185R/ D195N/E201R/E203N, D149Q/E185R/D195N/E201R/ E203N, D149N/E185R/D195Q/E201R/E203N, D149N/ E185R/D195N/E201R/E203Q, D149Q/E185R/D195Q/ E201R/E203N, D149Q/E185R/D195N/E201R/E203Q, D149N/E185R/D195Q/E201R/E203Q, D149Q/E185R/ D195Q/E201R/E203Q, E131D/K49R, E101N/N102F, E101N/N102Y, E101N/N102W, E101F/N102F, E101F/ N102Y, E101F/N102W, E101Y/N102F, E101Y/N102Y, E101Y/N102W, E101W/N102F, E101W/N102Y, E101W/ N102W, E101N/N102R, E101F/N102R, E101Y/N102R or E101W/N102F.

* * * * *